(12) United States Patent
Kay et al.

(10) Patent No.: US 7,622,463 B2
(45) Date of Patent: Nov. 24, 2009

(54) DIHYDRODIAZEPINES USEFUL AS INHIBITORS OF PROTEIN KINASES

(75) Inventors: David Kay, Purton (GB); Ronald Knegtel, Abingdon (GB); Jean-Damien Charrier, Wantage (GB); Heather Twin, Wantage (GB)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 152 days.

(21) Appl. No.: 11/706,070

(22) Filed: Feb. 13, 2007

(65) Prior Publication Data

US 2008/0167289 A1 Jul. 10, 2008

Related U.S. Application Data

(60) Provisional application No. 60/876,206, filed on Dec. 21, 2006, provisional application No. 60/849,353, filed on Oct. 4, 2006, provisional application No. 60/831,371, filed on Jul. 17, 2006, provisional application No. 60/772,992, filed on Feb. 14, 2006.

(51) Int. Cl.
*C07D 401/12* (2006.01)
*A61K 31/4545* (2006.01)

(52) U.S. Cl. .................. 514/220; 514/221; 540/495; 540/501

(58) Field of Classification Search ............ 540/495, 540/501; 514/220, 221
See application file for complete search history.

(56) References Cited

U.S. PATENT DOCUMENTS

| 3,880,855 | A | 4/1975 | Juby et al. |
|---|---|---|---|
| 2003/0191307 | A1 | 10/2003 | Blumenkopf et al. |
| 2004/0176380 | A1 | 9/2004 | Hoffmann et al. |

FOREIGN PATENT DOCUMENTS

| DE | 2418285 | A1 | 11/1974 |
|---|---|---|---|
| EP | 445467 | A1 | 3/1990 |
| WO | 0119825 | A1 | 3/2001 |
| WO | 0140215 | A1 | 6/2001 |
| WO | 03020722 | A1 | 3/2003 |
| WO | 2004076454 | A1 | 9/2004 |
| WO | 2005123736 | A1 | 12/2005 |
| WO | 2006058876 | A1 | 6/2006 |
| WO | 2009040556 | A1 | 4/2009 |
| WO | 2009042711 | A1 | 4/2009 |

OTHER PUBLICATIONS

International Search Report Received in the corresponding PCT Application No. PCT/US2007/003699.
Couture, Karine; Ple, Nelly; Turck, Alain; Queguiner, Guy, "A new route to aminodiazines via a metalation reaction. Synthesis of an aza analog of nevirapine," Electronic Conference on Heterocyclic Chemistry, [Proceedings], Jun. 24-Jul. 22, 1996 (1997).
Ple, Nelly; Turck, Alain; Couture, Karine; Queguiner, Guy, "A new route to aminodiazines via metalation reaction. Synthesis of an aza analog of nevirapine. Diazines", Synthesis (1996), (7), 838-842.
Phillips, Oludotun A.; Knaus, Edward E., "Synthesis of 6,7,8,9-tetrahydro-5H-pyrimido[4,5-b][1,4]diazepine-6,8-diones", Journal of Heterocyclic Chemistry (1993), 30(1), 283-5.
Boyle, Peter H.; Hughes, Enid M.; Khattab, Hassan A., "Synthesis of a 2,4-diaminodihydrohomopteridine,6-acetyl-2,4-diamino-7,8-dihydro-9H-pyrimido[4,5-b][1,4]diazepine, using a furazano[3,4-d]pyrimidine precursor", Tetrahedron (1991), 47(28), 5259-68.

*Primary Examiner*—Bruck Kifle
(74) *Attorney, Agent, or Firm*—Booyong Shimlim; Lisa A. Dixon; Vertex Pharmaceuticals Incorporated

(57) ABSTRACT

The present invention relates to compounds useful as inhibitors of protein kinase. The invention also provides pharmaceutically acceptable compositions comprising said compounds and methods of using the compositions in the treatment of various disease, conditions, or disorders. The invention also provides processes for preparing compounds of the inventions.

42 Claims, No Drawings

DIHYDRODIAZEPINES USEFUL AS INHIBITORS OF PROTEIN KINASES

CROSS REFERENCE TO RELATED APPLICATIONS

This non-provisional patent application claims priority to U.S. Provisional Application No. 60/876,206, filed Dec. 21, 2006; U.S. Provisional Application No. 60/849,353, filed Oct. 4, 2006; U.S. Provisional Application No. 60/831,371 filed Jul. 17, 2006; U.S. Provisional Application No. 60/772,992, filed Feb. 14, 2006; each of which is incorporated by reference in its entirety.

TECHNICAL FIELD OF THE INVENTION

The present invention relates to compounds useful as inhibitors of protein kinases. The invention also relates to pharmaceutically acceptable compositions comprising the compounds of the invention and methods of using the compositions in the treatment of various disorders. The invention also relates to processes for preparing the compounds of the invention.

BACKGROUND OF THE INVENTION

The search for new therapeutic agents has been greatly aided in recent years by a better understanding of the structure of enzymes and other biomolecules associated with diseases. One important class of enzymes that has been the subject of intensive study is protein kinases.

Protein kinases constitute a large family of structurally related enzymes that are responsible for the control of a variety of signal transduction processes within the cell (see Hardie, G. and Hanks, S. *The Protein Kinase Facts Book, I and II*, Academic Press, San Diego, Calif.: 1995). Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids etc). Sequence motifs have been identified that generally correspond to each of these kinase families (See, for example, Hanks, S. K., Hunter, T., *FASEB J.* 1995, 9, 576-596; Knighton et al., *Science* 1991, 253, 407-414; Hiles et al, *Cell* 1992, 70, 419-429; Kunz et al, *Cell* 1993, 73, 585-596; Garcia-Bustos et al, *EMBO J.* 1994, 13, 2352-2361).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., shock, heat shock, ultraviolet radiation, bacterial endotoxin, and $H_2O_2$), cytokines (e.g., interleukin-1 (IL-1) and tumor necrosis factor alpha (TNF-a), and growth factors (e.g., granulocyte macrophage-colony stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, survival and regulation of the cell cycle.

Many diseases are associated with abnormal cellular responses triggered by protein kinase-mediated events as described above. These diseases include, but are not limited to, cancer, autoimmune diseases, inflammatory diseases, bone diseases, metabolic diseases, neurological and neurodegenerative diseases, cardiovascular diseases, allergies and asthma, Alzheimer's disease and hormone related diseases. Accordingly, there has been a substantial effort in medicinal chemistry to find protein kinase inhibitors that are effective as therapeutic agents.

The Polo-like kinases (Plk) belong to a family of serine/threonine kinases that are highly conserved across the species, ranging from yeast to man (reviewed in Lowery D M et al., *Oncogene* 2005, 24; 248-259). The Plk kinases have multiple roles in cell cycle, including control of entry into and progression through mitosis.

Plk1 is the best characterized of the Plk family members. Plk1 is widely expressed and is most abundant in tissues with a high mitotic index. Protein levels of Plk1 rise and peak in mitosis (Hamanaka, R et al., *J Biol Chem* 1995, 270, 21086-21091). The reported substrates of Plk1 are all molecules that are known to regulate entry and progression through mitosis, and include CDC25C, cyclin B, p53, APC, BRCA2 and the proteasome. Plk1 is upregulated in multiple cancer types and the expression levels correlate with severity of disease (Macmillan, J C et al., *Ann Surg Oncol* 2001, 8, 729-740). Plk1 is an oncogene and can transform NIH-3T3 cells (Smith, M R et al., *Biochem Biophys Res Commun* 1997, 234, 397-405). Depletion or inhibition of Plk1 by siRNA, antisense, microinjection of antibodies, or transfection of a dominant negative construct of Plk1 into cells, reduces proliferation and viability of tumour cells in vitro (Guan, R et al., Cancer Res 2005, 65, 2698-2704; Liu, X et al., *Proc Natl Acad Sci USA* 2003, 100, 5789-5794, Fan, Y et al., *World J Gastroenterol* 2005, 11, 4596-4599; Lane, H A et al., *J Cell Biol* 1996, 135, 1701-1713). Tumour cells that have been depleted of Plk1 have activated spindle checkpoints and defects in spindle formation, chromosome alignment and separation and cytokinesis. Loss in viability has been reported to be the result of an induction of apoptosis. In contrast, normal cells have been reported to maintain viability on depletion of Plk1. In vivo knock down of Plk1 by siRNA or the use of dominant negative constructs leads to growth inhibition or regression of tumours in xenograft models.

Plk2 is mainly expressed during the G1 phase of the cell cycle and is localized to the centrosome in interphase cells. Plk2 knockout mice develop normally, are fertile and have normal survival rates, but are around 20% smaller than wild type mice. Cells from knockout animals progress through the cell cycle more slowly than in normal mice (Ma, S et al., *Mol Cell Biol* 2003, 23, 6936-6943). Depletion of Plk2 by siRNA or transfection of kinase inactive mutants into cells blocks centriole duplication. Downregulation of Plk2 also sensitizes tumour cells to taxol and promotes mitotic catastrophe, in part by suppression of the p53 response (Burns T F et al., *Mol Cell Biol* 2003, 23, 5556-5571).

Plk3 is expressed throughout the cell cycle and increases from G1 to mitosis. Expression is upregulated in highly proliferating ovarian tumours and breast cancer and is associated with a worse prognosis (Weichert, W et al., *Br J Cancer* 2004, 90, 815-821; Weichert, W et al., *Virchows Arch* 2005, 446, 442-450). In addition to regulation of mitosis, Plk3 is believed to be involved in Golgi fragmentation during the cell cycle and in the DNA-damage response. Inhibition of Plk3 by dominant negative expression is reported to promote p53- independent apoptosis after DNA damage and suppresses colony formation by tumour cells (Li, Z et al., *J Biol Chem* 2005, 280, 16843-16850).

Plk4 is structurally more diverse from the other Plk family members. Depletion of this kinase causes apoptosis in cancer cells (Li, J et al., *Neoplasia* 2005, 7, 312-323). Plk4 knockout mice arrest at E7.5 with a high fraction of cells in mitosis and partly segregated chromosomes (Hudson, J W et al., *Current Biology* 2001, 11, 441-446).

Molecules of the protein kinase family have been implicated in tumour cell growth, proliferation and survival. Accordingly, there is a great need to develop compounds useful as inhibitors of protein kinases. The evidence implicating the Plk kinases as essential for cell division is strong. Blockade of the cell cycle is a clinically validated approach to inhibiting tumour cell proliferation and viability. It would therefore be desirable to develop compounds that are useful as inhibitors of the Plk family of protein kinases (e.g., Plk1, Plk2, Plk3 and Plk4), that would inhibit proliferation and reduce viability of tumour cells, particularly as there is a strong medical need to develop new treatments for cancer, including treatments that would be administered orally.

SUMMARY OF THE INVENTION

Compounds of this invention, and pharmaceutically acceptable compositions thereof, are useful as inhibitors of protein kinases. In some embodiments, these compounds are useful as inhibitors of PLK protein kinases; in some embodiments, as inhibitors of PLK1 protein kinases. These compounds have the formula I, as defined herein, or a pharmaceutically acceptable salt thereof.

These compounds and pharmaceutically acceptable compositions thereof are useful for treating or preventing a variety of diseases, disorders or conditions, including, but not limited to, an autoimmune, inflammatory, proliferative, or hyperproliferative disease, a neurodegenerative disease, or an immunologically-mediated disease. The compounds provided by this invention are also useful for the study of kinases in biological and pathological phenomena; the study of intracellular signal transduction pathways mediated by such kinases; and the comparative evaluation of new kinase inhibitors.

DETAILED DESCRIPTION OF THE INVENTION

This invention provides compounds of Formula I:

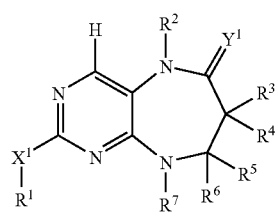

wherein
$X^1$ is a bond, O, $NR^8$, S, SO, or $SO_2$;
$Y^1$ is O or $NR^9$;
$R^1$ is H, $C_{1-10}$aliphatic, $C_{3-10}$cycloaliphatic, $C_{6-10}$aryl, 5-10 membered heteroaryl, or 3-10 membered heterocyclyl; wherein said $R^1$ is optionally substituted with 0-5 $J^1$; provided that when $X^1$ is a bond, $R^1$ is not H;

$R^2$ is H, $C_{1-10}$aliphatic, —($C_{1-10}$aliphatic)-($C_{3-10}$cycloaliphatic), $C_{3-8}$cycloaliphatic, halo$C_{1-4}$ aliphatic; wherein said $R^2$ is optionally substituted with 0-4 $J^2$;
each $R^3$, $R^4$, $R^5$, and $R^6$ is independently H, $C_{1-10}$aliphatic, $C_{3-10}$cycloaliphatic, $C_{6-10}$aryl, or 5-10 membered heteroaryl; wherein each $R^3$, $R^4$, $R^5$, and $R^6$ is optionally and independently substituted with 0-5 $J^3$, $J^4$, $J^5$, and $J^6$ respectively; and
$R^7$ is H, C(O)R, C(O)OR, or C(O)NRR', $C_{1-10}$aliphatic, $C_{3-10}$cycloaliphatic, $C_{6-10}$aryl, 5-10 membered heteroaryl, 3-10 membered heterocyclyl, —($C_{1-6}$aliphatic)-($C_{3-10}$cycloaliphatic), —($C_{1-6}$aliphatic)-($C_{6-10}$aryl), or —($C_{1-6}$aliphatic)-(5-10 membered heteroaryl); wherein said $R^7$ is optionally substituted with 0-5 $J^7$; or
$R^3$ and $R^4$, together with the carbon atom to which they are attached, optionally form a 3-8 membered saturated or partially unsaturated monocyclic ring containing 0-4 heteroatoms independently selected from O, N, and S; said monocyclic ring formed by $R^3$ and $R^4$ is optionally substituted with 0-4 $J^{34}$;
$R^5$ and $R^6$, together with the carbon atom to which they are attached, optionally form a 3-8 membered saturated or partially unsaturated monocyclic ring containing 0-4 heteroatoms independently selected from O, N, and S; said monocyclic ring formed by $R^5$ and $R^6$ is optionally substituted with 0-4 $J^{56}$;
$R^3$ and $R^5$, together with the carbon atoms to which they are attached, optionally form a 3-8 membered saturated or partially unsaturated monocyclic ring containing 0-4 heteroatoms independently selected from O, N, and S; said monocyclic ring formed by $R^3$ and $R^5$ is optionally substituted with 0-4 $J^{35}$;
$R^3$ and $R^7$, together with the atoms to which they are attached, optionally form a 4-8 membered saturated or partially unsaturated monocyclic ring containing 0-4 heteroatoms independently selected from O, N, and S; said monocyclic ring formed by $R^3$ and $R^7$ is optionally substituted with 0-4 $J^{37}$;
$R^5$ and $R^7$, together with the atoms to which they are attached, optionally form a 3-8 membered saturated or partially unsaturated monocyclic ring containing 0-4 heteroatoms independently selected from O, N, and S; said monocyclic ring formed by $R^5$ and $R^7$ is optionally substituted with 0-4 $J^{57}$;
$R^8$ is H, $C_{1-6}$aliphatic, $C_{3-8}$cycloaliphatic, C(O)R, C(O)OR, or C(O)NRR';
$R^9$ is H or unsubstituted $C_{1-6}$aliphatic; or
$R^2$ and $R^9$, together with the atoms to which they are attached, optionally form a 5-8 membered aromatic or nonaromatic monocyclic ring containing 2-4 heteroatoms independently selected from O, N, and S; said monocyclic ring formed by $R^2$ and $R^9$ is optionally substituted with 0-4 $J^{29}$;
each $J^1$ is independently $C_{1-6}$haloalkyl, halo, $NO_2$, CN, Q, or -Z-Q; or, two $J^1$ taken together can optionally form =O;
Z is $C_{1-6}$aliphatic optionally replaced with 0-3 occurrences of —NR—, —O—, —S—, —C(O)—, —C(=NR)—, —C(=NOR)—, —SO—, or —$SO_2$—; each Z is optionally substituted with 0-2 $J^Z$;
Q is H; $C_{1-6}$ aliphatic; a 3-8-membered aromatic or nonaromatic monocyclic ring having 0-3 heteroatoms independently selected from O, N, and S; or an 8-12 membered aromatic or nonaromatic bicyclic ring system having 0-5 heteroatoms independently selected from O, N, and S; each Q is optionally substituted with 0-5 $J^Q$;
each $J^2$ is halo or halo$C_{1-4}$ aliphatic;
each $J^3$, $J^4$, $J^5$, and $J^6$ is independently $C_{1-6}$ aliphatic, $C_{3-6}$cycloaliphatic, or —($C_{1-4}$alkyl)$_n$-$V^1$; wherein n is 0 or 1;

V$^1$ is halo(C$_{1-4}$aliphatic), —O(haloC$_{1-4}$aliphatic), halo, NO$_2$, CN, OH, OR", SH, SR", NH$_2$, NHR", N(R")$_2$, COH, COR", CO$_2$H, CO$_2$R", CONH$_2$, CONHR", CONR"$_2$, OCOR", OCONH$_2$, OCONHR", OCON(R")$_2$, NHCOR", NR"COR", NHCO$_2$R", NR"CO$_2$R", NHCO$_2$H, NR"CO$_2$H, NHCONH$_2$, NHCONHR", NHCON(R")$_2$, SO$_2$NH$_2$, SO$_2$NHR", SO$_2$N(R")$_2$, NHSO$_2$R", NR"SO$_2$R";

or V$^1$ is a cyclic group selected from C$_{3-6}$cycloaliphatic, phenyl, 5-6 membered heteroaryl, or 3-6 membered heterocyclyl; wherein said cyclic group is optionally substituted with 0-3 J$^V$;

R" is unsubstituted C$_{1-4}$ aliphatic;

or two of the same J$^3$, J$^4$, J$^5$, or J$^6$, bonded to the same atom, together can optionally form =O;

each J$^Z$ and J$^V$ is independently halo, C$_{1-6}$ aliphatic, C$_{3-6}$cycloaliphatic, NO$_2$, CN, —NH$_2$, —NH(C$_{1-4}$ aliphatic), —N(C$_{1-4}$ aliphatic)$_2$, —OH, —O(C$_{1-4}$ aliphatic), —CO$_2$H, —CO$_2$(C$_{1-4}$aliphatic), —O(haloC$_{1-4}$aliphatic), or halo(C$_{1-4}$aliphatic);

each J$^Q$, J$^7$, J$^{29}$, J$^{34}$, J$^{56}$, J$^{35}$, J$^{37}$, and J$^{57}$ is independently M or —Y-M;

each Y is independently an unsubstituted C$_{1-6}$aliphatic optionally replaced with 0-3 occurrences of —NR—, —O—, —S—, —C(O)—, —SO—, or —SO$_2$—;

each M is independently H, C$_{1-6}$ aliphatic, C$_{3-6}$cycloaliphatic, halo(C$_{1-4}$ aliphatic), —O(haloC$_{1-4}$ aliphatic), 3-6 membered heterocyclyl, halo, NO$_2$, CN, OH, OR', SH, SR', NH$_2$, NHR', N(R')$_2$, COH, COR', CO$_2$H, CO$_2$R', CONH$_2$, CONHR', CONR'$_2$, OCOR', OCONH$_2$, OCONHR', OCON(R')$_2$, NHCOR', NR'COR', NHCO$_2$R', NR'CO$_2$R', NHCO$_2$H, NR'CO$_2$H, NHCONH$_2$, NHCONHR', NHCON(R')$_2$, SO$_2$NH$_2$, SO$_2$NHR', SO$_2$N(R')$_2$, NHSO$_2$R', or NR'SO$_2$R';

R is H or unsubstituted C$_{1-6}$aliphatic;

R' is unsubstituted C$_{1-6}$aliphatic; or two R' groups, together with the atom to which they are bound, form an unsubstituted 3-8 membered saturated or partially unsaturated monocyclic ring having 0-1 heteroatoms independently selected from O, N, and S.

In one embodiment, R$^1$ is H, C$_{1-10}$aliphatic, C$_{3-10}$cycloaliphatic, C$_{6-10}$aryl, 5-10 membered heteroaryl, or 3-10 membered heterocyclyl; wherein said R$^1$ is optionally substituted with 0-5 J$^1$; provided that when X$^1$ is a bond, R$^1$ is not H; and the other variables are as defined herein.

In another embodiment, R$^7$ is H, C(O)R, C(O)OR, or C(O)NRR', C$_{1-10}$aliphatic, C$_{3-10}$cycloaliphatic, C$_{6-10}$aryl, 5-10 membered heteroaryl, 3-10 membered heterocyclyl, —(C$_{1-6}$aliphatic)-(C$_{3-10}$cycloaliphatic), —(C$_{1-6}$aliphatic)-(C$_{6-10}$aryl), —(C$_{1-6}$aliphatic)-(5-10 membered heteroaryl), or —(C$_{1-6}$aliphatic)-(3-6 membered heterocyclyl); wherein said R$^7$ is optionally substituted with 0-5 J$^7$; and the other variables are as defined herein.

In another embodiment, Q is H; C$_{1-6}$ aliphatic; a 3-8-membered aromatic or nonaromatic monocyclic ring having 0-3 heteroatoms independently selected from O, N, and S; or a 7-12 membered aromatic or nonaromatic bicyclic ring system having 0-5 heteroatoms independently selected from O, N, and S; each Q is optionally substituted with 0-5 J$^Q$; and the other variables are as defined herein.

In another embodiment, each M is independently H, C$_{1-6}$ aliphatic, C$_{3-6}$cycloaliphatic, halo(C$_{1-4}$ aliphatic), —O(haloC$_{1-4}$ aliphatic), 3-6 membered heterocyclyl, C$_{6-10}$aryl, halo, NO$_2$, CN, OH, OR', SH, SR', NH$_2$, NHR', N(R')$_2$, COH, COR', CO$_2$H, CO$_2$R', CONH$_2$, CONHR', CONR'$_2$, OCOR', OCONH$_2$, OCONHR', OCON(R')$_2$, NHCOR', NR'COR', NHCO$_2$R', NR'CO$_2$R', NHCO$_2$H, NR'CO$_2$H, NHCONH$_2$, NHCONHR', NHCON(R')$_2$, SO$_2$NH$_2$, SO$_2$NHR', SO$_2$N(R')$_2$, NHSO$_2$R', or NR'SO$_2$R', or two M taken together can optionally form =O; and the other variables are as defined herein.

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As described herein, a specified number range of atoms includes any integer therein. For example, a group having from 1-4 atoms could have 1, 2, 3, or 4 atoms.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted". In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

The term "stable", as used herein, refers to compounds that are not substantially altered when subjected to conditions to allow for their production, detection, recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation that has a single point of attachment to the rest of the molecule.

Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. Suitable aliphatic groups include, but are not limited to, linear or branched, substituted or unsubstituted alkyl, alkenyl, or alkynyl groups. Specific examples include, but are not limited to, methyl, ethyl, isopropyl, n-propyl, sec-butyl, vinyl, n-butenyl, ethynyl, and tert-butyl.

The term "cycloaliphatic" (or "carbocycle" or "carbocyclyl" or "cycloalkyl") refers to a monocyclic C3-C8 hydrocarbon or bicyclic C8-C12 hydrocarbon or bicyclic C7-C12 hydrocarbon that is completely saturated or that contains one or more units of unsaturation, but which is not aromatic, that has a single point of attachment to the rest of the molecule wherein any individual ring in said bicyclic ring system has 3-7 members. Suitable cycloaliphatic groups include, but are not limited to, cycloalkyl and cycloalkenyl groups. Specific examples include, but are not limited to, cyclohexyl, cyclopropenyl, and cyclobutyl.

The term "heterocycle", "heterocyclyl", or "heterocyclic" as used herein means non-aromatic, monocyclic, bicyclic, or tricyclic ring systems in which one or more ring members are an independently selected heteroatom. In some embodiments, the "heterocycle", "heterocyclyl", or "heterocyclic" group has three to fourteen ring members in which one or more ring members is a heteroatom independently selected from oxygen, sulfur, nitrogen, or phosphorus, and each ring in the system contains 3 to 7 ring members. In some embodiments, there are 1-4 heteroatoms in a ring system.

Suitable heterocycles include, but are not limited to, 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolane, benzodithiane, and 1,3-dihydro-imidazol-2-one.

Cyclic groups, (e.g., cycloaliphatic and heterocycles), can be linearly fused, bridged, or spirocyclic.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation.

The term "nonaromatic", as used herein, describes rings that are either saturated or partially unsaturated.

The term "alkoxy", or "thioalkyl", as used herein, refers to an alkyl group, as previously defined, attached through an oxygen ("alkoxy") or sulfur ("thioalkyl") atom.

The terms "haloalkyl", "haloalkenyl", "haloaliphatic", and "haloalkoxy" mean alkyl, alkenyl or alkoxy, as the case may be, substituted with one or more halogen atoms. The terms "halogen", "halo", and "hal" mean F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring".

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. In some embodiments, there are 1-4 heteroatoms in a ring system. The term "heteroaryl" may be used interchangeably with the term "heteroaryl ring" or the term "heteroaromatic". Suitable heteroaryl rings include, but are not limited to, 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

The term "protecting group" and "protective group" as used herein, are interchangeable and refer to an agent used to temporarily block one or more desired functional groups in a compound with multiple reactive sites. In certain embodiments, a protecting group has one or more, or preferably all, of the following characteristics: a) is added selectively to a functional group in good yield to give a protected substrate that is b) stable to reactions occurring at one or more of the other reactive sites; and c) is selectively removable in good yield by reagents that do not attack the regenerated, deprotected functional group. As would be understood by one skilled in the art, in some cases, the reagents do not attack other reactive groups in the compound. In other cases, the reagents may also react with other reactive groups in the compound. Exemplary protecting groups are detailed in Greene, T. W., Wuts, P. G in "Protective Groups in Organic Synthesis", Third Edition, John Wiley & Sons, New York: 1999 (and other editions of the book), the entire contents of which are hereby incorporated by reference. The term "nitrogen protecting group", as used herein, refers to an agents used to temporarily block one or more desired nitrogen reactive sites in a multifunctional compound. Preferred nitrogen protecting groups also possess the characteristics exemplified above, and certain exemplary nitrogen protecting groups are also detailed in Chapter 7 in Greene, T. W., Wuts, P. G in "Protective Groups in Organic Synthesis", Third Edition, John Wiley & Sons, New York: 1999, the entire contents of which are hereby incorporated by reference.

In some embodiments, an alkyl or aliphatic chain can be optionally replaced with another atom or group. This means that a methylene unit of the alkyl or the aliphatic chain is optionally replaced with said other atom or group. Examples of such atoms or groups would include, but are not limited to, —NR—, —O—, —C(O)—, —C(=N—CN)—, —C(=NR)—, —C(=NOR)—, —S—, —SO—, or —SO$_2$—. These atoms or groups can be combined to form larger groups. Examples of such groups include, but are not limited to, —OC(O)—, —C(O)CO—, —CO$_2$—, —C(O)NR—, —C(=N—CN), —NRCO—, —NRC(O)O—, —SO$_2$NR—, —NRSO$_{2-1}$—NRC(O)NR—, —OC(O)NR—, and —NRSO$_2$NR—, wherein R is defined herein.

Unless otherwise specified, the optional replacements form a chemically stable compound. Optional replacements can occur both within the chain and at either end of the chain; i.e., both at the point of attachment and/or also at the terminal end. Two optional replacements can also be adjacent to each other within a chain so long as it results in a chemically stable compound. The optional replacements can also completely replace all of the carbon atoms in a chain. For example, a C₃ aliphatic can be optionally replaced by —NR—, —C(O)—, and —NR— to form —NRC(O)NR— (a urea).

Unless otherwise specified, if the replacement occurs at the terminal end, the replacement atom is bound to an H on the terminal end. For example, if —CH₂CH₂CH₃ were optionally replaced with —O—, the resulting compound could be —OCH₂CH₃, —CH₂OCH₃, or —CH₂CH₂OH.

Unless otherwise stated, structures depicted herein are also meant to include all isomeric (e.g., enantiomeric, diastereomeric, geometric, conformational, and rotational forms of the structure). For example, the R and S configurations for each asymmetric center, (Z) and (E) double bond isomers, and (Z) and (E) conformational isomers are included in this invention. As would be understood to one skilled in the art, a substituent can freely rotate around any rotatable bonds. For example, a substituent drawn as

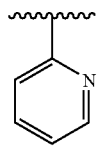

also represents

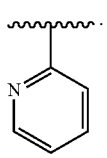

Therefore, single stereochemical isomers as well as enantiomeric, diastereomeric, geometric, conformational, or rotational mixtures of the present compounds are within the scope of the invention.

Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

The compounds of this invention can exist in free form for treatment, or where appropriate, as a pharmaceutically acceptable salt.

As used herein, the term "pharmaceutically acceptable salt" refers to salts of a compound which are, within the scope of sound medical judgment, suitable for use in contact with the tissues of humans and lower animals without undue toxicity, irritation, allergic response and the like, and are commensurate with a reasonable benefit/risk ratio.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. These salts can be prepared in situ during the final isolation and purification of the compounds. Acid addition salts can be prepared by 1) reacting the purified compound in its free-based form with a suitable organic or inorganic acid and 2) isolating the salt thus formed.

Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, salicylate, stearate, succinate, sulfate, tartrate, thiocyanate, p-toluenesulfonate, undecanoate, valerate salts, and the like. Salts derived from appropriate bases include alkali metal, alkaline earth metal, ammonium and N⁺(C₁₋₄alkyl)₄ salts. This invention also envisions the quaternization of any basic nitrogen-containing groups of the compounds disclosed herein. Water or oil-soluble or dispersible products may be obtained by such quaternization.

Base addition salts can be prepared by 1) reacting the purified compound in its acid form with a suitable organic or inorganic base and 2) isolating the salt thus formed. Base addition salts include alkali or alkaline earth metal salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower-alkyl sulfonate and aryl sulfonate. Other acids and bases, while not in themselves pharmaceutically acceptable, may be employed in the preparation of salts useful as intermediates in obtaining the compounds of the invention and their pharmaceutically acceptable acid or base addition salts.

The following abbreviations are used:
LG leaving group
TBTU O-(Benzotriazol-1-yl)-N,N,N',N'-tetramethyluronium tetrafluoroborate
DMSO dimethyl sulfoxide
DMA dimethyl acetamide
TCA trichloroacetic acid
ATP adenosine triphosphate
DEAD diethylazodicarboxylate
HEPES 4-(2-hydroxyethyl)-1-piperazineethanesulfonic acid
BSA bovine serum albumin
DTT dithiothreitol
MOPS 4-morpholinepropanesulfonic acid
NMR nuclear magnetic resonance
HPLC high performance liquid chromatography
LCMS liquid chromatography-mass spectrometry
TLC thin layer chromatography
Rt retention time In one aspect of this invention, $X^1$ is O, $NR^8$, or S. In some embodiments, $X^1$ is $NR^8$. In other aspects, $Y^1$ is O.

In another aspect of this invention, $R^1$ is optionally substituted $C_{6-10}$aryl or optionally substituted 5-10 membered heteroaryl.

In one embodiment, $R^1$ is optionally substituted $C_{6-10}$aryl, such as phenyl.

In one embodiment, $R^1$ is optionally substituted with $J^1$, wherein $J^1$ is —H, —O—$C_{1-6}$alkyl, halo, or —C(O)N(R)(O), wherein the R is —H.

In one embodiment, $R^1$ is optionally substituted with $J^1$, wherein $J^1$ is —H, —OCH$_3$, halo, or —C(O)N(R)(O), wherein the R is —H.

In one embodiment, $J^1$ is —OCH$_3$ or —C(O)N(R)ZQ, wherein Z is $C_{1-6}$aliphatic and Q is a 3-8-membered aromatic or nonaromatic monocyclic ring having 1-3 heteroatoms independently selected from O, N, and S; or an 8-12 membered aromatic or nonaromatic bicyclic ring system having 1-5 heteroatoms independently selected from O, N, and S; and Q is optionally substituted with 0-5 $J^Q$. In certain embodiments, Z is $C_{1-6}$alkyl and in more specific embodiments, Z is —CH$_2$—.

In one embodiment, $J^1$ is —OCH$_3$ or —C(O)N(R)ZQ, wherein Z is $C_{1-6}$aliphatic and Q is a 5-6-membered aromatic having 1 heteroatom selected from O and N (e.g., pyridine); wherein Q is optionally substituted with 0-5 $J^Q$. In certain embodiments, Z is $C_{1-6}$alkyl and in more specific embodiments, Z is —CH$_2$—.

In certain embodiments, Z is $C_{1-6}$alkyl and in more specific embodiments, Z is —CH$_2$—.

In one embodiment, $J^1$ is —OCH$_3$ or —C(O)N(R)(O), wherein the R is —H and the Q is $C_{1-6}$ alkyl, 3-6-membered cycloalkyl, a 7-12 nonaromatic bicyclic ring system, or a 8-12 nonaromatic bicyclic ring system, wherein each Q is substituted with 0-5 $J^Q$.

In one embodiment, $J^1$ is —OCH$_3$ or —C(O)N(R)(O), wherein the R is —H and the Q is 3-6-membered cycloalkyl, wherein each Q is substituted with 0-5 $J^Q$.

In one embodiment, $J^1$ is —OCH$_3$ or —C(O)N(R)(Q), wherein the R is —H and the Q is cyclohexyl, wherein each Q is substituted with 0-5 $J^Q$.

In one embodiment, $J^1$ is —OCH$_3$ or —C(O)N(R)(Q), wherein the R is —H and the Q is $C_{6-10}$aryl or 5-10 membered heteroaryl having 0-5 heteroatoms independently selected from O, N, and S; wherein each Q is substituted with 0-5 $J^Q$.

In one embodiment, $J^1$ is —OCH$_3$ or —C(O)N(R)(Q), wherein the R is —H and the Q is a 3-8-membered heterocyclic ring having 1 or 2 heteroatoms independently selected from O, N, and S; wherein each Q is substituted with 0-5 $J^Q$.

In one embodiment, $J^1$ is Q and Q is:

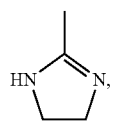

wherein Q is substituted with 0-5 $J^Q$.

In one embodiment, Q is substituted with 0, 1, or 2 $J^Q$.

In one embodiment, each $J^Q$ is independently F, —OH, —OR, or —OC(O)R'.

In one embodiment, each R' is independently $C_{1-6}$aliphatic, wherein the aliphatic is straight-chained.

In one embodiment, each R' is independently $C_{1-6}$alkyl, wherein the alkyl is straight-chained.

In one embodiment, R' is CH$_3$.

In another aspect, $R^2$ is optionally substituted $C_{1-10}$aliphatic or optionally substituted $C_{3-10}$cycloaliphatic.

In some embodiments, $R^3$ and $R^4$, together with the carbon atom to which they are attached, form an optionally substituted 3-6 membered monocyclic ring.

In other embodiments, $R^3$ and $R^5$, together with the carbon atoms to which they are attached, form an optionally substituted 3-6 membered monocyclic ring.

In yet other embodiments, $R^3$, $R^4$, $R^5$, and $R^6$ is independently an optionally substituted group selected from H, $C_{1-10}$aliphatic, $C_{3-10}$cycloaliphatic, $C_{6-10}$aryl, or 5-10 membered heteroaryl. In some embodiments, each $R^3$ and $R^4$ is independently H, $C_{1-6}$aliphatic, or $C_{3-8}$cycloaliphatic. In some embodiments, one of $R^3$ and $R^4$ is H and the other is $C_{1-6}$aliphatic or $C_{3-8}$cycloaliphatic.

In one embodiment, each $R^3$ and $R^4$ is independently H or $C_{1-3}$alkyl or $R^3$ and $R^4$, together with the carbon atoms to which they are attached, form an optionally substituted 3-4 membered monocyclic ring.

In one embodiment, one of $R^3$ and $R^4$ is H and the other is ethyl or (S)-methyl.

In one embodiment, one of $R^3$ and $R^4$ is H and the other is (R)-methyl.

In one embodiment, each $R^3$ and $R^4$ is methyl.

In one embodiment, $R^3$ and $R^4$, together with the carbon atoms to which they are attached, form an unsubstituted 3-4 membered monocyclic ring.

In one embodiment, $R^3$ and $R^4$, together with the carbon atoms to which they are attached, form an unsubstituted 3 membered monocyclic ring.

In one embodiment, $R^5$ is H.

In one embodiment, $R^6$ is H.

In some embodiments, $J^3$ and $J^4$ is independently halo.

In other embodiments, $R^5$ and $R^7$, together with the atoms to which they are attached, form an optionally substituted 3-6 membered saturated or partially unsaturated monocyclic ring.

In one aspect of this invention, $R^7$ is an optionally substituted group selected from $C_{1-10}$aliphatic, $C_{3-10}$cycloaliphatic, $C_{6-10}$aryl, 5-10 membered heteroaryl, and 3-10 membered heterocyclyl. In some aspects, $R^7$ is an optionally substituted group selected from $C_{1-10}$aliphatic, $C_{3-8}$cycloaliphatic, phenyl, a 5-membered heteroaryl, 2-pyridyl, 3-pyridyl, 4-pyridyl, 2,5-pyridazinyl, 3,5-pyrimidyl, and a 3-8 membered heterocyclyl. In other aspects, $R^7$ is not 3-amino-2,4-pyrimidine.

In one embodiment, $R^8$ is H.

One aspect of this invention provides a compound of formula II:

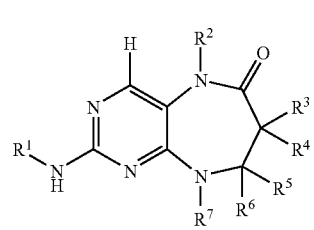

wherein
$R^1$ is optionally substituted $C_{6-10}$aryl or optionally substituted 5-10 membered heteroaryl;

R² is H or an optionally substituted group selected from C₁₋₁₀aliphatic and C₃₋₁₀cycloaliphatic;

each R³, R⁴, R⁵, and R⁶ is independently H, C₁₋₁₀aliphatic, or C₃₋₁₀cycloaliphatic; wherein each R³, R⁴, R⁵, and R⁶ is optionally substituted with 0-5 J³, J⁴, J⁵, and J⁶ respectively; or R³ and R⁴, together with the carbon atom to which they are attached, can form an optionally substituted 3-6 membered saturated or partially unsaturated monocyclic ring;

R³ and R⁵, together with the carbon atoms to which they are attached, can form an optionally substituted 3-6 membered saturated or partially unsaturated monocyclic ring;

R⁵ and R⁷, together with the atoms to which they are attached, can form an optionally substituted 3-6 membered saturated or partially unsaturated monocyclic ring;

R² and R⁹, together with the atoms to which they are attached, can form an optionally substituted 5-8 membered saturated or partially unsaturated monocyclic ring.

Another aspect of this invention provides a compound of formula III:

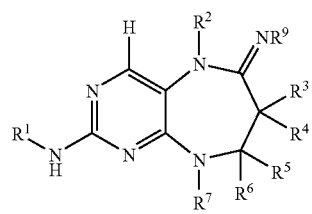

III wherein
R¹ is optionally substituted C₆₋₁₀aryl or optionally substituted 5-10 membered heteroaryl;

R² is H or an optionally substituted group selected from C₁₋₁₀aliphatic and C₃₋₁₀cycloaliphatic;

each R³, R⁴, R⁵, and R⁶ is independently H, C₁₋₁₀aliphatic, or C₃₋₁₀cycloaliphatic; wherein each R³, R⁴, R⁵, and R⁶ is optionally substituted with 0-5 J³, J⁴, J⁵, and J⁶ respectively; or R³ and R⁴, together with the carbon atom to which they are attached, can form an optionally substituted 3-6 membered saturated or partially unsaturated monocyclic ring;

R³ and R⁵, together with the carbon atoms to which they are attached, can form an optionally substituted 3-6 membered saturated or partially unsaturated monocyclic ring;

R⁵ and R⁷, together with the atoms to which they are attached, can form an optionally substituted 3-6 membered saturated or partially unsaturated monocyclic ring;

R² and R⁹, together with the atoms to which they are attached, can form an optionally substituted 5-8 membered saturated or partially unsaturated monocyclic ring.

In some embodiments, each J³, J⁴, J⁵, and J⁶ is independently C₁₋₆ aliphatic, C₃₋₆cycloaliphatic, or —(C₁₋₄alkyl)ₙ-V¹; wherein n is 0 or 1;

V¹ is halo(C₁₋₄aliphatic), —O(haloC₁₋₄ aliphatic), halo, NO₂, CN, OH, OR", SH, SR", NH₂, NHR", N(R")₂, COH, COR", CO₂H, CO₂R", CONH₂, CONHR", CONR'₂, OCOR", OCONH₂, OCONHR", OCON(R")₂, NHCOR", NR"COR", NHCO₂R", NR"CO₂R", NHCO₂H, NR"CO₂H, NHCONH₂, NHCONHR", NHCON(R")₂, SO₂NH₂, SO₂NHR", SO₂N(R")₂, NHSO₂R", NR"SO₂R";

R" is unsubstituted C₁₋₄ aliphatic;

or two of the same J³, J⁴, J⁵, or J⁶, bonded to the same atom, together can optionally form =O.

In some embodiments, the variables are as depicted in the species disclosed herein.

In some embodiments, the compounds of this invention are represented in Table 1.

TABLE 1

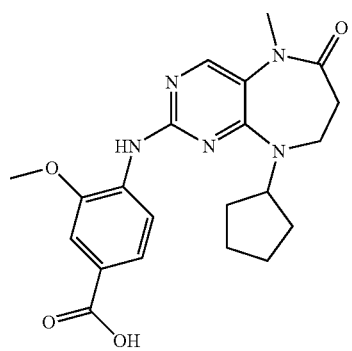

I-1

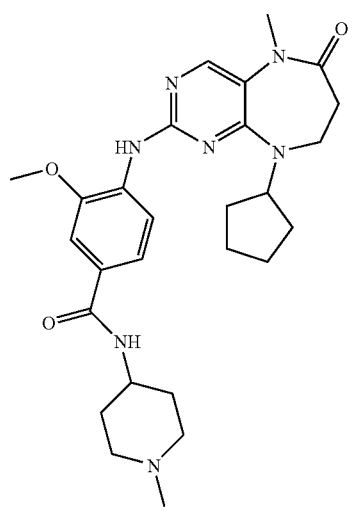

I-2

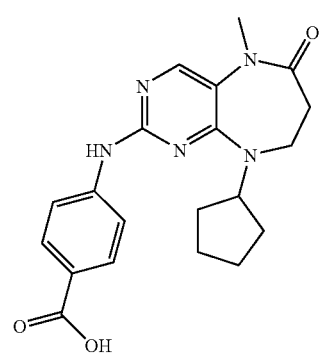

I-3

TABLE 1-continued
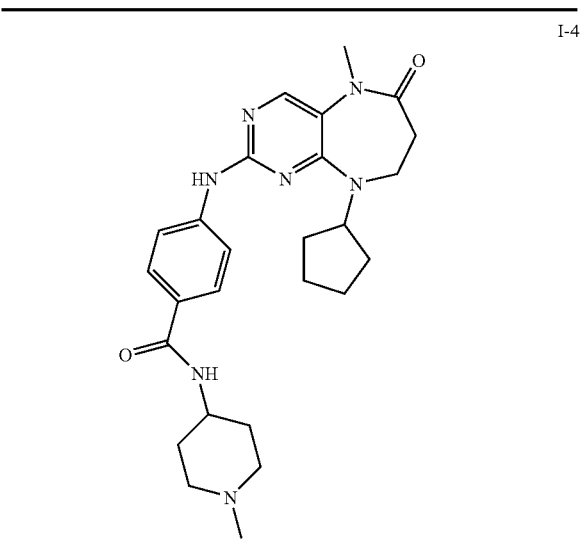
I-4
I-5
I-6
TABLE 1-continued
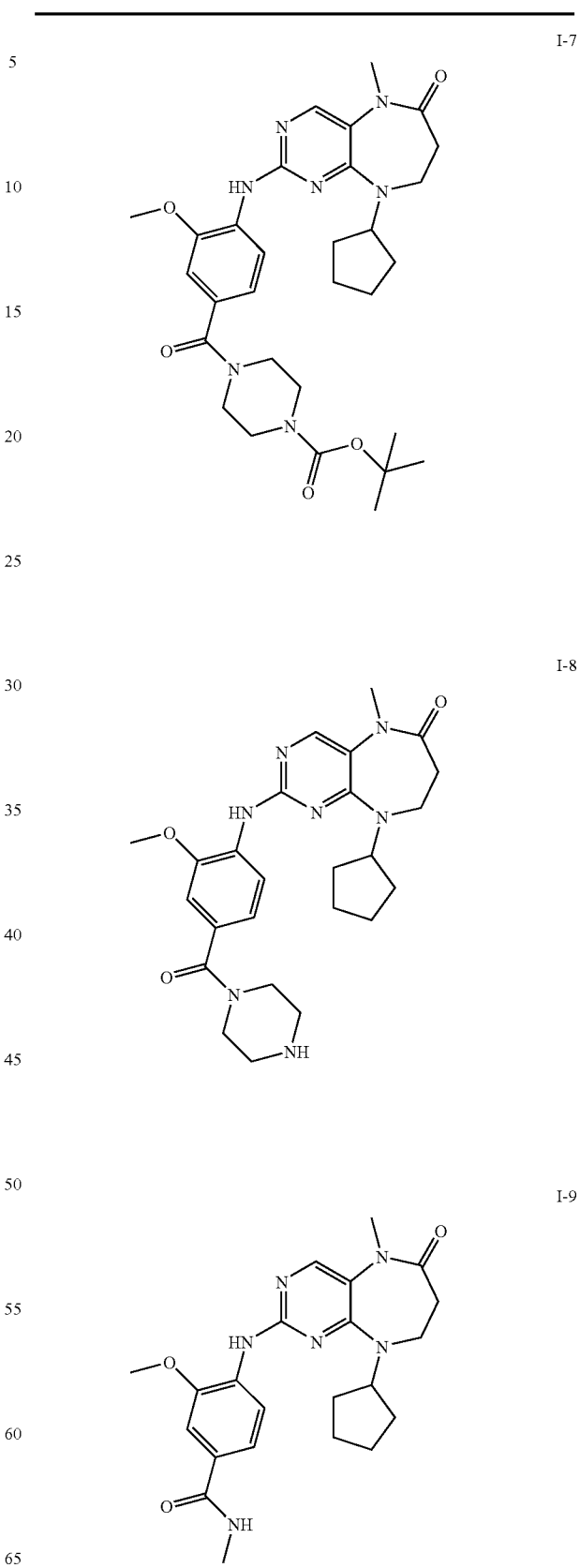
I-7
I-8
I-9

TABLE 1-continued
I-10
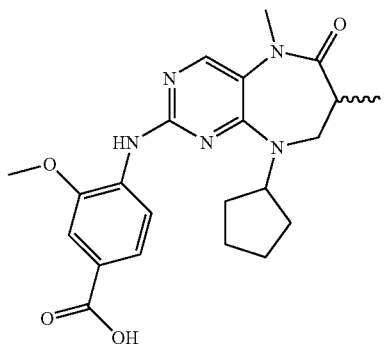
I-11
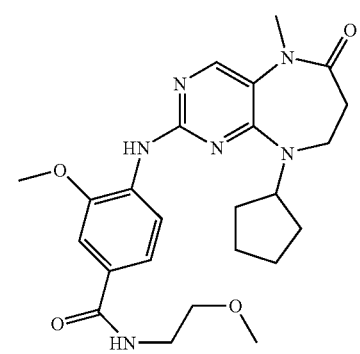
I-12
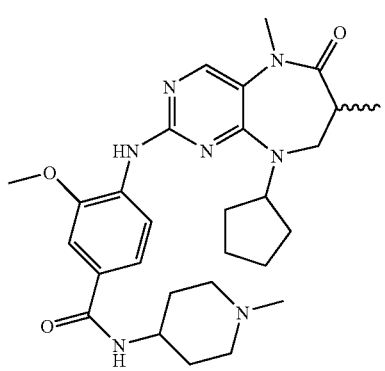
I-14
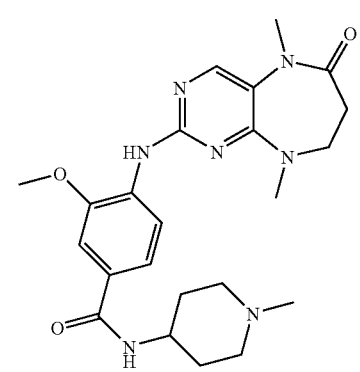
TABLE 1-continued
I-15
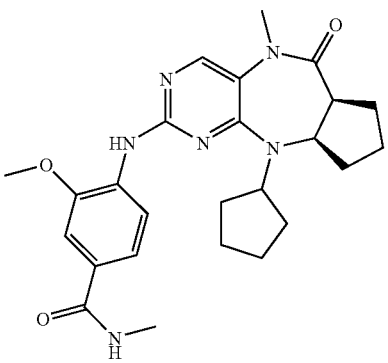
I-16
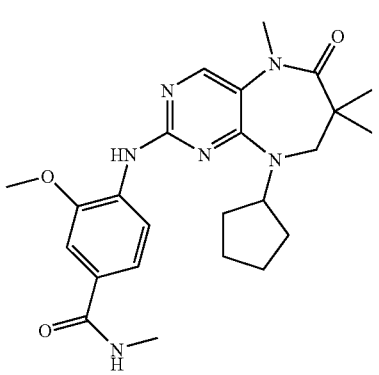
I-17
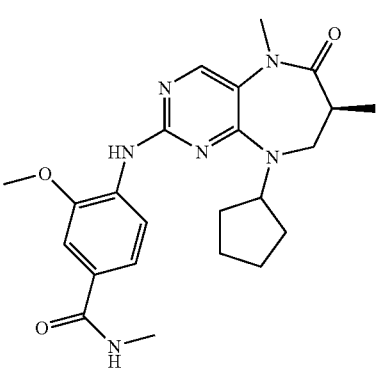
I-18
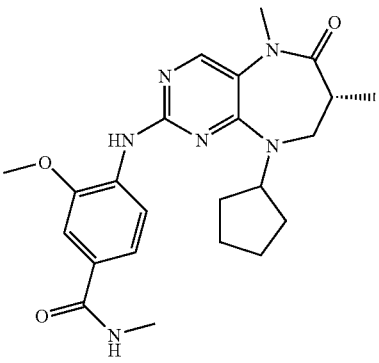

TABLE 1-continued
I-19
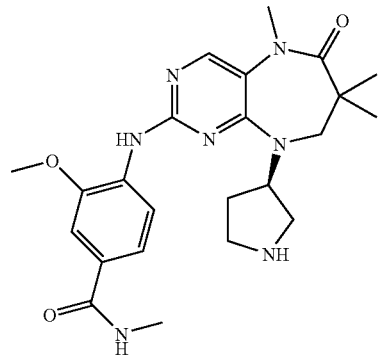
I-20
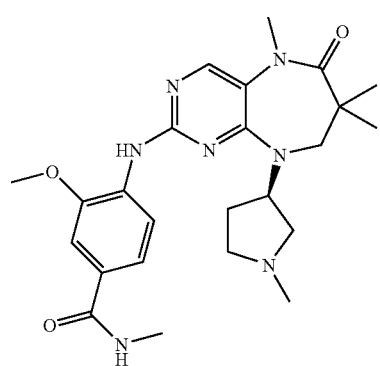
I-21
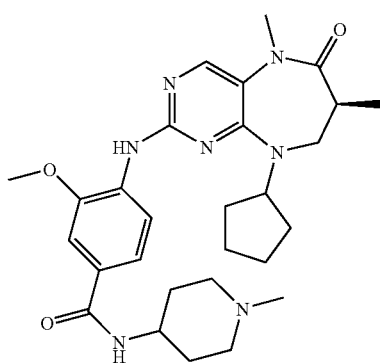
I-22
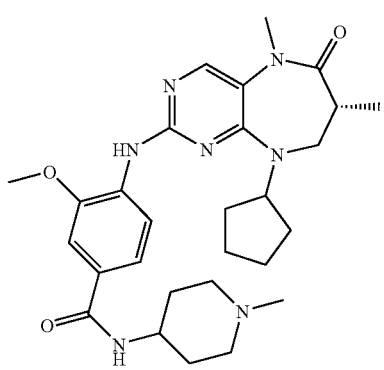
TABLE 1-continued
I-23
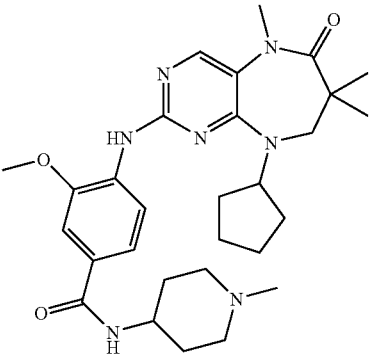
I-24
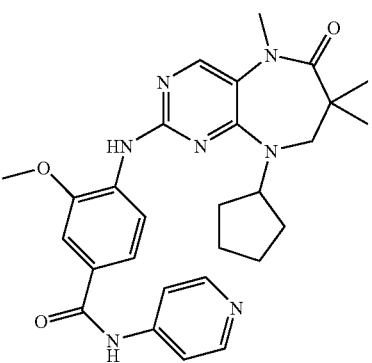
I-25
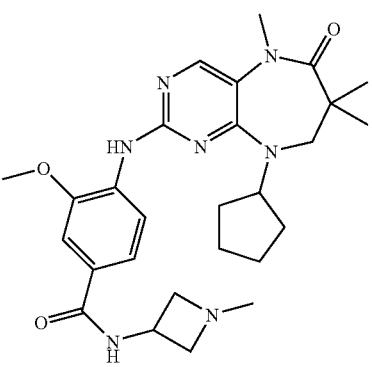
I-26
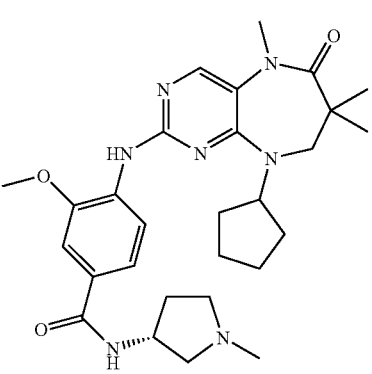

TABLE 1-continued
I-27
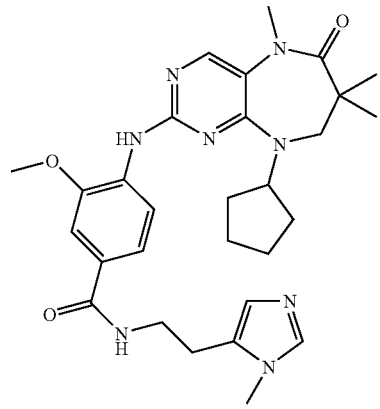
I-28
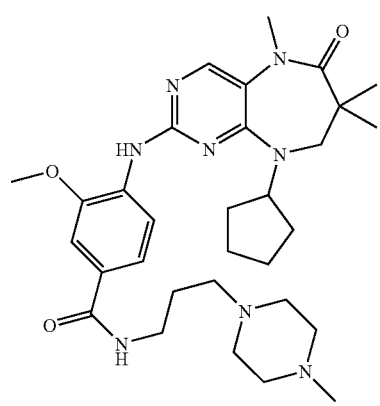
I-29
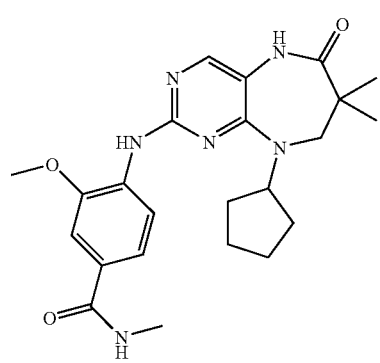
I-30
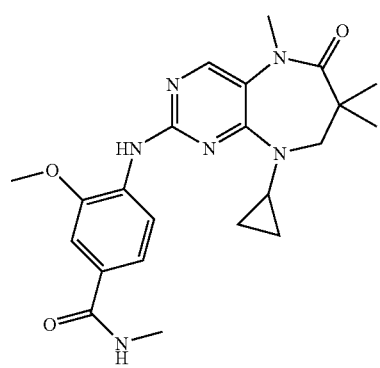
TABLE 1-continued
I-31
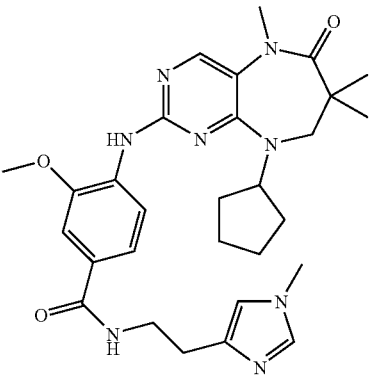
I-32
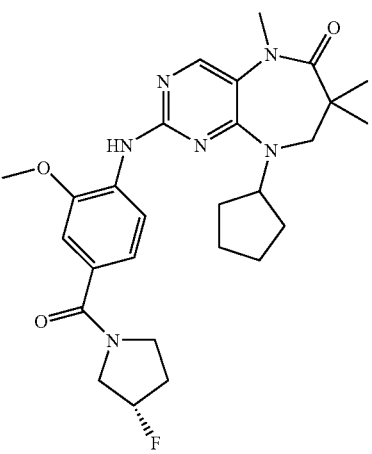
I-33
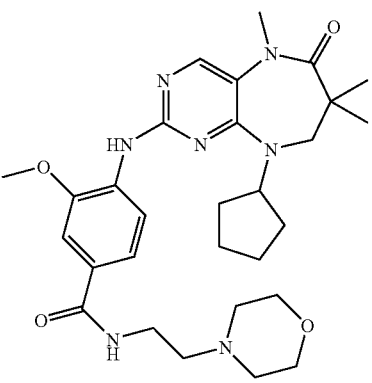

TABLE 1-continued
I-34
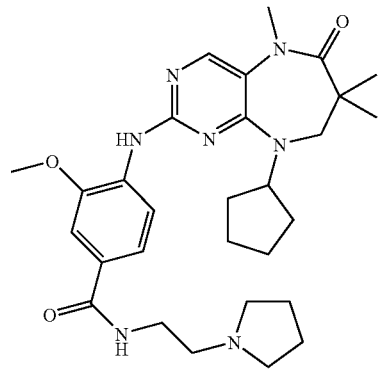
I-35
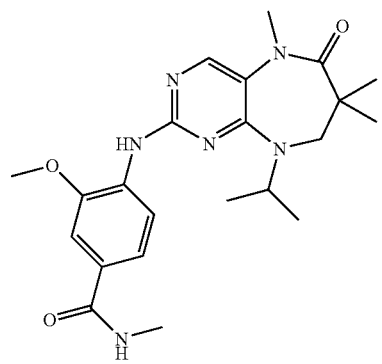
I-36
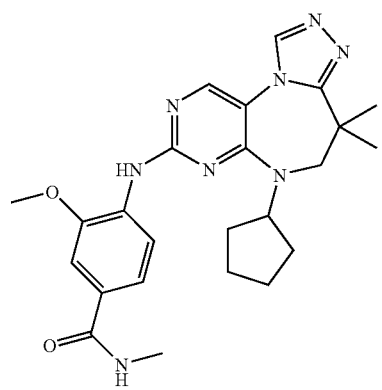
I-37
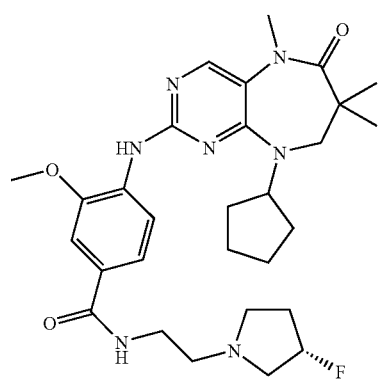
TABLE 1-continued
I-38
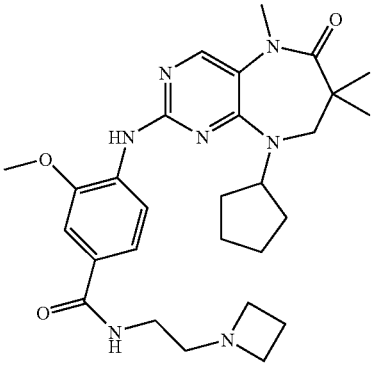
I-39
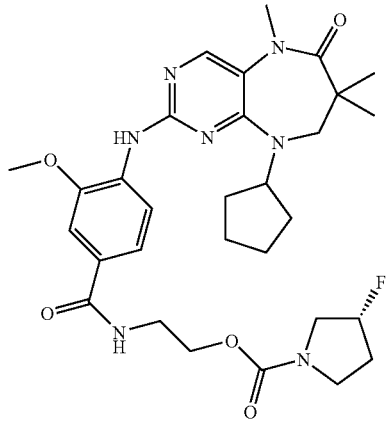
I-40
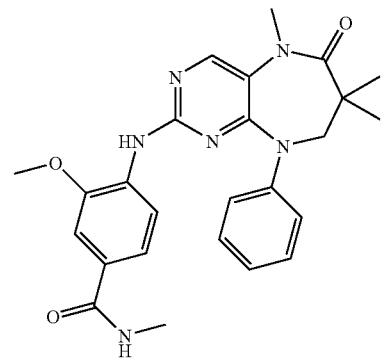
I-41
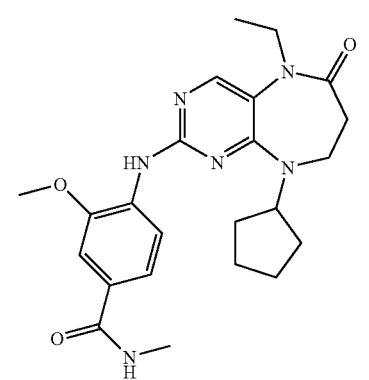

TABLE 1-continued
I-42
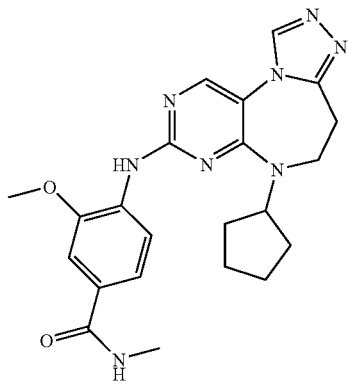
I-43
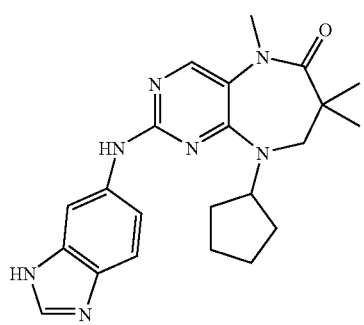
I-44
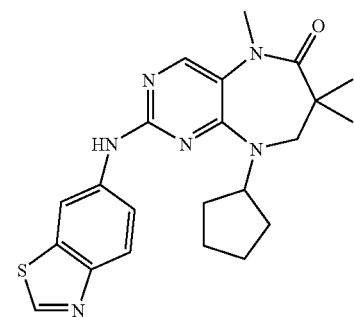
I-45
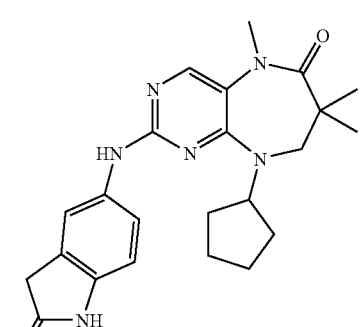
TABLE 1-continued
I-46
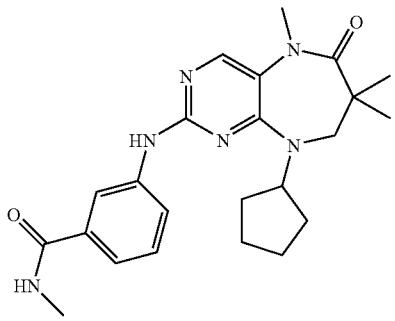
I-47
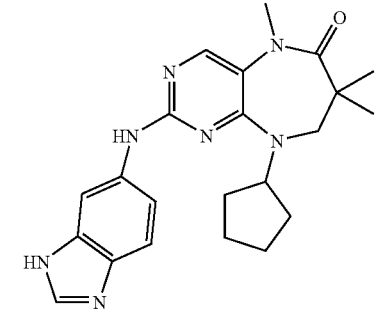
I-48
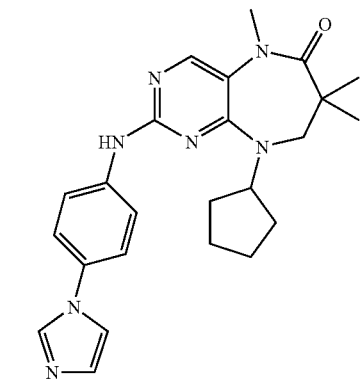
I-49
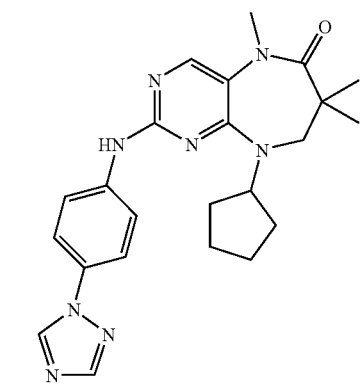

TABLE 1-continued
I-50
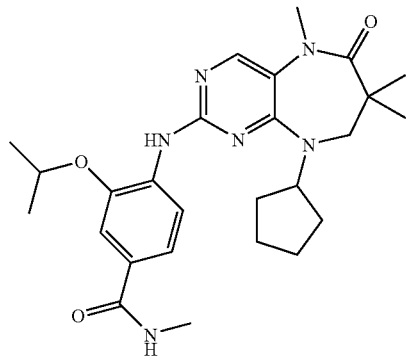
I-51
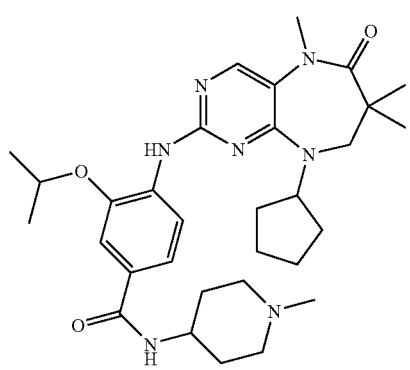
I-52
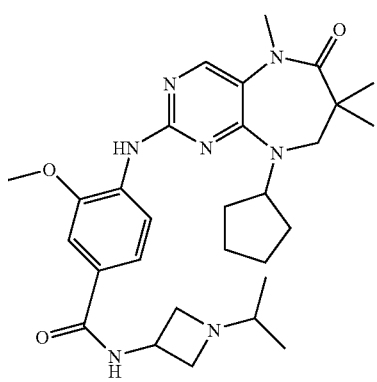
I-53
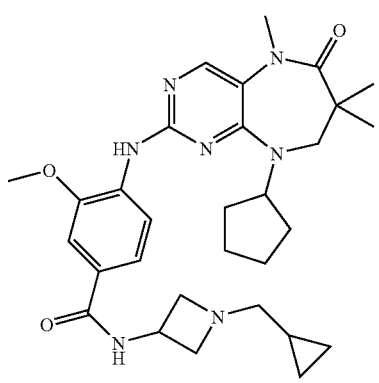
TABLE 1-continued
I-54
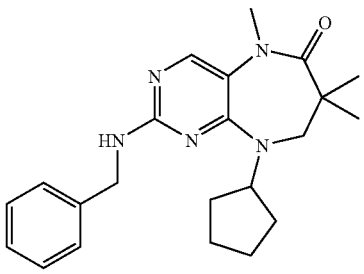
I-55
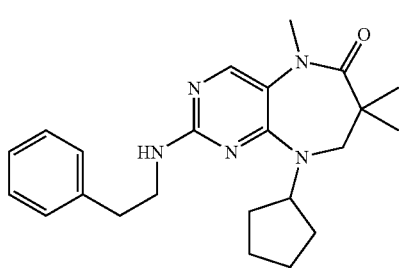
I-56
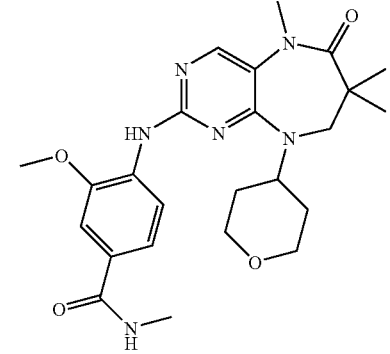
I-57
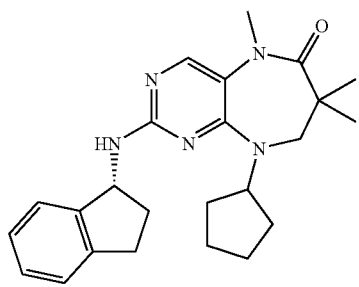

TABLE 1-continued
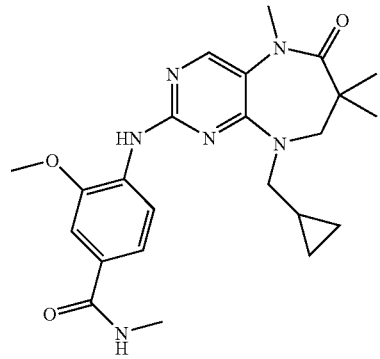
I-58
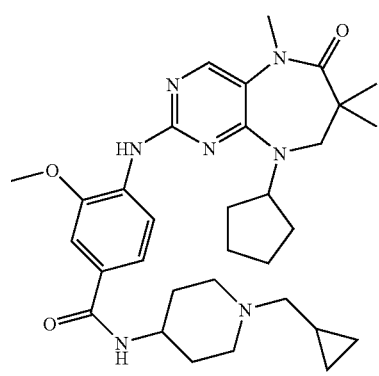
I-59
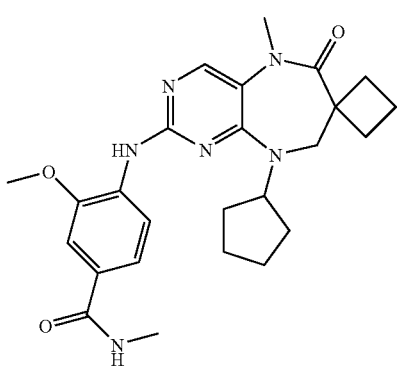
I-60
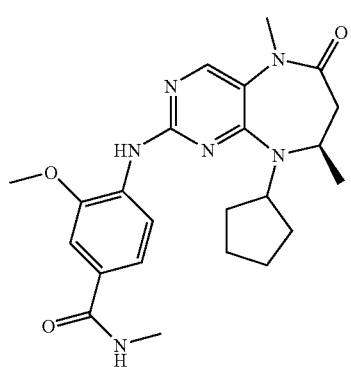
I-61
TABLE 1-continued
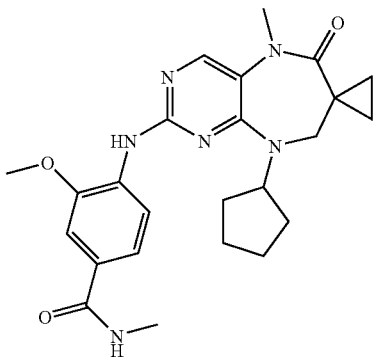
I-62
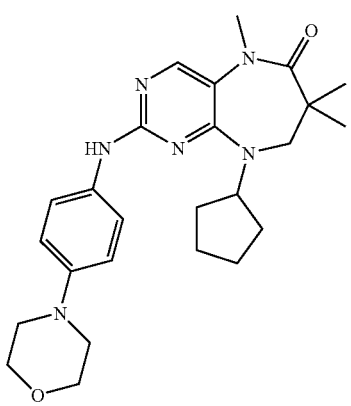
I-63
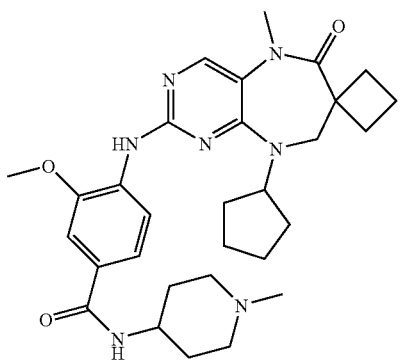
I-64
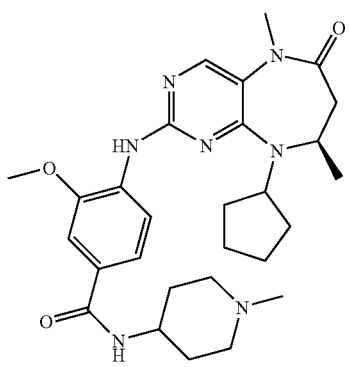
I-65

TABLE 1-continued
I-66
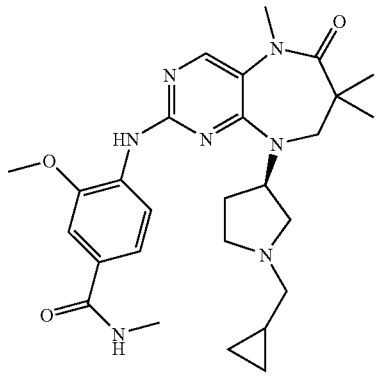
I-67
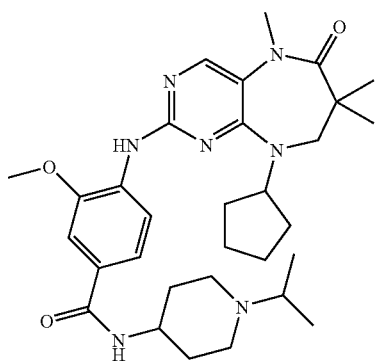
I-68
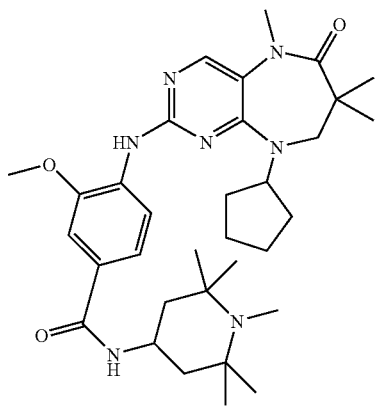
I-69
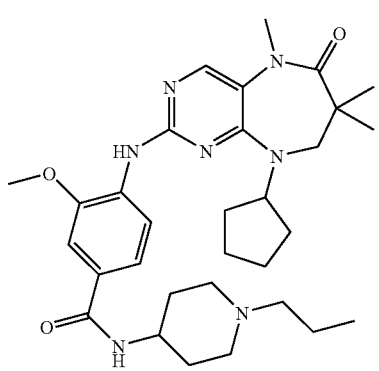
TABLE 1-continued
I-70
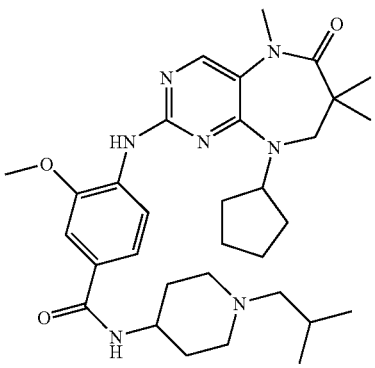
I-71
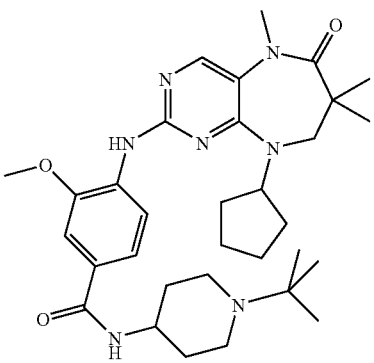
I-72
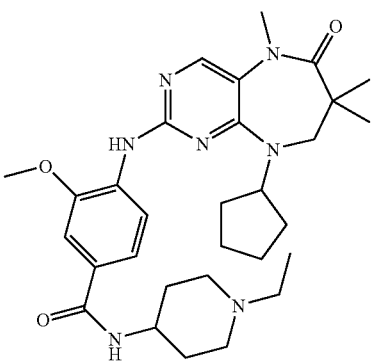

TABLE 1-continued
I-73
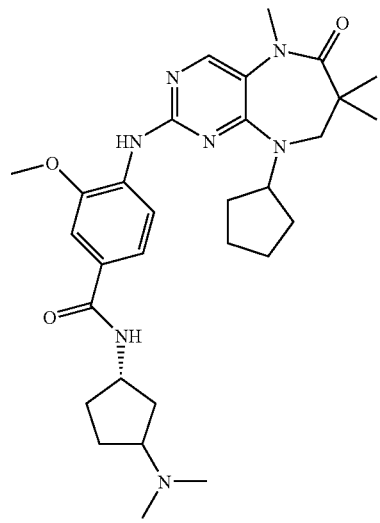
I-74
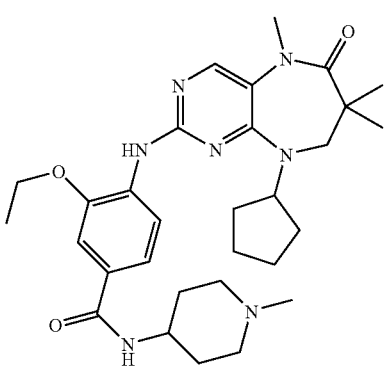
I-75
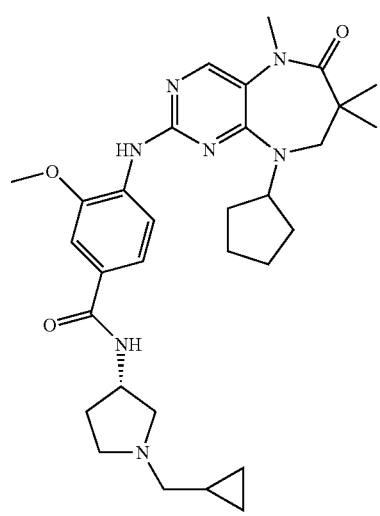
TABLE 1-continued
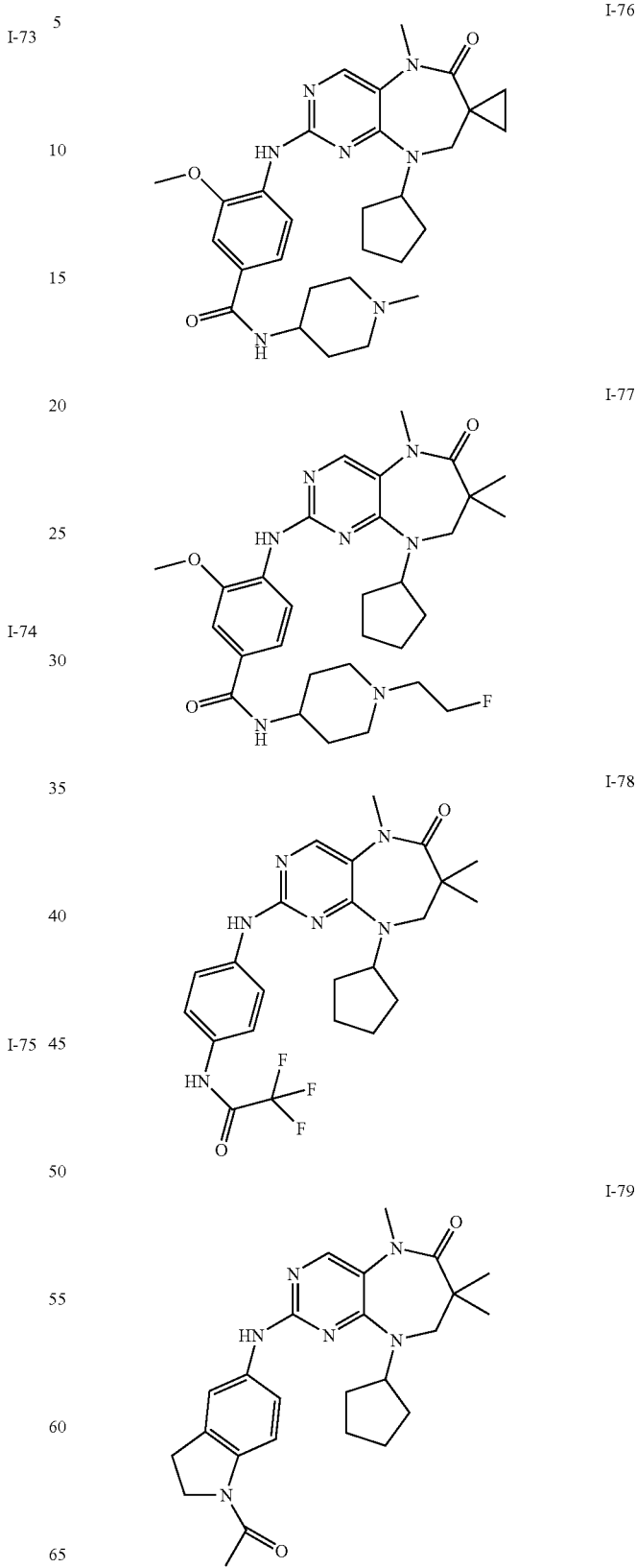

TABLE 1-continued
I-80
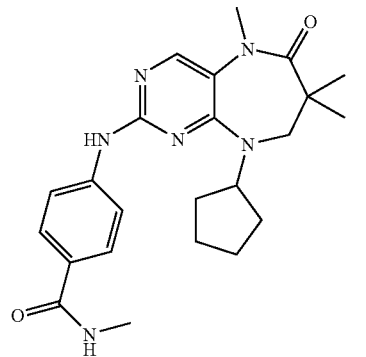
I-81
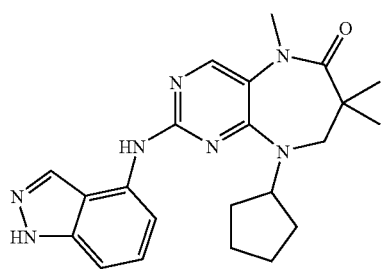
I-82
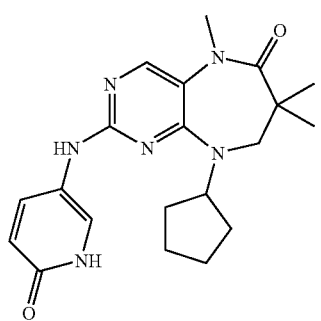
I-83
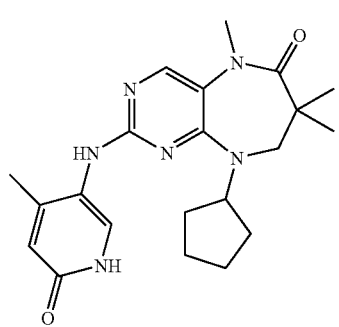
TABLE 1-continued
I-84
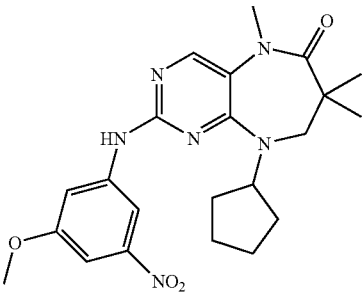
I-85
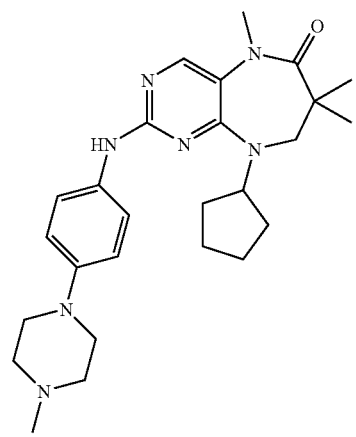
I-86
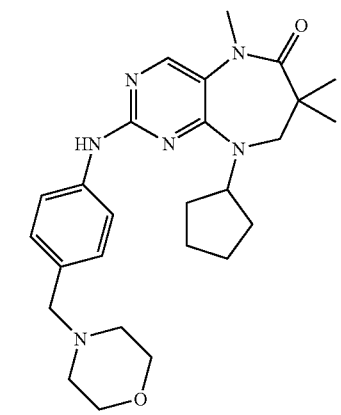
I-87
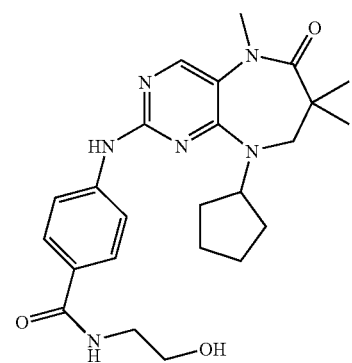

TABLE 1-continued
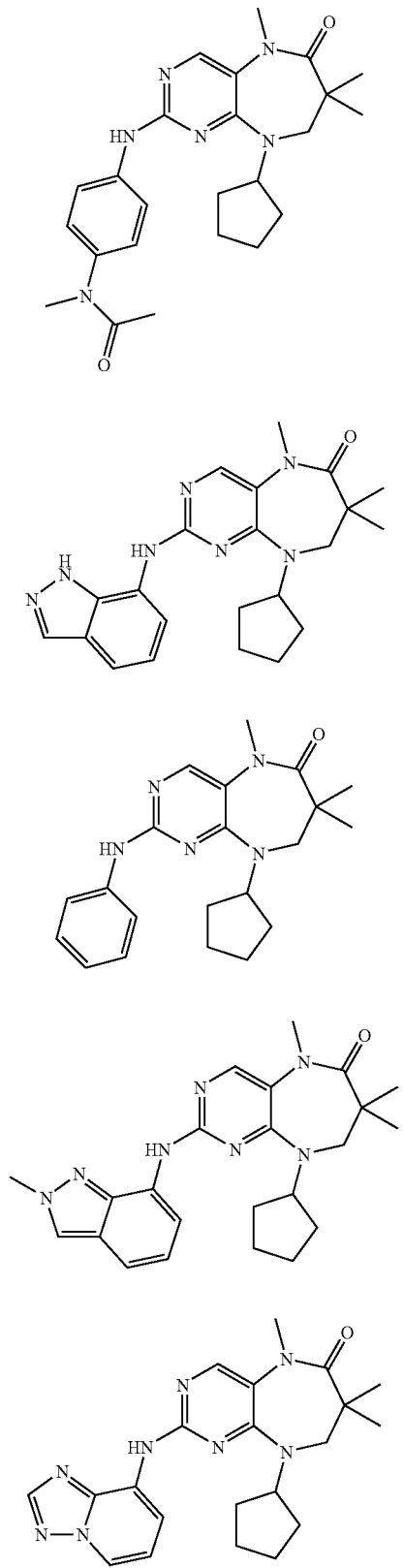
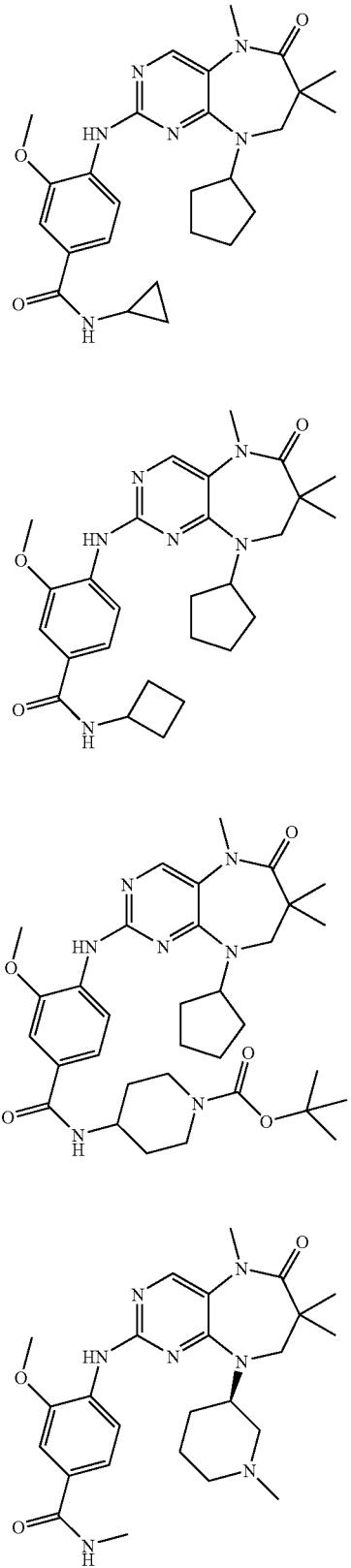

TABLE 1-continued
I-97
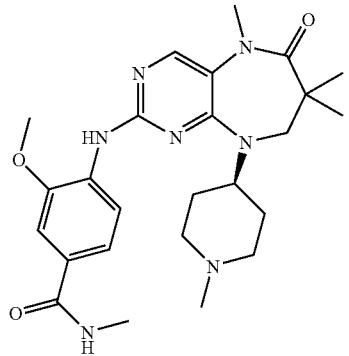
I-98
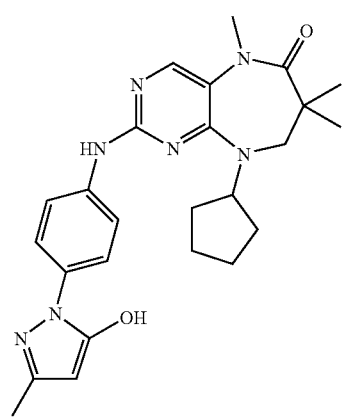
I-99
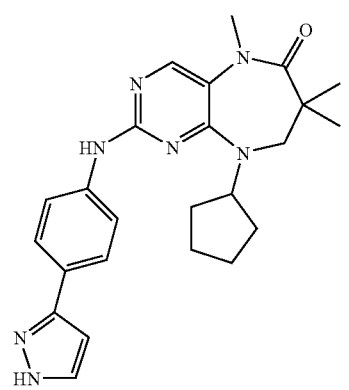
I-100
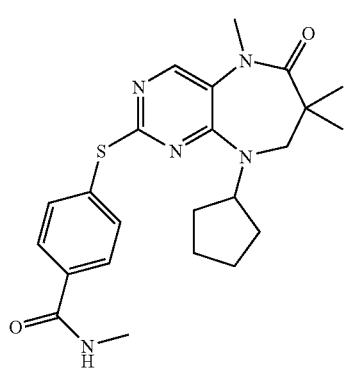
TABLE 1-continued
I-101
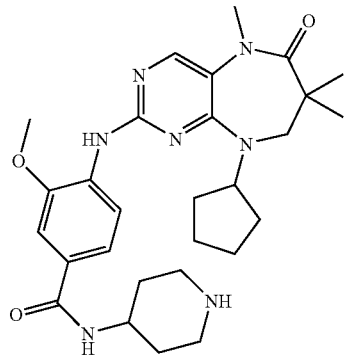
I-102
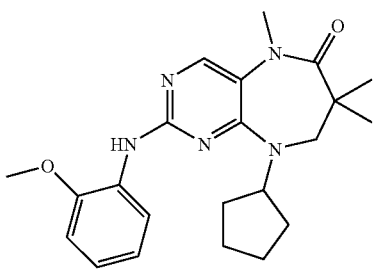
I-103
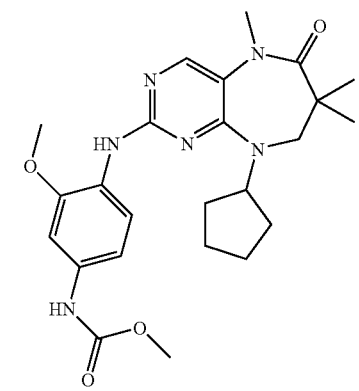
I-104
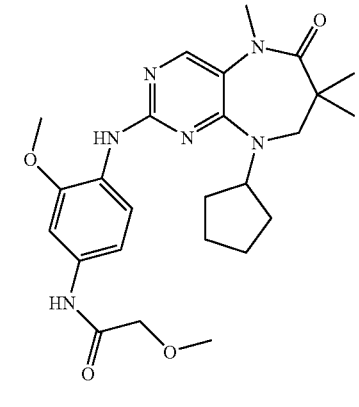

TABLE 1-continued
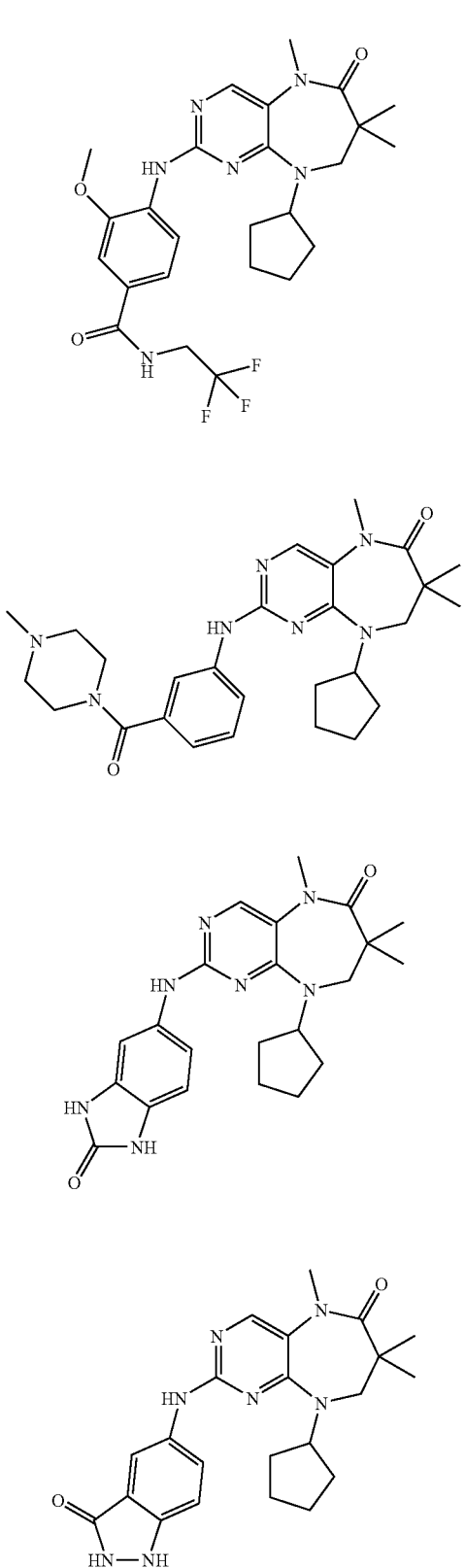
TABLE 1-continued
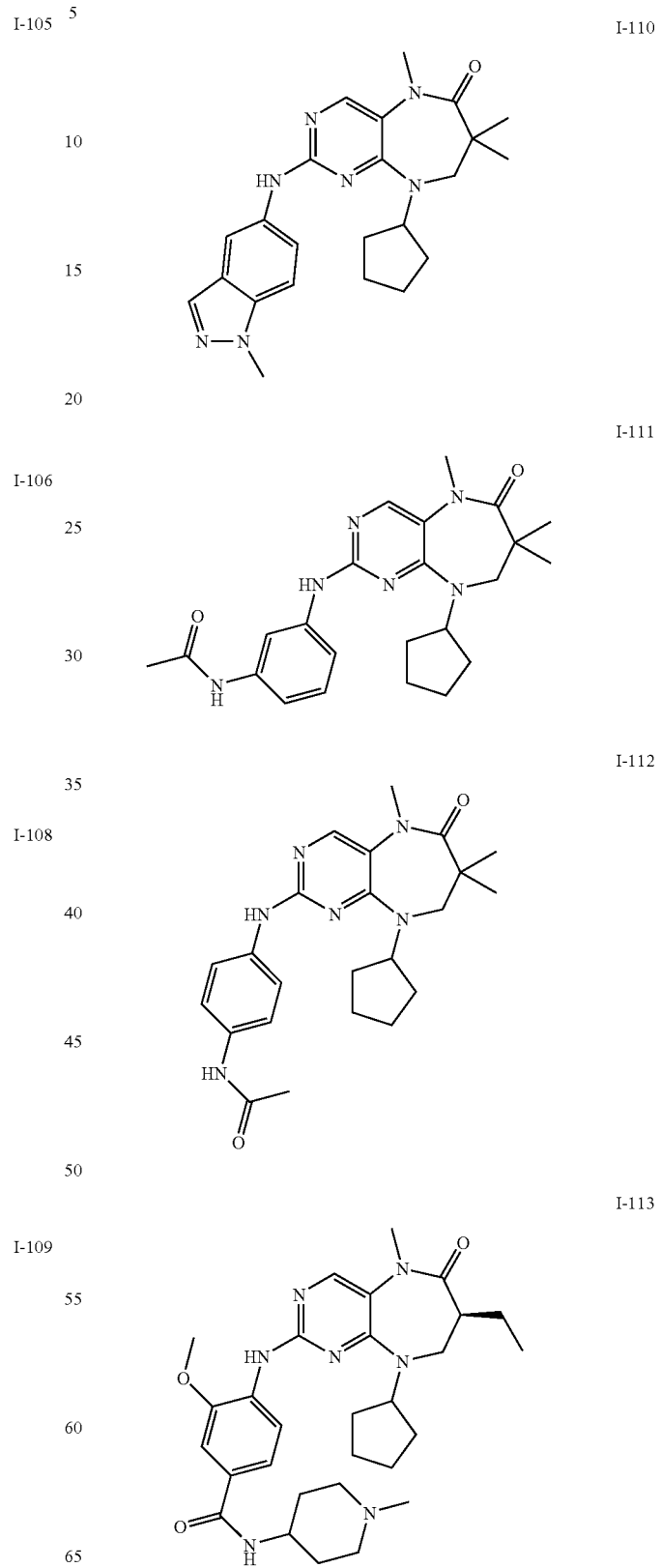

TABLE 1-continued
I-114
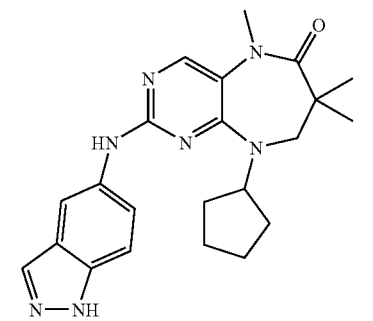
I-115
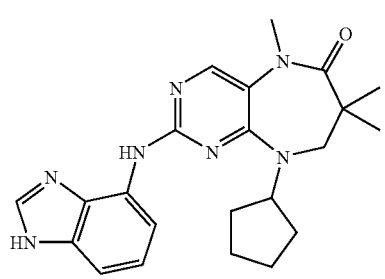
I-116
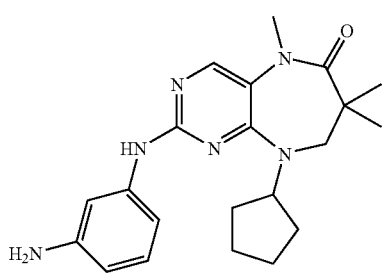
I-117
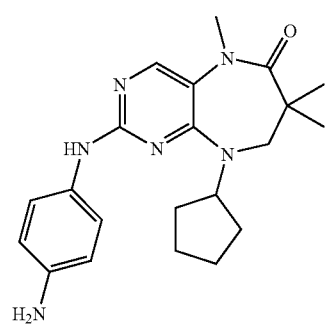
TABLE 1-continued
I-118
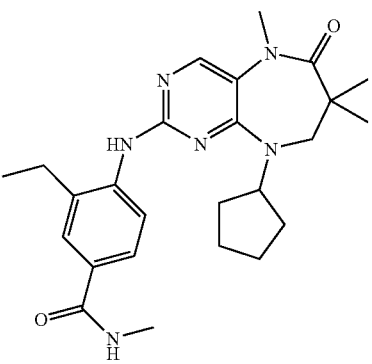
I-119
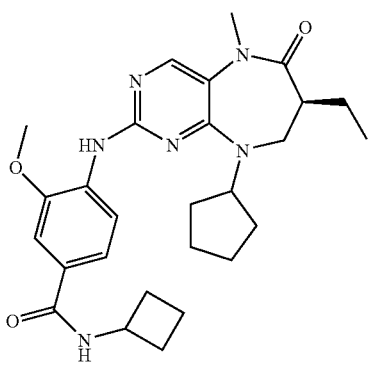
I-120
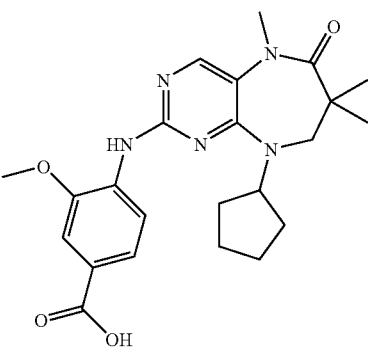
I-121
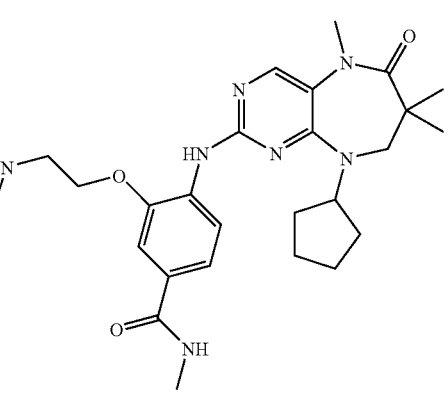

TABLE 1-continued
I-122
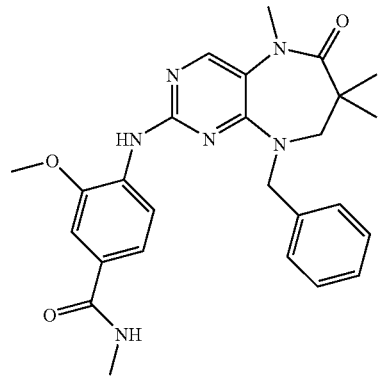
I-123
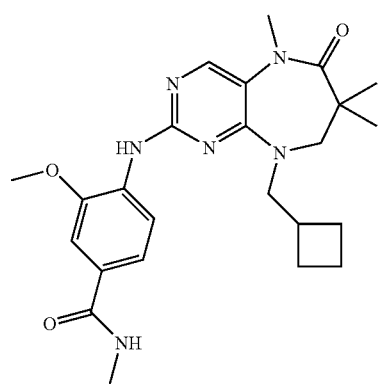
I-124
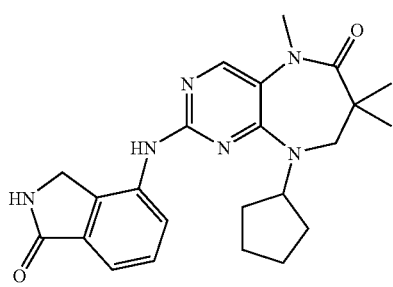
I-125
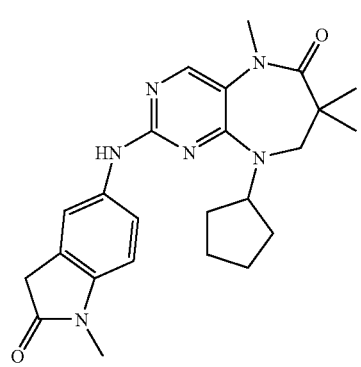
TABLE 1-continued
I-126
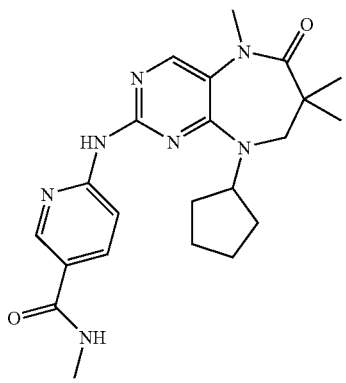
I-127
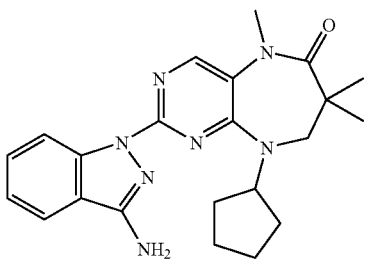
I-128
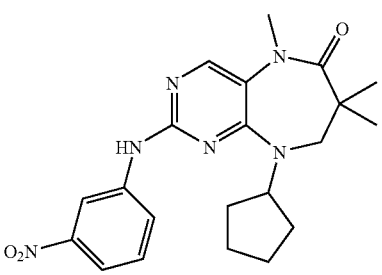
I-129
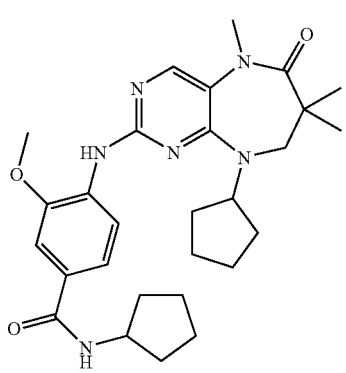

TABLE 1-continued
I-130
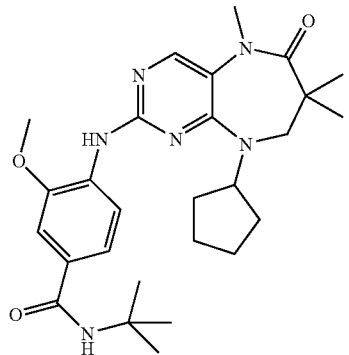
I-131
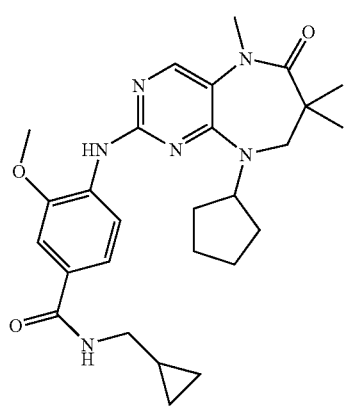
I-132
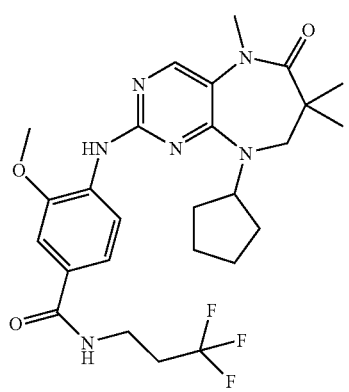
I-133
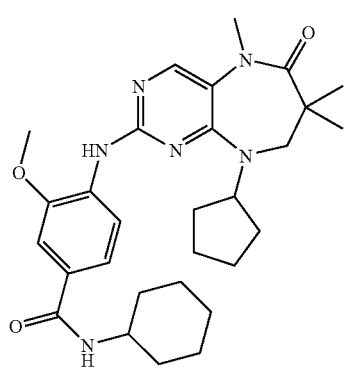
TABLE 1-continued
I-134
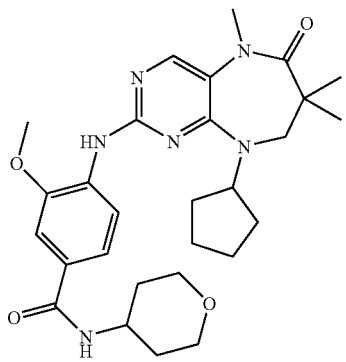
I-135
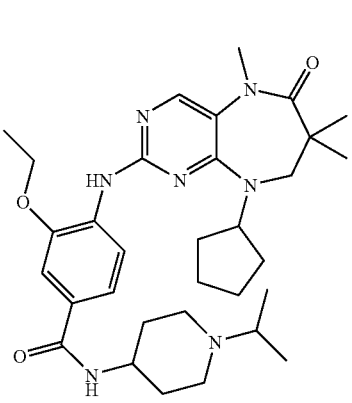
I-136
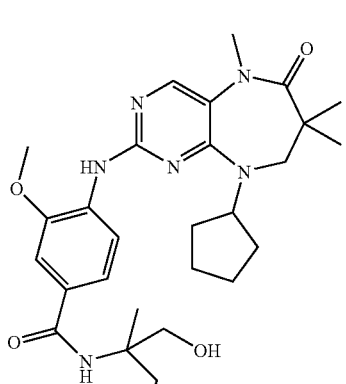
I-137
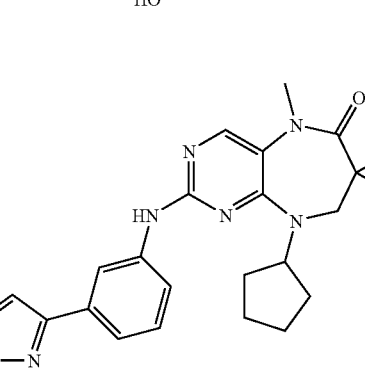

TABLE 1-continued
I-138
I-139
I-140
I-141
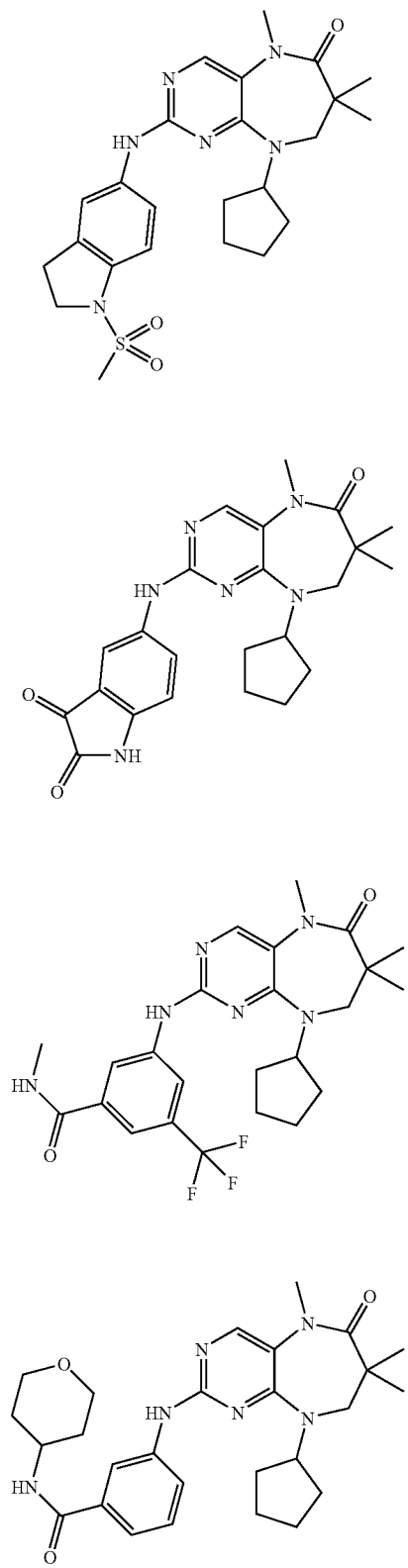
TABLE 1-continued
I-142
I-143
I-144
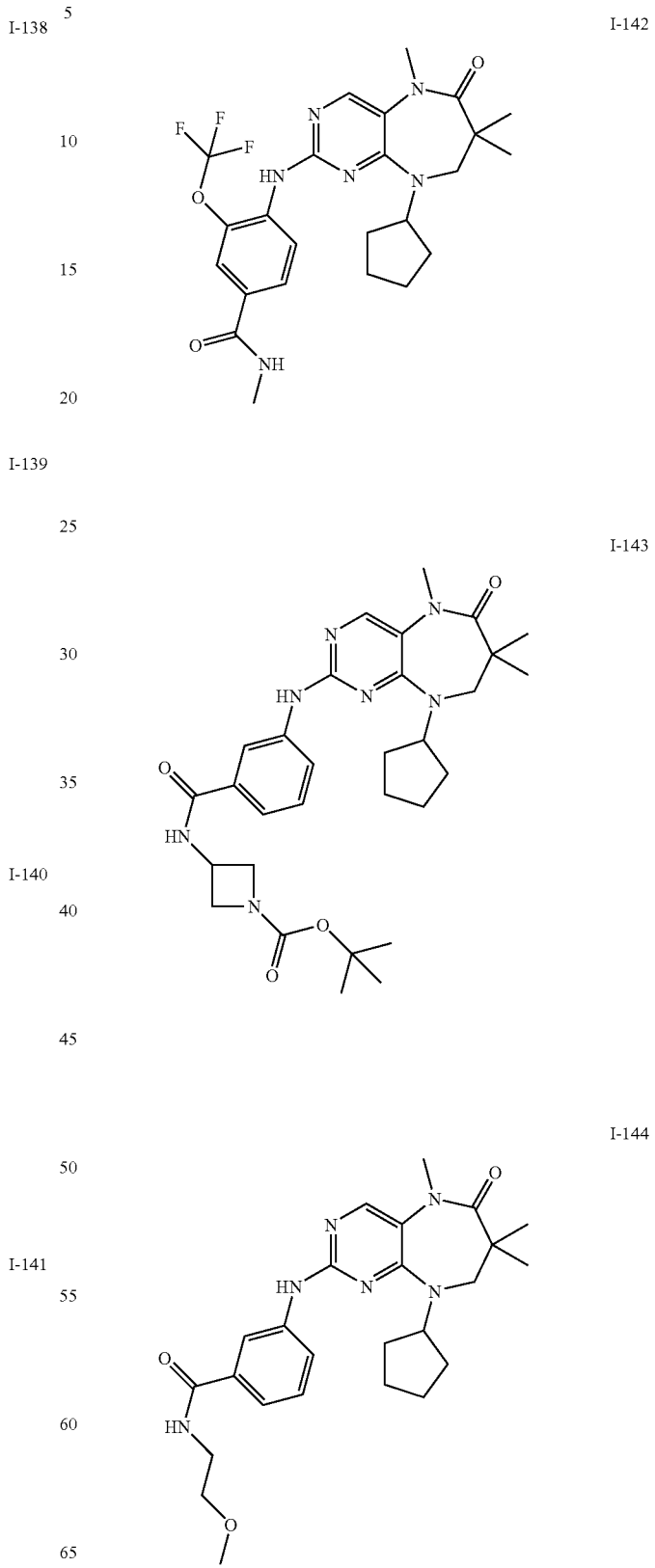

TABLE 1-continued
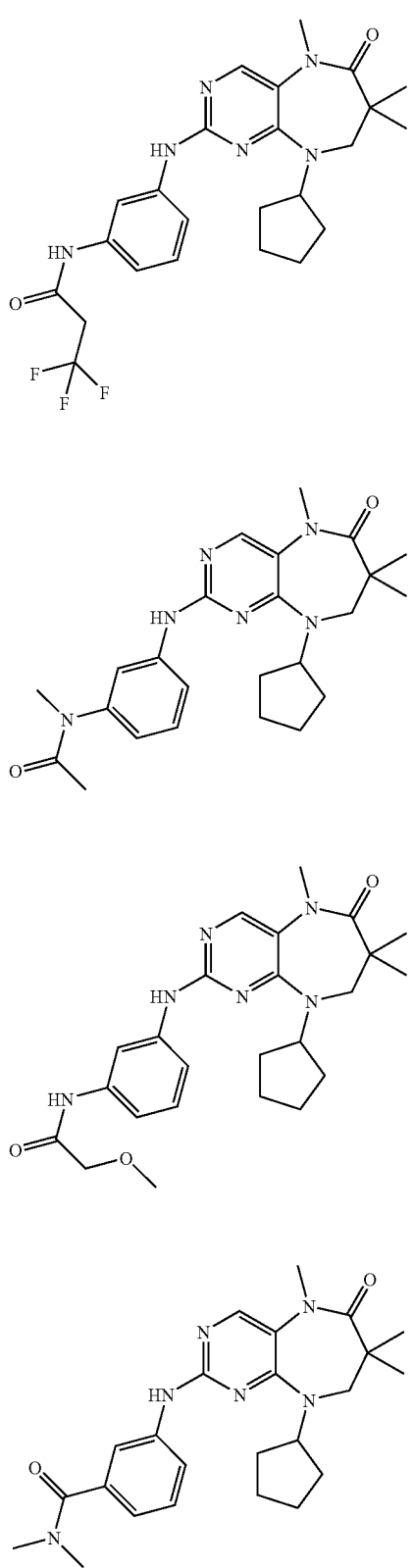
I-145
I-146
I-147
I-148
TABLE 1-continued
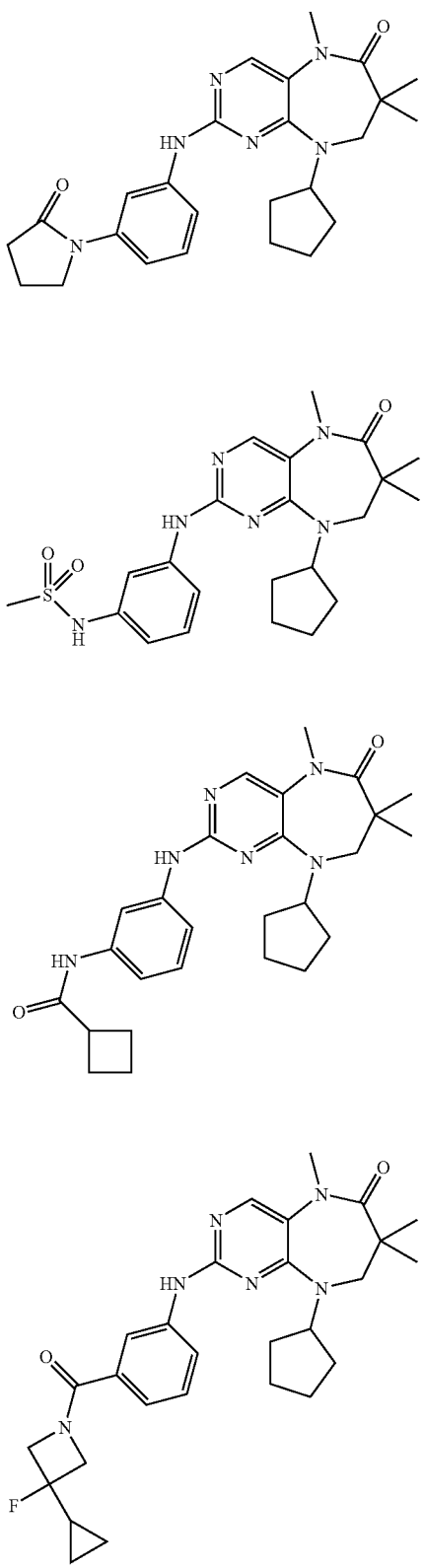
I-149
I-150
I-151
I-152

TABLE 1-continued
I-153 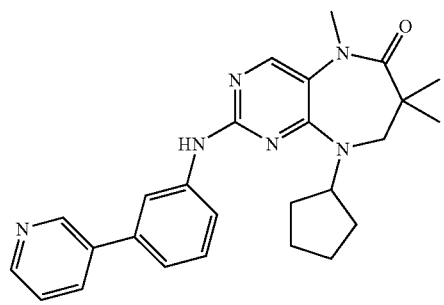
I-154 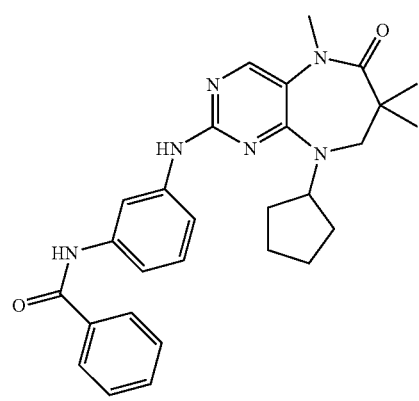
I-155 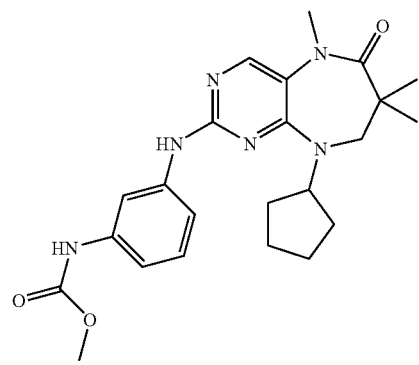
I-156 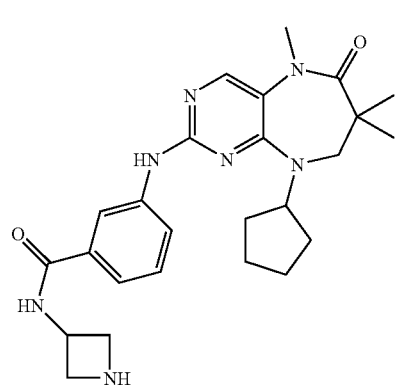
TABLE 1-continued
I-157 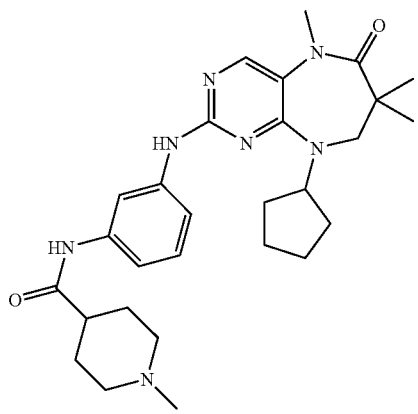
I-158 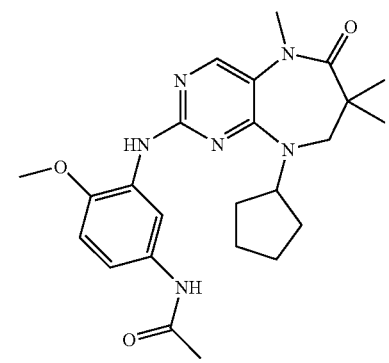
I-159 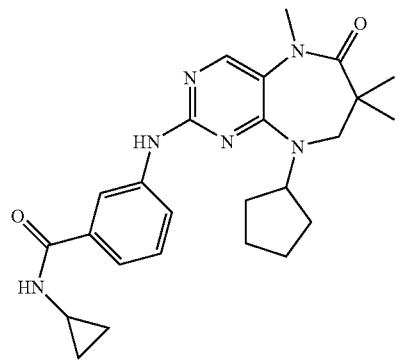
I-160 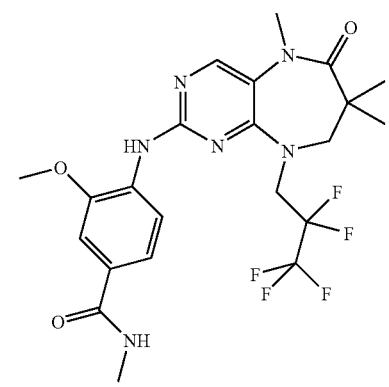

TABLE 1-continued
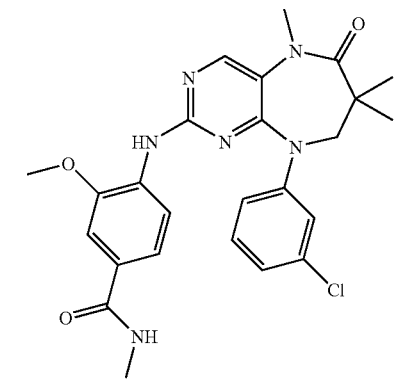
I-161
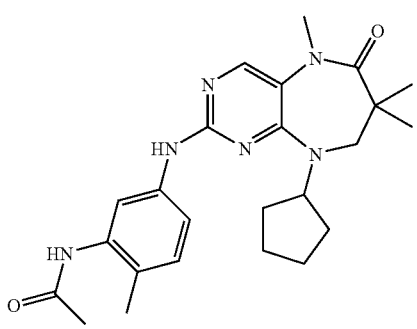
I-162
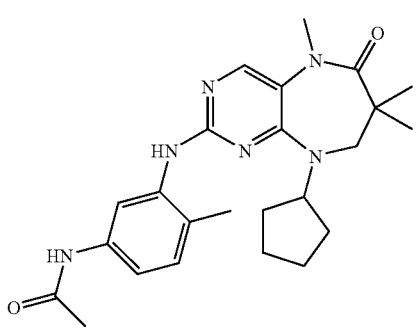
I-163
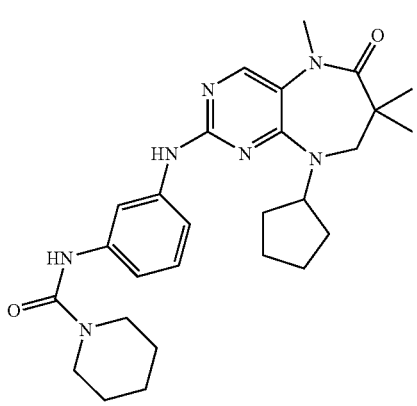
I-164
TABLE 1-continued
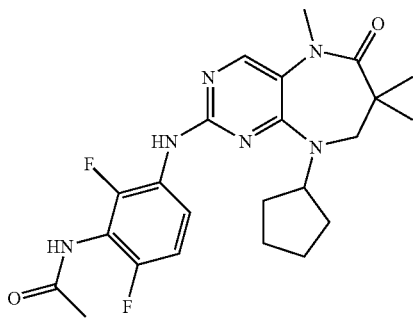
I-165
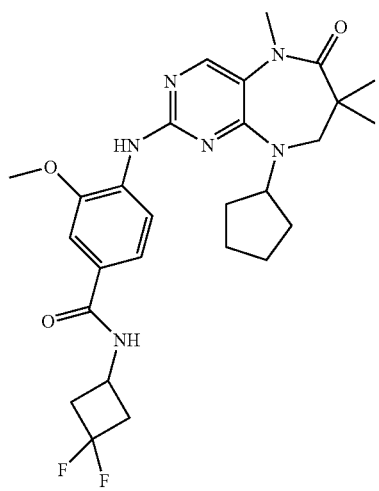
I-166
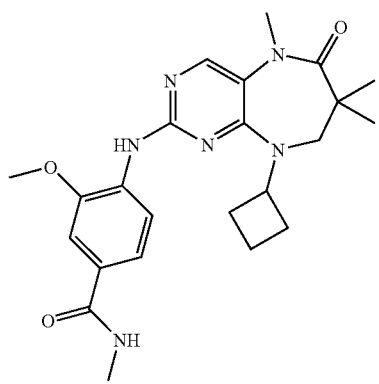
I-167

TABLE 1-continued
I-168
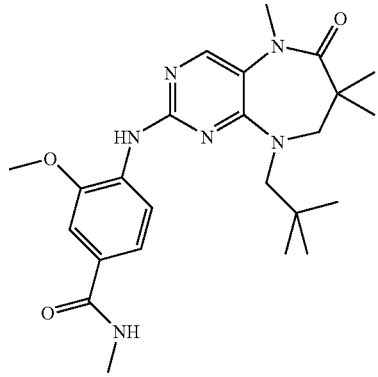
I-169
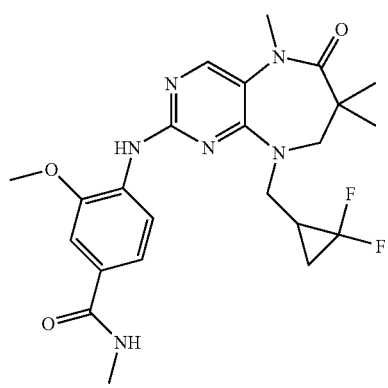
I-170
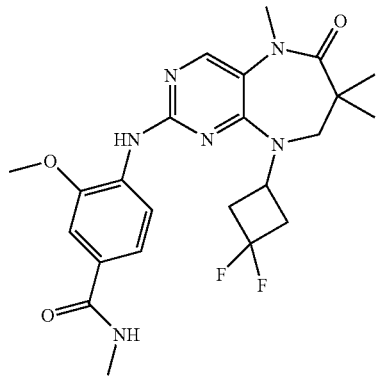
TABLE 1-continued
I-171
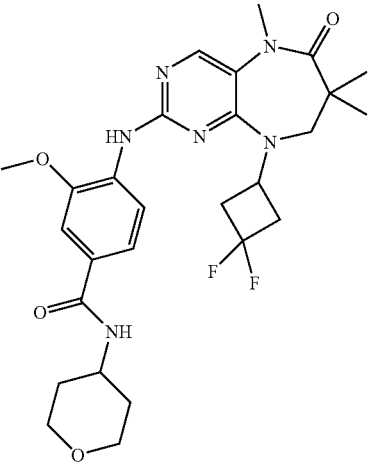
I-172
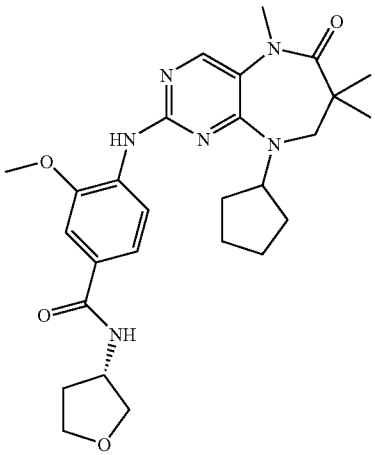
I-173
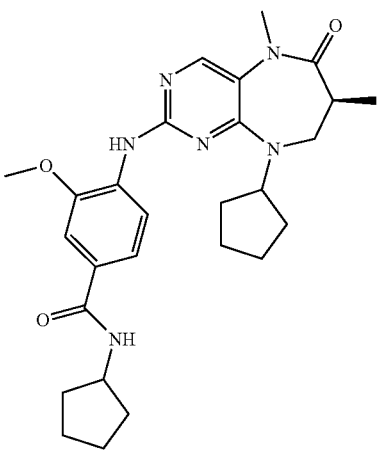

TABLE 1-continued
I-174
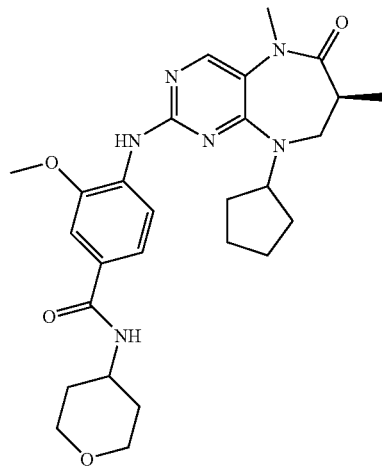
I-175
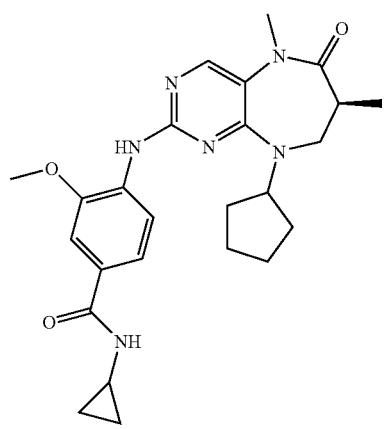
I-176
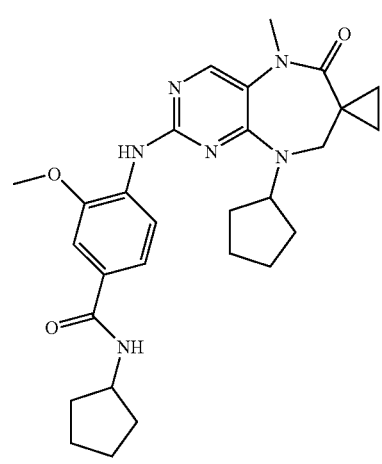
TABLE 1-continued
I-177
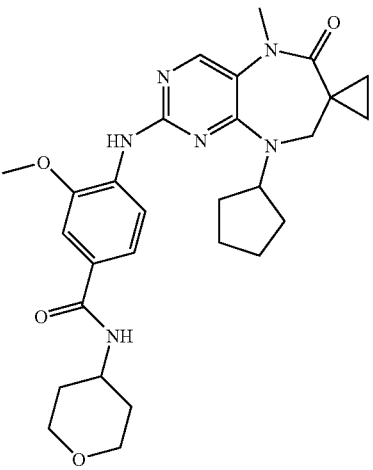
I-178
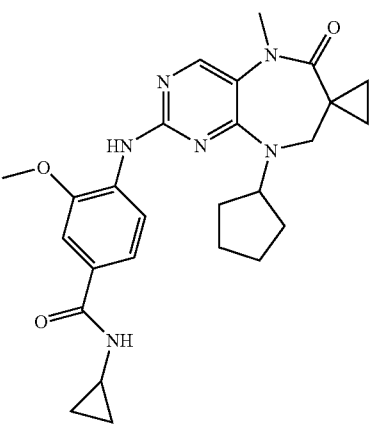
I-179
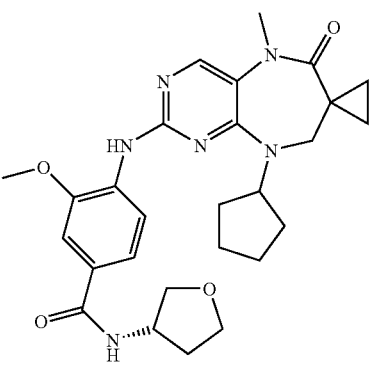

TABLE 1-continued
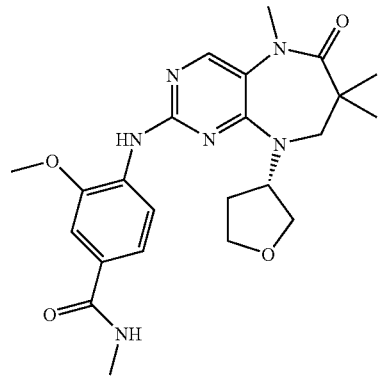
I-180
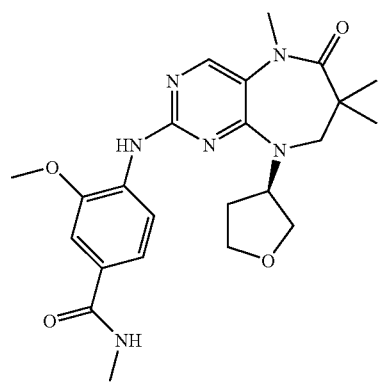
I-181
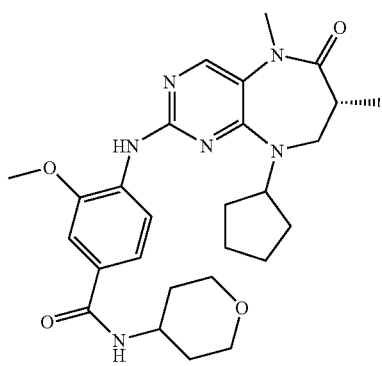
I-182
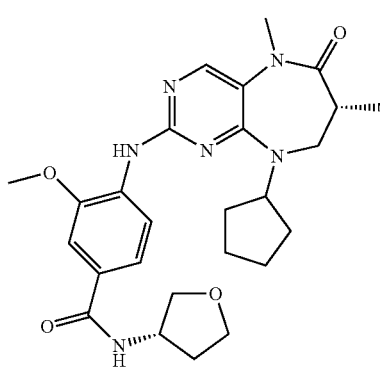
I-183
TABLE 1-continued
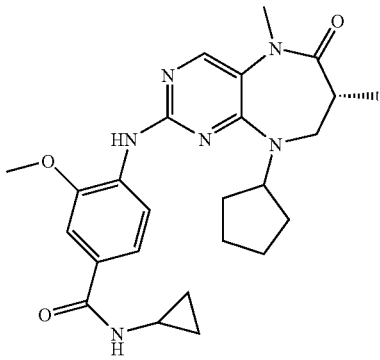
I-184
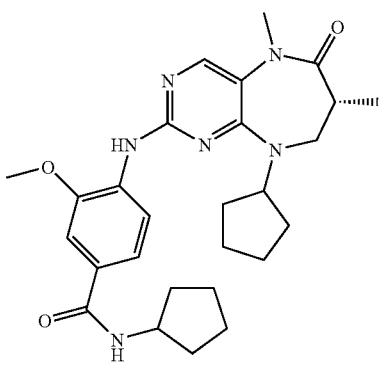
I-185
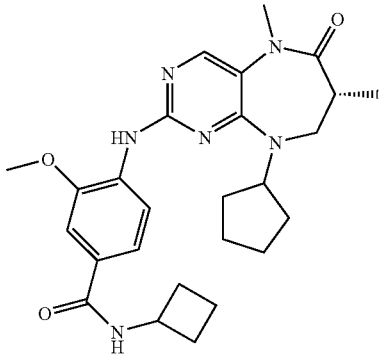
I-186
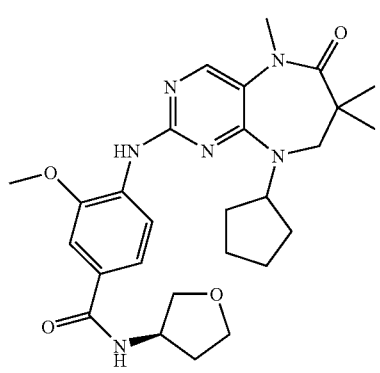
I-187

TABLE 1-continued
I-188
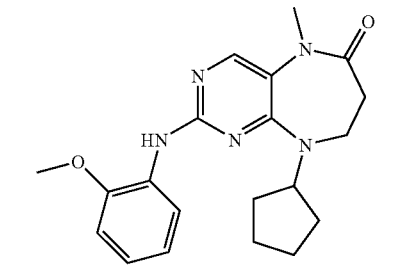
I-189
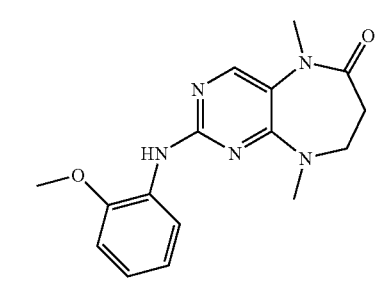
I-190
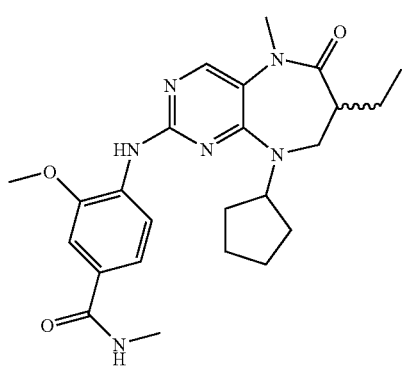
I-191
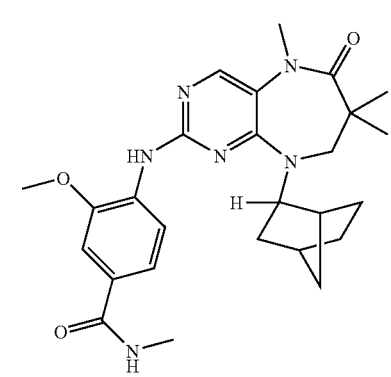
TABLE 1-continued
I-192
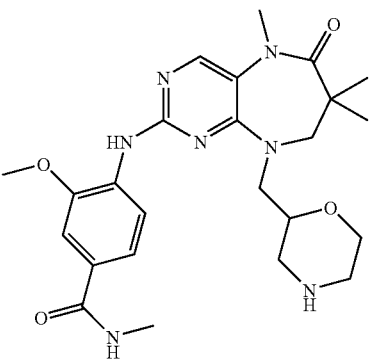
I-193
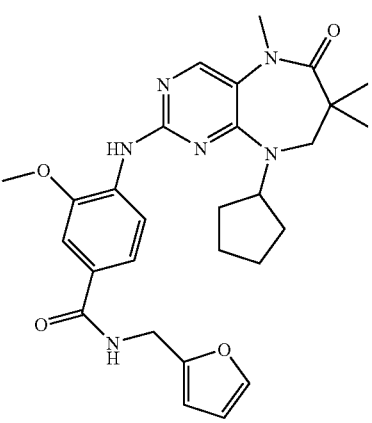
I-194
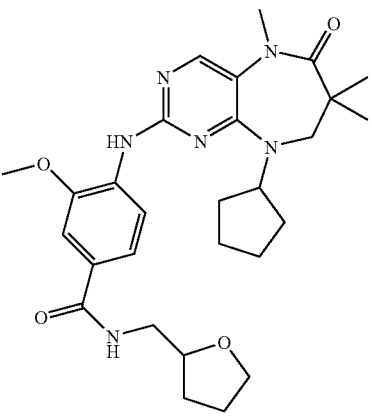

TABLE 1-continued
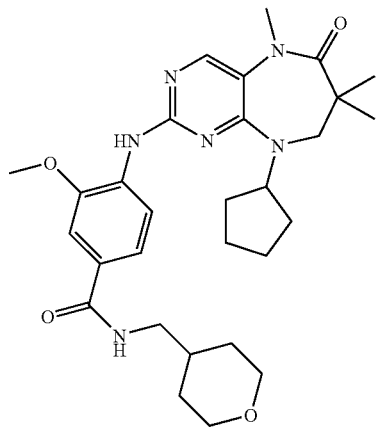
I-195
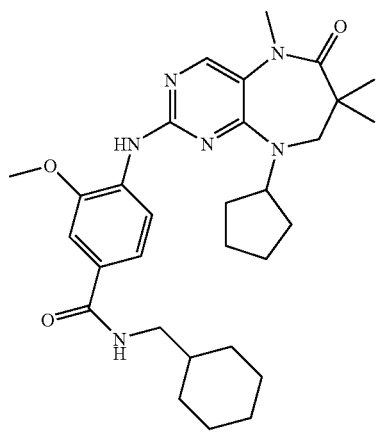
I-196
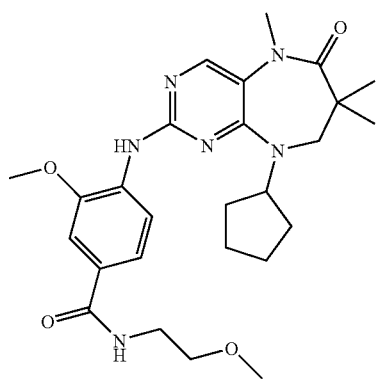
I-197
TABLE 1-continued
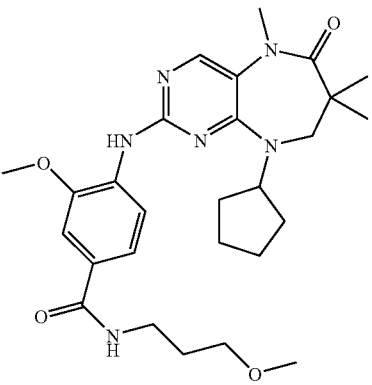
I-198
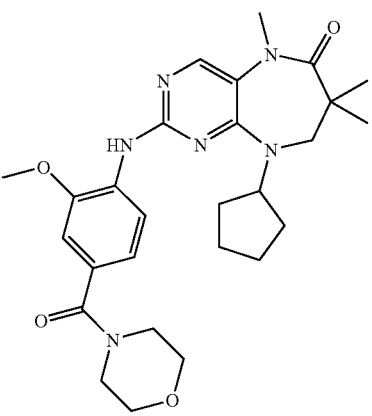
I-199
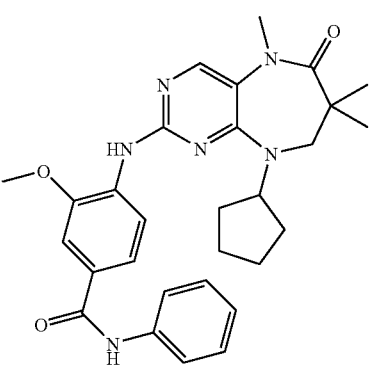
I-200

TABLE 1-continued
I-201
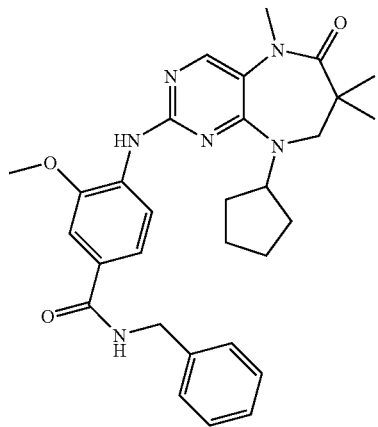
I-202
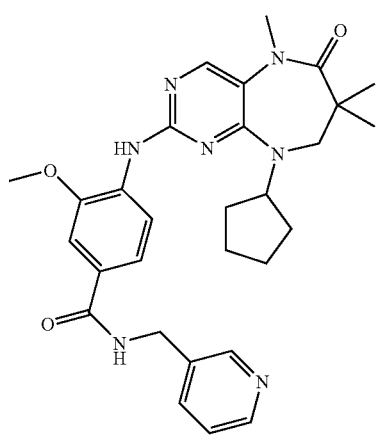
I-203
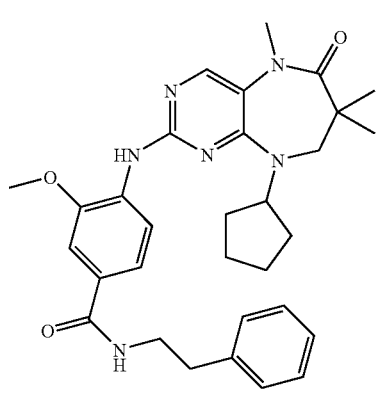
TABLE 1-continued
I-204
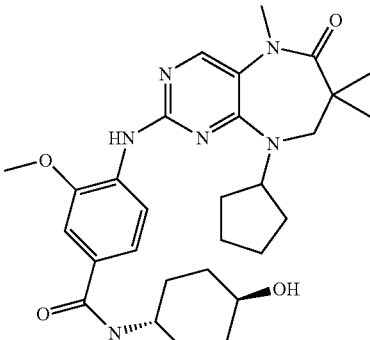
I-205
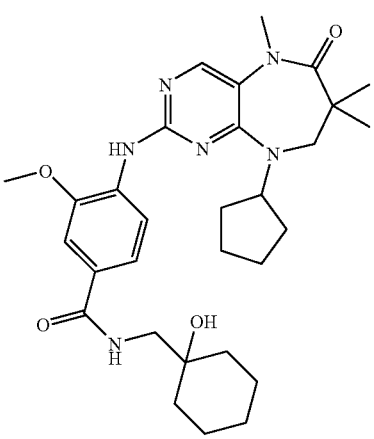
I-206
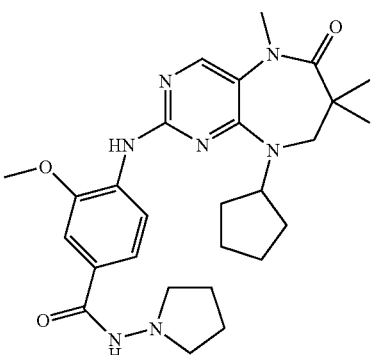
I-207
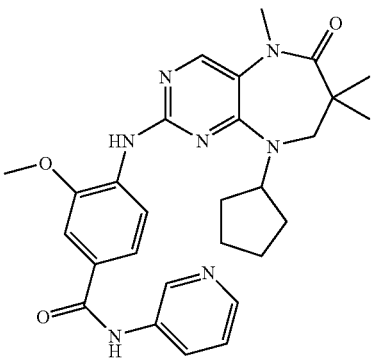

TABLE 1-continued
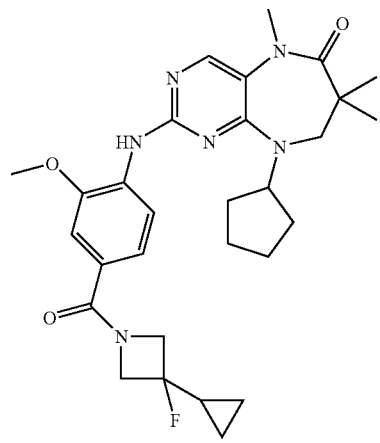
I-208
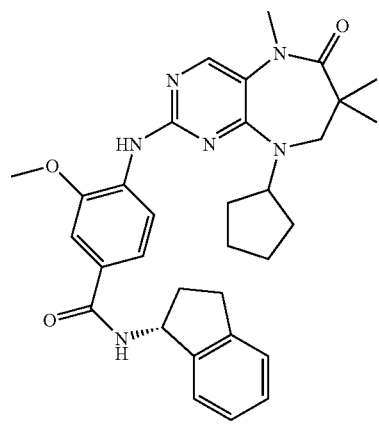
I-209
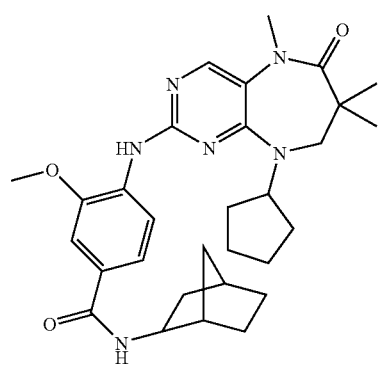
I-210
TABLE 1-continued
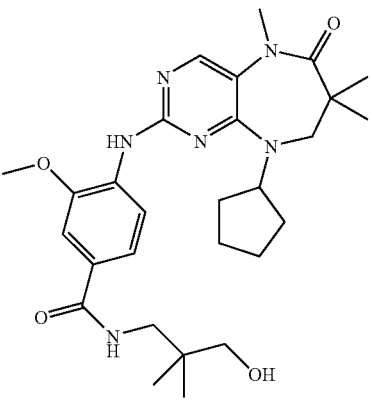
I-211
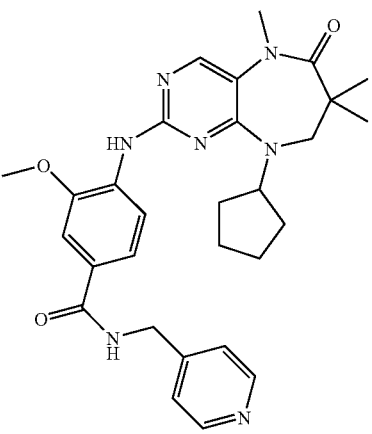
I-212
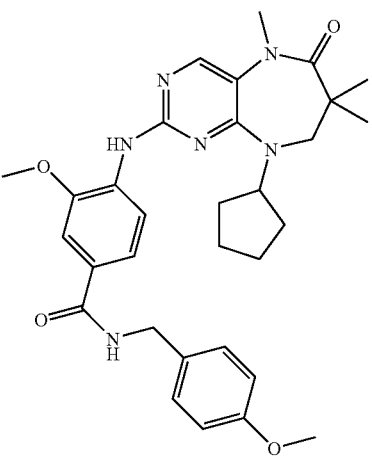
I-213

TABLE 1-continued
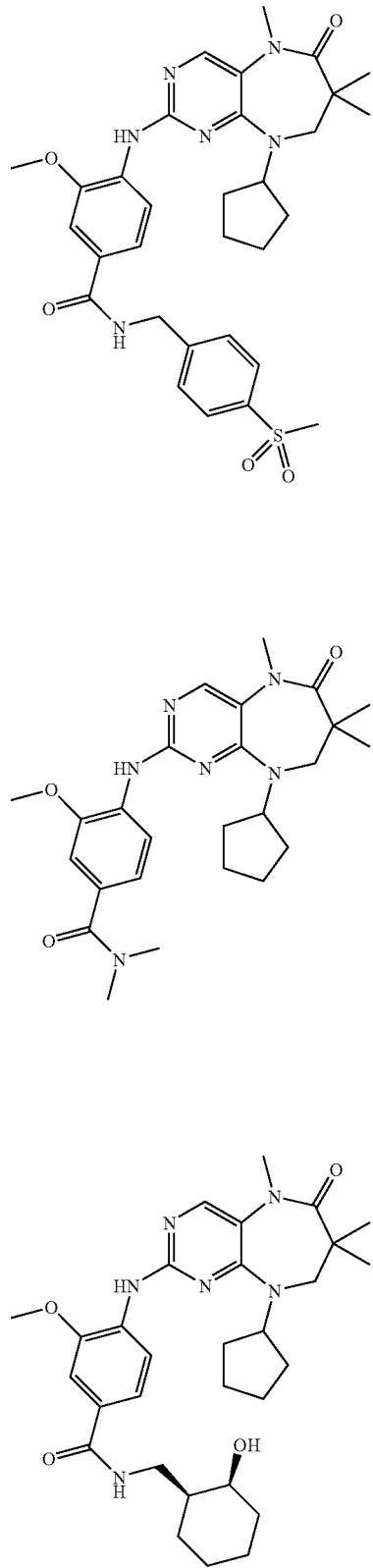
I-214
I-215
I-216
TABLE 1-continued
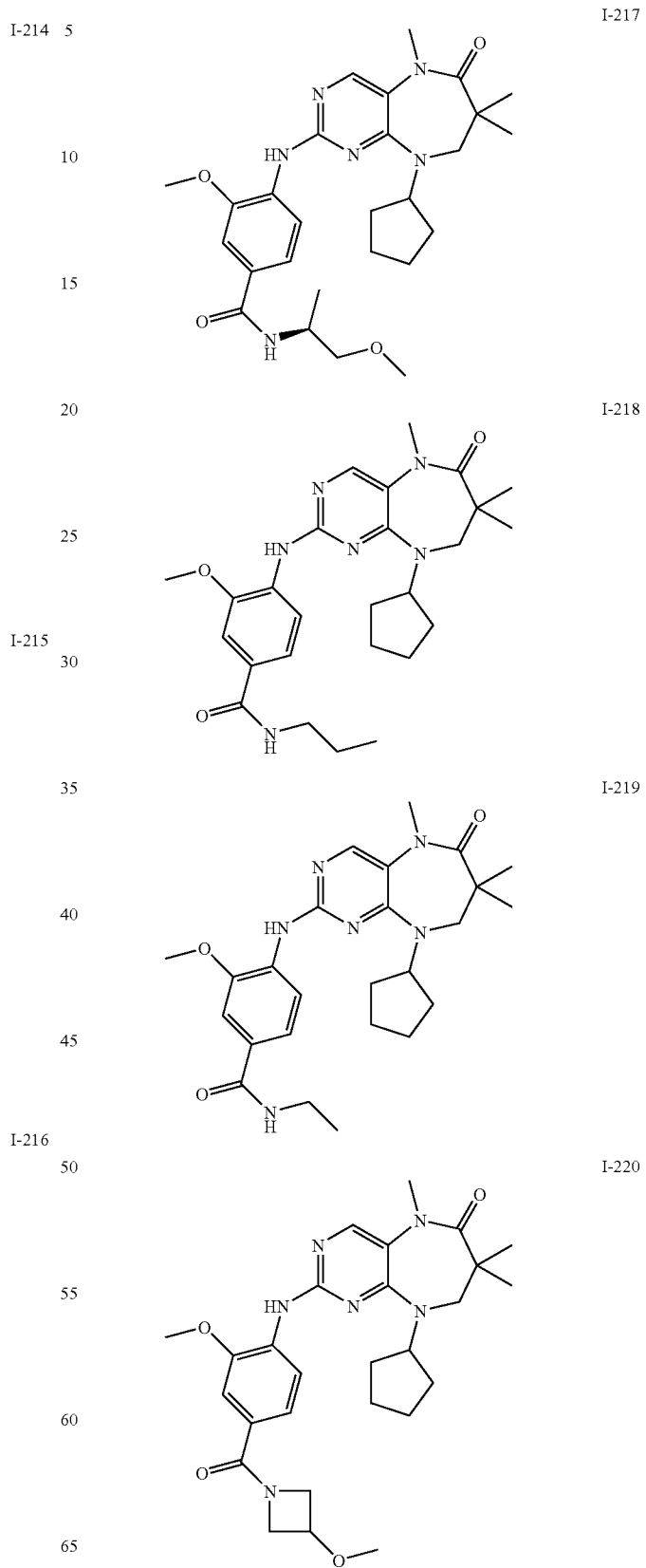
I-217
I-218
I-219
I-220

TABLE 1-continued
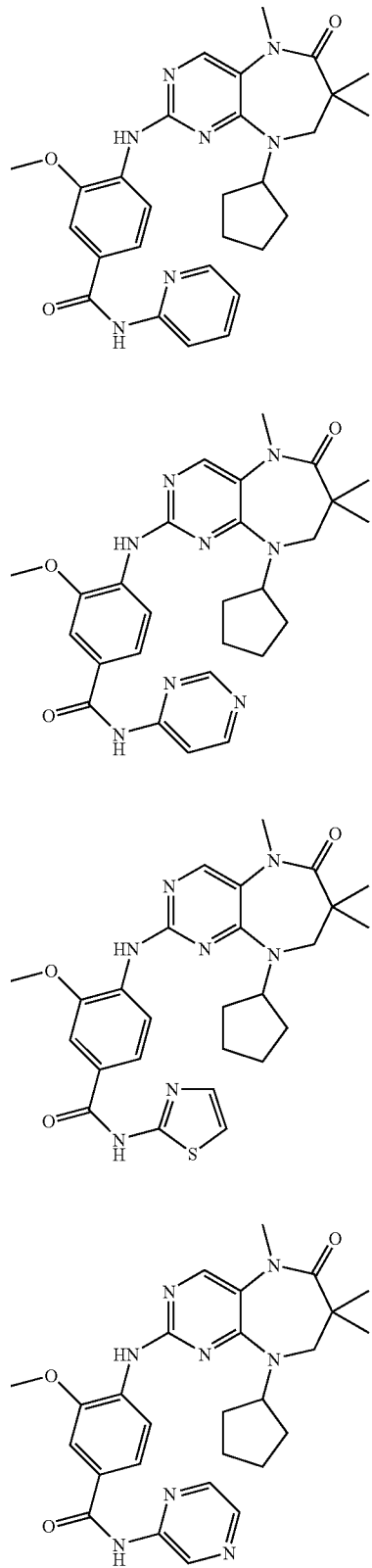
I-221
I-222
I-223
I-224
TABLE 1-continued
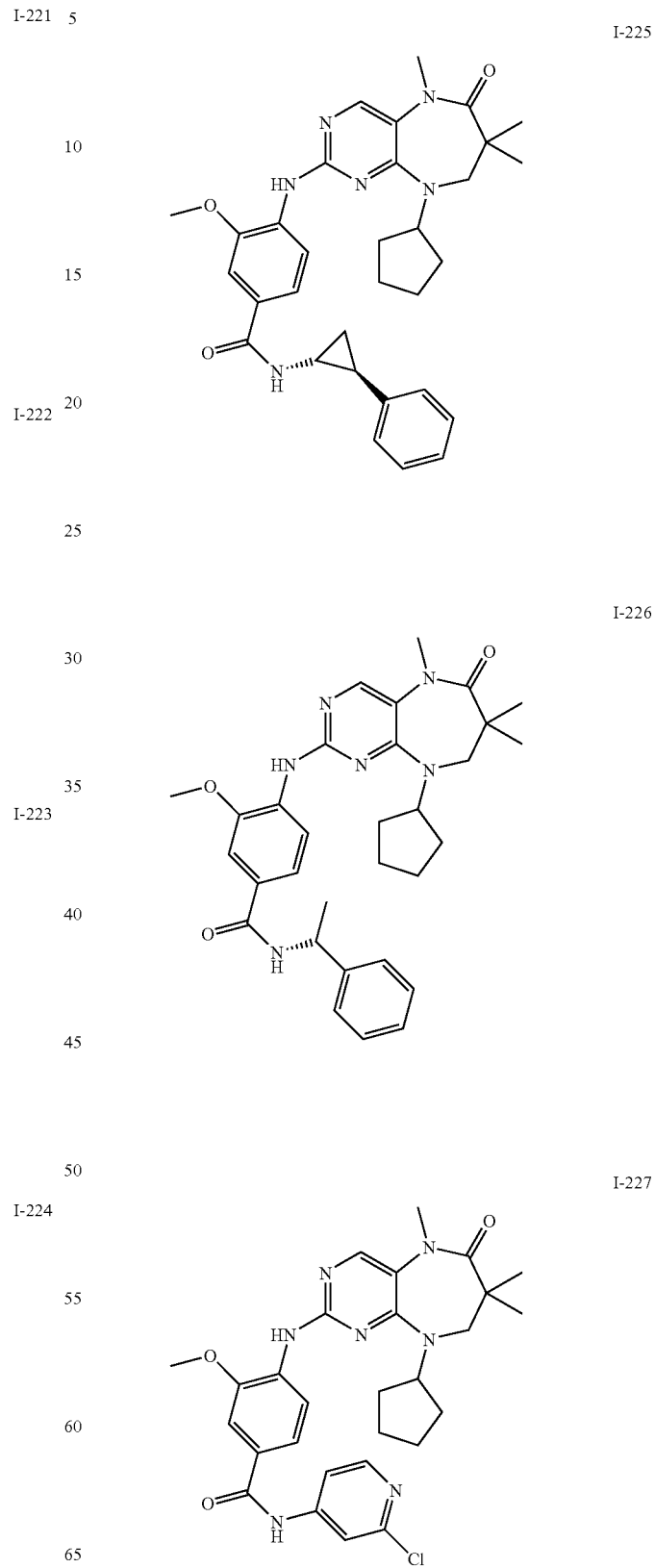
I-225
I-226
I-227

TABLE 1-continued
I-228
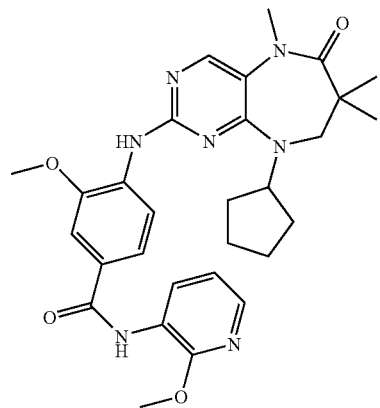
I-229
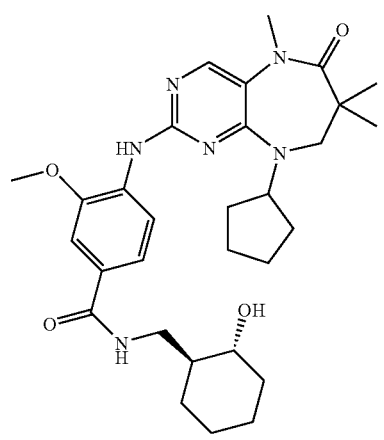
I-230
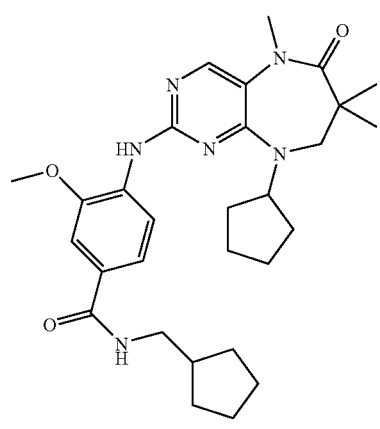
TABLE 1-continued
I-231
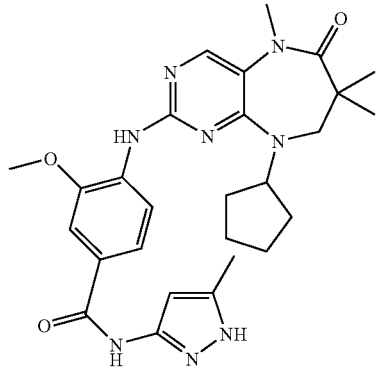
I-232
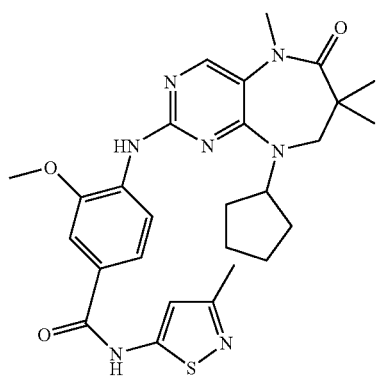
I-233
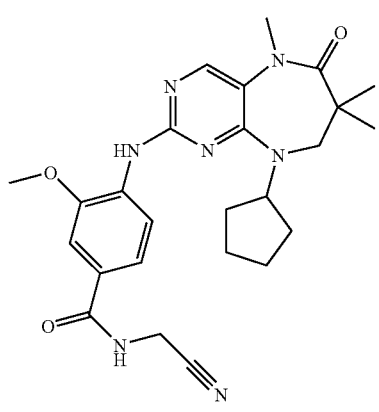

TABLE 1-continued
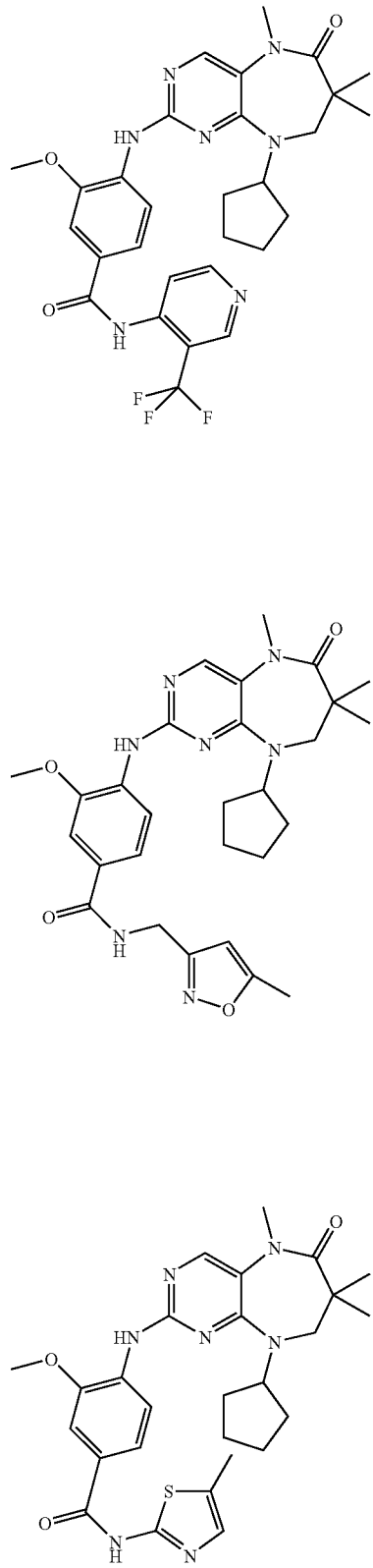
I-234
I-235
I-236
TABLE 1-continued
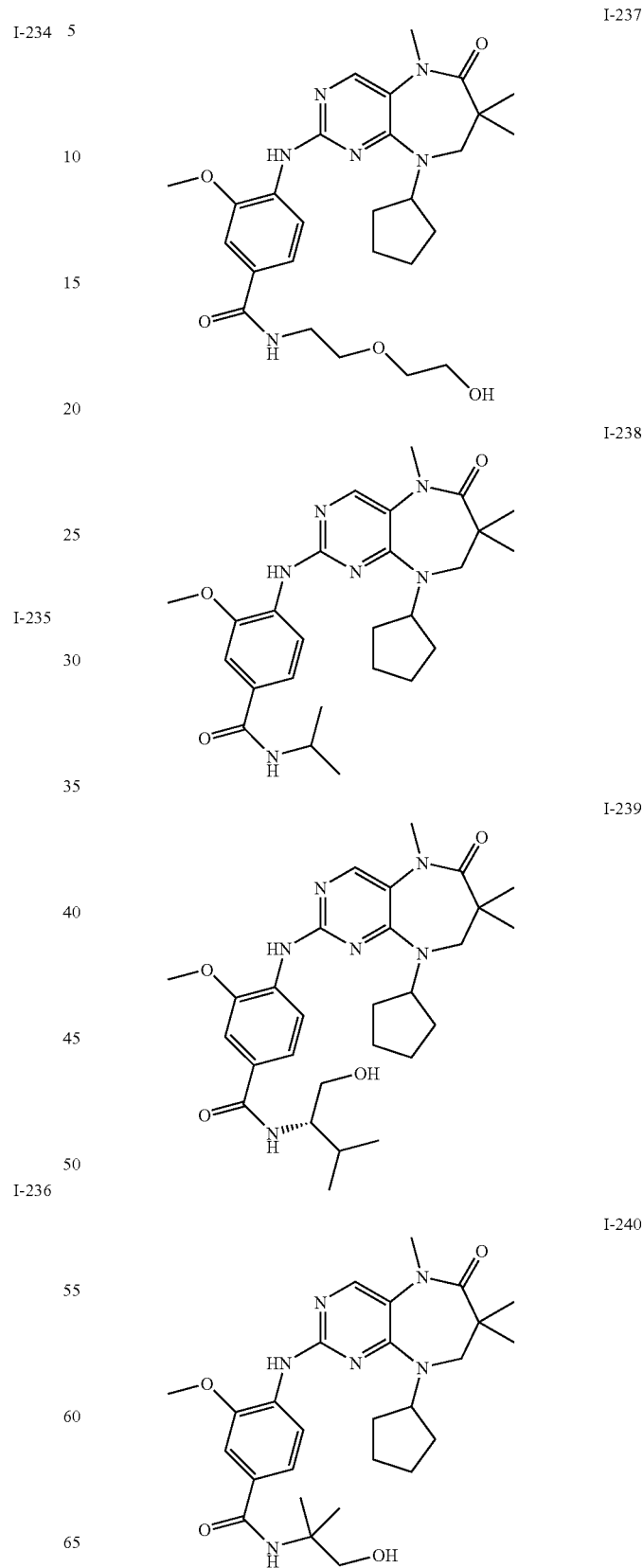
I-237
I-238
I-239
I-240

TABLE 1-continued
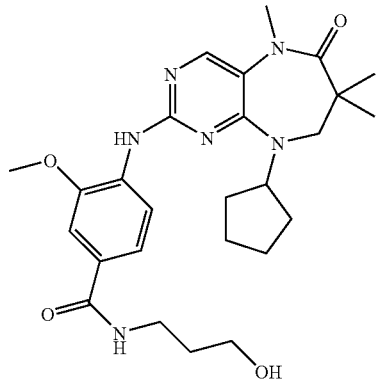
I-241
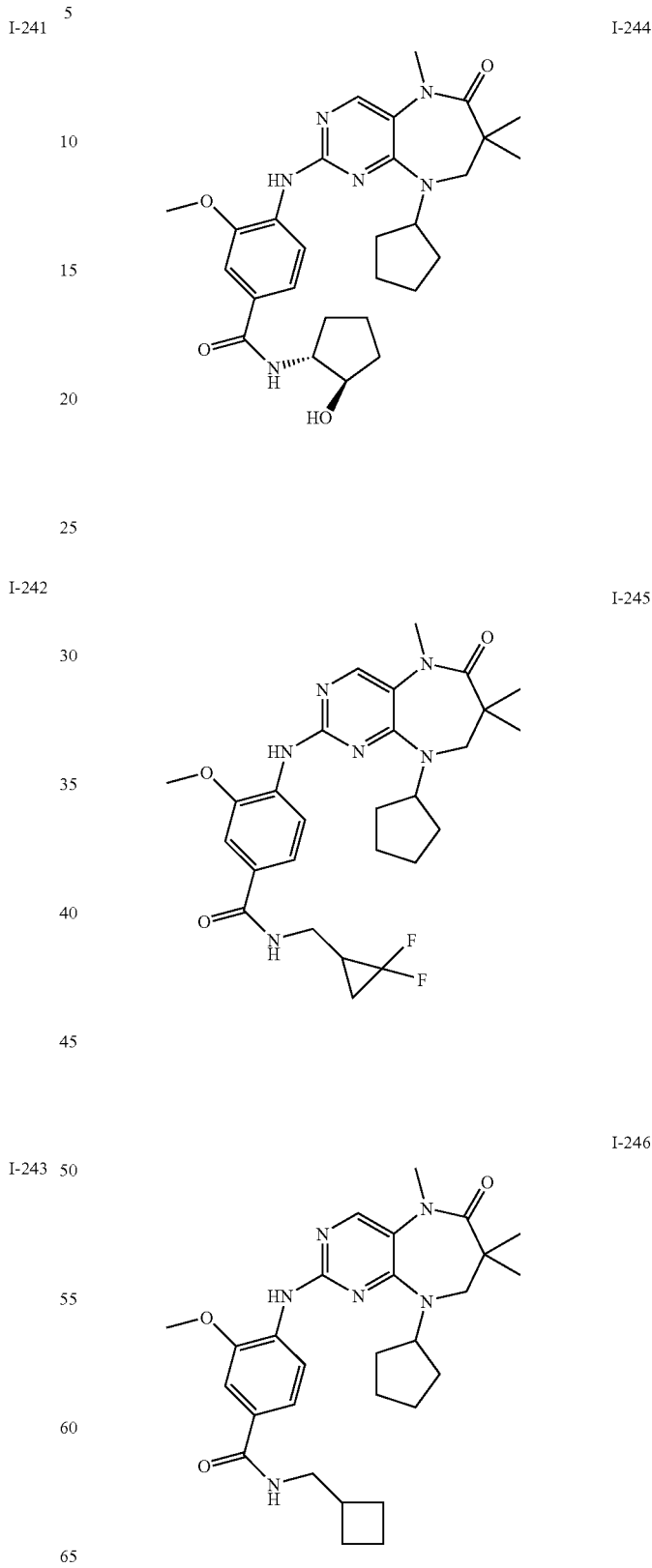
I-242
I-243
I-244
I-245
I-246

TABLE 1-continued
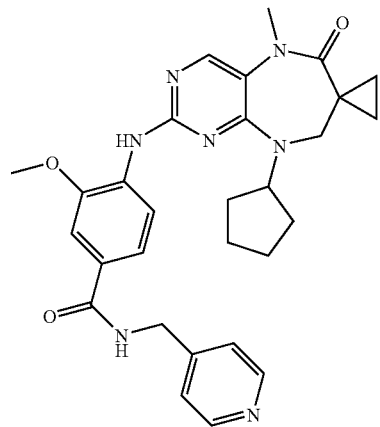
I-247
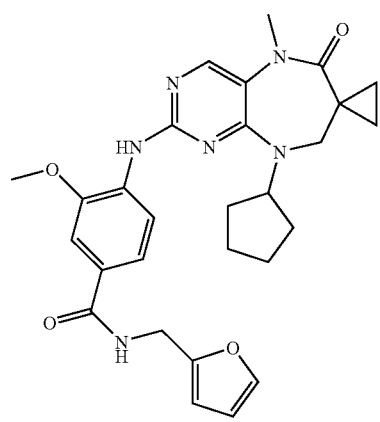
I-248
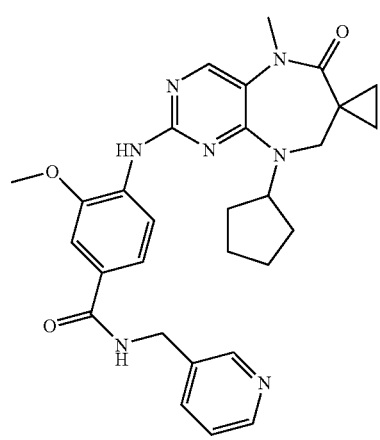
I-249
TABLE 1-continued
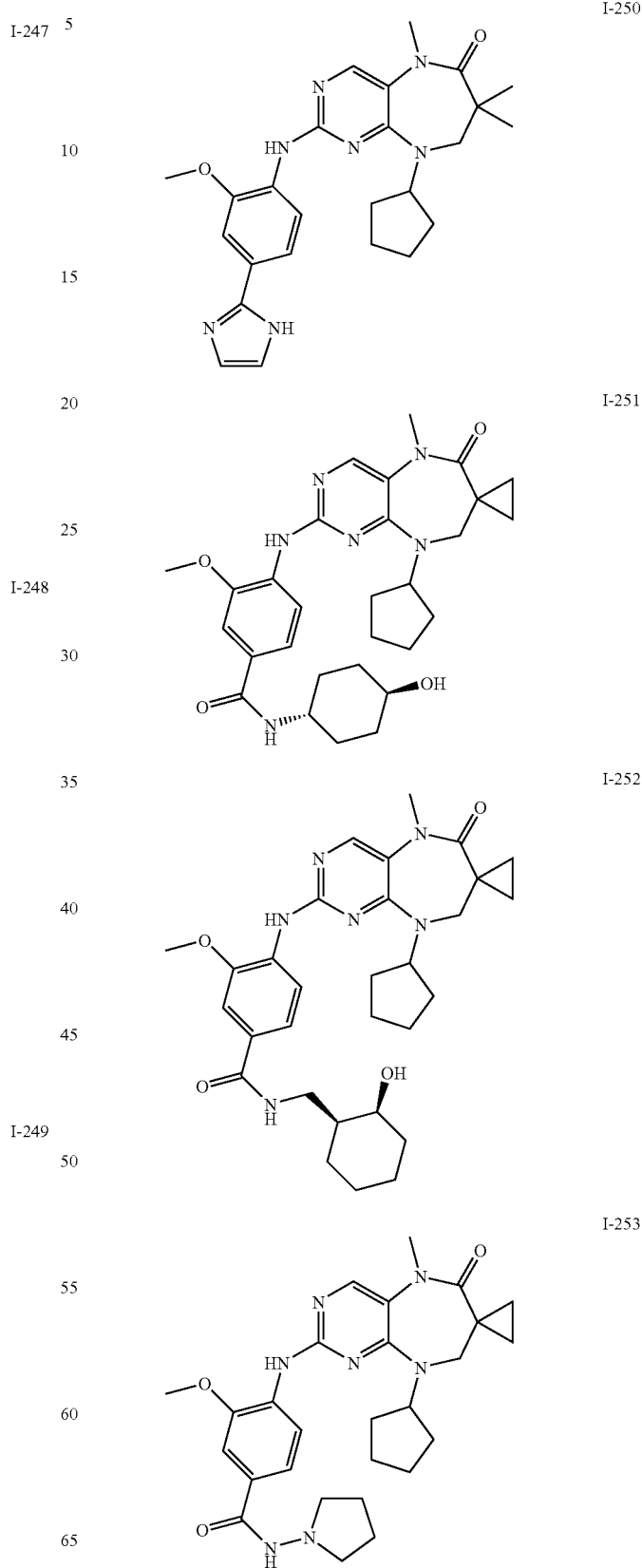

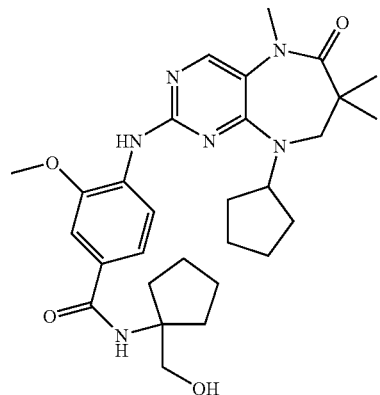
I-254
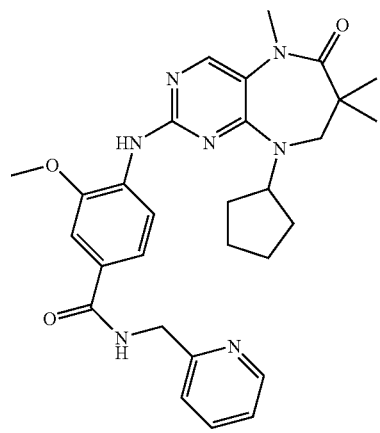
I-255
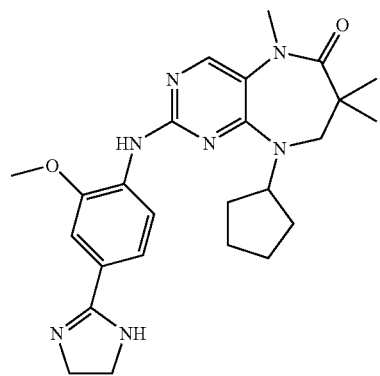
I-256
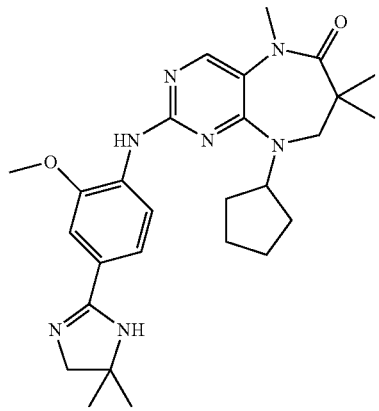
I-257
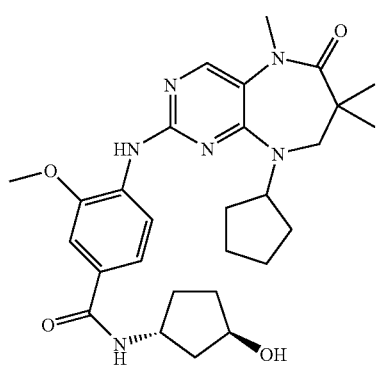
I-258
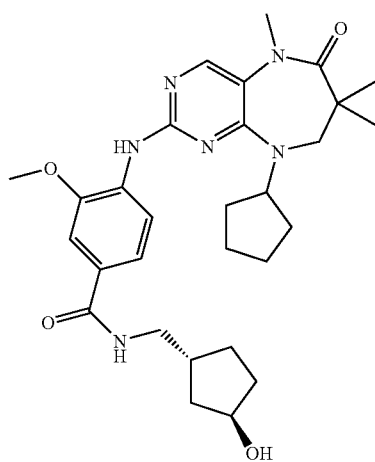
I-259

TABLE 1-continued
I-260
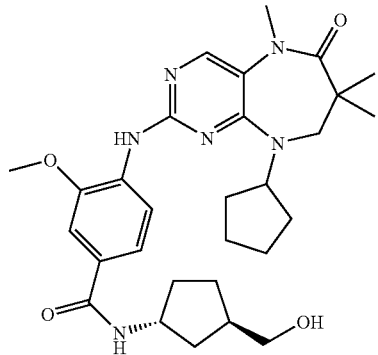
I-261
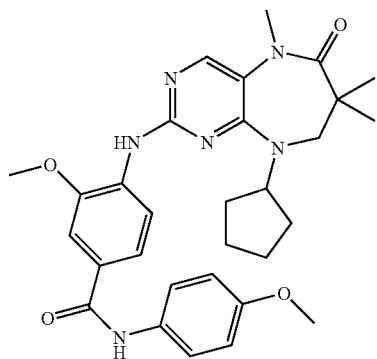
I-262
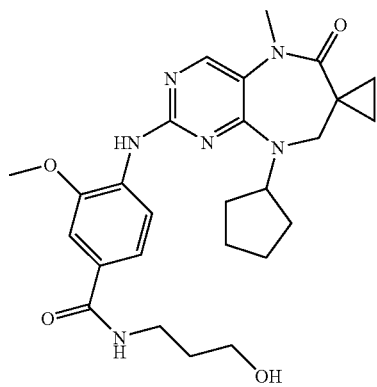
I-263
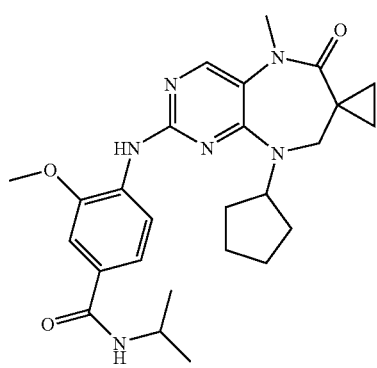
TABLE 1-continued
I-264
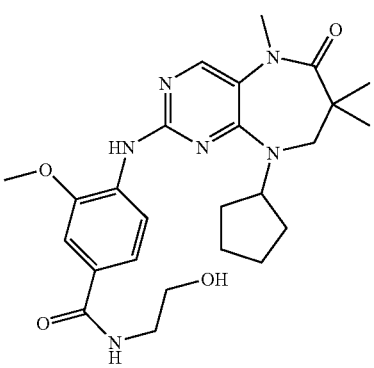
I-265
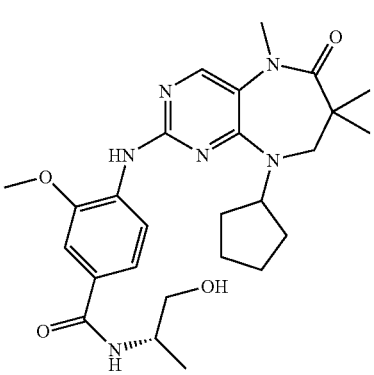
I-266
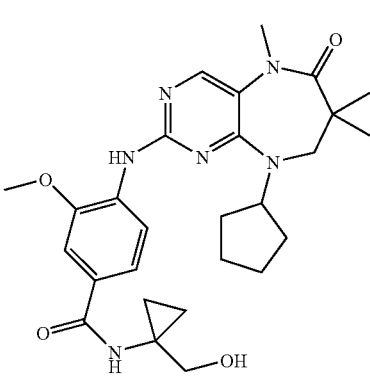
I-267
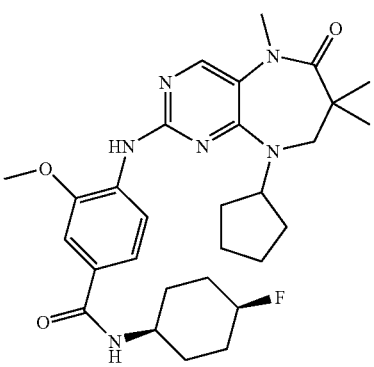

TABLE 1-continued
I-268
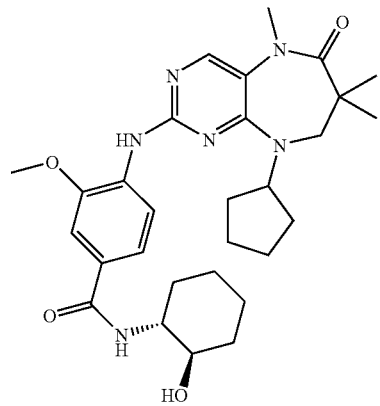
I-269
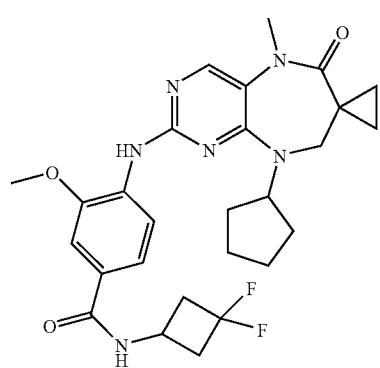
I-270
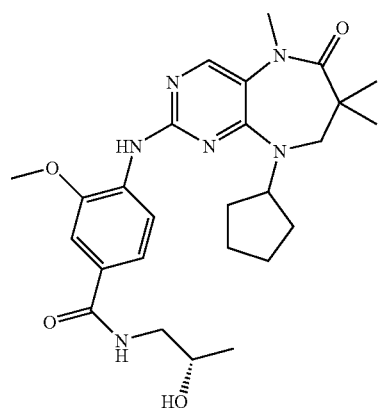
I-271
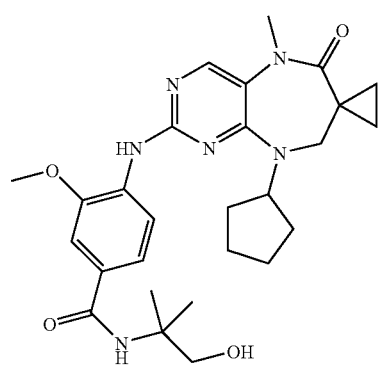
TABLE 1-continued
I-272
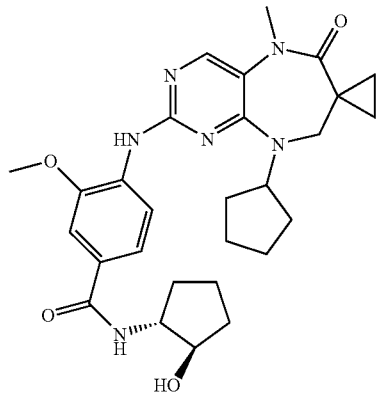
I-273
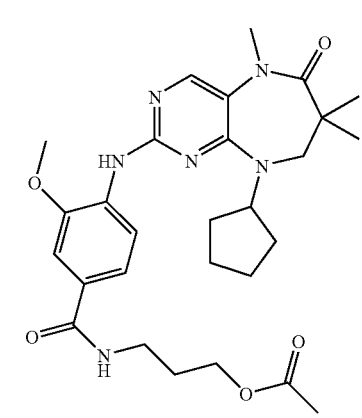
I-274
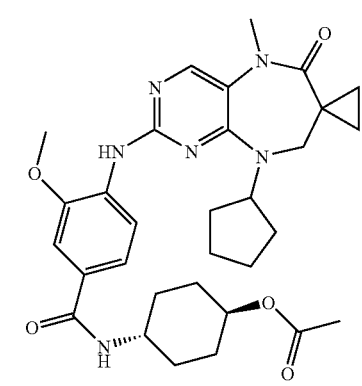
I-275
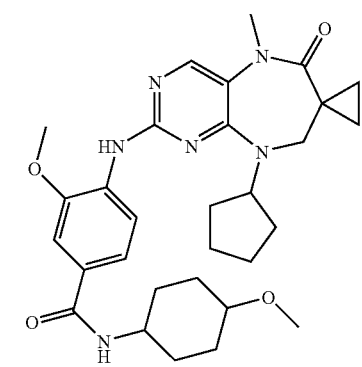

TABLE 1-continued
I-276
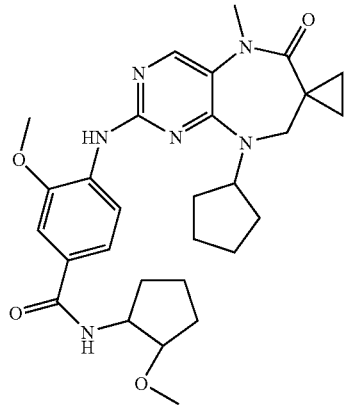
I-277
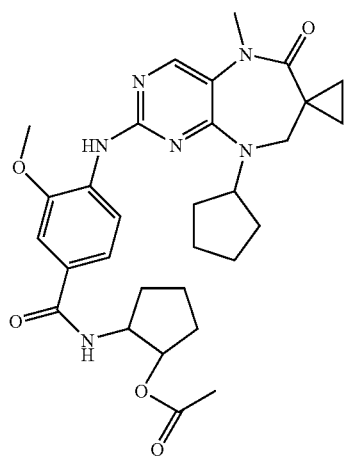
I-278
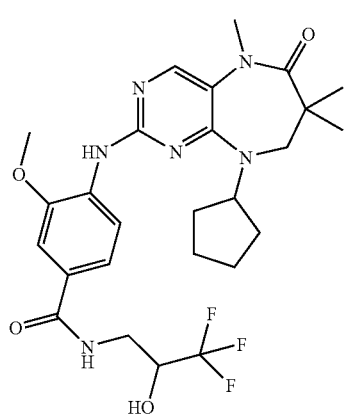
TABLE 1-continued
I-279
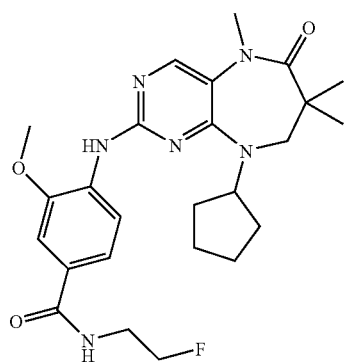
I-280

I-281
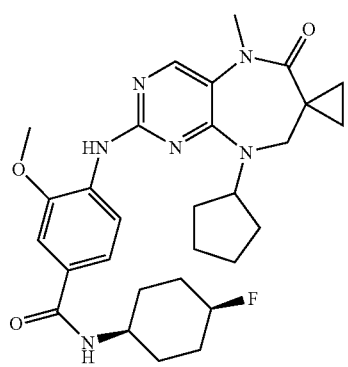
I-282
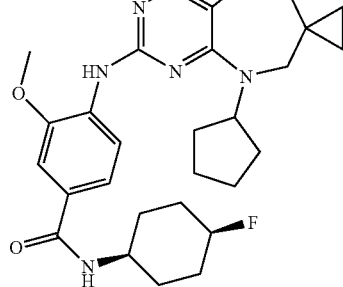

TABLE 1-continued
I-283
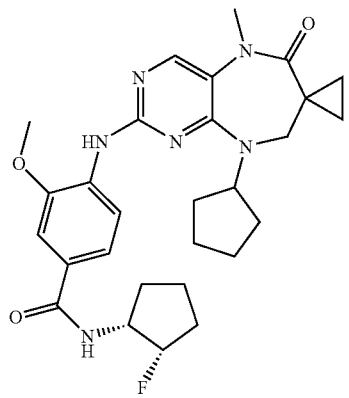
I-284
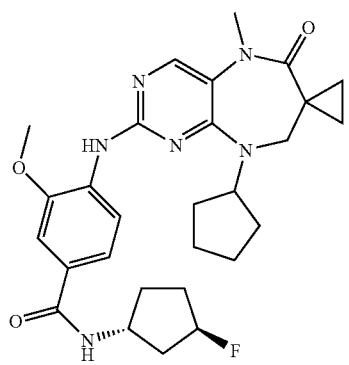
I-285
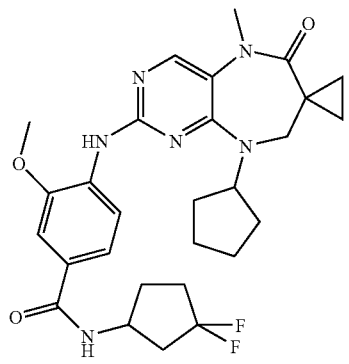
I-286
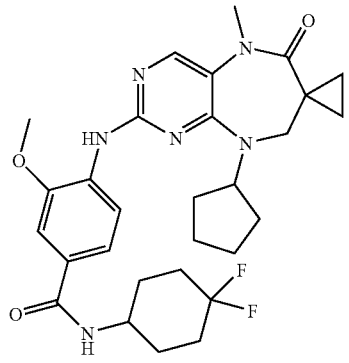
TABLE 1-continued
I-287
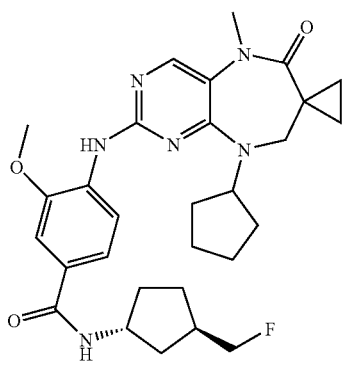
General Synthetic Methodology
The compounds of this invention may be prepared in general by methods such as those depicted in the general schemes below, and the preparative examples that follow. Unless otherwise indicated, all variables in the following schemes are as defined herein.
Scheme 1

-continued

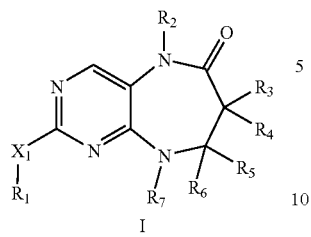
I

Scheme 1 above shows a general synthetic route for preparing compounds of formula I where $Y^1$=O, Starting material 1 (wherein $LG_1$ and $LG_2$ can be, but not restricted to, chlorine atoms) reacts with β-aminoester 2 to give adduct 3. Reduction of the nitro group, followed by cyclo-condensation gives bicyclic compound 4. The amide N—H can be functionalized at this stage to give 5. $LG_2$ can finally be used as a handle for preparation of the compounds of formula I. In this last step $LG_2$ can, for example, be displaced with amines or be engaged in palladium assisted coupling reactions known to one skilled in the art (e.g., Suzuki, Stille).

Alternatively, the compound of formula 3, after reduction of the nitro group, can be first functionalized to form a compound of formula 3-b;

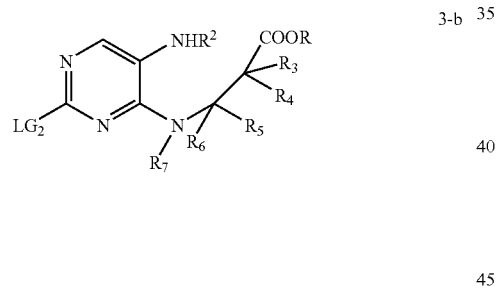

which can subsequently be cyclized to form the compound of formula 5.

-continued

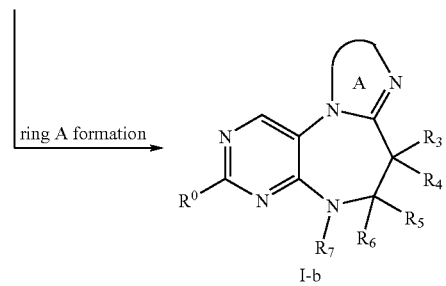
I-b
$R^0$ = $LG_2$ 5-b
$R^0$ = $R^1X^1$ I-b

Scheme 2 above shows a general synthetic route for preparing compounds of this invention where $Y^1$ is $NR^9$. The lactam functional group in 5 or I (either in 5 where $LG_2$ is still present or in I if it has already been derivatised as $R^1X^1$) can be engaged into a functional group transformation to form an amidine group (either 5-a where $LG_2$ is still present or I-a if it has already been derivatised as $R^1X^1$).

Alternatively, Scheme 2 above also shows a general synthetic route for preparing compounds of this invention where $Y^1$=N and $R^2$ and $R^9$ are taken together to form ring A. The lactam functional group in 5 or I (either in 5 where $LG_2$ is still present or in I if it has already been derivatised as $R^1X^1$) can be engaged in a multi-step cyclisation sequence to form ring A (either 5-b where $LG_2$ is still present or I-b if it has already been derivatised as $R^1X^1$).

Scheme 3

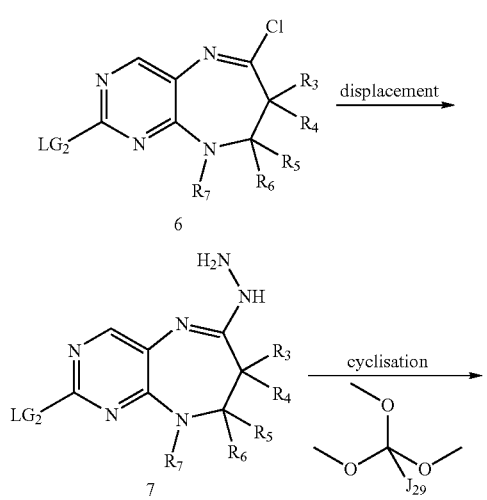

Scheme 2

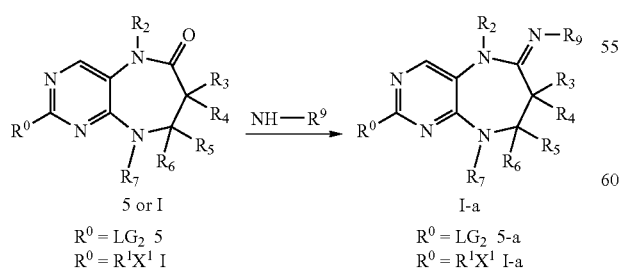
5 or I
$R^0$ = $LG_2$ 5
$R^0$ = $R^1X^1$ I

I-a
$R^0$ = $LG_2$ 5-a
$R^0$ = $R^1X^1$ I-a

-continued

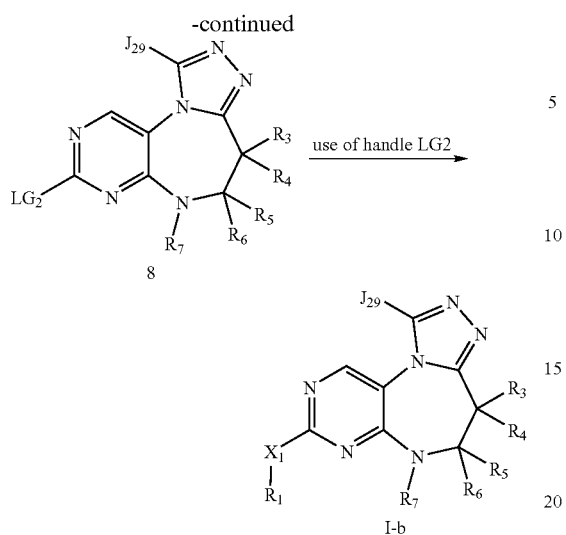

Scheme 3 above shows a general synthetic route for preparing compounds of this invention where $Y^1$ is $NR^9$ and $R^2$ and $R^9$ are taken together to form a triazole ring. Activation of the lactam functional group in 4, followed by displacement with hydrazine lead to intermediates of formula 7. Compounds of formula I-b were finally obtain by cyclisation of derivatives 7 and subsequent displacement with $HX_1$—$R_1$.

Scheme 4

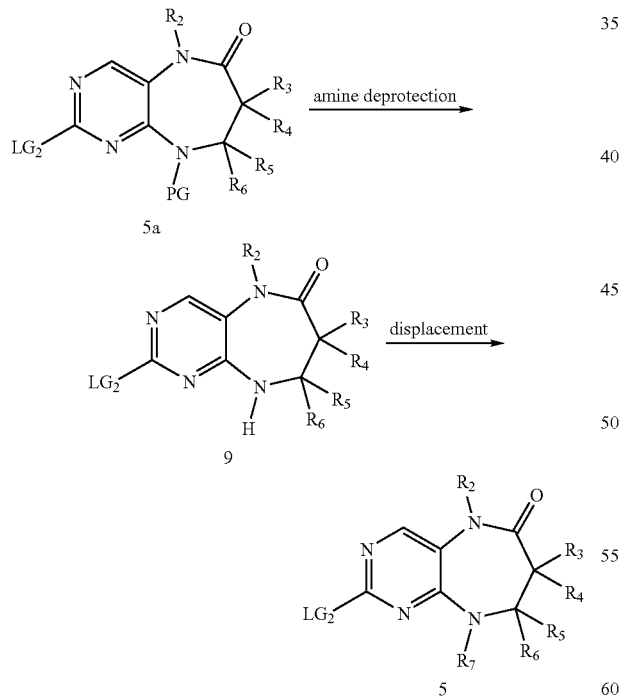

Scheme 4 above shows another general synthetic route for preparing compounds 5 of this invention. Compounds of formula 5a, containing a protecting group on the amine, can be prepared like previously shown (see compound 5 scheme 1). Deprotection of amines 5a, followed by substitution of the free amines of 9 with the desired $R^7$-halides can be achieved by methods well known in the art.

Accordingly, this invention also provides a process for preparing a compound of this invention.

One embodiment of this invention provides a process for preparing a compound of formula I:

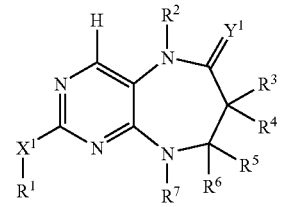

I wherein
$Y^1$ is O and $X^1$, $R^1$, $R^2$, $R^3$, $R^4$, $R^5$, $R^6$, and $R^7$ are as defined herein;
comprising reacting a compound of formula 5;

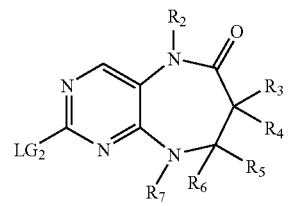

5 wherein
$R^2$, $R^3$, $R^4$, $R^5$, $R^6$, and $R^7$ are as defined herein; and $LG_2$ is a suitable leaving group, such as halo, with $X^1R^1$ under suitable conditions to form the compound of formula I. $X^1R^1$ can displace $LG_2$ in a variety of ways known to one skilled in the art. For example, if $X^1$ is $NHR^8$, O, or S, then $X^1R^1$ can displace $LG_2$ in the presence of suitable base or acid, solvent, and conditions. Suitable displacement reactions are known to one skilled in the art and can be found in a variety of resources, including "March's Advanced Organic Chemistry". A sulfur linker (wherein $X^1$ is S) can be oxidized under suitable oxidation conditions to form compounds wherein $X^1$ is SO or $SO_2$. Compounds of formula I, wherein $X^1$ is a bond and $R^1$ is bonded to $X^1$ via a carbon atom, can be formed under suitable cross-coupling conditions. In these cross coupling reactions, one of the starting materials is $R^1$ bonded to a cross-coupling group. This starting material can react with the compound of formula 5 under cross coupling conditions to form compounds of formula I, wherein $X^1$ is a bond and $R^1$ is bonded to $X^1$ via a carbon atom.

The term "cross-coupling reaction", as used herein, refers to a reaction in which a carbon-carbon bond is formed with the aid of a metal catalyst. Usually, one of the carbon atoms is bonded to a functional group (a "cross-coupling group") while the other carbon atom is bonded to a halogen. Examples of cross coupling reactions include, but are not limited to, Suzuki couplings, Stille couplings, and Negishi couplings.

The term "cross-coupling group", as used herein, refers to a functional group capable of reacting with another functional group (e.g., halo) in a cross coupling reaction to form a carbon-carbon ("C—C") bond. In some embodiments, the C—C bond is formed between two aromatic groups.

The term "cross coupling condition", as used herein, refers to the chemical conditions (e.g., temperature, length of time of reaction, volume of solvent required) required in order to enable the cross coupling reaction to occur.

Examples of cross-coupling groups and their respective cross-coupling conditions include, but are not limited to, boronic acids and boronic esters with Suzuki coupling conditions, $SnBu_3$ with Stille coupling conditions, and ZnX with Negishi coupling conditions.

All three of these coupling conditions typically involve the use of a catalyst, a suitable solvent, and optionally a base. Suzuki coupling conditions involve the use of a palladium catalyst and a suitable solvent. Examples of suitable palladium catalysts include, but are not limited to, $PdCl_2(PPh_3)_2$, $Pd(Ph_3)_4$, and $PdCl_2(dppf)$. Suitable bases include, but are not limited to, $K_2CO_3$ and $Na_2CO_3$. Suitable solvents include, but are not limited to, tetrahydrofuran, toluene, and ethanol.

Stille coupling conditions involve the use of a catalyst (usually palladium, but sometimes nickel), a suitable solvent, and other optional reagents. Examples of suitable catalysts include, but are not limited to, $PdCl_2(PPh_3)_2$, $Pd(Ph_3)_4$, and $PdCl_2(dppf)$. Suitable solvents include, but are not limited to, tetrahydrofuran, toluene, and dimethylformamide.

Negishi coupling conditions involve the use of a catalyst (palladium or nickel) and a suitable solvent. Examples of suitable catalysts include, but are not limited to $Pd_2(dba)_3$, $Ni(PPh_3)_2Cl_2$, $PdCl_2(PPh_3)_2$, and $Pd(Ph_3)_4$. Suitable solvents include, but are not limited to, tetrahydrofuran, toluene, and dimethylformamide.

Suzuki, Stille, and Negishi conditions are known to one skilled in the art and are described in more detail in a variety of references, including "March's Advanced Organic Chemistry".

As would be understood by one skilled in the art, cross coupling groups are formed from coupling groups precursors. A "coupling group precursor" is a reagent or group of reagents used to form a cross-coupling group. Examples include, but are not limited to, bis(pinacolato)diborane for the formation of boronate esters, trimethylborates for the formation of boronic acids, $Bu_3SnCl$ for the formation of stannanes, and $ZnCl_2$ for the formation zincates in Negishi coupling reactions. Examples of suitable coupling group formation conditions include, but are not limited to, making boronic esters via palladium-mediated catalysis; making boronic acids by hydrolyzing boronic esters; making stannanes via a two step process: 1) halogen metal exchange followed by 2) transmetallation with Bu3SnCl; and making zincates via a two step process: 1) halogen metal exchange followed by 2) addition of $ZnCl_2$.

Another embodiment provides a process for forming a compound of formula 5 comprising reacting a compound of formula 4;

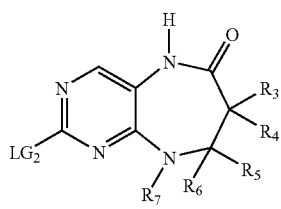

4 wherein $R^3$, $R^4$, $R^5$, $R^6$, and $R^7$ are as defined herein; and $LG_2$ is a suitable leaving group, such as halo;

with $R^2$-$LG_3$, wherein $LG_3$ is a leaving group capable of being displaced by an NH-amide. Examples of leaving groups include, but are not limited to, halo, tosylate, and mesylate.

Another embodiment provides a process for forming a compound of formula 4 comprising reacting a compound of formula 3;

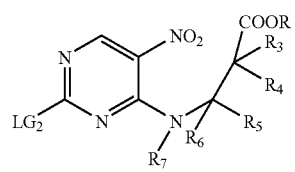

3 under a two step process. The first step involves reduction of the nitro group under suitable reduction conditions, such as iron powder, $SnCl_2$, zinc powder, indium/HCl, or $H_2/Pd$ to form a compound of formula 3-a:

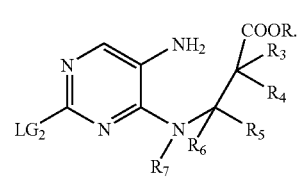

3-a

The second step involves cyclocondensation of the amine with the carboxylic ester of formula 3-a, resulting in the compound of formula 4. Cyclocondensations typically occur in the presence of an acid or a base. In some embodiments, this two-step process occurs in situ. One example of an in situ condition involves treating the nitro-compound with iron powder in glacial acetic acid.

Another aspect of this invention provides an alternative way of forming the compounds of formula 5. Instead of directly cyclizing the compound of formula 3-a to form the compound of formula 4, the amino intermediate can be functionalized first to form the compound of formula 3-b

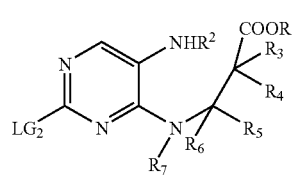

3-b under suitable conditions known to one skilled in the art. For example, the amino group can react with $R^2$-$LG_3$, wherein $LG_3$ is a leaving group capable of being displaced by an amine. Examples of leaving groups include, but are not limited to, halo, tosylate, and mesylate.

This compound can then be cyclized under suitable cyclocondensation conditions to form the compound of formula 5.

Another embodiment of this invention provides a process for forming the compound of formula 3; comprising reacting the compound of formula 2;

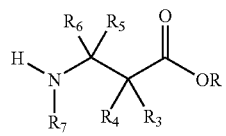

with a compound of formula 1;

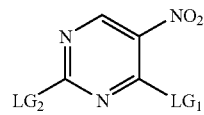

under suitable displacement conditions to form the compound of formula 3. Suitable displacement conditions typically comprise of a suitable solvent and a suitable base or acid. Examples of suitable displacement conditions include, but are not limited to, $K_2CO_3$ and acetone, Hunig's base/THF.

Another aspect of this invention provides a process for making compounds of formula I wherein $Y^1$ is $NR^9$. One embodiment involves reacting the compound of formula I wherein $Y^1$ is O and $X^1$, $R^1$, $R^2$, $R^3$, $R^4$, $R^5$, $R^6$, and $R^7$ are as defined herein; under suitable conditions known in the art for converting amides into amidines, to form a compound of formula I wherein $Y^1$ is $NR^9$ (shown in Scheme II as I-a). Suitable conditions typically involve an amine ($R^1$—$NHR^9$), a suitable solvent, and an activated intermediate deriving from an amide (e.g., a thioamide prepared from an amide and Lawesson's Reagent).

In another aspect, the compound of formula 5 can be subject to similar amide-converting conditions to form a compound of formula 5-a. The $LG_2$ group in 5-a or 5-b can be used as a handle for preparation of the compounds of this invention. In this last step $LG_2$ can, for example, be displaced with amines or be engaged in palladium assisted coupling reactions (e.g., Suzuki, Stille).

In some embodiments, the compounds of formula 1 or 5, wherein $Y^1$ is O and $X^1$, $R^1$, $R^2$, $R^3$, $R^4$, $R^5$, $R^6$, and $R^7$ are as defined herein, can be converted into cyclic amidines, wherein $R^2$ and $R^9$ are taken together to form ring A. These cyclic amidines (shown in Scheme II as I-b) can be made via a multi-step cyclisation sequence. Ring A can vary in size (e.g. 5-8 membered ring) and in degree of unsaturation. For example, formation of ring A can be carried out using methods similar to the ones reported in: *J. Am. Chem. Soc,* 103 (14), 4186-4194, 1981; *J. Het. Chem.,* 19(1), 193-200, 1982; *Angew. Chem.,* 43(4), 478-482, 2004; *Scientia Pharm.,* 57(1), 27-38, 1989; *Tetrahedron Lett.,* 16(2), 449-469, 2005; *J. Org. Chem.,* 59 (17), 5084-5087, 1994. The $LG_2$ group in 5-a or 5-b can be used as a handle for preparation of the compounds of this invention. In this last step $LG_2$ can, for example, be displaced with amines or be engaged in palladium assisted coupling reactions (e.g., Suzuki, Stille).

Another aspect of this invention provides compounds that are inhibitors of protein kinases, and thus are useful for the treatment of the diseases, disorders, and conditions, along with other uses described herein. In another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

The present invention provides compounds and compositions that are useful as inhibitors of protein kinases. In some embodiments, the protein kinases are PLK. In some embodiments, PLK1.

As inhibitors of protein kinases, the compounds and compositions of this invention are particularly useful for treating or lessening the severity of a disease, condition, or disorder where a protein kinase is implicated in the disease, condition, or disorder. In one aspect, the present invention provides a method for treating or lessening the severity of a disease, condition, or disorder where a protein kinase is implicated in the disease state. In another aspect, the present invention provides a method for treating or lessening the severity of a kinase disease, condition, or disorder where inhibition of enzymatic activity is implicated in the treatment of the disease. In another aspect, this invention provides a method for treating or lessening the severity of a disease, condition, or disorder with compounds that inhibit enzymatic activity by binding to the protein kinase. Another aspect provides a method for treating or lessening the severity of a kinase disease, condition, or disorder by inhibiting enzymatic activity of the kinase with a protein kinase inhibitor.

In some embodiments, said protein kinase inhibitor is a PLK inhibitor.

One aspect of the invention relates to a method of inhibiting protein kinase activity in a patient, which method comprises administering to the patient a compound of formula I, or a composition comprising said compound.

In some embodiments, said method is used to treat or prevent a condition selected from autoimmune diseases, inflammatory diseases, proliferative and hyperproliferative diseases, immunologically-mediated diseases, bone diseases, metabolic diseases, neurological and neurodegenerative diseases, cardiovascular diseases, hormone related diseases, allergies, asthma, and Alzheimer's disease. In some embodiments, said protein kinase in PLK. In other embodiments, said condition is selected from a proliferative disorder and a neurodegenerative disorder.

Depending upon the particular protein kinase-mediated conditions to be treated or prevented, additional drugs, which are normally administered to treat or prevent that condition, may be administered together with the inhibitors of this invention. For example, chemotherapeutic agents or other anti-proliferative agents may be combined with the protein kinase inhibitors of this invention to treat proliferative diseases.

Those additional agents may be administered separately, as part of a multiple dosage regimen, from the protein kinase inhibitor-containing compound or composition. Alternatively, those agents may be part of a single dosage form, mixed together with the protein kinase inhibitor in a single composition.

As inhibitors of protein kinases, the compounds and compositions of this invention are also useful in biological samples. One aspect of the invention relates to inhibiting protein kinase activity in a biological sample, which method comprises contacting said biological sample with a compound of formula I or a composition comprising said compound. The term "biological sample", as used herein, means an in vitro or an ex vivo sample, including, without limitation, cell cultures or extracts thereof; biopsied material obtained from a mammal or extracts thereof; and blood, saliva, urine, feces, semen, tears, or other body fluids or extracts thereof.

Inhibition of protein kinase activity in a biological sample is useful for a variety of purposes that are known to one of skill in the art. Examples of such purposes include, but are not limited to, blood transfusion, organ-transplantation, and biological specimen storage.

Another aspect of this invention relates to the study of protein kinases in biological and pathological phenomena; the study of intracellular signal transduction pathways mediated by such protein kinases; and the comparative evaluation of new protein kinase inhibitors. Examples of such uses include, but are not limited to, biological assays such as enzyme assays and cell-based assays.

The activity of the compounds as protein kinase inhibitors may be assayed in vitro, in vivo or in a cell line. In vitro assays include assays that determine inhibition of either the kinase activity or ATPase activity of the activated kinase. Alternate in vitro assays quantitate the ability of the inhibitor to bind to the protein kinase and may be measured either by radiolabelling the inhibitor prior to binding, isolating the inhibitor/kinase complex and determining the amount of radiolabel bound, or by running a competition experiment where new inhibitors are incubated with the kinase bound to known radioligands. Detailed conditions for assaying a compound utilized in this invention as an inhibitor of PLK1, PLK2, PLK3, and PLK4 are set forth in the Examples below.

One aspect of this invention provides compounds that are useful for the treatment of diseases, disorders, and conditions characterized by excessive or abnormal cell proliferation. Such diseases include, a proliferative or hyperproliferative disease, and a neurodegenerative disease.

Examples of proliferative and hyperproliferative diseases include, without limitation, cancer.

The term "cancer" includes, but is not limited to, the following cancers: breast; ovary; cervix; prostate; testis, genitourinary tract; esophagus; larynx, glioblastoma; neuroblastoma; stomach; skin, keratoacanthoma; lung, epidermoid carcinoma, large cell carcinoma, small cell carcinoma, lung adenocarcinoma; bone; colon; colorectal; adenoma; pancreas, adenocarcinoma; thyroid, follicular carcinoma, undifferentiated carcinoma, papillary carcinoma; seminoma; melanoma; sarcoma; bladder carcinoma; liver carcinoma and biliary passages; kidney carcinoma; myeloid disorders; lymphoid disorders, Hodgkin's, hairy cells; buccal cavity and pharynx (oral), lip, tongue, mouth, pharynx; small intestine; colon-rectum, large intestine, rectum; brain and central nervous system; chronic myeloid leukemia (CML), and leukemia. The term "cancer" includes, but is not limited to, the following cancers: myeloma, lymphoma, or a cancer selected from gastric, renal, or and the following cancers: head and neck, oropharangeal, non-small cell lung cancer (NSCLC), endometrial, hepatocarcinoma, Non-Hodgkins lymphoma, and pulmonary.

For the avoidance of doubt, the term "cancer" also includes, but is not limited to, the following cancers: epidermoid Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal; rectum, Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma] hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, undifferentiated thyroid cancer, multiple endocrine neoplasia type 2A, multiple endocrine neoplasia type 2B, familial medullary thyroid cancer, pheochromocytoma, paraganglioma; and Adrenal glands: neuroblastoma. Thus, the term "cancerous cell" as provided herein, includes a cell afflicted by any one of the above-identified conditions.

In some embodiments, the compounds of this invention are useful for treating cancer, such as colorectal, thyroid, breast, and lung cancer; and myeloproliferative disorders, such as polycythemia vera, thrombocythemia, myeloid metaplasia with myelofibrosis, chronic myelogenous leukemia, chronic myelomonocytic leukemia, hypereosinophilic syndrome, juvenile myelomonocytic leukemia, and systemic mast cell disease.

In some embodiments, the compounds of this invention are useful for treating hematopoietic disorders, in particular, acute-myelogenous leukemia (AML), chronic-myelogenous leukemia (CML), acute-promyelocytic leukemia (APL), and acute lymphocytic leukemia (ALL).

Examples of neurodegenerative diseases include, without limitation, Alzheimer's disease.

Another aspect of this invention provides a method for the treatment or lessening the severity of a disease selected from a proliferative or hyperproliferative disease, or a neurodegenerative disease, comprising administering an effective amount of a compound, or a pharmaceutically acceptable composition comprising a compound, to a subject in need thereof.

In certain embodiments, an "effective amount" of the compound or pharmaceutically acceptable composition is that amount effective in order to treat said disease. The compounds and compositions, according to the method of the present invention, may be administered using any amount and any route of administration effective for treating or lessening the severity of said disease.

In some embodiments, said disease is a protein-kinase mediated condition. In some embodiments, said disease is a PLK-mediated disease.

The term "protein kinase-mediated condition", as used herein, means any disease or other deleterious condition in which a protein kinase plays a role. Such conditions include, without limitation, autoimmune diseases, inflammatory diseases, proliferative and hyperproliferative diseases, immunologically-mediated diseases, bone diseases, metabolic diseases, neurological and neurodegenerative diseases, cardiovascular diseases, hormone related-diseases, allergies, asthma, and Alzheimer's disease.

The term "PLK-mediated condition", as used herein means any disease or other deleterious condition in which PLK plays a role. Such conditions include, without limitation, a proliferative or hyperproliferative disease, or a neurodegenerative disease.

In another aspect of the present invention, pharmaceutically acceptable compositions are provided, wherein these compositions comprise any of the compounds as described herein, and optionally comprise a pharmaceutically acceptable carrier, adjuvant or vehicle.

In certain embodiments, these compositions optionally further comprise one or more additional therapeutic agents.

For example, chemotherapeutic agents or other anti-proliferative agents may be combined with the compounds of this invention to treat proliferative diseases and cancer. Examples of known chemotherapeutic agents include, but are not limited to, Gleevec™, adriamycin, dexamethasone, vincristine, cyclophosphamide, fluorouracil, topotecan, taxol, interferons, and platinum derivatives.

Other examples of agents the inhibitors of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and antiviral agents; agents for treating blood disorders such as corticosteroids, anti-leukemic agents, and growth factors; and agents for treating immunodeficiency disorders such as gamma globulin.

As described herein, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The protein kinase inhibitors or pharmaceutical salts thereof may be formulated into pharmaceutical compositions for administration to animals or humans. These pharmaceutical compositions, which comprise an amount of the protein inhibitor effective to treat or prevent a protein kinase-mediated condition and a pharmaceutically acceptable carrier, are another embodiment of the present invention. In some embodiments, said protein kinase-mediated condition is a PLK-mediated condition.

The exact amount of compound required for treatment will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect. In a preferred embodiment, compounds of this invention are administered orally.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

In addition to the compounds of this invention, pharmaceutically acceptable derivatives or prodrugs of the compounds of this invention may also be employed in compositions to treat or prevent the above-identified disorders.

The compounds of this invention can also exist as pharmaceutically acceptable derivatives.

A "pharmaceutically acceptable derivative" is an adduct or derivative which, upon administration to a patient in need, is capable of providing, directly or indirectly, a compound as otherwise described herein, or a metabolite or residue thereof. Examples of pharmaceutically acceptable derivatives include, but are not limited to, esters and salts of such esters.

A "pharmaceutically acceptable derivative or prodrug" means any pharmaceutically acceptable ester, salt of an ester or other derivative of a compound of this invention which, upon administration to a recipient, is capable of providing, either directly or indirectly, a compound of this invention or an inhibitorily active metabolite or residue thereof. Particularly favoured derivatives or prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds of this invention include, without limitation, esters, amino acid esters, phosphate esters, metal salts and sulfonate esters.

Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intraarticular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include, but are not limited to, cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of protein kinase inhibitor that may be combined with the carrier materials to produce a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of inhibitor will also depend upon the particular compound in the composition.

According to another embodiment, the invention provides methods for treating or preventing a protein kinase-mediated condition (in some embodiments, a PLK-mediated condition) comprising the step of administering to a patient one of the above-described pharmaceutical compositions. The term "patient", as used herein, means an animal, preferably a human.

In some embodiments, said method is used to treat or prevent a condition selected from a proliferative disorder, such as cancer, a neurodegenerative disorder, an autoimmune disorder, an inflammatory disorder, and an immunologically-mediated disorder. In some embodiments, said method is used to treat or prevent a condition selected from cancers such as cancers of the breast, colon, prostate, skin, pancreas, brain, genitourinary tract, lymphatic system, stomach, larynx and lung, including lung adenocarcinoma and small cell lung cancer; stroke, diabetes, myeloma, hepatomegaly, cardiomegaly, Alzheimer's disease, cystic fibrosis, and viral disease, or any specific disease described above.

The compounds of this invention may be prepared in general by methods known to those skilled in the art. Those compounds may be analyzed by known methods, including but not limited to LCMS (liquid chromatography mass spectrometry) and NMR (nuclear magnetic resonance). Compounds of this invention may be also tested according to these examples. It should be understood that the specific conditions shown below are only examples, and are not meant to limit the scope of the conditions that can be used for making, analyzing, or testing the compounds of this invention. Instead, this invention also includes conditions known to those skilled in that art for making, analyzing, and testing the compounds of this invention.

EXAMPLES

As used herein, the term "Rt(min)" refers to the HPLC retention time, in minutes, associated with the compound. Unless otherwise indicated, the HPLC method utilized to obtain the reported retention time is as follows:

Column: ACE C8 column, 4.6×150 mm

Gradient: 0-100% acetonitrile+methanol 50:50 (20 mM Tris phosphate)

Flow rate: 1.5 mL/minute

Detection: 225 nm.

Mass spec. samples were analyzed on a MicroMass Quattro Micro mass spectrometer operated in single MS mode with electrospray ionization. Samples were introduced into the mass spectrometer using chromatography.

$^1$H-NMR spectra were recorded at 400 MHz using a Bruker DPX 400 instrument. The following compounds of formula I were prepared and analyzed as follows.

Compounds I-1 to I-273 and I-278 to I-282 were prepared and characterized as follows in the Examples below.

Example 1

4-(9-Cyclopentyl-6,7,8,9-tetrahydro-5-methyl-6-oxo-5H-pyrimido[4,5-b][1,4]diazepin-2-ylamino)-3-methoxybenzoic acid (I-1)

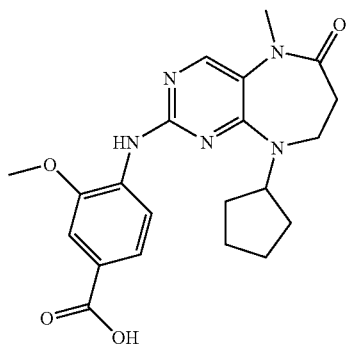

111

Method A: Methyl 3-(N-cyclopentyl-N-(2-chloro-5-nitropyrimidin-4-yl)amino)propionate

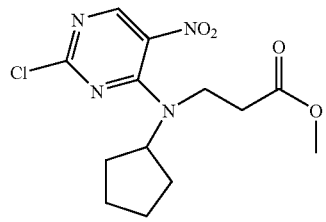

Methyl 3-(cyclopentylamino)propanoate (1.78 g, 10.4 m mole) and potassium carbonate (1.52 g, 11.0 m mol) in acetone (25 ml) was stirred at 0° C. during the addition of a solution of 2,4-dichloro-5-nitropyrimidine (2.04 g, 10.4 m mol) in acetone (15 ml). The mixture was stirred at ambient temperature overnight, concentrated and diluted with ethyl acetate/water. The mixture was extracted ×3 with ethyl acetate, dried over magnesium sulphate and concentrated to an amber oil which solidified on standing. Flash chromatography on silica gel eluting with 30% ethyl acetate/petrol gave methyl 3-(N-cyclopentyl-N-(2-methyl-5-nitropyrimidin-4-yl)amino)propionate as a pale yellow solid (2.24 g, 65%). NMR CDCl$_3$ 1.50-2.07 (8H, m), 2.70-2.82 (2H, m), 3.65-3.90 (6H, m), 8.72 (1H, s).

Method B: 2-Chloro-9-cyclopentyl-8,9-dihydro-5H-pyrimido[4,5-b][1,4]diazepin-6(7H)-one

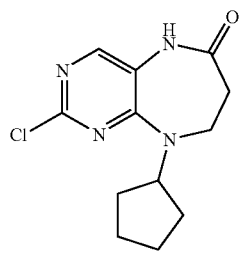

Methyl 3-(N-cyclopentyl-N-(2-chloro-5-nitropyrimidin-4-yl)amino)propionate (2.0 g, 6.1 mmol) in glacial acetic acid at 70° C. was treated in portions with iron powder (0.7 g, 12.4 mmol) over 6 hours. The mixture was concentrated and triturated with dichloromethane and filtered. The filtrate was absorbed onto silica gel and soxhlet extracted over 7 hours with ethyl acetate. The extract was concentrated to a black oil and triturated with methanol to give pale brown crystals of 2-chloro-9-cyclopentyl-8,9-dihydro-5H-pyrimido[4.5-b][1,4]diazepin-6(7H)-one (499 mg, 31%). NMR 1.46-1.58 (4H, m), 1.60-1.72 (2H, m), 1.75-1.85 (2H, m), 2.64 H, d), 3.55 (2H, d), 4.92-5.03 (1H, m), 7.83 (1H, s), 9.72 (1H, s).

112

Method C: 2-Chloro-9-cyclopentyl-8,9-dihydro-5-methyl-5H-pyrimido[4,5-b][1,4]diazepin-6(7H)-one

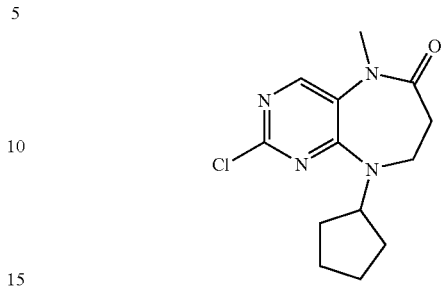

2-Chloro-9-cyclopentyl-8,9-dihydro-5H-pyrimido[4.5-b][1,4]diazepin-6(7H)-one (474.7 mg, 1.78 mmol) and methyl iodide (0.122 ml, 1.96 mmol) in DMA (4.5 ml) stirred at −10° C. and treated with sodium hydride 60% oil dispersion (75 mg, 1.87 mmol). The mixture was warmed to 0° C. for 20 min and then to 20° C. for 40 min. A further 0.12 ml methyl iodide and 8 mg sodium hydride were added and the mixture stirred at ambient overnight. Ice was added and the mixture concentrated under reduced pressure. The residual oil was treated dropwise with water (6 ml), filtered and the buff solid dried under high vacuum at 60° C. (486 mg, 98%). NMR DMSO D$^6$ 1.45-1.72 (6H, m), 1.76-1.91 (2H, m), 2.61 (2H, d), 3.18 (3H, s), 3.64 (2H, d), 4.65-4.74 (1H, m), 8.15 (1H, s).

Method D: 4-(9-Cyclopentyl-6,7,8,9-tetrahydro-5-methyl-6-oxo-5H-pyrimido[4,5-b][1,4]diazepin-2-ylamino)-3-methoxybenzoic acid (I-1)

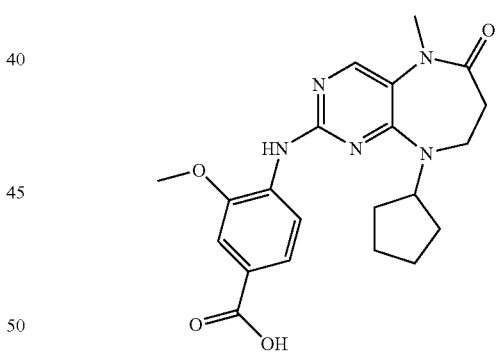

2-Chloro-9-cyclopentyl-8,9-dihydro-5-methyl-5H-pyrimido[4,5-b][1,4]diazepin-6(7H)-one (150 mg, 0.536 mmol) in ethanol (2.25 ml) and water (9 ml) was treated with conc. HCl (0.088 ml) and 4-amino-3-methoxy benzoic acid (134 mg, 0.804 mmol). The mixture was stirred at 90° C. 24 hours, concentrated and the residue triturated with methanol/ether, filtered and the solid washed with ethanol then ether to give 4-(9-cyclopentyl-6,7,8,9-tetrahydro-5-methyl-6-oxo-5H-pyrimido[4,5-b][1,4]diazepin-2-ylamino)-3-methoxybenzoic acid as a buff powder (185.5 mg, 84%). NMR DMSO D$^6$ 1.51-1.79 (6H, m), 1.82-1.93 (2H, m), 2.70-2.75 (2H m), 3.18 (3H, s), 3.72-3.78 (2H, m), 3.98 (3H, s), 4.81-4.93 (1H, m), 7.57-7.64 (2H, m), 8.15-8.22 (2H, m), 9.46 (1H, br s); HPLC rt(min): 6.57.

Example 2

Method E: 4-(9-cyclopentyl-6,7,8,9-tetrahydro-5-methyl-6-oxo-5H-pyrimido[4,5-b][1,4]diazepin-2-ylamino)-3-methoxy-N-(1-methylpiperidin-4-yl)benzamide (I-2)

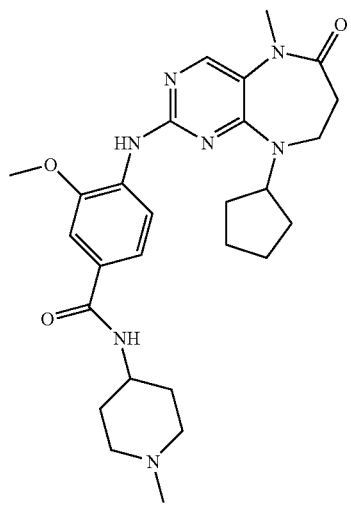

Cyclopentyl-6,7,8,9-tetrahydro-5-methyl-6-oxo-5H-pyrimido[4,5-b][1,4]diazepin-2-ylamino)-3-methoxybenzoic acid (150 mg, 0.365 mmol) in dichloromethane (5 ml) was treated with diisopropylethylamine (0.127 ml, 0.73 mmol) and TBTU (127 mg, 0.394 mmol). The mixture was stirred for 25 min then treated with 4-amino-1-methylpiperidine (52 mg, 0.453 mmol) and stirred overnight. The mixture was diluted with ethyl acetate, washed with aqueous sodium hydrogen carbonate, x2 with 0.02 M sodium hydroxide solution, brine, dried over magnesium sulphate and concentrated. Trituration with ethyl acetate/ether gave 4-(9-cyclopentyl-6,7,8,9-tetrahydro-5-methyl-6-oxo-5H-pyrimido[4,5-b][1,4]diazepin-2-ylamino)-3-methoxy-N-(1-methylpiperidin-4-yl)benzamide as a colourless solid (132 mg, 71%). 1H NMR DMSO $D^6$ 1.50-2.08 (14H, m), 2.21 (3H, s), 2.55-2.65 (2H, m), 2.77-2.87 (2H, m), 3.21 (3H, s), 3.60-3.70 (2H, m), 3.70-3.82 (1H, m), 3.98 (3H, s), 4.80-4.90 (1H, m), 7.42-7.52 (2H, m), 7.75 (1H, s), 8.10-8.18 (2H, m), 8.40 (1H, d); HPLC rt(min): 9.60.

Example 3

4-(9-Cyclopentyl-6,7,8,9-tetrahydro-5-methyl-6-oxo-5H-pyrimido[4,5-b][1,4]diazepin-2-ylamino)-benzoic acid (I-3)

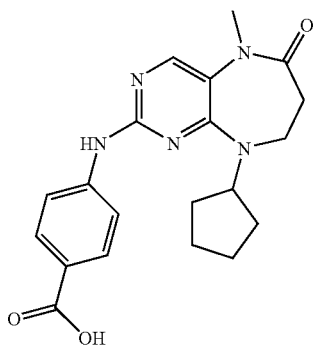

Prepared from 2-chloro-9-cyclopentyl-8,9-dihydro-5-methyl-5H-pyrimido[4,5-b][1,4]diazepin-6(7H)-one and 4-aminobenzoic acid using method D. NMR DMSO $D^6$ 1.59-1.80 (6H, m), 1.90-1.98 (2H, m), 2.70-2.75 (2H m), 3.18 (3H, s), 3.71-3.75 (2H, m), 4.91 (1H, m), 7.77 (2H, d), 7.94 (2H, d), 8.17 (1H, s), 10.65 (1H, br s). HPLC rt(min): 6.39.

Example 4

4-(9-cyclopentyl-6,7,8,9-tetrahydro-5-methyl-6-oxo-5H-pyrimido[4,5-b][1,4]diazepin-2-ylamino)-N-(1-methylpiperidin-4-yl)benzamide (I-4)

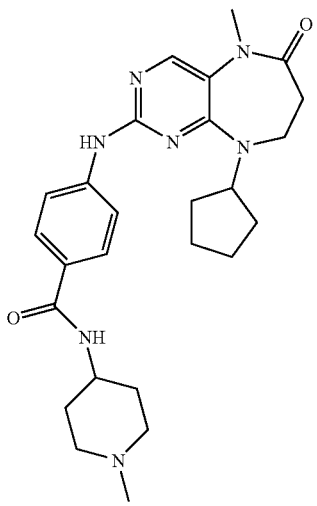

Prepared from compound I-3 and 4-amino-1-methylpiperidine using method E. $^1$H NMR DMSO $D^6$ 1.62-2.05 (14H, m), 2.23 (3H, s), 2.60-2.68 (2H, m), 2.77-2.86 (2H, m), 3.23 (3H, s), 3.65-3.70 (2H, m), 3.78 (1H, m), 4.91 (1H, m), 7.76-7.85 (4H, m), 8.00 (1H, d), 8.11 (1H, s), 9.50 (1H, s); HPLC rt(min): 7.50.

Example 5

4-(9-cyclopentyl-6,7,8,9-tetrahydro-5-methyl-6-oxo-5H-pyrimido[4,5-b][1,4]diazepin-2-ylamino)-3-methoxy-N-[1-(tert-butoxycarbonyl)piperidin-4-yl]benzamide (I-5)

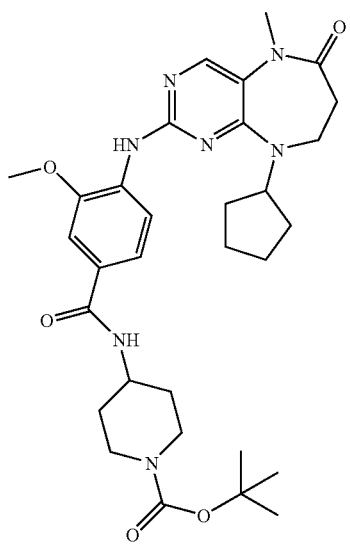

Prepared from compound I-1 and 4-amino-1-(tert-butoxycarbonyl)piperidine using method E. NMR DMSO D⁶ 1.41 (9H, s), 1.37-1.98 (14H, m), 2.57-2.63 (2H, m), 2.80 (2H, m), 3.17 (3H, s), 3.61-3.69 (2H, m), 3.91 (3H, s), 3.97 (1H, m), 4.83 (1H, m), 7.47-7.52 (2H, m), 8.07-8.15 (3H, m), 8.27 (1H, m); HPLC rt(min): 10.07.

Example 6

Method F: 4-(9-cyclopentyl-6,7,8,9-tetrahydro-5-methyl-6-oxo-5H-pyrimido[4,5-b][1,4]diazepin-2-ylamino)-3-methoxy-N-(piperidin-4-yl)benzamide (I-6)

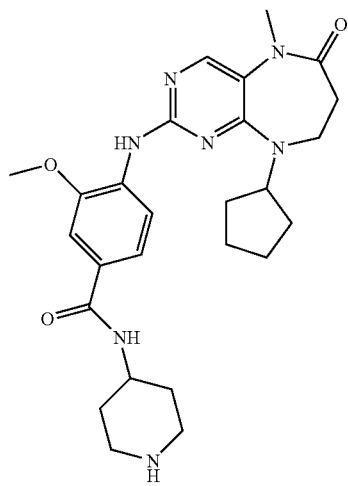

To a solution of 4-(9-cyclopentyl-6,7,8,9-tetrahydro-5-methyl-6-oxo-5H-pyrimido[4,5-b][1,4]diazepin-2-ylamino)-3-methoxy-N-[1-(tert-butoxycarbonyl)piperidin-4-yl]benzamide (I-5) (72 mg, 0.12 mmol) in dichloromethane (3 ml) was added trifluoroacetic acid at 0° C. The reaction mixture was stirred for 30 minutes at 0° C., 60 minutes at room temperature and then solvents were evaporated. The residue was triturated in diethyl ether and the solid filtered to give the TFA salt of the title compound as an off-white solid (70 mg, 95%). 1H NMR DMSO D⁶ 1.55-2.04 (14H, m), 2.62-2.70 (2H, m), 2.98-3.08 (2H, m), 3.19 (3H, s), 3.40-3.48 (2H, m), 3.65-3.71 (2H, m), 3.97 (3H, s), 4.09 (1H, m), 4.89 (1H, m), 7.49-7.56 (2H, m), 8.10 (1H, s), 8.19 (1H, d), 8.30-8.40 (2H, d), 8.60-8.69 (2H, m); HPLC rt(min): 7.53.

Example 7

4-(9-cyclopentyl-6,7,8,9-tetrahydro-5-methyl-6-oxo-5H-pyrimido[4,5-b][1,4]diazepin-2-ylamino)-3-methoxyphenyl-(4-tert-butoxycarbonypiperazin-1-yl)methanone (I-7)

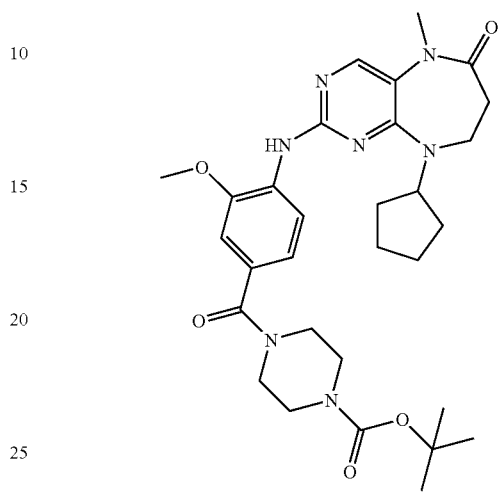

Prepared from compound I-1 and N-tert-butoxycarbonylpiperazine using method E. NMR DMSO D⁶ 1.41 (9H, s), 1.55-1.95 (10H, m), 2.57-2.62 (2H, m), 3.18 (3H, s), 3.27-3.63 (8H, m), 3.90 (3H, s), 4.80 (1H, m), 6.96 (1H, d), 7.05 (1H, s), 7.72 (1H, s), 8.07 (1H, s), 8.30 (1H, d); HPLC rt(min): 9.98.

Example 8

4-(9-cyclopentyl-6,7,8,9-tetrahydro-5-methyl-6-oxo-5H-pyrimido[4,5-b][1,4]diazepin-2-ylamino)-3-methoxyphenyl(piperazin-1-yl)methanone (I-8)

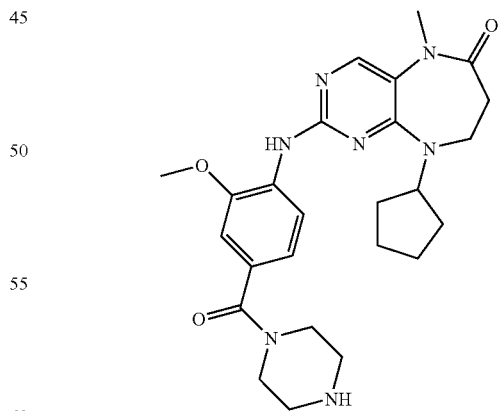

Prepared from compound I-7 using method F. NMR DMSO D⁶ 1.50-1.91 (8H, m), 2.65-2.73 (2H, m), 3.15-3.22 (7H, m), 7.63-7.70 (6H, m), 3.94 (3H, s), 4.80 (1H, m), 7.12 (1H, d), 7.20 (1H, s), 8.04 (1H, d), 8.10 (1H, s), 9.02-9.11 (2H, m). HPLC rt(min): 7.81.

Example 9

4-(9-cyclopentyl-6,7,8,9-tetrahydro-5-methyl-6-oxo-5H-pyrimido[4,5-b][1,4]diazepin-2-ylamino)-3-methoxy-N-methylbenzamide (I-9)

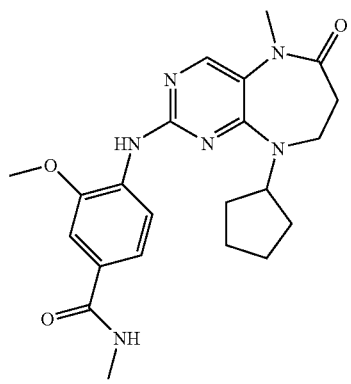

Prepared using the appropriate reagents according to method E. NMR DMSO D⁶ 1.62-1.73 (6H, m), 1.92-1.97 (2H, m), 2.58-2.60 (2H, m), 2.78-2.80 (3H, m), 3.17 (3H, s), 3.62-3.64 (2H, m), 3.94 (3H, s), 4.82 (1H, m), 7.46-7.50 (2H, m), 7.73 (1H, s), 8.08 (1H, s), 8.35 (1H, m), 8.38 (1H, m); HPLC rt(min): 8.45; MS (ES⁺) 425, (ES⁻) 423.

Example 10

4-(9-cyclopentyl-6,7,8,9-tetrahydro-5,7-dimethyl-6-oxo-5H-pyrimido[4,5-b][1,4]diazepin-2-ylamino)-3-methoxybenzoic acid (I-10)

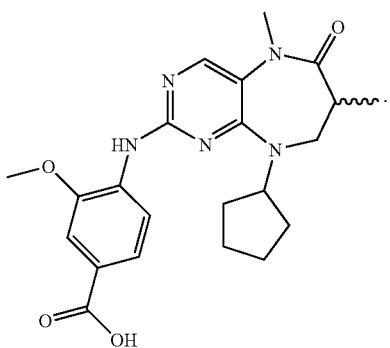

Prepared using the appropriate reagents according to method D. NMR DMSO D⁶ 1.08 (3H, d), 1.48-1.86 (7H, m), 1.98-2.10 (1H, m), 2.90-3.00 (1H, m), 3.20 (3H, s), 3.37 (1H, d), 3.56 (1H, t), 3.95 (3H, s), 4.72-4.85 (1H, m), 7.56 (1H, s), 7.60 (1H, d), 8.13 (1H, s), 8.31 (1H, d), 8.66 (1H, br s); HPLC rt(min): 7.47; MS (ES⁺) 426, (ES⁻) 424.

Example 11

4-(9-cyclopentyl-6,7,8,9-tetrahydro-5-methyl-6-oxo-5H-pyrimido[4,5-b][1,4]diazepin-2-ylamino)-3-methoxy-N-(2-methoxyethyl)benzamide (I-11)

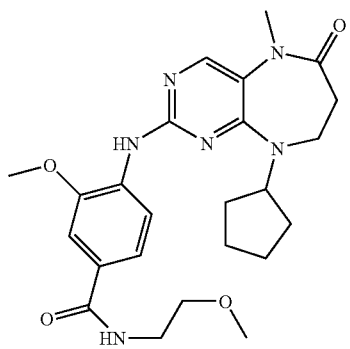

Prepared using the appropriate reagents according to method E. NMR DMSO D⁶ 1.62-1.73 (6H, m), 1.90-2.0 (2H, m), 2.54-2.60 (2H, m), 3.17 (3H, s), 3.25 (3H, s), 3.42-3.46 (4H, m), 3.62-3.64 (2H, m), 3.95 (3H, s), 4.82 (1H, m), 7.49-7.52 (2H, m), 7.74 (1H, s), 8.09 (1H, s), 8.41 (2H, m); HPLC rt(min): 8.65; MS (ES⁺) 469, (ES⁻) 467.

Example 12

4-(9-cyclopentyl-6,7,8,9-tetrahydro-5,7-dimethyl-6-oxo-5H-pyrimido[4,5-b][1,4]diazepin-2-ylamino)-3-methoxy-N-(1-methylpiperidin-4-yl)benzamide (I-12)

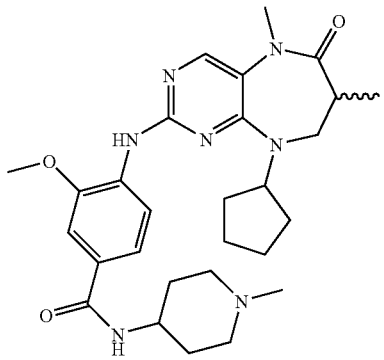

Prepared using the appropriate reagents according to method E. NMR DMSO D⁶ 1.03 (3H, d), 1.50-2.15 (14H, m), 2.18 (3H, s), 2.76-2.90 (3H, m), 3.20 (3H, s), 3.28-3.48 (2H, m), 3.70-3.80 (1H, m), 3.98 (3H, s), 7.49-7.52 (2H, m), 7.74 (1H, s), 8.05-8.12 (2H, m), 8.40 (1H, d); HPLC rt(min): 8.95; MS (ES⁺) 522, (ES⁻) 520.

Example 13

Method G: Ethyl 4-(9-cyclopentyl-6,7,8,9-tetrahydro-5-methyl-6-oxo-5H-pyrimido[4,5-b][1,4]diazepin-2-ylamino)piperidin-1-carboxylate (I-13)

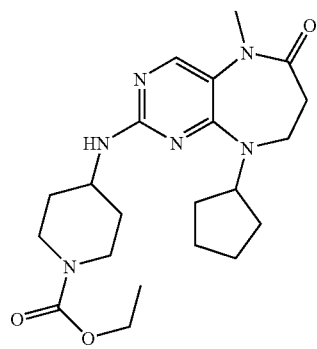

2-Chloro-9-cyclopentyl-8,9-dihydro-5-methyl-5H-pyrimido[4,5-b][1,4]diazepin-6(7H)-one (100 mg, 0.357 mmol) and ethyl 4-aminopiperidine-1-carboxylate (129 μl, 0.714 mmol) in isopropylalcohol (2 ml) were heated at 90° C. for 24 hours. Diisopropylethylamine (125 μl, 0.714 mmol) was added and the reaction mixture was heated at 105° C. for another 24 hours. The crude mixture was concentrated in vacuo and purified by reverse phase preparative HPLC [Waters Sunfire C18, 10 uM, 100 Å column, gradient 10%-95% B (solvent A: 0.05% TFA in water; solvent B: CH3CN) over 16 minutes at 25 mL/min] to afford the title compound (18 mg) as an off-white powder. NMR DMSO $D^6$ 1.20 (3H, t), 1.28-1.91 (14H, m), 2.80-2.96 (2H, m), 3.11 (3H, s), 3.50-3.58 (2H, m), 3.70-3.85 (1H, m), 3.90-3.98 (2H, m), 4.03 (2H, q), 4.60-4.70 (1H, m), 6.65 (1H, br s), 7.88 (1H, s); HPLC rt(min): 8.09; MS (ES$^+$) 417, (ES$^-$) 415.

Example 14

4-(6,7,8,9-tetrahydro-5,9-dimethyl-6-oxo-5H-pyrimido[4,5-b][1,4]diazepin-2-ylamino)-3-methoxy-N-(1-methylpiperidin-4-yl)benzamide (I-14)

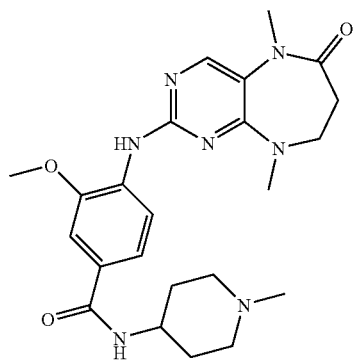

Prepared using the appropriate reagents according to method D. NMR DMSO $D^6$ 1.65-1.67 (2H, m), 1.83-1.85 (2H, m), 2.33-2.36 (3H, m), 2.50-2.53 (2H, m), 2.60-2.63 (2H, m), 3.07 (3H, s), 3.18 (3H, s), 3.29 (3H, s), 3.69-3.71 (2H, m), 3.94 (3H, s), 7.48-7.53 (2H, m), 7.75 (1H, s), 8.11 (2H, m), 8.46 (1H, m); HPLC rt(min): 6.75; MS (ES$^+$) 454, (ES$^-$) 452.

Example 15

4-((3aR,10aS)-4-cyclopentyl-9-methyl-10-oxo-1,2,3,3a,4,9,10,10a-octahydro-4,5,7,9-tetraaza-benzo[f]azulen-6-ylamino)-3-methoxy-N-methylbenzamide (I-15)

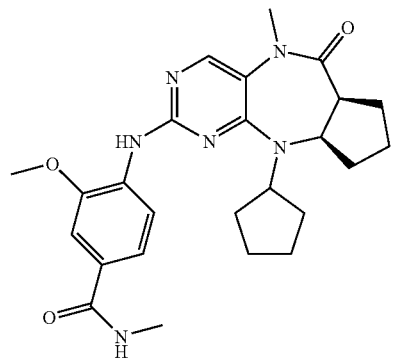

Prepared using the appropriate reagents according to method D. NMR DMSO $D^6$ 1.40-1.60 (9H, m), 1.66-1.69 (2H, m), 1.79 (1H, m), 1.86-1.87 (2H, m), 2.04 (1H, m), 2.15 (1H, m), 2.80 (3H, d), 3.20 (3H, s), 3.92 (3H, s), 4.14 (1H, m), 7.55 (1H, d), 7.57 (1H, s), 7.95 (1H, d), 8.22 (1H, s), 8.44 (1H, d), 8.95 (1H, br s); HPLC rt(min): 9.45; MS (ES$^+$) 465, (ES$^-$) 463.

Example 16

4-(9-cyclopentyl-6,7,8,9-tetrahydro-5,7,7-trimethyl-6-oxo-5H-pyrimido[4,5-b][1,4]diazepin-2-ylamino)-3-methoxy-N-methylbenzamide (I-16)

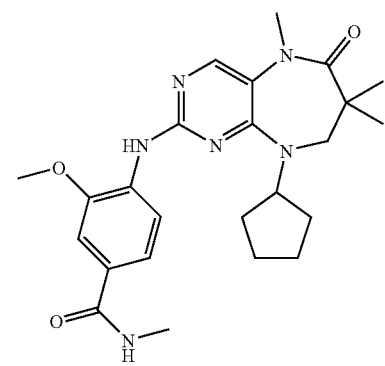

Prepared using the appropriate reagents according to method D. NMR DMSO $D^6$ 1.10 (6H, s), 1.62-1.65 (4H, m), 1.74 (2H, m), 1.88 (2H, m), 2.79 (3H, d), 3.19 (3H, s), 3.36-3.40 (2H, m), 3.94 (3H, s), 5.18 (1H, m), 7.45-7.50 (2H, m), 7.68 (1H, s), 7.99 (1H, s), 8.30 (1H, m), 8.37 (1H, d); HPLC rt(min): 9.23; MS (ES$^+$) 453, (ES$^-$) 451.

Example 17

4-((S)-9-cyclopentyl-6,7,8,9-tetrahydro-5,7-dimethyl-6-oxo-5H-pyrimido[4,5-b][1,4]diazepin-2-ylamino)-3-methoxy-N-methylbenzamide (I-17)

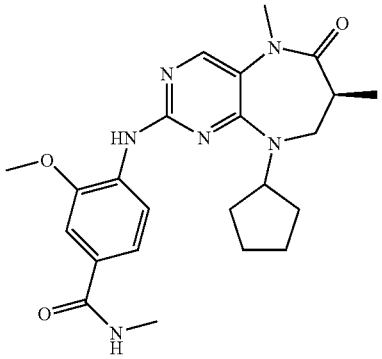

Prepared using the appropriate reagents according to method D. NMR DMSO D$^6$ 1.03-1.07 (3H, m), 1.55-1.61 (4H, m), 1.70-1.78 (4H, m), 1.99 (1H, m), 2.80 (3H, m), 3.18 (3H, s), 3.56-3.61 (2H, m), 3.94 (3H, s), 4.80 (1H, m), 7.50-7.52 (1H, m), 7.58 (1H, m), 8.07-8.10 (1H, m), 8.13 (1H, br s), 8.47 (1H, m), 9.25 (1H, br s); HPLC rt(min): 8.92; MS (ES$^+$) 439, (ES$^-$) 437.

Example 18

4-((R)-9-cyclopentyl-6,7,8,9-tetrahydro-5,7-dimethyl-6-oxo-5H-pyrimido[4,5-b][1,4]diazepin-2-ylamino)-3-methoxy-N-methylbenzamide (I-18)

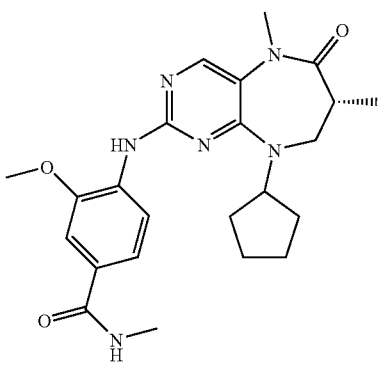

Prepared using the appropriate reagents according to method D. NMR DMSO D$^6$ 1.03-1.07 (3H, m), 1.56-1.60 (4H, m), 1.72-1.78 (4H, m), 1.98 (1H, m), 2.80 (3H, m), 3.19 (3H, m), 3.57-3.63 (2H, m), 3.94 (3H, s), 4.81 (1H, m), 7.50-7.53 (1H, m), 7.60 (1H, m), 8.06 (1H, d), 8.15 (1H, m), 8.50 (1H, d), 9.49 (1H, br s); HPLC rt(min): 8.92; MS (ES$^+$) 439, (ES$^-$) 437.

Example 19

4-(6,7,8,9-tetrahydro-5,7,7-trimethyl-6-oxo-9-((R)-pyrrolidin-3-yl)-5H-pyrimido[4,5-b][1,4]diazepin-2-ylamino)-3-methoxy-N-methylbenzamide (I-19)

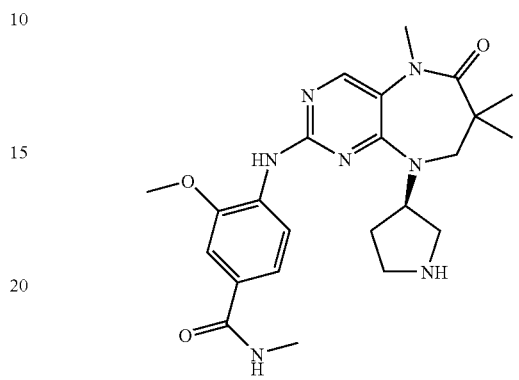

Prepared using the appropriate reagents according to method D. NMR DMSO D$^6$ 1.118 (3H, s), 1.124 (3H, s), 2.04 (1H m), 2.27 (1H, m), 2.80 (3H, d), 3.11-3.28 (5H, m), 3.40-3.56 (4H, m), 3.93 (3H, s), 5.42 (1H, quint.), 7.53-7.57 (2H, m), 8.10 (1H, s), 8.17 (1H, d), 8.39 (1H, q), 8.55 (1H, br s), 9.05 (1H, br s), 9.12 (1H, br s); HPLC rt(min): 6.14; MS (ES$^+$) 454, (ES$^-$) 452.

Example 20

4-(6,7,8,9-tetrahydro-5,7,7-trimethyl-9-((R)-1-methylpyrrolidin-3-yl)-6-oxo-5H-pyrimido[4,5-b][1,4]diazepin-2-ylamino)-3-methoxy-N-methylbenzamide (I-20)

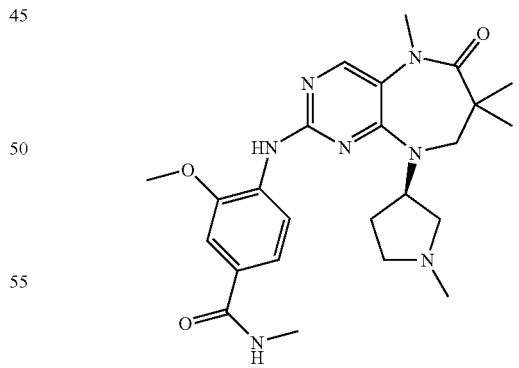

Prepared using the appropriate reagents according to method D. NMR DMSO D$^6$ 1.11-1.15 (6H, m), 2.00-2.41 (2H m), 2.80 (3H, d), 2.85-2.95 (3H, m), 3.10-3.40 (5H, m), 3.51-3.80 (4H, m), 3.93 (3H, s), 5.36-5.60 (1H, m), 7.56-7.59 (2H, m), 8.04-8.13 (2H, m), 8.46 (1H, m), 8.93-9.13 (1H, br s), 10.38-10.77 (1H, br s); HPLC rt(min): 7.25; MS (ES$^+$) 468, (ES$^-$) 466.

Example 21

4-((S)-9-cyclopentyl-6,7,8,9-tetrahydro-5,7-dimethyl-6-oxo-5H-pyrimido[4,5-b][1,4]diazepin-2-ylamino)-3-methoxy-N-(1-methylpiperidin-4-yl)benzamide (I-21)

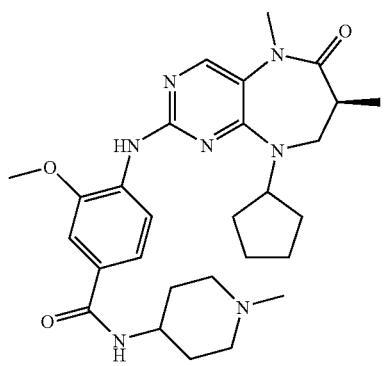

Prepared using the appropriate reagents according to method E. NMR DMSO $D^6$ 1.06-1.07 (3H, d), 1.56-2.03 (14H, m), 2.70 (3H, d), 3.09 (3H, m), 3.19 (3H, s), 3.58-3.64 (2H, m), 3.95 (3H, s), 4.04 (1H, m), 4.84 (1H, m), 7.56-7.64 (2H, m), 8.08 (1H, d), 8.22 (1H, s), 8.59 (1H, d), 9.61 (1H, br s), 10.77 (1H, br s); HPLC rt(min): 9.00; MS (ES$^+$) 522, (ES$^-$) 520.

Example 22

4-((R)-9-cyclopentyl-6,7,8,9-tetrahydro-5,7-dimethyl-6-oxo-5H-pyrimido[4,5-b][1,4]diazepin-2-ylamino)-3-methoxy-N-(1-methylpiperidin-4-yl)benzamide (I-22)

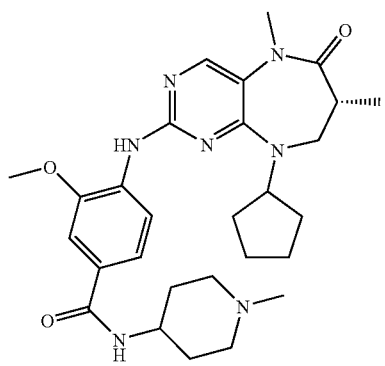

Prepared using the appropriate reagents according to method E. NMR DMSO $D^6$ 1.06-1.07 (3H, d), 1.56-1.98 (14H, m), 2.71 (3H, d), 3.02-3.08 (3H, m), 3.19 (3H, s), 3.58-3.64 (2H, m), 3.95 (3H, s), 4.05 (1H, m), 4.83 (1H, m), 7.57-7.64 (2H, m), 8.09 (1H, m), 8.23 (1H, s), 8.60 (1H, d), 9.64 (1H, br s), 10.81 (1H, br s); HPLC rt(min): 9.11; MS (ES$^+$) 522, (ES$^-$) 520.

Example 23

4-(9-cyclopentyl-6,7,8,9-tetrahydro-5,7,7-trimethyl-6-oxo-5H-pyrimido[4,5-b][1,4]diazepin-2-ylamino)-3-methoxy-N-(1-methylpiperidin-4-yl)benzamide (I-23)

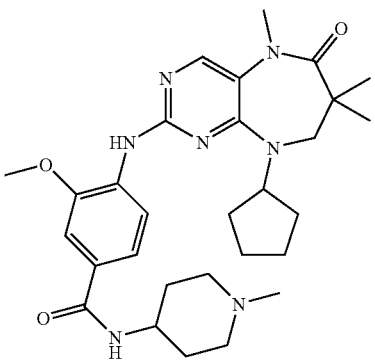

Prepared using the appropriate reagents according to method E. NMR DMSO $D^6$ 1.20 (6H, s), 1.55-2.08 (12H, m), 2.70 (3H, s), 3.00-3.14 (2H, m), 3.52 (3H, s), 3.50-3.85 (4H, m), 3.96 (3H, s), 3.98-4.08 (1H, m), 5.07-5.18 (1H, m), 7.56 (1H, d), 7.65 (1H, s), 8.07 (1H, d), 8.10 (1H, s), 8.57 (1H, d), 9.50 (1H, br s), 10.60 (1H, br s); HPLC rt(min): 9.55; MS (ES$^+$) 536, (ES$^-$) 534.

Example 24

4-(9-cyclopentyl-6,7,8,9-tetrahydro-5,7,7-trimethyl-6-oxo-5H-pyrimido[4,5-b][1,4]diazepin-2-ylamino)-3-methoxy-N-(pyridin-4-yl)benzamide (I-24)

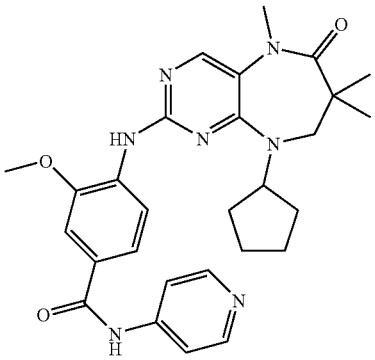

Prepared using the appropriate reagents according to method E. NMR DMSO $D^6$ 1.20 (6H, s), 1.55-1.90 (8H, m), 3.19 (3H, s), 3.50-3.60 (2H, m), 4.04 (3H, s), 5.13-5.22 (1H, m), 7.85 (1H, d), 7.90 (1H, s), 8.11 (1H, s), 8.31 (1H, d), 8.45 (2H, d), 8.77 (2H, d), 9.18 (1H, br s), 11.78 (1H, s); HPLC rt(min): 9.94; MS (ES$^+$) 516, (ES$^-$) 514.

Example 25

Method H: 4-(9-cyclopentyl-6,7,8,9-tetrahydro-5,7,7-trimethyl-6-oxo-5H-pyrimido[4,5-b][1,4]diazepin-2-ylamino)-3-methoxy-N-(1-methylazetidin-3-yl)benzamide (I-25)

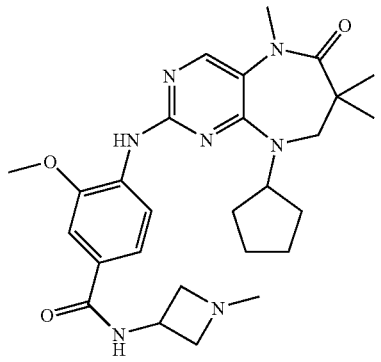

4-(9-cyclopentyl-6,7,8,9-tetrahydro-5,7,7-trimethyl-6-oxo-5H-pyrimido[4,5-b][1,4]diazepin-2-ylamino)-N-(azetidin-3-yl)-3-methoxybenzamide (69 mg, 0.14 mmol) was dissolved in methanol (1.5 ml). 37% aqueous formaldehyde (66 µl, 0.84 mmol) and sodium cyanoborohydride (26 mg, 0.42 mmol) were successively added. The reaction mixture was stirred at room temperature for 2 hours. The crude mixture was diluted with 2N HCl then, basified with a saturated solution of NaHCO$_3$. The mixture was extracted twice with ethyl acetate. The combined organic phases were dried (MgSO$_4$ and concentrated in vacuo.

The title compound (33 mg) was obtained as a white solid after crystallization from ethyl acetate. NMR DMSO D$^6$ 1.10 (6H, s), 1.55-1.69 (4H, m), 1.69-1.80 (2H, m), 1.82-1.95 (2H, m), 2.28 (3H, s), 3.01 (2H, t), 3.38 (2H, s), 3.57 (2H, t), 3.95 (3H, s), 4.39-4.50 (1H, m), 5.12-5.25 (1H, m), 7.43-7.52 (2H, m), 7.71 (1H, s), 8.00 (1H, s), 8.38 (1H, d), 8.63 (1H, d); HPLC rt(min): 9.60; MS (ES$^+$) 508, (ES$^-$) 506.

Example 26

4-(9-cyclopentyl-6,7,8,9-tetrahydro-5,7,7-trimethyl-6-oxo-5H-pyrimido[4,5-b][1,4]diazepin-2-ylamino)-3-methoxy-N—((R)-1-methylpyrrolidin-3-yl)benzamide (I-26)

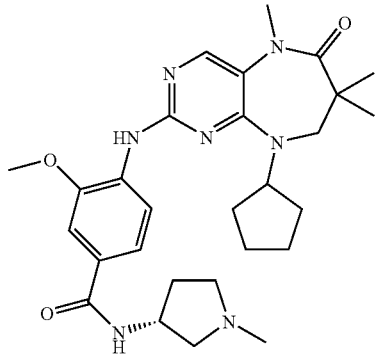

Prepared using the appropriate reagents according to method H. NMR DMSO D$^6$ 1.01 (6H, s), 1.52-1.94 (9H, m), 2.12-2.20 (1H, m), 2.27 (3H, s), 2.35-2.42 (1H, m), 2.8-2.68 (2H, m), 3.19 (3H, s), 3.38 (2H, s), 3.95 (3H, s), 4.36-4.47 5.13-5.26 (1H, m), 7.46-7.56 (2H, m), 7.69 (1H, s), 7.99 (1H, s), 8.33-8.41 (2H, m); HPLC rt(min): 9.71; MS (ES$^+$) 522, (ES$^-$) 520.

Example 27

4-(9-cyclopentyl-6,7,8,9-tetrahydro-5,7,7-trimethyl-6-oxo-5H-pyrimido[4,5-b][1,4]diazepin-2-ylamino)-3-methoxy-N-(2-(1-methyl-1H-imidazo-5-yl)ethyl)benzamide (I-27)

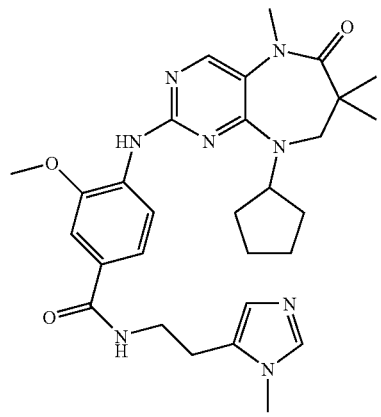

Prepared using the appropriate reagents according to method E. NMR DMSO D$^6$ 1.01 (6H, s), 1.55-1.94 (8H, m), 2.77-2.85 (2H, m), 3.20 (3H, s), 3.38 (2H, s), 3.45-3.50 (2H, m), 3.58 (3H, s), 5.15-5.25 (1H, m), 6.73 (1H, s), 7.45-7.55 (2H, m), 7.70 (1H, s), 7.99 (1H, s), 8.49 (1H, d), 8.55-8.59 (1H, m); HPLC rt(min): 9.10; MS (ES$^+$) 547, (ES$^-$) 545.

Example 28

4-(9-cyclopentyl-6,7,8,9-tetrahydro-5,7,7-trimethyl-6-oxo-5H-pyrimido[4,5-b][1,4]diazepin-2-ylamino)-3-methoxy-N-(3-(4-methylpiperazin-1-yl)propyl)benzamide (I-28)

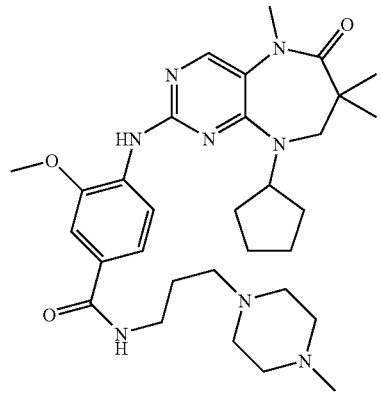

Prepared using the appropriate reagents according to method E. NMR DMSO D$^6$ 1.10 (6H, s), 1.53-1.95 (12H, m), 2.15 (3H, s), 2.20-2.45 (8H, m), 3.19 (3H, s), 3.22-3.30 (2H, m), 3.38 (2H, s), 3.94 (3H, s), 5.10-5.21 (1H, m), 7.48 (1H, d), 7.49 (1H, s), 7.69 (1H, s), 7.99 (1H, s), 8.30-8.40 (2H, m); HPLC rt(min): 9.37; MS (ES$^+$) 579, (ES$^-$) 577.

Example 29

4-(9-cyclopentyl-6,7,8,9-tetrahydro-7,7-dimethyl-6-oxo-5H-pyrimido[4,5-b][1,4]diazepin-2-ylamino)-3-methoxy-N-methylbenzamide (I-29)

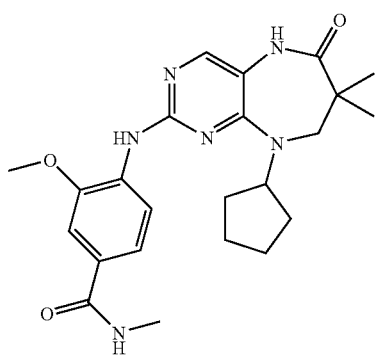

Prepared using the appropriate reagents according to method D. NMR DMSO D$^6$ 1.15 (6H, s), 1.59-1.60 (4H, m), 1.75-1.82 (4H, m), 2.80 (3H, d), 3.45 (2H, m), 3.93 (3H, s), 5.21 (1H, m), 7.48 (1H, m), 7.56 (1H, s), 7.79 (1H, s), 8.05 (1H, m), 8.44 (1H, m), 9.00 (1H, v br s), 9.76 (1H, s); HPLC rt(min): 8.97; MS (ES$^+$) 439, (ES$^-$) 437.

Example 30

4-(9-cyclopropyl-6,7,8,9-tetrahydro-5,7,7-trimethyl-6-oxo-5H-pyrimido[4,5-b][1,4]diazepin-2-ylamino)-3-methoxy-N-methylbenzamide (I-30)

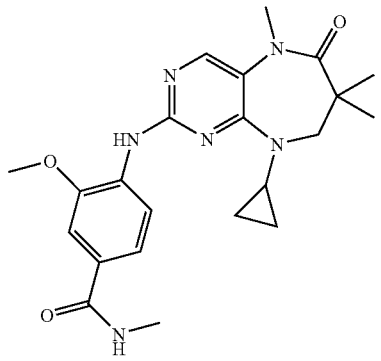

Prepared using the appropriate reagents according to method D. NMR DMSO D$^6$ 0.83 (2H, m), 0.96 (2H, q), 1.16 (6H, s), 2.79 (3H, d), 3.09 (1H, m), 3.17 (3H, s), 3.71 (2H, s), 3.96 (3H, s), 7.52-7.56 (2H, m), 8.12 (1H, s), 8.38 (1H, q), 8.53 (1H, d), 9.12 (1H, br s); HPLC rt(min): 8.26; MS (ES$^+$) 425, (ES$^-$) 423.

Example 31

4-(9-cyclopentyl-6,7,8,9-tetrahydro-5,7,7-trimethyl-6-oxo-5H-pyrimido[4,5-b][1,4]diazepin-2-ylamino)-3-methoxy-N-(2-(1-methyl-1H-imidazo-4-yl)ethyl)benzamide (I-31)

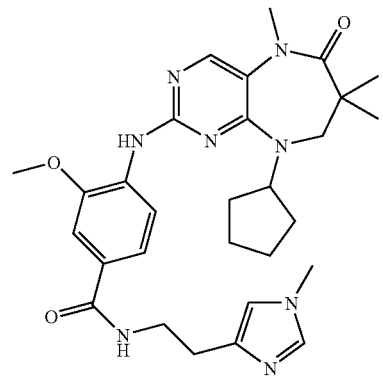

Prepared using the appropriate reagents according to method E. NMR DMSO D$^6$ 1.10 (6H, s), 1.55-1.68 (4H, m), 1.70-1.78 (2H, m), 1.83-1.93 (2H, m), 2.70 (2H, t), 3.19 (3H, s), 3.39 (2H, s), 3.93-3.51 (2H, m), 3.60 (3H, s), 3.95 (3H, s), 5.14-5.25 (1H, m), 6.91 (1H, s), 7.43-7.52 (3H, m), 7.65 (1H, s), 7.99 (1H, s), 8.37 (1H, d), 8.41-8.46 (1H, m); HPLC rt(min): 9.16; MS (ES$^+$) 547, (ES$^-$) 545.

Example 32

9-Cyclopentyl-2-[4-((S)-3-fluoro-pyrrolidine-1-carbonyl)-2-methoxyphenylamino]-5,7,7-trimethyl-5,7,8,9-tetrahydropyrimido[4,5-b][1,4]diazepin-6-one (I-32)

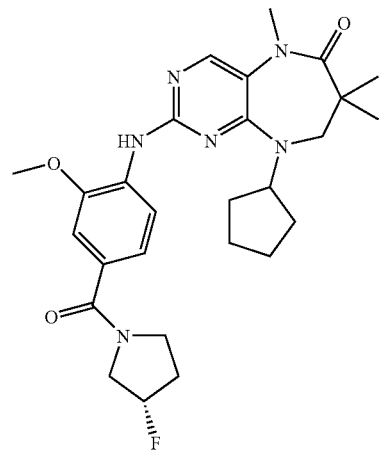

Prepared using the appropriate reagents according to method E. NMR DMSO D$^6$ 1.15 (6H, s), 1.60-2.27 (10H, m), 3.25 (3H, s), 3.43 (2H, s), 3.65-3.90 (4H, m), 3.98 (3H, s), 5.18-5.29 (1H, m), 5.30-5.53 (1H, m), 7.15-7.25 (2H, m), 7.73 (1H, s), 8.03 (1H, s), 8.39 (1H, d); HPLC rt(min): 9.67; MS (ES$^+$) 411, (ES$^-$) 409.

Example 33

4-(9-cyclopentyl-6,7,8,9-tetrahydro-5,7,7-trimethyl-6-oxo-5H-pyrimido[4,5-b][1,4]diazepin-2-ylamino)-3-methoxy-N-(2-morpholinoethyl)benzamide (I-33)

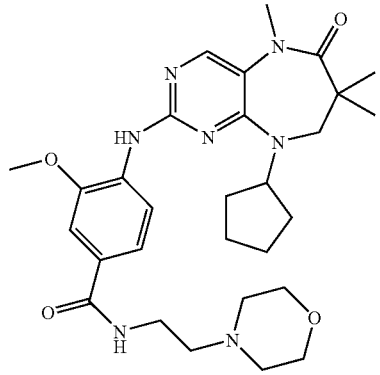

Prepared using the appropriate reagents according to method E. NMR DMSO D$^6$ 1.10 (6H, s), 1.55-1.92 (8H, m), 2.38-2.52 (6H, m), 3.19 (3H, s), 3.38 (2H, s), 3.36-3.44 (2H, m), 3.54-3.63 (4H, m), 3.94 (3H, s), 5.12-5.22 (1H, m), 7.45 (1H, d), 7.49 (1H, s), 7.69 (1H, s), 7.99 (1H, s), 8.26 (1H, br s), 8.37 (1H, d); HPLC rt(min): 9.26; MS (ES$^+$) 552, (ES$^-$) 550.

Example 34

4-(9-cyclopentyl-6,7,8,9-tetrahydro-5,7,7-trimethyl-6-oxo-5H-pyrimido[4,5-b][1,4]diazepin-2-ylamino)-3-methoxy-N-(2-(pyrrolidin-1-yl)ethyl)benzamide (I-34)

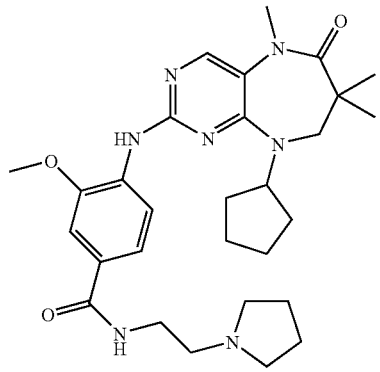

Prepared using the appropriate reagents according to method E. NMR DMSO D$^6$ 1.10 (6H, s), 1.55-1.93 (12H, m), 2.52-2.73 (6H, m), 3.19 (3H, s), 3.39 (2H, s), 2.28-2.46 (2H, m), 3.95 (3H, s), 5.13-5.22 (1H, m), 7.43-7.50 (2H, m), 7.69 (1H, s), 7.99 (1H, s), 8.34-8.42 (2H, m); HPLC rt(min): 9.17; MS (ES$^+$) 536, (ES$^-$) 534.

Example 35

4-(6,7,8,9-tetrahydro-9-isopropyl-5,7,7-trimethyl-6-oxo-5H-pyrimido[4,5-b][1,4]diazepin-2-ylamino)-3-methoxy-N-methylbenzamide (I-35)

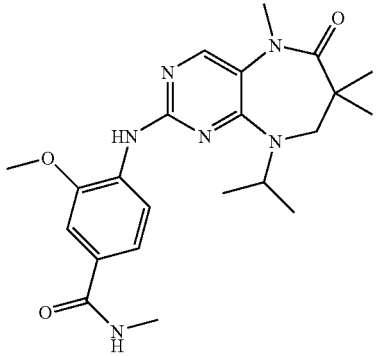

Prepared using the appropriate reagents according to method D. NMR DMSO D$^6$ 1.11 (6H, s), 1.23 (6H, d), 2.80 (3H, d), 3.18 (3H, s), 3.50 (2H, s), 3.95 (3H, s), 5.09 (1H, hept), 7.53 (1H, dd), 7.57 (1H, d), 8.01 (1H, s), 8.07 (1H, d), 8.41 (1H, q), 9.15 (1H, br s); HPLC rt(min): 8.63; MS (ES$^+$) 527, (ES$^-$) 525.

Example 36

4-(6-Cyclopentyl-4,4-dimethyl-5,6-dihydro-4H-2,3,6,7,9,10b-hexaazabenzo[e]azulen-8-ylamino)-3-methoxy-N-methylbenzamide (I-36)

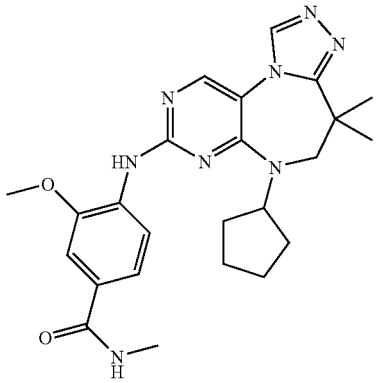

Method I: 8-Chloro-6-Cyclopentyl-4,4-dimethyl-5,6-dihydro-4H-2,3,6,7,9,10b-hexaazabenzo[e]azulene

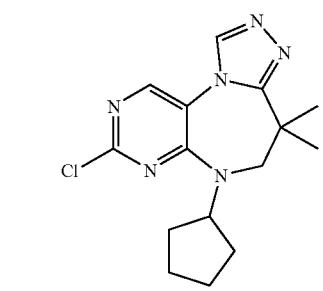

2-Chloro-9-cyclopentyl-8,9-dihydro-7,7-dimethyl-5H-pyrimido[4,5-b][1,4]diazepin-6(7H)-one (0.21 g, 0.73 mmol) in phosphorus oxychloride (6 ml) was heated at 110° C. for 4 hours. The reaction mixture was concentrated in vacuo and redissolved in dichloromethane (4 ml). This latest solution was then added dropwise to a 1M solution of hydrazine in tetrahydrofuran (7.27 ml, 7.27 mmol). The reaction mixture was stirred overnight at room temperature. A saturated solution of NaHCO₃ was added and the mixture was extracted with ethyl acetate. The organic layer was dried (MgSO₄), filtered and concentrated in vacuo. The resulting mixture was dissolved in trimethylorthoformate (4 ml) and heated to 110° C. for 90 minutes. The reactionnel mixture was evaporated in vacuo and purified by silica gel chromatography eluting with ethyl acetate to give the title compound as an off-white solid (0.16 g, 69% yield). NMR DMSO $D^6$ 1.37 (6H, s), 1.52-1.88 (8H, m), 3.44 (2H, s), 5.23 (1H, quint.), 8.56 (1H, s), 9.02 (1H, s); MS (ES⁺) 319.

4-(6-Cyclopentyl-4,4-dimethyl-5,6-dihydro-4H-2,3,6,7,9,10b-hexaazabenzo[e]azulen-8-ylamino)-3-methoxy-N-methylbenzamide (I-36)

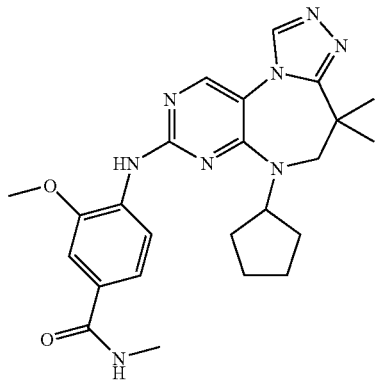

Prepared using the appropriate reagents according to method D. NMR DMSO $D^6$ 1.41 (6H, s), 1.55-1.90 (8H, m), 2.80 (3H, d), 3.50 (2H, s), 3.94 (3H, s), 5.27 (1H, quint.), 7.51 (1H, dd), 7.57 (1H, d), 8.08 (1H, d), 8.47 (1H, q), 8.51 (1H, s), 8.97 (1H, br s), 9.12 (1H, s); HPLC rt(min): 8.54; MS (ES⁺) 463, (ES⁻) 461.

Example 37

4-(9-cyclopentyl-6,7,8,9-tetrahydro-5,7,7-trimethyl-6-oxo-5H-pyrimido[4,5-b][1,4]diazepin-2-ylamino)-N-(2-((S)-3-fluoropyrrolidin-1-yl)ethyl)-3-methoxy-benzamide (I-37)

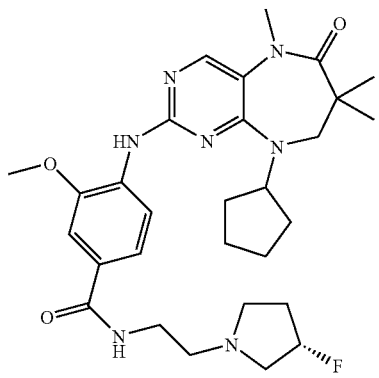

Prepared using the appropriate reagents according to method E. NMR DMSO $D^6$ 1.16 (6H, s), 1.62-2.04 (9H, m), 2.08-2.50 (2H, m), 2.60-3.00 (5H, m), 3.25 (3H, s), 3.43-3.48 (2H, m), 3.44 (2H, s), 4.00 (3H, s), 5.17-5.38 (2H, m), 7.51 (1H, d), 7.56 (1H, s), 7.74 (1H, s), 8.05 (1H, s), 8.35-8.48 (1H, m), 8.43 (1H, d); HPLC rt(min): 9.57; MS (ES⁺) 554, (ES⁻) 552.

Example 38

4-(9-cyclopentyl-6,7,8,9-tetrahydro-5,7,7-trimethyl-6-oxo-5H-pyrimido[4,5-b][1,4]diazepin-2-ylamino)-N-(2azetidin-1-yl)ethyl)-3-methoxybenzamide (I-38)

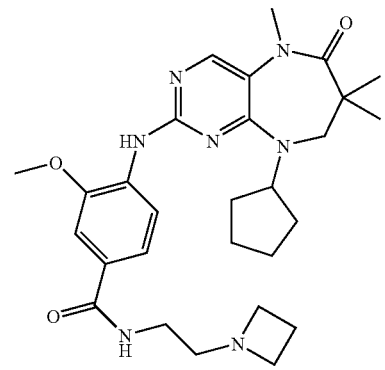

Prepared using the appropriate reagents according to method E. NMR DMSO $D^6$ 1.10 (6H, s), 1.55-2.04 (10H. m), 2.35-2.55 (2H, m), 3.08-3.25 (6H, m), 3.20 (3H, s), 3.38 (2H, s), 3.75-3.95 (1H, m), 3.94 (3H, s), 5.15-5.25 (1H, m), 7.46 (1H, s), 7.50 (1H, s), 7.68 (1H, s), 7.80 (1H, s), 8.24-8.30 (1H, m), 8.36 (1H, d); HPLC rt(min): 9.31; MS (ES⁺) 522, (ES⁻) 520.

Example 39

(R)-3-Fluoro-pyrrolidine-1-carboxylic acid 2-[4-(9-cyclopentyl-5,7,7-trimethyl-6-oxo-6,7,8,9-tetrahydro-5H-pyrimido[4,5-b][1,4]diazepin-2-ylamino)-3-methoxybenzoylamino]-ethyl ester (I-39)

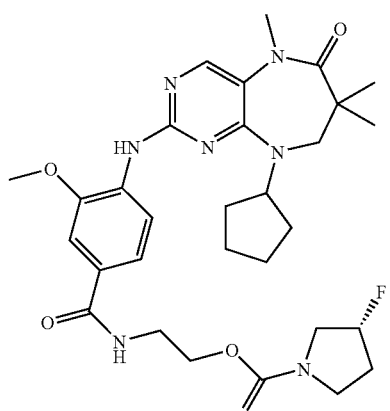

Prepared using the appropriate reagents according to method E. NMR DMSO $D^6$ 1.10 (6H, s), 1.55-1.96 (8H, m), 2.05-2.15 (2H, m), 3.19 (3H, s), 3.88 (2H, s), 3.45-3.58 (6H, m), 3.94 (3H, s), 4.09-4.20 (2H, m), 7.46 (1H, d), 7.50 (1H, s), 7.72 (1H, s), 7.99 (1H, s), 8.37 (1H, d), 8.43-8.47 (1H, m); HPLC rt(min): 9.49; MS (ES+) 598, (ES−) 596.

Example 40

4-(6,7,8,9-tetrahydro-5,7,7-trimethyl-6-oxo-9-phenyl-5H-pyrimido[4,5-b][1,4]diazepin-2-ylamino)-3-methoxy-N-methylbenzamide (I-40)

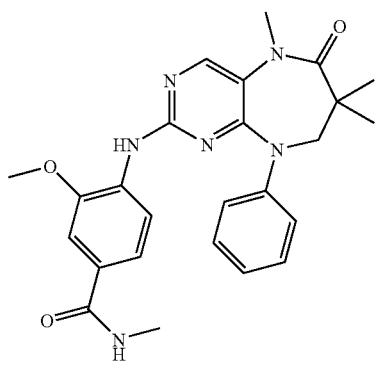

Prepared using the appropriate reagents according to method D. NMR DMSO D$^6$ 1.29 (6H, s), 2.78 (3H, d), 3.29 (3H, s), 3.89 (3H, s), 3.93 (2H, s), 6.86 (1H, dd), 7.08 (1H, d), 7.38-7.42 (3H, m), 7.52-7.57 (1H, m), 7.61 (2H, t), 8.26-8.30 (2H, m), 8.86 (1H, br s); HPLC rt(min): 8.59; MS (ES+) 461, (ES−) 459.

Example 41

4-(9-cyclopentyl-5-ethyl-6,7,8,9-tetrahydro-6-oxo-5H-pyrimido[4,5-b][1,4]diazepin-2-ylamino)-3-methoxy-N-methylbenzamide (I-41)

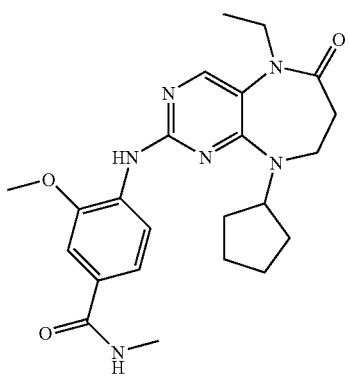

Prepared using the appropriate reagents according to method D. NMR DMSO D$^6$ 1.00 (3H, t), 1.56-1.76 (6H, m), 1.88-2.02 (2H, m), 2.50-2.56 (2H, m), 2.79 (3H, d), 3.61-3.64 (2H, m), 3.70 (2H, q), 3.94 (3H, s), 4.74 (1H, dt), 7.47 (1H, dd), 7.51 (1H, d), 7.86 (1H, br s), 8.13 (1H, s), 8.28-8.33 (1H, m), 8.36 (1H, d); HPLC rt(min): 8.76; MS (ES+) 439, (ES−) 437.

Example 42

4-(6-Cyclopentyl-5,6-dihydro-4H-2,3,6,7,9,10b-hexaazabenzo[e]azulen-8-ylamino)-3-methoxy-N-methylbenzamide (I-42)

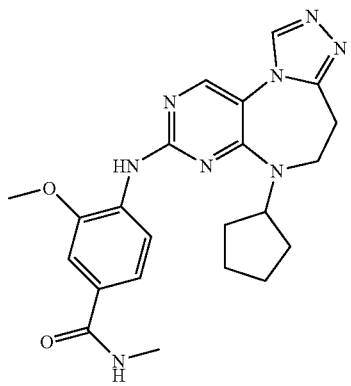

Prepared using the appropriate reagents according to method D. NMR DMSO D$^6$ 1.63-1.71 (4H, m), 1.73-1.85 (2H, m), 1.88-2.00 (2H, m), 2.85 (3H, d), 3.26-3.31 (2H, m), 3.62-3.67 (2H, m), 3.99 (3H, s), 5.26 (1H, dt), 7.53 (1H, dd), 7.57 (1H, d), 8.02 (1H, s), 8.34 (1H, d), 8.34-8.39 (1H, m), 8.45 (1H, s), 9.01 (1H, s); HPLC rt(min): 7.88; MS (ES+) 435, (ES−) 433.

Example 43

2-(1H-benzo[d]imidazol-6-ylamino)-9-cyclopentyl-8,9-dihydro-5,7,7-trimethyl-5H-pyrimido[4,5-b][1,4]diazepin-6(7H)-one (I-43)

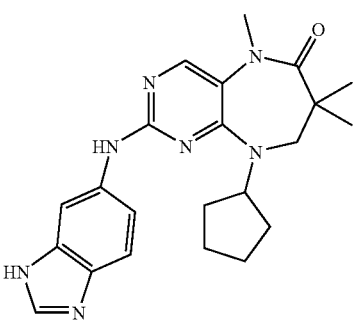

Prepared using the appropriate reagents according to method D. NMR DMSO D$^6$ 1.12 (6H, s), 1.52-1.65 (4H, m), 1.66-1.76 (2H, m), 1.82-1.93 (2H, m), 3.20 (3H, s), 3.40 (2H, s), 5.25 (1H, dt), 7.69-7.76 (2H, m), 7.97 (1H, s), 8.26 (1H, br s), 9.31 (1H, br s), 9.67 (1H, br s); HPLC rt(min): 8.52; MS (ES+) 406, (ES−) 404.

Example 44

2-(benzo[d]thiazol-6-ylamino)-9-cyclopentyl-8,9-dihydro-5,7,7-trimethyl-5H-pyrimido[4,5-b][1,4]diazepin-6(7H)-one (I-44)

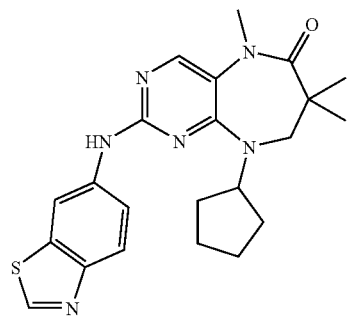

Prepared using the appropriate reagents according to method D. NMR DMSO $D^6$ 1.13 (6H, s), 1.57-1.68 (4H, m), 1.69-1.79 (2H, m), 1.82-1.94 (2H, m), 3.20 (3H, s), 3.43 (2H, s), 5.22 (1H, dt), 7.62 (1H, dd), 7.97 (1H, s), 7.99 (1H, d), 8.65 (1H, br s), 9.21 (1H, s), 9.70 (1H, br s); HPLC rt(min): 9.99; MS (ES$^+$) 423, (ES$^-$) 421.

Example 45

2-(2-oxoindolin-5-ylamino)-9-cyclopentyl-8,9-dihydro-5,7,7-trimethyl-5H-pyrimido[4,5-b][1,4]diazepin-6(7H)-one (I-45)

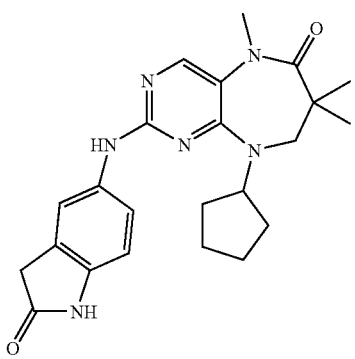

Prepared using the appropriate reagents according to method D. NMR DMSO $D^6$ 1.13 (6H, s), 1.47-1.63 (4H, m), 1.64-1.78 (2H, m), 1.79-1.90 (2H, m), 3.17 (3H, s), 3.45 (2H, s), 3.47 (2H, s), 5.13 (1H, dt), 6.79 (1H, d), 7.29 (1H, d), 7.49 (1H, s), 7.83 (1H, s), 9.60 (1H, br s), 10.33 (1H, s); HPLC rt(min): 8.59; MS (ES$^+$) 421, (ES$^-$) 419.

Example 46

3-(9-cyclopentyl-6,7,8,9-tetrahydro-5,7,7-trimethyl-6-oxo-5H-pyrimido[4,5-b][1,4]diazepin-2-ylamino)-N-methylbenzamide (I-46)

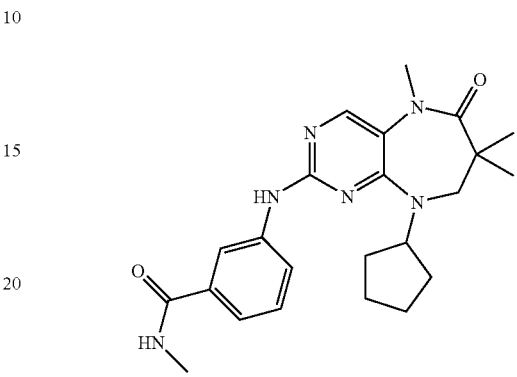

Prepared using the appropriate reagents according to method D. NMR DMSO $D^6$ 1.13 (6H, s), 1.50-1.62 (4H, m), 1.62-1.75 (2H, m), 1.78-1.90 (2H, m), 2.77 (3H, d), 3.19 (3H, s), 3.44 (2H, s), 7.39 (1H, dd), 7.47 (1H, d), 7.59 (1H, d), 7.94 (1H, s), 8.19 (1H, dd), 8.34-8.39 (1H, m), 9.85 (1H, br s); HPLC rt(min): 8.80; MS (ES$^+$) 423, (ES$^-$) 421.

Example 47

2-(1H-indazo-6-ylamino)-9-cyclopentyl-8,9-dihydro-5,7,7-trimethyl-5H-pyrimido[4,5-b][1,4]diazepin-6(7H)-one (I-47)

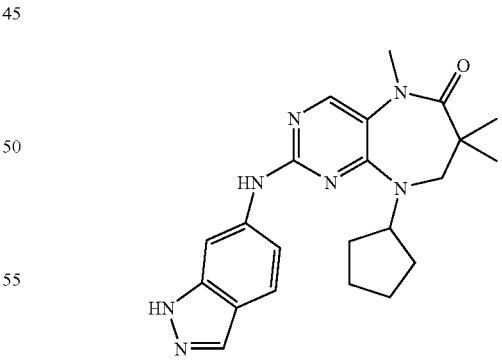

Prepared using the appropriate reagents according to method D. NMR DMSO $D^6$ 1.14 (6H, s), 1.51-1.77 (6H, m), 1.81-1.90 (2H, m), 3.19 (3H, s), 3.46 (2H, s), 5.21 (1H, dt), 7.25 (1H, dd), 7.69 (1H, d), 7.85 (1H, s), 7.93 (1H, s), 8.01 (1H, s), 9.98 (1H, br s), 12.97 (1H, br s); HPLC rt(min): 9.25; MS (ES$^+$) 406, (ES$^-$) 404.

Example 48

2-(4-(1H-imidazol-1-yl)phenylamino)-9-cyclopentyl-8,9-dihydro-5,7,7-trimethyl-5H-pyrimido[4,5-b][1,4]diazepin-6(7H)-one (I-48)

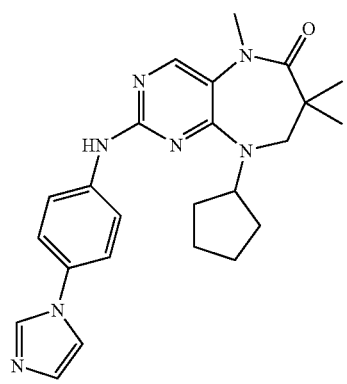

Prepared using the appropriate reagents according to method D. NMR DMSO D$^6$ 1.12 (6H, s), 1.56-1.69 (4H, m), 1.70-1.77 (2H, m), 1.83-1.94 (2H, m), 3.19 (3H, s), 3.42 (2H, s), 5.23 (1H, dt), 7.69 (1H, s), 7.72 (1H, s), 7.87-7.93 (2H, m), 7.93 (1H, s), 8.01 (1H, s), 8.23 (1H, dd), 9.58 (1H, s), 9.79 (1H, br s); HPLC rt(min): 9.75; MS (ES$^+$) 432, (ES$^-$) 430.

Example 49

2-(4-(1H-1,2,4-triazol-1-yl)phenylamino)-9-cyclopentyl-8,9-dihydro-5,7,7-trimethyl-5H-pyrimido[4,5-b][1,4]diazepin-6(7H)-one (I-49)

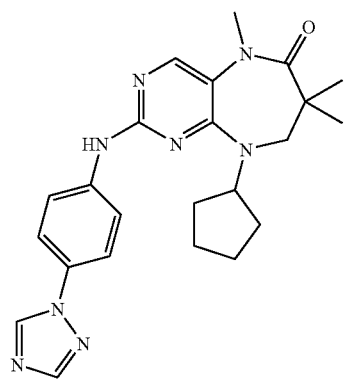

Prepared using the appropriate reagents according to method D. NMR DMSO D$^6$ 1.13 (6H, s), 1.57-1.68 (4H, m), 1.69-1.79 (2H, m), 1.82-1.95 (2H, m), 3.19 (3H, s), 3.45 (2H, s), 5.19 (1H, dt), 7.75-7.83 (4H, m), 7.96 (1H, s), 8.22 (1H, s), 9.23 (1H, s), 9.88 (1H, br s); HPLC rt(min): 9.45; MS (ES$^+$) 433, (ES$^-$) 431.

Example 50

4-(9-cyclopentyl-6,7,8,9-tetrahydro-5,7,7-trimethyl-6-oxo-5H-pyrimido[4,5-b][1,4]diazepin-2-ylamino)-3-isopropoxy-N-methylbenzamide (I-50)

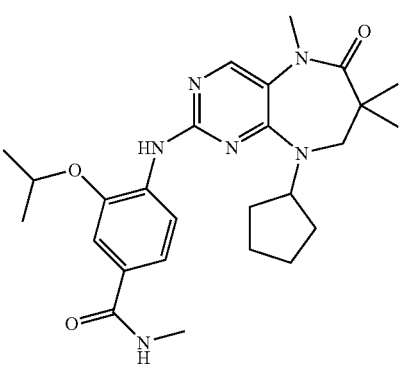

Prepared using the appropriate reagents according to method D. NMR DMSO D$^6$ 1.10 (6H, s), 1.36 (6H, d), 1.57-1.70 (4H, m), 1.70-1.81 (2H, m), 1.85-1.94 (2H, m), 2.78 (3H, d), 3.19 (3H, s), 3.39 (2H, s), 4.68-4.78 (1H, m), 5.08-5.18 (1H, m), 7.44 (1H, d), 7.50 (1H, s), 7.62 (1H, s), 7.98 (1H, s), 8.30-8.35 (1H, m), 8.38 (1H, d); HPLC rt(min): 9.84; MS (ES$^+$) 481, (ES$^-$) 479.

Example 51

4-(9-cyclopentyl-6,7,8,9-tetrahydro-5,7,7-trimethyl-6-oxo-5H-pyrimido[4,5-b][1,4]diazepin-2-ylamino)-3-isopropoxy-N-(1-methylpiperidin-4-yl)benzamide (I-51)

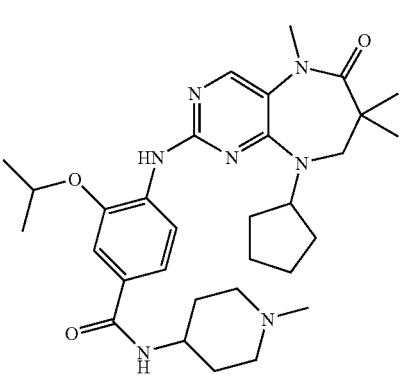

Prepared using the appropriate reagents according to method D. NMR DMSO D$^6$ 1.10 (6H, s), 1.35 (6H, d), 1.55-2.05 (14H, m), 2.19 (3H, s), 2.78-2.87 (2H, m), 3.19 (3H, s), 3.39 (2H, s), 3.22-3.30 (1H, m), 4.73-4.82 (1H, m), 5.09-5.20 (1H, m), 7.47 (1H, d), 7.52 (1H, s), 7.34 (1H, s), 7.98 (1H, s), 8.09 (1H, d), 8.38 (1H, d); HPLC rt(min): 10.05; MS (ES$^+$) 564, (ES$^-$) 562.

Example 52

4-(9-cyclopentyl-6,7,8,9-tetrahydro-5,7,7-trimethyl-6-oxo-5H-pyrimido[4,5-b][1,4]diazepin-2-ylamino)-N-(1-isopropylazetidin-3-yl)-3-methoxybenzamide (I-52)

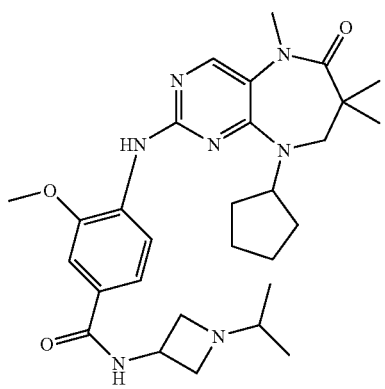

Prepared using the appropriate reagents according to method H. NMR DMSO D$^6$ 0.89 (6H, d), 1.10 (6H, s), 1.55-1.93 (8H, m), 2.32-2.42 (1H, m), 2.90-3.06 (2H, m), 3.19 (3H, s), 3.38 (2H, s), 3.48-3.61 (2H, m), 3.95 (3H, s), 4.35-4.47 (1H, m), 5.17-5.26 (1 h, m), 7.49 (1H, d), 7.50 (1H, s), 7.71 (1H, s), 7.99 (1H, s), 8.38 (1H, d), 8.63 (1H, br s); HPLC rt(min): 9.60; MS (ES$^+$) 536, (ES$^-$) 534.

Example 53

4-(9-cyclopentyl-6,7,8,9-tetrahydro-5,7,7-trimethyl-6-oxo-5H-pyrimido[4,5-b][1,4]diazepin-2-ylamino)-N-(1-(cyclopropylmethyl)azetidin-3-yl)-3-methoxybenzamide (I-53)

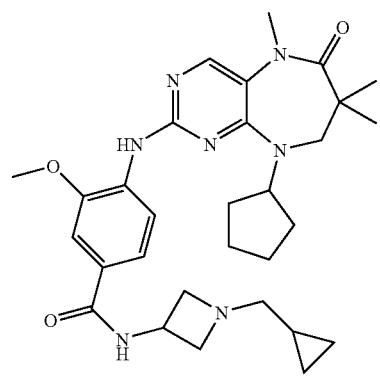

Prepared using the appropriate reagents according to method H. NMR DMSO D$^6$ 0.00-0.05 (2H, m), 0.30-0.35 (2H, m), 0.50-0.71 (1H, m), 1.00 (6H, s), 1.47-1.85 (8H, m), 2.17-2.26 (2H, m), 2.88-3.00 (2H m), 3.09 (3H, s), 3.29 (2H, s), 3.48-3.57 (2H, m), 3.85 (3H, s), 4.32-4.42 (1H, m), 5.04-5.14 (1H, m), 7.38 (1H, d), 4.41 (1H, s), 7.61 (1H, s), 7.90 (1H, s), 8.28 (1H, d), 8.53 (1H, d); HPLC rt(min): 9.68; MS (ES$^+$) 548, (ES$^-$) 546.

Example 54

Method J: 2-(benzylamino)-9-cyclopentyl-8,9-dihydro-5,7,7-trimethyl-5H-pyrimido[4,5-b][1,4]diazepin-6(7H)-one (I-54)

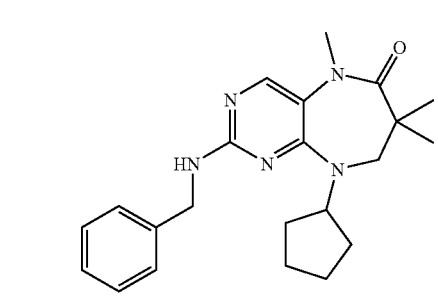

To 2-Chloro-9-cyclopentyl-8,9-dihydro-5,7,7-trimethyl-5H-pyrimido[4,5-b][1,4]diazepin-6(7H)-one (50 mg, 0.162 mmol) in "butanol (2 ml), was added benzylamine (71 µl, 0.648 mmol) and diisopropylethylamine (113 µl, 0.648 mmol). The reaction mixture was heated to 140° C. in a microwave for 90 minutes. The crude mixture was concentrated in vacuo and purified by reverse phase preparative HPLC [Waters Sunfire C18, 10 uM, 100 Å column, gradient 10%-95% B (solvent A: 0.05% TFA in water; solvent B: CH3CN) over 16 minutes at 25 mL/min] to afford the title compound (33 mg) as an off-white powder. NMR DMSO D$^6$ 1.10 (6H, s), 1.46-1.58 (4H, m), 1.60-1.74 (4H, m), 3.13 (3H, s), 3.42 (2H, s), 4.52 (2H, d), 4.95-5.04 (1H, m), 7.24-7.30 (1H, m), 7.31-7.39 (4H, m), 7.83 (1H, s), 8.64 (1H, br s); HPLC rt(min): 10.36; MS (ES$^+$) 380, (ES$^-$) 378.

Example 55

9-cyclopentyl-8,9-dihydro-5,7,7-trimethyl-2-(phenethylamino)-5H-pyrimido[4,5-b][1,4]diazepin-6(7H)-one (I-55)

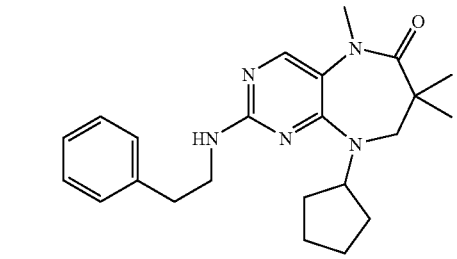

Prepared using the appropriate reagents according to method J. NMR DMSO D$^6$ 1.07 (6H, s), 1.51-1.60 (4H, m), 1.62-1.72 (2H, m), 1.77-1.89 (2H, m), 2.78-2.84 (2H, m), 3.13 (3H, s), 3.31 (2H, d), 3.36-3.45 (2H, m), 5.18-5.28 (1H, m), 7.17-7.24 (3H, m), 7.26-7.32 (2H, m), 7.78 (1H, s); HPLC rt(min): 10.64; MS (ES$^+$) 394, (ES$^-$) 392.

Example 56

4-(6,7,8,9-tetrahydro-9-(tetrahydro-2H-pyran-4-yl)-5,7,7-trimethyl-6-oxo-5H-pyrimido[4,5-b][1,4]diazepin-2-ylamino)-3-methoxy-N-methylbenzamide (I-56)

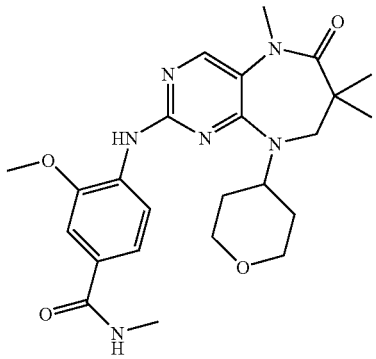

Prepared using the appropriate reagents according to method D. NMR DMSO D$^6$ 1.15 (6H, s), 1.63 (2H, br d), 1.91 (2H, dq), 2.82 (3H, d), 3.18 (3H, s), 3.37 (2H, t), 3.57 (2H, s), 3.94 (3H, s), 4.01 (2H, dd), 4.92 (1H, tt), 7.57 (1H, dd), 7.60 (1H, d), 8.06 (1H, d), 8.09 (1H, s), 8.51 (1H, q), 9.32 (1H, br s); HPLC rt(min): 7.94; MS (ES$^+$) 469, (ES$^-$) 467.

Example 57

2-((R)-2,3-dihydro-1H-inden-1-ylamino)-9-cyclopentyl-8,9-dihydro-5,7,7-trimethyl-5H-pyrimido[4,5-b][1,4]diazepin-6(7H)-one (I-57)

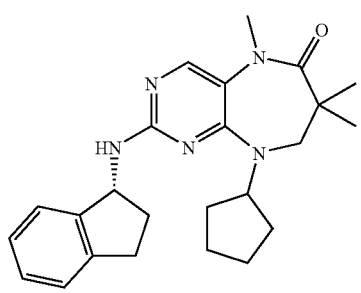

Prepared using the appropriate reagents according to method J. NMR DMSO D$^6$ 1.08 (6H, s), 1.41-1.57 (4H, m), 1.59-1.82 (4H, m), 1.91-2.04 (1H, m), 2.36-2.45 (1H, m), 2.74-2.84 (1H, m), 2.90-2.98 (1H, m), 3.15 (3H, s), 3.29 (2H, d), 5.01-5.16 (1H, m), 5.32-5.44 (1H, m), 6.94 (1H, br s), 7.11-7.24 (4H, m), 7.81 (1H, s); HPLC rt(min): 10.83; MS (ES$^+$) 406, (ES$^-$) 404.

Example 58

4-(9-(cyclopropylmethyl)-6,7,8,9-tetrahydro-5,7,7-trimethyl-6-oxo-5H-pyrimido[4,5-b][1,4]diazepin-2-ylamino)-3-methoxy-N-methylbenzamide (I-58)

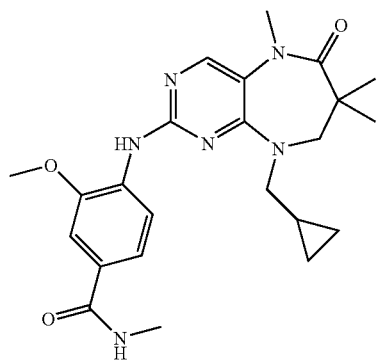

Prepared using the appropriate reagents according to method D. NMR DMSO D$^6$ 0.27-0.35 (2H, m), 0.47-0.53 (2H, m), 1.15-1.25 (7H, m), 2.80 (3H, d), 3.19 (3H, s), 3.66 (2H, d), 3.72 (2H, s), 3.94 (3H, s), 7.51 (1H, dd), 7.57 (1H, d), 8.03 (1H, s), 8.07 (1H, d), 8.46 (1H, q), 9.15 (1H, br s); HPLC rt(min): 8.72; MS (ES$^+$) 439, (ES$^-$) 437.

Example 59

4-(9-cyclopentyl-6,7,8,9-tetrahydro-5,7,7-trimethyl-6-oxo-5H-pyrimido[4,5-b][1,4]diazepin-2-ylamino)-N-(1-(cyclopropylmethyl)piperidin-4-yl)-3-methoxybenzamide (I-59)

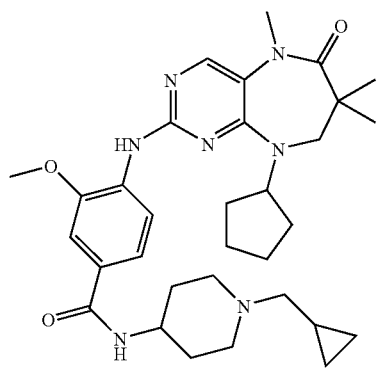

Prepared using the appropriate reagents according to method H. NMR DMSO D$^6$ 0.00-0.05 (2H, m), 0.30-0.35 (2H, m), 0.50-0.71 (1H, m), 1.00 (6H, s), 1.47-1.85 (8H, m), 2.17-2.26 (2H, m), 2.88-3.00 (2H m), 3.09 (3H, s), 3.29 (2H, s), 3.48-3.57 (2H, m), 3.85 (3H, s), 4.32-4.42 (1H, m), 5.04-5.14 (1H, m), 7.38 (1H, d), 4.41 (1H, s), 7.61 (1H, s), 7.90 (1H, s), 8.28 (1H, d), 8.53 (1H, d); HPLC rt(min): 9.68; MS (ES$^+$) 548, (ES$^-$) 546.

Example 60

4-(9'-cyclopentyl-5'-methyl-6'-oxo-5',6',8',9'-tetrahydrospiro[cyclobutane-1,7'-pyrimido[4,5-b][1,4]diazepine]-2'-ylamino)-3-methoxy-N-methylbenzamide (I-60)

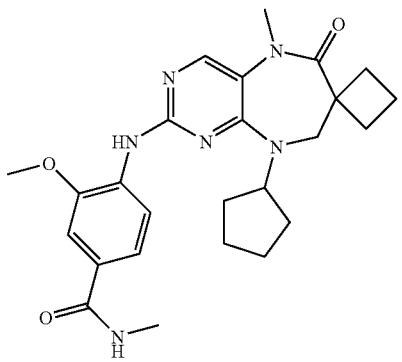

Prepared using the appropriate reagents according to method D. NMR DMSO $D^6$ 1.67-1.89 (9H, m), 2.08-2.10 (2H, m), 2.30-2.40 (3H, m), 2.85 (3H, d), 3.27 (3H, s), 3.70 (2H, s), 3.99 (3H, s), 4.88 (1H, quint.), 7.52 (1H, d), 7.56 (1H, s), 7.79 (1H, s), 8.11 (1H, s), 8.40 (1H, d), 8.44 (1H, d); HPLC rt(min): 9.30; MS (ES$^+$) 465, (ES$^-$) 463.

Example 61

4-((R)-9-cyclopentyl-6,7,8,9-tetrahydro-5,8-dimethyl-6-oxo-5H-pyrimido[4,5-b][1,4]diazepin-2-ylamino)-3-methoxy-N-methylbenzamide (I-61)

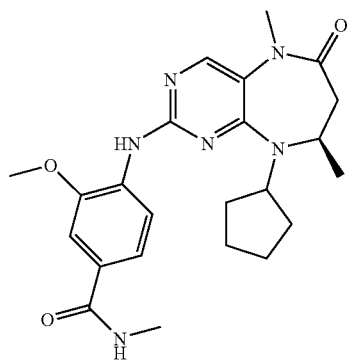

Prepared using the appropriate reagents according to method D. NMR DMSO $D^6$ 1.18 (3H, d), 1.31-1.49 (1H, m), 1.60-1.81 (5H, m), 1.90-1.96 (1H, m), 1.97-2.02 (1H, m), 2.33-2.40 (2H, m), 2.78 (3H, d), 3.19 (3H, s), 3.96 (3H, s), 4.03 (1H, t), 4.66 (1H, quint.), 7.46 (1H, d), 7.50 (1H, s), 7.78 (1H, m), 8.10 (1H, s), 8.30-8.34 (2H, m); HPLC rt(min): 8.70; MS (ES$^+$) 439, (ES$^-$) 437.

Example 62

4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxy-N-methylbenzamide (I-62)

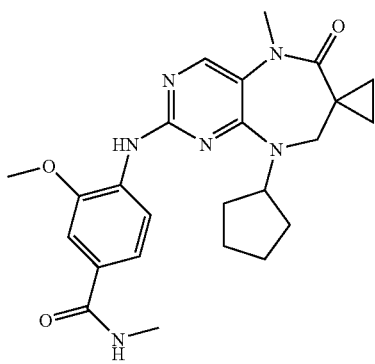

Prepared using the appropriate reagents according to method D. NMR DMSO $D^6$ 0.66-0.69 (2H, m), 0.88-0.92 (2H, m), 1.48-1.72 (6H, m), 1.85-1.91 (2H, m), 2.78 (3H, d), 3.17 (3H, s), 3.48 (2H, s), 3.94 (3H, s), 4.85 (1H, quint.), 7.46 (1H, d), 7.49 (1H, s), 7.69 (1H, s), 7.90 (1H, s), 8.33 (1H, m), 8.40 (1H, d); HPLC rt(min): 8.80; MS (ES$^+$) 451, (ES$^-$) 449.

Example 63

2-(4-morpholinophenylamino)-9-cyclopentyl-8,9-dihydro-5,7,7-trimethyl-5H-pyrimido[4,5-b][1,4]diazepin-6(7H)-one (I-63)

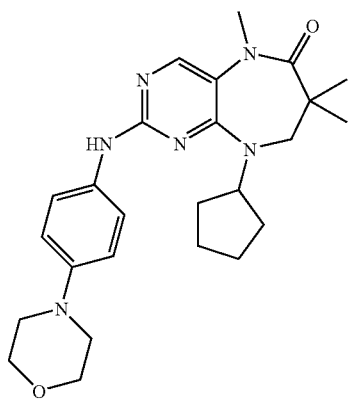

Prepared using the appropriate reagents according to method D. NMR DMSO $D^6$ 1.14 (6H, s), 1.48-1.85 (8H, m), 3.10 (4H, t), 3.16 (3H, s), 3.48 (2H, s), 3.75 (4H, t), 5.11 (1H, dt), 6.98 (2H, d), 7.38 (2H, d), 7.84 (1H, s), 10.01 (1H, br s); HPLC rt(min): 9.47; MS (ES$^+$) 451, (ES$^-$) 449.

Example 64

4-(9'-cyclopentyl-5'-methyl-6'-oxo-5',6',8',9'-tetrahydrospiro[cyclobutane-1,7'-pyrimido[4,5-b][1,4]diazepine]-2'-ylamino)-3-methoxy-N-(1-methylpiperidin-4-yl)benzamide (I-64)

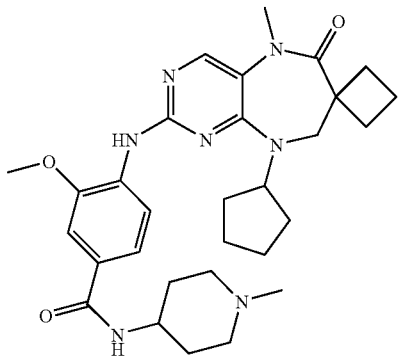

Prepared using the appropriate reagents according to method D. NMR DMSO $D^6$ 1.53-1.71 (9H, m), 1.78-1.99 (6H, m), 2.08-2.12 (2H, m), 2.20-2.33 (6H, m), 2.77-2.96 (2H, m), 3.19 (3H, s), 3.65 (2H, s), 3.75-3.84 (1H, m), 3.95 (3H, s), 4.83 (1H, quint.), 7.48 (1H, d), 7.50 (1H, s), 7.73 (1H, s), 8.06 (1H, s), 8.13 (1H, br d), 8.37 (1H, d); HPLC rt(min): 9.50; MS (ES$^+$) 548, (ES$^-$) 546.

Example 65

4-((R)-9-cyclopentyl-6,7,8,9-tetrahydro-5,8-dimethyl-6-oxo-5H-pyrimido[4,5-b][1,4]diazepin-2-ylamino)-3-methoxy-N-(1-methylpiperidin-4-yl)benzamide (I-65)

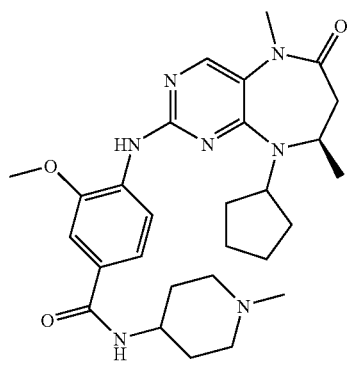

Prepared using the appropriate reagents according to method D. NMR DMSO $D^6$ 1.27 (3H, d), 1.33-1.42 (1H, m), 1.56-1.79 (9H), 1.91-2.02 (4H, m), 2.20 (3H, s), 2.41-2.54 (1H, m), 2.66-2.75 (1H, m), 2.76-2.86 (2H, m), 3.21 (3H, s), 3.71-3.79 (1H, m), 3.94 (3H, s), 4.00-4.05 (1H, m), 4.64 (1H, quint.), 7.48 (1H, d), 7.49 (1H, s), 7.74 (1H, s), 8.11 (1H, s), 8.13 (1H, s), 8.32 (1H, d); HPLC rt(min): 8.50; MS (ES$^+$) 522, (ES$^-$) 520.

Example 66

4-(9-((R)-1-cyclopropylmethyl)pyrrolidin-3-yl)-6,7,8,9-tetrahydro-5,7,7-trimethyl-6-oxo-5H-pyrimido[4,5-b][1,4]diazepin-2-ylamino)-3-methoxy-N-methylbenzamide (I-66)

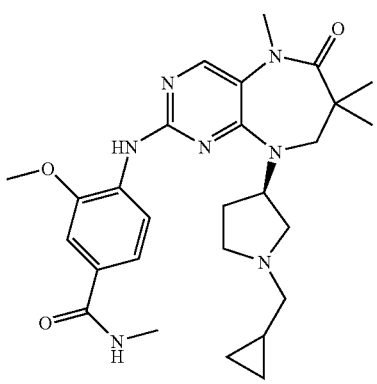

Prepared using the appropriate reagents according to method D. NMR DMSO $D^6$ 0.27-0.35 (2H, m), 0.47-0.53 (2H, m), 1.15-1.25 (7H, m), 2.80 (3H, d), 3.19 (3H, s), 3.66 (2H, d), 3.72 (2H, s), 3.94 (3H, s), 7.51 (1H, dd), 7.57 (1H, d), 8.03 (1H, s), 8.07 (1H, d), 8.46 (1H, q), 9.15 (1H, br s); HPLC rt(min): 7.93; MS (ES$^+$) 508, (ES$^-$) 507.

Example 67

4-(9-cyclopentyl-6,7,8,9-tetrahydro-5,7,7-trimethyl-6-oxo-5H-pyrimido[4,5-b][1,4]diazepin-2-ylamino)-N-(1-(isopropylpiperidin-4-yl)-3-methoxybenzamide (I-67)

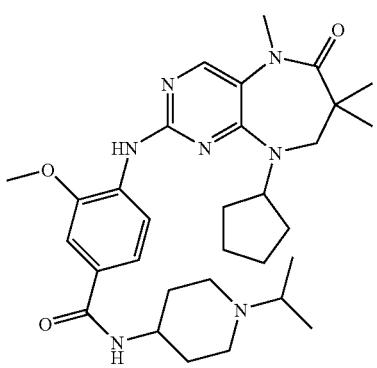

Prepared using the appropriate reagents according to method H. NMR CDCl$_3$ 1.05 (6H, d), 1.13 (6H, s), 1.40-2.41 (13H, m), 2.78-2.95 (3H, m), 3.20 (3H, s), 3.30 (2H, s), 3.90 (3H, s), 3.90-4.01 (1H, m), 5.18-5.30 (1H, m), 5.96-6.01 (1H, m), 7.17 (1H, d), 7.19 (1H, s), 7.34 (1H, s), 7.55 (1H, s), 7.78 (1H, s), 8.41 (1H, d); HPLC rt(min): 9.06; MS (ES$^+$) 564, (ES$^-$) 562.

Example 68

4-(9-cyclopentyl-6,7,8,9-tetrahydro-5,7,7-trimethyl-6-oxo-5H-pyrimido[4,5-b][1,4]diazepin-2-ylamino)-3-methoxy-N-(1,2,2,6,6-pentamethylpiperidin-4-yl)-benzamide (I-68)

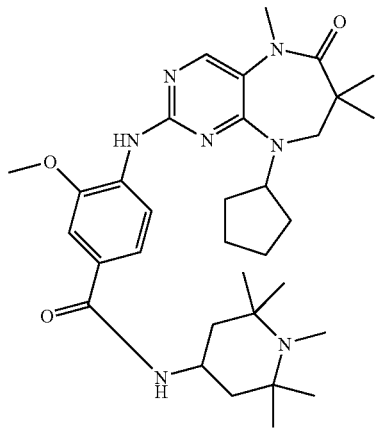

Prepared using the appropriate reagents according to method E. NMR CDCl₃ 1.07 (12H, s), 1.20 (6H, s), 1.40-1.95 (11H, m), 2.28 (3H, s), 3.22 (3H, s), 3.30 (2H, s), 3.90 (3H, s), 4.30-4.40 (1H, m), 5.20-5.29 (1H, m), 5.33-5.43 (1H, m), 7.16 (1H, d), 7.19 (1H, s), 7.36 (1H, s), 7.56 (1H, s), 7.78 (1H, s), 8.41 (1H, d); HPLC rt(min): 9.07; MS (ES⁺) 591, (ES⁻) 590.

Example 69

4-(9-cyclopentyl-6,7,8,9-tetrahydro-5,7,7-trimethyl-6-oxo-5H-pyrimido[4,5-b][1,4]diazepin-2-ylamino)-3-methoxy-N-(1-(propylpiperidin-4-yl)benzamide (I-69)

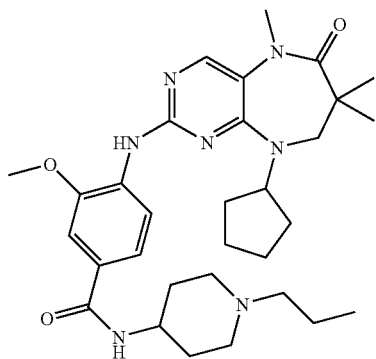

Prepared using the appropriate reagents according to method H. NMR CDCl₃ 0.85 (3H, t), 1.13 (6H, s), 1.17-1.21 (2H, m), 1.47-2.40 (19H, m), 2.90-2.99 (2H, m), 3.22 (3H, s), 3.30 (2H, s), 3.90 (3H, s), 3.91-4.02 (1H, m), 5.18-5.28 (1H, m), 5.95-6.00 (1H, m), 7.16 (1H, d), 7.18 (1H, s), 7.34 (1H, s), 7.55 (1H, s), 7.78 (1H, s), 8.41 (1H, d); HPLC rt(min): 9.45; MS (ES⁺) 564, (ES⁻) 562.

Example 70

4-(9-cyclopentyl-6,7,8,9-tetrahydro-5,7,7-trimethyl-6-oxo-5H-pyrimido[4,5-b][1,4]diazepin-2-ylamino)-N-(1-(isobutylpiperidin-4-yl)-3-methoxybenzamide (I-70)

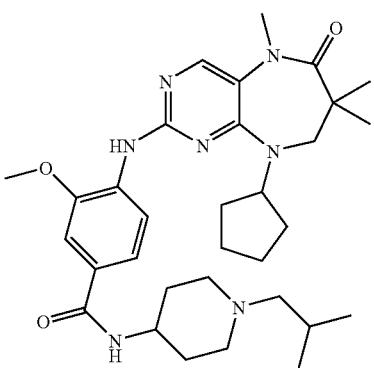

Prepared using the appropriate reagents according to method H. NMR CDCl₃ 0.85 (6H, d), 1.13 (6H, s), 1.41-2.15 (16H, m), 2.75-2.85 (2H, m), 3.23 (3H, s), 3.30 (2H, s), 3.90 (3H, s), 3.90-3.97 (1H, m), 5.20-5.29 (1H, m), 5.91-5.97 (1H, m), 7.14 (1H, s), 7.20 (1H, s), 7.34 (1H, s), 7.55 (1H, s), 7.78 (1H, s), 8.41 (1H, d); HPLC rt(min): 9.83; MS (ES⁺) 578, (ES⁻) 576.

Example 71

4-(9-cyclopentyl-6,7,8,9-tetrahydro-5,7,7-trimethyl-6-oxo-5H-pyrimido[4,5-b][1,4]diazepin-2-ylamino)-N-(1-tert-butylpiperidin-4-yl)-3-methoxybenzamide (I-71)

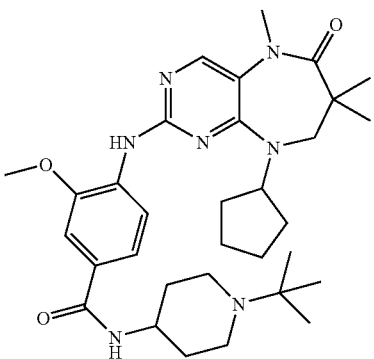

Prepared using the appropriate reagents according to method E. NMR CDCl₃ 1.10 (9H, s), 1.13 (6H, s), 1.40-2.09 (12H, m), 2.26-2.36 (2H, m), 2.97-3.10 (2H, m), 3.23 (3H, s), 3.30 (2H, s), 3.90 (3H, s), 3.30-3.10 (1H, m), 5.18-5.28 (1H, m), 5.95-6.01 (1H, m), 7.15 (1H, d), 7.20 (1H, s), 7.35 (1H, s), 7.55 (1H, s), 7.78 (1H, s), 8.41 (1H, d); HPLC rt(min): 8.83; MS (ES⁺) 578, (ES⁻) 576.

Example 72

4-(9-cyclopentyl-6,7,8,9-tetrahydro-5,7,7-trimethyl-6-oxo-5H-pyrimido[4,5-b][1,4]diazepin-2-ylamino)-N-(1-(ethylpiperidin-4-yl)-3-methoxybenzamide
(I-72)

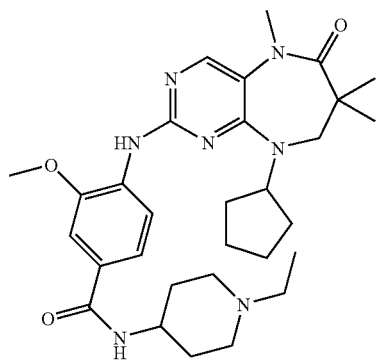

Prepared using the appropriate reagents according to method H. NMR CDCl$_3$ 1.22 (3H, t), 1.26 (6H, s), 1.50-2.18 (11H, m), 2.20-2.34 (2H, m), 2.58 (2H, q), 3.06-3.13 (2H, m), 3.32 (3H, s), 3.39 (2H, s), 4.00 (3H, s), 4.02-4.15 (1H, m), 5.27-5.37 (1H, m), 6.00-6.07 (1H, m), 7.25 (1H, d), 7.28 (1H, s), 7.43 (1H, s), 7.65 (1H, s), 7.87 (1H, s), 8.50 (1H, s); HPLC rt(min): 9.12; MS (ES$^+$) 550, (ES$^-$) 548.

Example 73

4-(9-cyclopentyl-6,7,8,9-tetrahydro-5,7,7-trimethyl-6-oxo-5H-pyrimido[4,5-b][1,4]diazepin-2-ylamino)-N—((S)-1-isoipropylpyrrolidin-3-yl)-3-methoxybenzamide (I-73)

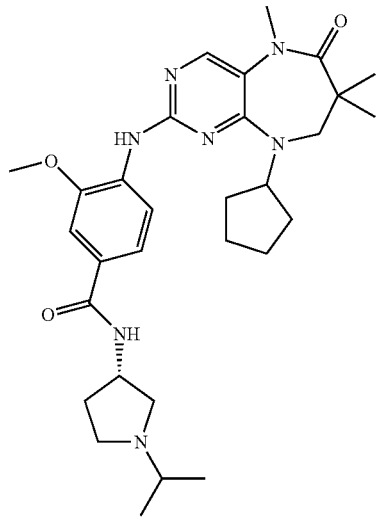

Prepared using the appropriate reagents according to method H. NMR DMSO D$^6$ 1.02-1.14 (12H, m), 1.53-2.23 (10H, m), 2.08-2.15 (1H, m), 2.45-3.00 (4H, m), 3.19 (3H, s), 3.38 (2H, s), 3.95 (3H, s), 4.40 (1H, m), 5.19 (1H, m), 7.47- 7.53 (2H, m), 7.70 (1H, s), 7.99 (1H, s), 8.33-8.40 (2H, m); HPLC rt(min): 9.42; MS (ES$^+$) 551, (ES$^-$) 549.

Example 74

4-(9-cyclopentyl-6,7,8,9-tetrahydro-5,7,7-trimethyl-6-oxo-5H-pyrimido[4,5-b][1,4]diazepin-2-ylamino)-3-ethoxy-N-(1-methylpiperidin-4-yl)benzamide
(I-74)

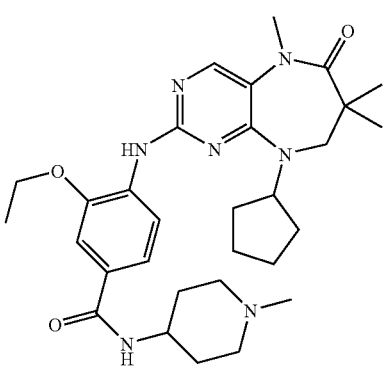

Prepared using the appropriate reagents according to method D. NMR CDCl$_3$ 1.18 (6H, s), 1.43 (3H, t), 1.50 (2H, br m), 1.69 (6H, br m), 1.97 (4H, br m), 2.22 (2H, br m), 2.32 (3H, s), 2.89 (2H, br m), 3.21 (3H, s), 3.31 (2H, s), 4.05 (1H, br m), 4.15 (2H, q), 5.22 (1H, m), 6.10 (NH), 7.17 (1H, m), 7.31 (1H, s), 7.60 (NH), 7.78 (1H, s), 8.41 (1H, m); HPLC rt(min): 9.93; MS (ES$^+$) 550, (ES$^-$) 548.

Example 75

4-(9-cyclopentyl-6,7,8,9-tetrahydro-5,7,7-trimethyl-6-oxo-5H-pyrimido[4,5-b][1,4]diazepin-2-ylamino)-N—((S)-1-(cyclopropylmethyl)pyrrolidin-3-yl)-3-methoxybenzamide (I-75)

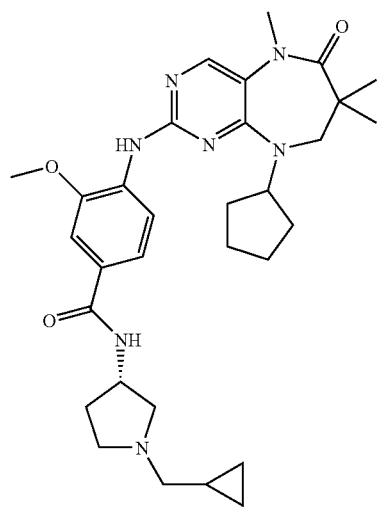

Prepared using the appropriate reagents according to method H. NMR DMSO D$^6$ -0.01 (2H, q), 0.35 (2H, m), 0.76 (1H, hept), 1.00 (6H, s), 1.45-1.85 (9H, m), 2.07 (1H, m), 2.18

(2H, d), 2.35-2.47 (2H, m), 2.60-2.75 (2H, m), 3.09 (3H, s), 3.28 (2H, s), 3.85 (3H, s), 4.31 (1H, hex), 5.09 (1H, quint), 7.40-7.47 (2H, m), 7.60 (1H, s), 7.90 (1H, s), 8.24-8.29 (2H, m); HPLC rt(min): 9.67; MS (ES$^+$) 562, (ES$^-$) 561.

Example 76

4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxy-N-(1-methylpiperidin-4-yl)benzamide (I-76)

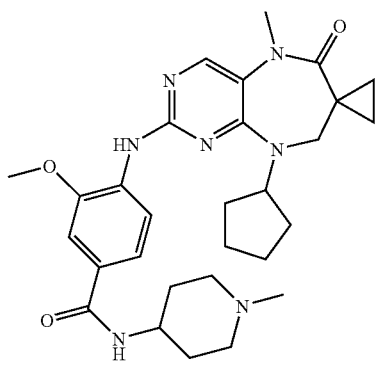

Prepared using the appropriate reagents according to method D. NMR DMSO D$^6$ 0.73-0.75 (2H, m), 0.91-0.98 (2H, m), 1.51-1.79 (8H, m), 1.84-2.00 (5H, m), 2.31-2.42 (4H, m), 2.95-3.05 (2H, m), 3.23 (3H, s), 3.54 (2H, s), 3.81-3.94 (1H, m), 4.01 (3H, s), 4.91 (1H, quin), 7.54 (1H, d), 7.55 (1H, s), 7.58 (1H, s), 8.05 (1H, s), 8.20 (1H, d), 8.45 (1H, d); HPLC rt(min): 8.90; MS (ES$^+$) 532, (ES$^-$) 534.

Example 77

4-(-9-cyclopentyl-6,7,8,9-tetrahydro-5,7,7-trimethyl-6-oxo-5H-pyrimido[4,5-b][1,4]diazepin-2-ylamino)-N-(1-(2-fluoroethyl)piperidin-4-yl)-3-methoxybenzamide (I-77)

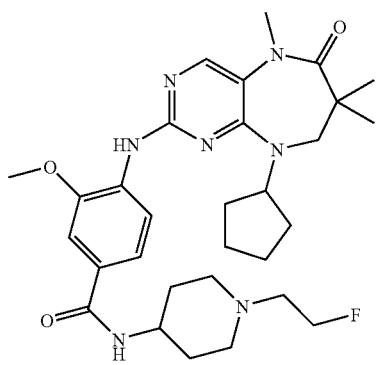

Prepared using the appropriate reagents according to method H. NMR CDCl$_3$ 1.13 (6H, s), 1.40-1.80 (7H, m), 1.85-1.95 (2H, m), 1.97-2.05 (2H, m), 2.23-2.34 (2H, m), 2.66-2.78 (2H, m), 2.93-3.02 (2H, m), 3.23 (3H, s), 3.30 (2H, s), 3.91 (3H, s), 3.90-4.04 (1H, m), 1.45-1.64 (2H, m), 5.16-5.28 (1H, m), 5.85-5.95 (1H, m), 7.15 (1H, d), 7.20 (1H, s), 7.34 (1H, s), 7.56 (1H, s), 7.78 (1H, s), 8.42 (1H, d); HPLC rt(min): 9.58; MS (ES$^+$) 568, (ES$^-$) 566.

Example 78

N-(4-(9-cyclopentyl-6,7,8,9-tetrahydro-5,7,7-trimethyl-6-oxo-5H-pyrimido[4,5-b][1,4]diazepin-2-ylamino)phenyl)-2,2,2-trifluoroacetamide (I-78)

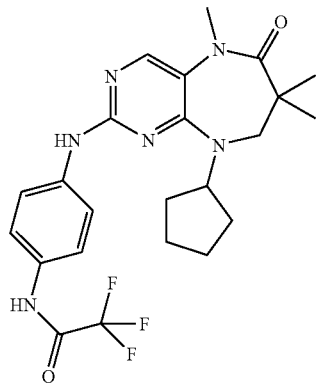

Prepared using the appropriate reagents according to method D. NMR DMSO D$^6$ 1.15 (6H, s), 1.52-1.68 (4H, m), 1.69-1.78 (2H, m), 1.79-1.94 (2H, m), 3.17 (3H, s), 3.43 (2H, s), 5.16 (1H, dt), 7.60 (2H, d), 7.65 (2H, d), 7.92 (1H, s), 9.64 (1H, br s), 11.19 (1H, s); HPLC rt(min): 9.90; MS (ES$^+$) 477, (ES$^-$) 475.

Example 79

2-(1-acetylindolin-5-ylamino)-9-cyclopentyl-8,9-dihydro-5,7,7-trimethyl-5H-pyrimido[4,5-b][1,4]diazepin-6(7H)-one (I-79)

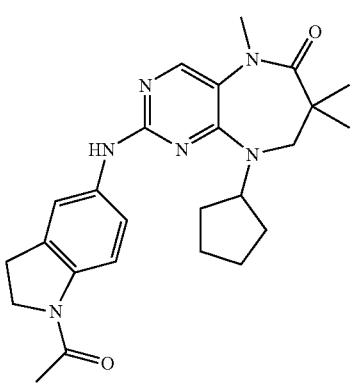

Prepared using the appropriate reagents according to method D. NMR DMSO D$^6$ 1.12 (6H, s), 1.50-1.68 (4H, m), 1.69-1.77 (2H, m), 1.78-1.88 (2H, m), 2.14 (3H, s), 3.12 (2H, t), 3.16 (3H, s), 3.44 (2H, s), 4.10 (2H, t), 5.15 (1H, dt), 7.26 (1H, d), 7.54 (1H, s), 7.86 (1H, s), 7.97 (1H, d), 9.65 (1H, br s); HPLC rt(min): 9.37; MS (ES$^+$) 449, (ES$^-$) 447.

Example 80

4-(9-cyclopentyl-6,7,8,9-tetrahydro-5,7,7-trimethyl-6-oxo-5H-pyrimido[4,5-b][1,4]diazepin-2-ylamino)-N-methylbenzamide (I-80)

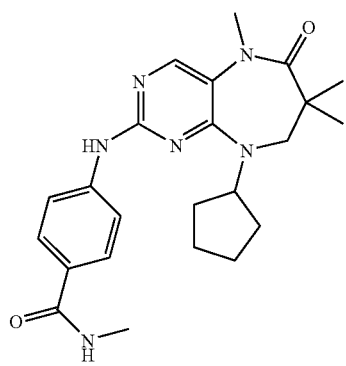

Prepared using the appropriate reagents according to method D. NMR DMSO D$^6$ 1.13 (6H, s), 1.55-1.69 (4H, m), 1.70-1.80 (2H, m), 1.82-1.93 (2H, m), 2.78 (3H, d), 3.18 (3H, s), 3.45 (2H, s), 5.20 (1H, dt), 7.71 (2H, d), 7.79 (2H, d), 7.97 (1H, s), 8.27-8.34 (1H, m), 9.86 (1H, br s); HPLC rt(min): 8.73; MS (ES$^+$) 423, (ES$^-$) 421.

Example 81

2-(1H-indazol-4-ylamino)-9-cyclopentyl-8,9-dihydro-5,7,7-trimethyl-5H-pyrimido[4,5-b][1,4]diazepin-6(7H)-one (I-81)

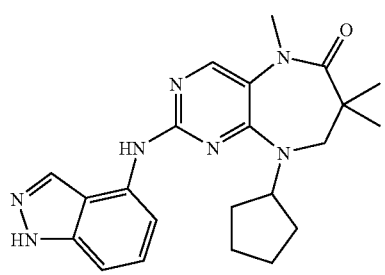

Prepared using the appropriate reagents according to method D. NMR DMSO D$^6$ 1.13 (6H, s), 1.41-1.79 (8H, m), 3.20 (3H, s), 3.44 (2H, s), 5.10 (1H, dt), 7.22-7.34 (2H, m), 7.51-7.59 (1H, m), 7.95 (1H, s), 8.27 (1H, s), 9.91 (1H, br s), 13.10 (1H, br s); HPLC rt(min): 9.32; MS (ES$^+$) 406, (ES$^-$) 404.

Example 82

2-(1,6-dihydro-6-oxopyridin-3-ylamino)-9-cyclopentyl-8,9-dihydro-5,7,7-trimethyl-5H-pyrimido[4,5-b][1,4]diazepin-6(7H)-one (I-82)

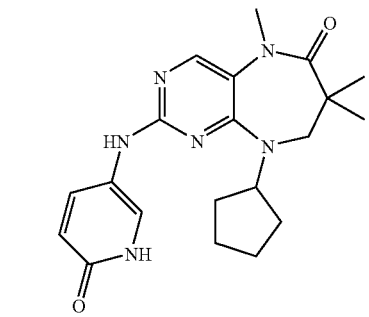

Prepared using the appropriate reagents according to method D. NMR DMSO D$^6$ 1.12 (6H, s), 1.48-1.84 (8H, m), 3.16 (3H, s), 3.45 (2H, s), 5.00-5.09 (1H, m), 6.39 (1H, d), 7.54 (1H, d), 7.61 (1H, s), 7.81 (1H, s), 9.45 (1H, br s); HPLC rt(min): 7.77; MS (ES$^+$) 383, (ES$^-$) 381.

Example 83

2-(1,6-dihydro-4-methyl-6-oxopyridin-3-ylamino)-9-cyclopentyl-8,9-dihydro-5,7,7-trimethyl-5H-pyrimido[4,5-b][1,4]diazepin-6(7H)-one (I-83)

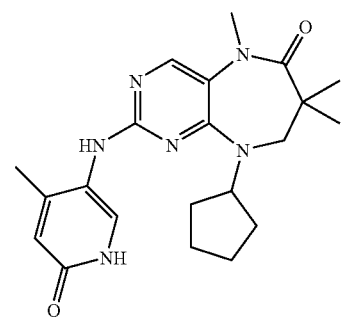

Prepared using the appropriate reagents according to method D. NMR DMSO D$^6$ 1.13 (6H, s), 1.39-1.78 (8H, m), 2.04 (3H, s), 3.16 (3H, s), 3.48 (2H, s), 6.30 (1H, s), 7.49 (1H, s), 7.75 (1H, br s), 9.39 (1H, br s); HPLC rt(min): 7.86; MS (ES$^+$) 397, (ES$^-$) 395.

Example 84

2-(3-methoxy-5-nitrophenylamino)-9-cyclopentyl-8,9-dihydro-5,7,7-trimethyl-5H-pyrimido[4,5-b][1,4]diazepin-6(7H)-one (I-84)

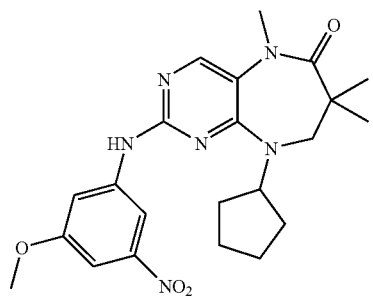

Prepared using the appropriate reagents according to method D. NMR DMSO $D^6$ 1.11 (6H, s), 1.56-1.77 (6H, m), 1.83-1.96 (2H, m), 3.19 (3H, s), 3.42 (2H, s), 3.86 (3H, s), 5.29 (1H, dt), 7.33 (1H, t), 7.60 (1H, t), 8.01 (1H, s), 8.41 (1H, t), 9.88 (1H, br s); HPLC rt(min): 10.48; MS (ES$^+$) 441, (ES$^-$) 439.

Example 85

2-(4-(4-methylpiperazin-1-yl)phenylamino)-9-cyclopentyl-8,9-dihydro-5,7,7-trimethyl-5H-pyrimido[4,5-b][1,4]diazepin-6(7H)-one (I-85)

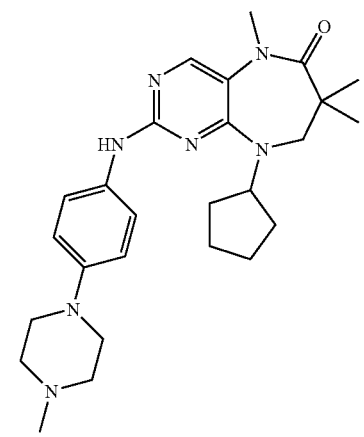

Prepared using the appropriate reagents according to method D. NMR DMSO $D^6$ 1.13 (6H, s), 1.51-1.65 (4H, m), 1.66-1.75 (2H, m), 1.76-1.86 (2H, m), 2.88 (3H, s), 2.86-2.94 (2H, m), 3.17 (3H, s), 3.12-3.24 (2H, m), 3.45 (2H, s), 3.53 (2H, d), 3.79 (2H, d), 5.13 (1H, dt), 7.00 (2H, d), 7.46 (2H, d), 7.90 (1H, s), 9.75 (1H, br s), 9.86 (1H, br s); HPLC rt(min): 9.66; MS (ES$^+$) 464, (ES$^-$) 462.

Example 86

2-(4-morpholinomethyl)phenylamino)-9-cyclopentyl-8,9-dihydro-5,7,7-trimethyl-5H-pyrimido[4,5-b][1,4]diazepin-6(7H)-one (I-86)

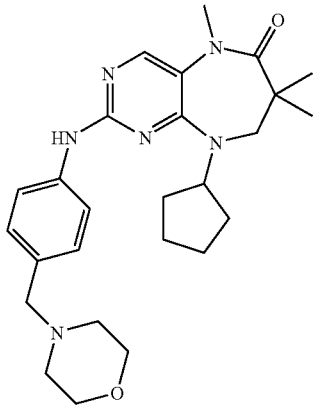

Prepared using the appropriate reagents according to method D. NMR DMSO $D^6$ 1.11 (6H, s), 1.53-1.67 (4H, m), 1.69-1.78 (2H, m), 1.80-1.94 (2H, m), 3.02-3.17 (2H, m), 3.19 (3H, s), 3.26 (2H, d), 3.40 (2H, s), 3.62 (2H, t), 3.97 (2H, d), 4.28 (2H, d), 5.21 (1H, dt), 7.39 (2H, d), 7.79 (2H, d), 7.97 (1H, s), 9.62 (1H, br s), 9.75 (1H, br s); HPLC rt(min): 9.82; MS (ES$^+$) 465, (ES$^-$) 463.

Example 87

4-(9-cyclopentyl-6,7,8,9-tetrahydro-5,7,7-trimethyl-6-oxo-5H-pyrimido[4,5-b][1,4]diazepin-2-ylamino)-N-(2-hydroxyethyl)benzamide (I-87)

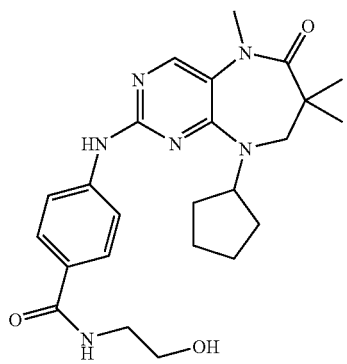

Prepared using the appropriate reagents according to method D. NMR DMSO $D^6$ 1.11 (6H, s), 1.56-1.66 (4H, m), 1.68-1.81 (2H, m), 1.83-1.95 (2H, m), 3.20 (3H, s), 3.20-3.28 (2H, m), 3.41 (2H, s), 4.40 (2H, t), 5.23 (1H, dt), 7.86 (2H, d), 7.92-7.99 (4H, m), 8.01 (1H, s), 9.80 (1H, br s); HPLC rt (min): 8.74; MS (ES$^+$) 453, (ES$^-$) 451.

Example 88

N-(4-(9-cyclopentyl-6,7,8,9-tetrahydro-5,7,7-trimethyl-6-oxo-5H-pyrimido[4,5-b][1,4]diazepin-2-ylamino)phenyl)-N-methylacetamide (I-88)

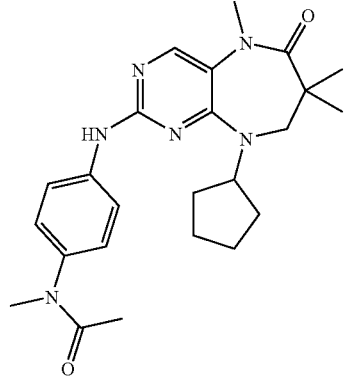

Prepared using the appropriate reagents according to method D. NMR DMSO D$^6$ 1.11 (6H, s), 1.52-1.65 (4H, m), 1.66-1.73 (2H, m), 1.77 (3H, s), 1.77-1.86 (2H, m), 3.13 (3H, s), 3.18 (3H, s), 3.44 (2H, s), 5.13 (1H, dt), 7.29 (2H, d), 7.65 (2H, d), 7.93 (1H, s), 9.80 (1H, br s); HPLC rt(min): 9.38; MS (ES$^+$) 437, (ES$^-$) 435.

Example 89

2-(1H-indazo-7-ylamino)-9-cyclopentyl-8,9-dihydro-5,7,7-trimethyl-5H-pyrimido[4,5-b][1,4]diazepin-6(7H)-one (I-89)

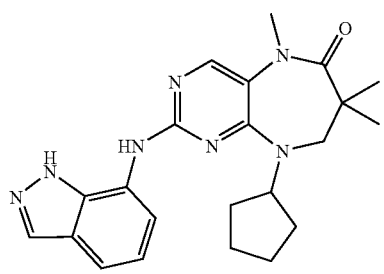

Prepared using the appropriate reagents according to method D. NMR DMSO D$^6$ 1.13 (6H, s), 1.40-1.79 (8H, m), 3.20 (3H, s), 3.45 (2H, s), 5.09 (1H, dt), 7.25-7.34 (2H, m), 7.53 (1H, d), 7.94 (1H, s), 8.26 (1H, s), 9.95 (1H, br s), 13.11 (1H, br s); HPLC rt(min): 9.33; MS (ES$^+$) 406, (ES$^-$) 404.

Example 90

9-cyclopentyl-8,9-dihydro-5,7,7-trimethyl-2-(phenylamino)-5H-pyrimido[4,5-b][1,4]diazepin-6(7H)-one (I-90)

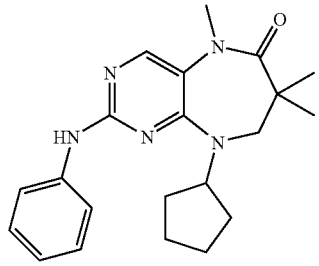

Prepared using the appropriate reagents according to method D. NMR DMSO D$^6$ 1.13 (6H, s), 1.51-1.89 (8H, m), 3.18 (3H, s), 3.45 (2H, s), 5.16 (1H, dt), 7.07 (1H, t), 7.34 (2H, t), 7.59 (2H, d), 7.91 (1H, s), 9.77 (1H, br s); HPLC rt(min): 10.38; MS (ES$^+$) 366, (ES$^-$) 364.

Example 91

2-(2-methyl-2H-indazol-7-ylamino)-9-cyclopentyl-8,9-dihydro-5,7,7-trimethyl-5H-pyrimido[4,5-b][1,4]diazepin-6(7H)-one (I-91)

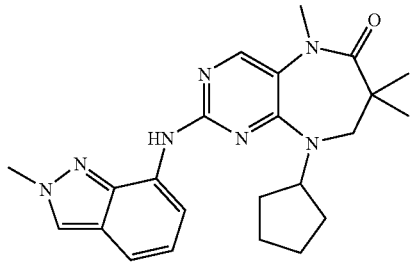

Prepared using the appropriate reagents according to method D. NMR DMSO D$^6$ 1.15 (6H, s), 1.53-1.78 (6H, m), 1.81-1.93 (2H, m), 3.19 (3H, s), 3.53 (2H, s), 4.22 (3H, s), 5.18 (1H, dt), 7.05 (1H, t), 7.47 (1H, d), 7.80 (1H, d), 8.02 (1H, s), 8.43 (1H, s), 9.60 (1H, br s); HPLC rt(min): 10.19; MS (ES$^+$) 420.

Example 92

Method K: 2-([1,2,4]triazolo[1,5-a]pyridin-8-ylamino)-9-cyclopentyl-8,9-dihydro-5,7,7-trimethyl-5H-pyrimido[4,5-b][1,4]diazepin-6(7H)-one (I-92)

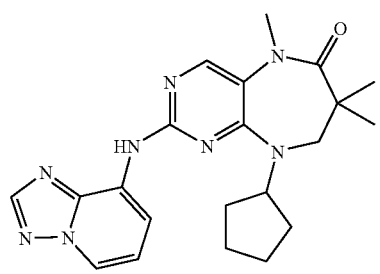

To 2-Chloro-9-cyclopentyl-8,9-dihydro-5,7,7-trimethyl-5H-pyrimido[4,5-b][1,4]diazepin-6(7H)-one (50 mg, 0.16 mmol) and triazolopyridinamine (22 mg, 0.16 mmol) in dioxane (1.5 mL) was added xantphos (2.8 mg, 0.005 mmol), palladium(II) acetate (0.7 mg, 0.003 mmol) and cesium carbonate (106 mg, 0.32 mmol). The reaction mixture was heated to 160° C. in a microwave for 40 minutes. The crude mixture was filtered through a path of celite and washed with methanol. The resulting mixture was concentrated in vacuo and purified by reverse phase preparative HPLC [Waters Sunfire C18, 10 uM, 100 Å column, gradient 10%-95% B (solvent A: 0.05% TFA in water; solvent B: CH3CN) over 16 minutes at 25 mL/min] to afford the title compound as a TFA salt (6.2 mg). NMR DMSO $D^6$ 1.13 (6H, s), 1.53-1.66 (4H, m), 1.68-1.77 (2H, m), 1.81-1.90 (2H, m), 3.20 (3H, s), 3.46 (2H, s), 5.15 (1H, dt), 7.21 (1H, t), 8.05 (1H, s), 8.23 (1H, d), 8.53 (1H, s), 8.64 (1H, d), 9.05 (1H, br s); HPLC rt(min): 9.71; MS (ES+) 407, (ES−) 405.

Example 93

4-(9-cyclopentyl-6,7,8,9-tetrahydro-5,7,7-trimethyl-6-oxo-5H-pyrimido[4,5-b][1,4]diazepin-2-ylamino)-N-cyclopropyl-3-methoxybenzamide (I-93)

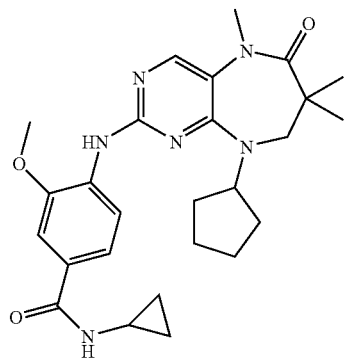

Prepared using the appropriate reagents according to method E. NMR DMSO $D^6$ 0.55-0.59 (2H, m), 0.68-0.73 (2H, m), 1.09 (6H, s), 1.54-1.68 (4H, m), 1.70-1.78 (2H, m), 1.83-1.95 (2H, m), 2.79-2.84 (1H, m), 3.19 (3H, s), 3.38 (2H, s), 4.03 (3H, s), 5.16-5.22 (1H, m), 7.43-7.47 (2H, m), 7.70 (1H, br s), 7.99 (1H, s), 8.32-8.35 (2H, m); HPLC rt(min): 9.60; MS (ES+) 479, (ES−) 477.

Example 94

4-(9-cyclopentyl-6,7,8,9-tetrahydro-5,7,7-trimethyl-6-oxo-5H-pyrimido[4,5-b][1,4]diazepin-2-ylamino)-N-cyclobutyl-3-methoxybenzamide (I-94)

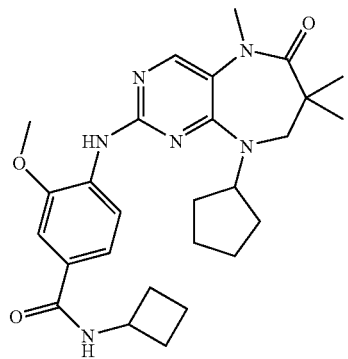

Prepared using the appropriate reagents according to method E. NMR DMSO $D^6$ 1.10 (6H, s), 1.58-1.78 (8H, m), 1.84-1.91 (2H, m), 2.03-2.13 (2H, m), 2.18-2.23 (2H, m), 3.19 (3H, s), 3.38 (2H, s), 3.95 (3H, s), 4.37-4.46 (1H, m), 5.15-5.23 (1H, m), 7.46-7.49 (2H, m), 7.69 (1H, s), 7.99 (1H, s), 8.36 (1H, d), 8.46 (1H, d); HPLC rt(min): 10.10; MS (ES+) 493, (ES−) 491.

Example 95

4-[4-(9-cyclopentyl-5,7,7-trimethyl-6-oxo-6,7,8,9-tetrahydro-5H-pyrimido[4,5-b][1,4]diazepin-2-ylmethyl)-3-methoxybenzoylamino]-piperidine-1-carboxylic acid tert-butyl ester (I-95)

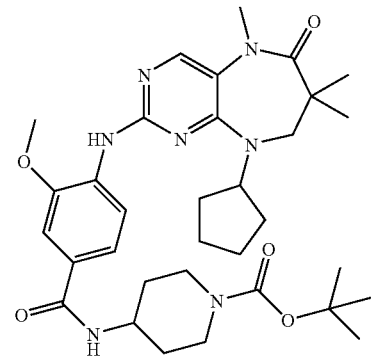

Prepared using the appropriate reagents according to method D. NMR DMSO $D^6$ 1.15 (6H, s), 1.45 (3H, s), 1.48 (9H, s), 1.64-1.97 (10H, m), 2.90 (2H, br s), 3.25 (3H, s), 3.44 (2H, s), 4.01 (3H, s), 4.02-4.10 (2H, br s), 5.21-5.32 (1H, m), 7.51-7.54 (2H, m), 7.76 (1H, s), 8.06 (1H, s), 8.18 (1H, d), 8.43 (1H, s); HPLC rt(min): 10.50; MS (ES+) 622, (ES−) 620.

Example 96

4-(6,7,8,9-tetrahydro-5,7,7-trimethyl-9-((R)-1-methylpiperidine-3-yl)-6-oxo-5H-pyrimido[4,5-b][1,4]diazepin-2-ylamino)-3-methoxy-N-methylbenzamide (I-96)

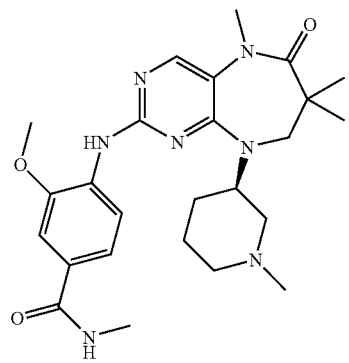

Prepared using the appropriate reagents according to method D. NMR DMSO $D^6$ 1.08 (3H, s), 1.10 (3H, s), 1.5-1.92 (5H, m), 2.00-2.10 (2H, m), 2.23 (3H, s), 2.79 (3H, d), 2.87 (1H, br d), 3.18 (3H, s), 3.42 (2H, s), 3.94 (3H, s), 4.86

(1H, tt), 7.45 (1H, dd), 7.49 (1H, d), 7.66 (1H, s), 7.99 (1H, s), 8.30 (1H, q), 8.38 (1H, d); HPLC rt(min): 7.64; MS (ES⁺) 482, (ES⁻) 480.

Example 97

4-(6,7,8,9-tetrahydro-5,7,7-trimethyl-9-((R)-1-methylpiperidine-4-yl)-6-oxo-5H-pyrimido[4,5-b][1,4]diazepin-2-ylamino)-3-methoxy-N-methylbenzamide (I-97)

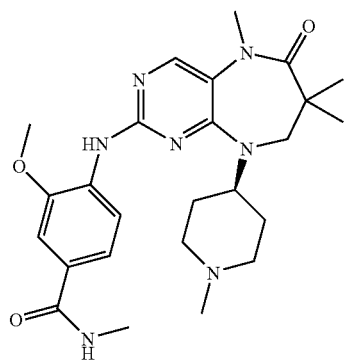

Prepared using the appropriate reagents according to method D. NMR DMSO D⁶ 1.09 (6H, s), 1.66 (2H, br d), 1.83 (2H, dq), 2.00-2.15 (2H, m), 2.24 (3H, s), 2.79 (3H, d), 2.92 (2H, br d), 3.18 (3H, s), 3.38 (2H, s), 3.94 (3H, s), 4.71 (1H, tt), 7.47 (1H, dd), 7.50 (1H, d), 7.68 (1H, s), 7.98 (1H, s), 8.25-8.34 (2H, m); HPLC rt(min): 7.28; MS (ES⁺) 482, (ES⁻) 480.

Example 98

2-(4-(5-hydroxy-3-methyl-1H-pyrazol-1-yl)phenylamino)-9-cyclopentyl-8,9-dihydro-5,7,7-trimethyl-5H-pyrimido[4,5-b][1,4]diazepin-6(7H)-one (I-98)

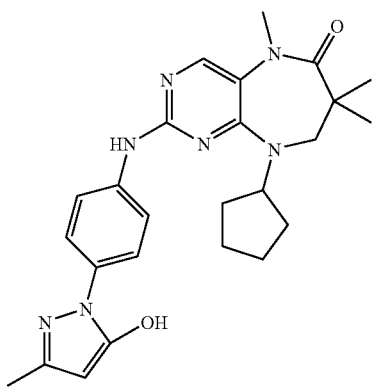

Prepared using the appropriate reagents according to method D. NMR DMSO D⁶ 1.14 (6H, s), 1.51-1.77 (6H, m), 1.81-1.92 (2H, m), 2.12 (3H, s), 3.19 (3H, s), 3.46 (2H, s), 5.17 (1H, dt), 5.36 (1H, s), 7.56-7.68 (4H, m), 7.90 (1H, s), 9.79 (1H, br s); HPLC rt(min): 8.75; MS (ES⁺) 462, (ES⁻) 460.

Example 99

2-(4-(1H-pyrazol-3-yl)phenylamino)-9-cyclopentyl-8,9-dihydro-5,7,7-trimethyl-5H-pyrimido[4,5-b][1,4]diazepin-6(7H)-one (I-99)

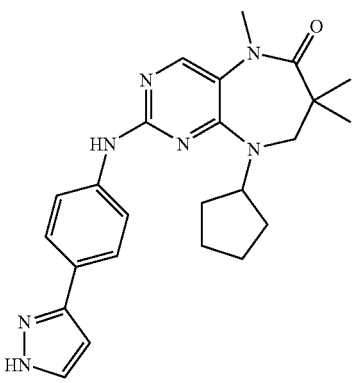

Prepared using the appropriate reagents according to method D. NMR DMSO D⁶ 1.15 (6H, s), 1.55-1.78 (6H, m), 1.82-1.93 (2H, m), 3.19 (3H, s), 3.48 (2H, s), 5.19 (1H, dt), 6.67 (1H, d), 7.62 (2H, d), 7.70 (1H, d), 7.78 (2H, d), 7.92 (1H, s), 9.93 (1H, br s); HPLC rt(min): 8.45; MS (ES⁺) 432, (ES⁻) 430.

Example 100

4-(9-cyclopentyl-6,7,8,9-tetrahydro-5,7,7-trimethyl-6-oxo-5H-pyrimido[4,5-b][1,4]diazepin-2-ylthio)-N-methylbenzamide (I-100)

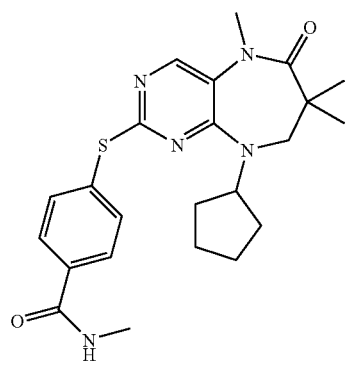

Method L: 4-(9-cyclopentyl-6,7,8,9-tetrahydro-5,7,7-trimethyl-6-oxo-5H-pyrimido[4,5-b][1,4]diazepin-2-ylthio)-benzoic acid

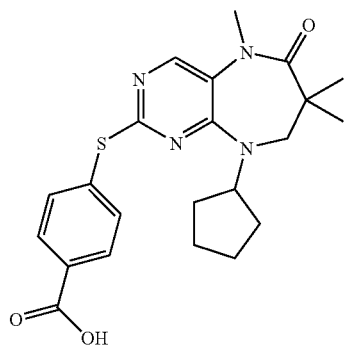

A solution of 2-Chloro-9-cyclopentyl-8,9-dihydro-5,7,7-trimethyl-5H-pyrimido[4,5-b][1,4]diazepin-6(7H)-one (100 mg, 0.324 mmol) and 4-mercaptobenzoic acid (50 mg, 0.324 mmol) in acetonitrile (5 mL) was heated under reflux for 4 hours. Additional 4-mercaptobenzoic acid (50 mg, 0.324 mmol) was added and the reaction mixture was heated under reflux for 16 hours. After cooling, the crude reaction mixture was filtered through Celite and washed with acetonitrile. The crude product was purified by column chromatography (0%-10% MeOH:CH$_2$Cl$_2$) and triturated with MeOH to give the title compound (37 mg, 27% yield) as a white solid. NMR DMSO D$^6$ 1.03 (6H, s), 1.20-1.38 (6H, m), 1.42-1.53 (2H, m), 3.17 (3H, s), 3.27 (2H, s), 4.47 (1H, dt), 7.72 (2H, dd), 7.99 (2H, dd), 8.02 (1H, s); MS (ES$^+$) 427, (ES$^-$) 425.

4-(9-cyclopentyl-6,7,8,9-tetrahydro-5,7,7-trimethyl-6-oxo-5H-pyrimido[4,5-b][1,4]diazepin-2-ylthio)-N-methyl-benzamide (I-100) has been Prepared using the appropriate reagents according to method D.

NMR DMSO D$^6$ 1.03 (6H, s), 1.22-1.44 (6H, m), 1.46-1.58 (2H, m), 2.80 (3H, d), 3.17 (3H, s), 3.28 (2H, s), 4.51 (1H, dt), 7.68 (2H, d), 7.91 (2H, d), 8.02 (1H, s), 8.47-8.53 (1H, m); HPLC rt(min): 8.86; MS (ES$^+$) 440, (ES$^-$) 438.

Example 101

2-(9-cyclopentyl-6,7,8,9-tetrahydro-5,7,7-trimethyl-6-oxo-5H-pyrimido[4,5-b][1,4]diazepin-2-ylamino)-3-methoxy-N-(piperidin-4-yl)benzamide (I-101)

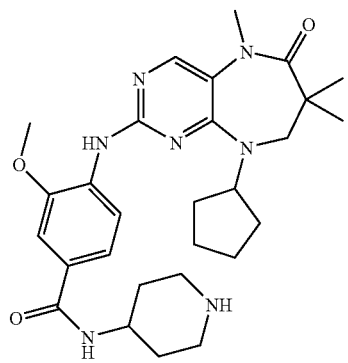

Prepared using the appropriate reagents according to method F. NMR MeOD 1.21 (6H, s), 1.61-1.85 (8H, m), 2.02-2.15 (4H, m), 2.85 (2H, br t), 3.23 (2H, br d), 3.39 (3H, s), 3.48 (2H, s), 4.02 (3H, s), 4.03-4.10 (1H, m), 5.36 (1H, quint), 7.50-7.54 (2H, m), 7.94 (1H, s), 8.48 (1H, d); HPLC rt(min): 9.00; MS (ES$^+$) 522, (ES$^-$) 520.

Example 102

2-(2-methoxyphenylamino)-9-cyclopentyl-8,9-dihydro-5,7,7-trimethyl-5H-pyrimido[4,5-b][1,4]diazepin-6(7H)-one (I-102)

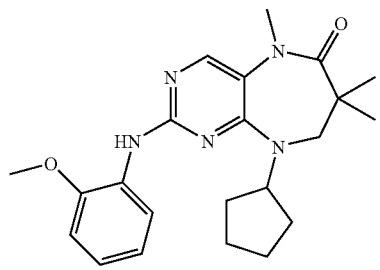

Prepared using the appropriate reagents according to method D. NMR DMSO D$^6$ 1.14 (6H, s), 1.48-1.84 (8H, m), 3.18 (3H, s), 3.49 (2H, s), 3.87 (3H, s), 5.07 (1H, dt), 6.99 (1H, dt), 7.14 (1H, dt), 7.19 (1H, dt), 7.83 (1H, d), 7.94 (1H, s), 9.13 (1H, br s); HPLC rt(min): 10.65; MS (ES$^+$) 396, (ES$^-$) 394.

Example 103

Methyl 4-(9-cyclopentyl-5,7,7-trimethyl-6-oxo-6,7,8,9-tetrahydro-5H-pyrimido[4,5-b][1,4]diazepin-2-ylamino)-3-methoxyphenylcarbamate (I-103)

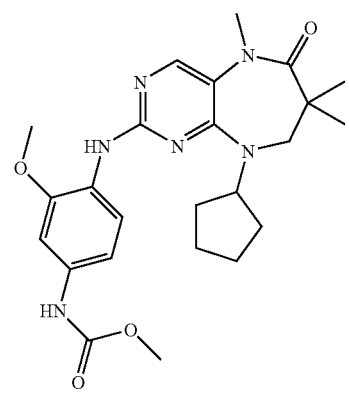

Prepared using the appropriate reagents according to method D. NMR DMSO D$^6$ 1.10 (6H, s), 1.56 (4H, br m), 1.71 (2H, br m), 1.82 (2H, br m), 3.17 (3H, s), 3.35 (2H, s), 3.66 (3H, s), 3.81 (3H, s), 5.11 (1H, br m), 6.96 (1H, dd), 7.23 (1H, s), 7.44 (1H, s), 7.90 (1H, s), 7.98 (1H, d), 9.46 (1H br s); HPLC rt(min): 9.60; MS (ES$^+$) 469, (ES$^-$) 467.

Example 104

N-(4-(9-cyclopentyl-5,7,7-trimethyl-6-oxo-6,7,8,9-tetrahydro-5H-pyrimido[4,5-b][1,4]diazepin-2-ylamino)-3-methoxyphenyl)-2-methoxyacetamide (I-104)

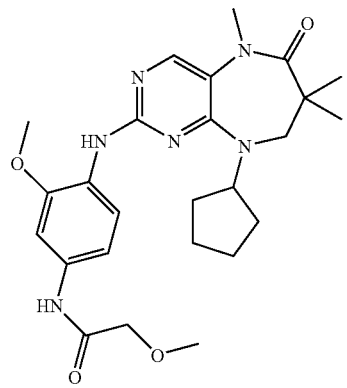

Prepared using the appropriate reagents according to method D. NMR DMSO D$^6$ 1.09 (6H, s), 1.57 (4H, br m), 1.71 (2H, br m), 1.84 (2H, br m), 3.18 (3H, s), 3.35 (2H, s), 3.39 (3H, s), 3.83 (3H, s), 3.98 (2H, s), 5.13 (1H, br m), 7.23 (1H, dd), 7.46 (2H, s), 7.92 (1H, s), 8.06 (1H, d), 9.60 (1H, br s); HPLC rt(min): 9.50; MS (ES$^+$) 483, (ES$^-$) 481.

Example 105

[4-(9-cyclopentyl-6,7,8,9-tetrahydro-5,7,7-trimethyl-6-oxo-5H-pyrimido][4,5-b][1,4]diazepin-2-ylamino)-N-(2,2,2-trifluoroethyl)-3-methoxybenzamide (I-105)

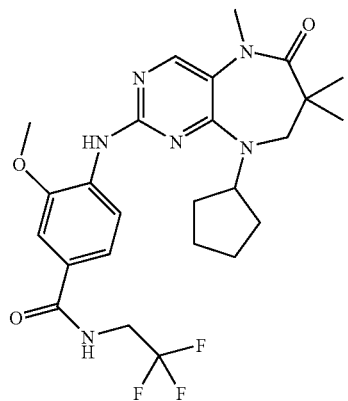

Prepared using the appropriate reagents according to method D. NMR DMSO D$^6$ 1.10 (6H, s), 1.63 (4H, br m), 1.75 (2H, br m), 1.89 (2H, br m), 3.19 (3H, s), 3.38 (2H, s), 3.95 (3H, s), 4.10 (2H, m), 5.20 (1H, m), 7.54 (2H, m), 7.73 (NH), 8.00 (1H, s), 8.43 (1H, m), 8.41 (1H, s); HPLC rt(min): 9.94; MS (ES$^+$) 521, (ES$^-$) 519.

Example 106

9-cyclopentyl-5,7,7-trimethyl-2-[3-(4-methylpiperazine-1-carbonyl)-phenylamino]-5,7,8,9-tetrahydropyrimido[4,5-b][1,4]diazepin-6-one (I-106)

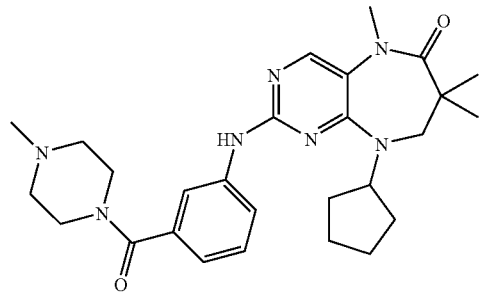

Prepared using the appropriate reagents according to method D. NMR DMSO D$^6$ 1.10 (6H, s), 1.57 (4H, br m), 1.71 (2H, br m), 1.85 (2H, br m), 2.82-3.34 (8H, br m), 3.19 (3H, s), 3.36 (3H, s), 5.23 (1H, m), 6.97 (1H, m), 7.31 (1H, m), 7.69 (1H, m), 7.96 (2H, m), 9.33 (1H, s); HPLC rt(min): 9.12; MS (ES$^+$) 492, (ES$^-$) 490.

Example 107

Method M: 4-(9-cyclopentyl-6,7,8,9-tetrahydro-5,7,7-trimethyl-6-oxo-5H-pyrimido[4,5-b][1,4]diazepin-2-yloxy)-3-methoxybenzoic acid (I-107)

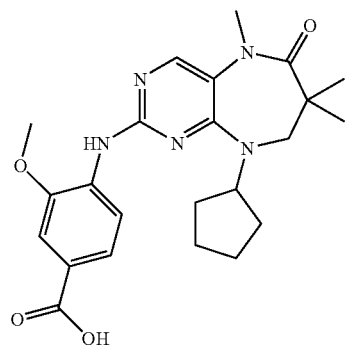

To 2-Chloro-9-cyclopentyl-8,9-dihydro-5,7,7-trimethyl-5H-pyrimido[4,5-b][1,4]diazepin-6(7H)-one (100 mg, 0324 mmol) in DMF (5 mL) was added vanillic acid (55 mg, 0.324 mmol) and potassium carbonate (90 mg, 0.648 mmol). The reaction mixture was heated at 80° C. for 48 hours. After cooling, the solvent was removed in vacuo and the residue taken up in methanol and purified by reverse phase preparative HPLC [Waters Sunfire C18, 10 uM, 100 Å column, gradient 10%-95% B (solvent A: 0.05% TFA in water; solvent B: CH3CN) over 16 minutes at 25 mL/min] to afford the title compound as a TFA salt (12 mg, 7% yield). NMR DMSO D$^6$ 1.06 (6H, s), 1.23-1.37 (2H, m), 1.38-1.50 (2H, m), 1.51-1.62 (4H, m), 3.18 (3H, s), 3.34 (2H, s), 3.76 (3H, s), 4.58 (1H, dt), 7.26 (1H, d), 7.56-7.62 (2H, m), 7.99 (1H, s); HPLC rt(min): 7.18; MS (ES$^+$) 441, (ES$^-$) 439.

Example 108

2-(2,3-dihydro-2-oxo-1H-benzo[d]imidazol-6-ylamino)-9-cyclopentyl-8,9-dihydro-5,7,7-trimethyl-5H-pyrimido[4,5-b][1,4]diazepin-6(7H)-one (I-108)

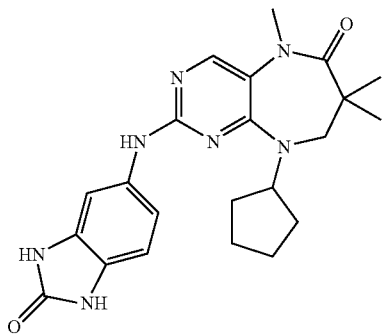

Prepared using the appropriate reagents according to method D. NMR DMSO $D^6$ 1.14 (6H, s), 1.44-1.76 (6H, m), 1.78-1.92 (2H, m), 3.17 (3H, s), 3.46 (2H, s), 5.13 (1H, dt), 6.89 (1H, d), 7.05 (1H, d), 7.13 (1H, s), 7.81 (1H, s), 9.75 (1H, br s), 10.57 (1H, s), 10.67 (1H, s); HPLC rt(min): 8.21; MS (ES$^+$) 422, (ES$^-$) 420.

Example 109

2-(2,3-dihydro-3-oxo-1H-indazol-5-ylamino)-9-cyclopentyl-8,9-dihydro-5,7,7-trimethyl-5H-pyrimido[4,5-b][1,4]diazepin-6(7H)-one (I-109)

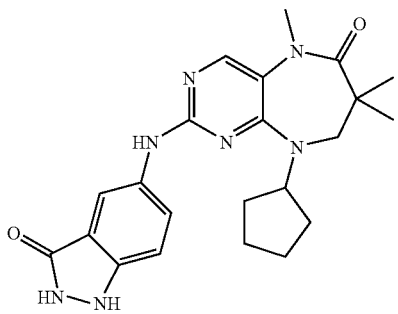

Prepared using the appropriate reagents according to method D. NMR DMSO $D^6$ 1.14 (6H, s), 1.50-1.74 (6H, m), 1.79-1.90 (2H, m), 3.18 (3H, s), 3.46 (2H, s), 5.18 (1H, dt), 7.27 (1H, d), 7.37 (1H, dd), 7.85 (1H, s), 7.88 (1H, s), 9.76 (1H, br s), 11.28 (1H, br s); HPLC rt(min): 8.01; MS (ES$^+$) 422, (ES$^-$) 420.

Example 110

2-(1-methyl-1H-indazol-5-ylamino)-9-cyclopentyl-8,9-dihydro-5,7,7-trimethyl-5H-pyrimido[4,5-b][1,4]diazepin-6(7H)-one (I-110)

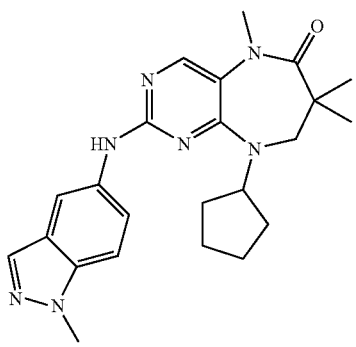

Prepared using the appropriate reagents according to method D. NMR DMSO $D^6$ 1.15 (6H, s), 1.43-1.77 (6H, m), 1.78-1.88 (2H, m), 3.18 (3H, s), 3.48 (2H, s), 4.05 (3H, s), 5.14 (1H, dt), 7.48 (1H, dd), 7.66 (1H, d), 7.87 (1H, s), 7.96 (1H, s), 7.99 (1H, s), 10.01 (1H, br s); HPLC rt(min): 9.65; MS (ES$^+$) 420, (ES$^-$) 418.

Example 111

N-(3-(9-cyclopentyl-6,7,8,9-tetrahydro-5,7,7-trimethyl-6-oxo-5H-pyrimido[4,5-b][1,4]diazepin-2-ylamino)phenyl)acetamide (I-111)

Prepared using the appropriate reagents according to method D. HPLC rt(min): 8.95; MS (ES$^+$) 423, (ES$^-$) 421.

Example 112

N-(4-(9-cyclopentyl-6,7,8,9-tetrahydro-5,7,7-trimethyl-6-oxo-5H-pyrimido[4,5-b][1,4]diazepin-2-ylamino)phenyl)acetamide (I-112)

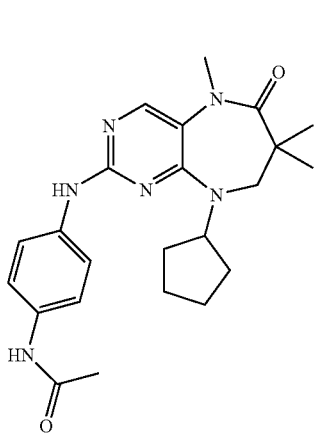

Prepared using the appropriate reagents according to method D. HPLC rt(min): 8.74; MS (ES+) 423, (ES−) 421.

Example 113

4-((S)-9-cyclopentyl-7-ethyl-6,7,8,9-tetrahydro-5-methyl-6-oxo-5H-pyrimido[4,5-b][1,4]diazepin-2-ylamino)-3-methoxy-N-(1-methylpiperidin-4-yl)benzamide (I-113)

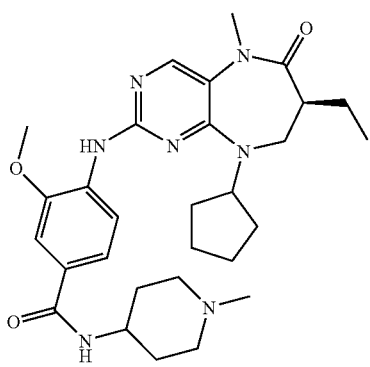

Prepared using the appropriate reagents according to method D. NMR DMSO $D^6$ 0.88 (3H, t), 1.04 (1H, d), 1.25-1.36 (1H, m), 1.52-1.85 (11H, m), 1.95-2.12 (3H, m), 2.20 (3H, s), 2.57-2.64 (1H, m), 2.78-2.83 (2H, m), 3.20 (3H, s), 3.41-3.45 (2H, m), 3.75-3.80 (1H, m), 3.95 (3H, s), 4.78 (1H, quint), 7.48 (1H, d), 7.49 (1H, s), 7.75 (1H, s), 8.07 (1H, d), 8.10 (1H, s), 8.39 (1H, d); HPLC rt(min): 9.70; MS (ES+) 536, (ES−) 534.

Example 114

2-(1H-indazo-5-ylamino)-9-cyclopentyl-8,9-dihydro-5,7,7-trimethyl-5H-pyrimido[4,5-b][1,4]diazepin-6(7H)-one (I-114)

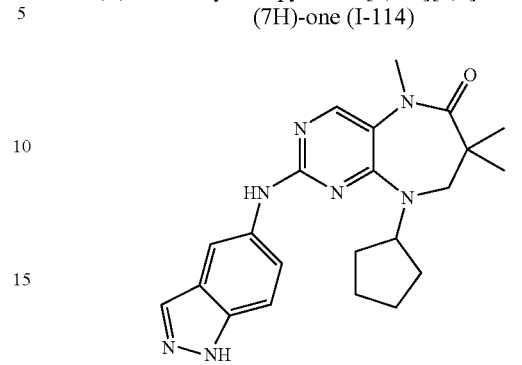

Prepared using the appropriate reagents according to method D. NMR DMSO $D^6$ 1.14 (6H, s), 1.44-1.93 (8H, m), 3.18 (3H, s), 3.47 (2H, s), 5.14 (1H, dt), 7.43 (1H, dd), 7.55 (1H, d), 7.86 (1H, s), 7.98 (1H, s), 8.02 (1H, s), 9.92 (1H, br s), 13.06 (1H, br s); HPLC rt(min): 8.99; MS (ES+) 406, (ES−) 404.

Example 115

2-(1H-benzo[d]imidazol-4-ylamino)-9-cyclopentyl-8,9-dihydro-5,7,7-trimethyl-5H-pyrimido[4,5-b][1,4]diazepin-6(7H)-one (I-115)

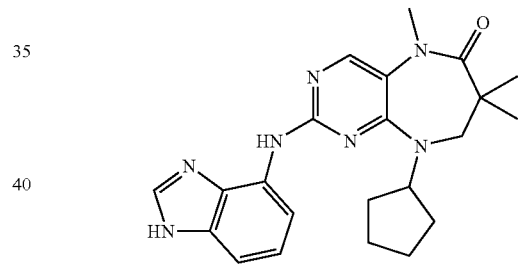

Prepared using the appropriate reagents according to method D. NMR DMSO $D^6$ 1.13 (6H, s), 1.38-1.73 (8H, m), 3.20 (3H, s), 3.42 (2H, s), 4.96 (1H, dt), 7.42 (1H, t), 7.50 (1H, d), 7.70 (1H, d), 8.01 (1H, s), 9.09 (1H, br s), 9.85 (1H, br s); HPLC rt(min): 9.37; MS (ES+) 406, (ES−) 404.

Example 116

2-(3-aminophenylamino)-9-cyclopentyl-8,9-dihydro-5,7,7-trimethyl-5H-pyrimido[4,5-b][1,4]diazepin-6(7H)-one (I-116)

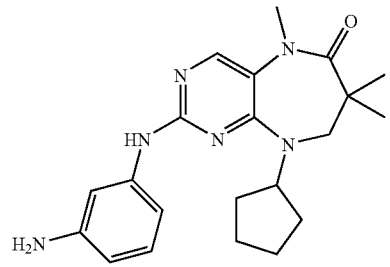

Prepared using the appropriate reagents according to method D. NMR DMSO D$^6$ 1.12 (6H, s), 1.53-1.73 (6H, m), 1.80-1.92 (2H, m), 3.18 (3H, s), 3.43 (2H, s), 5.19 (1H, dt), 6.61 (1H, d), 7.14-7.24 (3H, m), 7.89 (1H, s), 9.67 (1H, br s); HPLC rt(min): 9.16; MS (ES$^+$) 381, (ES$^-$) 379.

Example 117

2-(4-aminophenylamino)-9-cyclopentyl-8,9-dihydro-5,7,7-trimethyl-5H-pyrimido[4,5-b][1,4]diazepin-6(7H)-one (I-117)

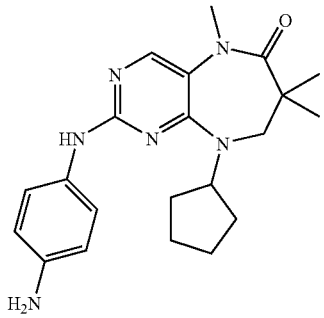

Prepared using the appropriate reagents according to method D. NMR DMSO D$^6$ 1.12 (6H, s), 1.50-1.92 (8H, m), 3.18 (3H, s), 3.43 (2H, s), 5.16 (1H, dt), 7.01-7.10 (2H, m), 7.50-7.63 (2H, m), 7.89 (1H, s), 9.67 (1H, br s); HPLC rt(min): 8.76; MS (ES$^+$) 381, (ES$^-$) 379.

Example 118

4-(9-cyclopentyl-6,7,8,9-tetrahydro-5,7,7-trimethyl-6-oxo-5H-pyrimido[4,5-b][1,4]diazepin-2-ylamino)-3-ethyl-N-methylbenzamide (I-118)

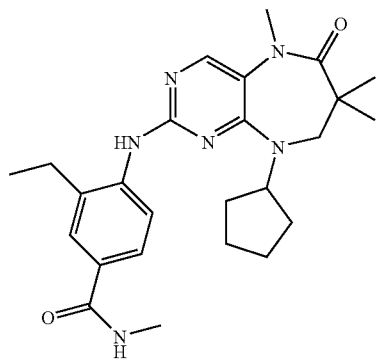

Prepared using the appropriate reagents according to method D. NMR DMSO D$^6$ 1.13 (6H, s), 1.18 (3H, t), 1.44 (2H, br m), 1.57-1.69 (6H, br m), 2.51 (2H, q), 2.64 (3H, m), 2.79 (3H, s), 3.45 (3H, s), 4.95 (1H, m), 7.69 (2H, m), 7.78 (1H, m), 7.87 (1H, s), 8.38 (1H, s); HPLC rt(min): 9.24; MS (ES$^+$) 451, (ES$^-$) 449.

Example 119

4-((S)-9-cyclopentyl-7-ethyl-6,7,8,9-tetrahydro-5-methyl-6-oxo-5H-pyrimido[4,5-b][1,4]diazepin-2-ylamino)-N-cyclobutyl-3-methoxybenzamide (I-119)

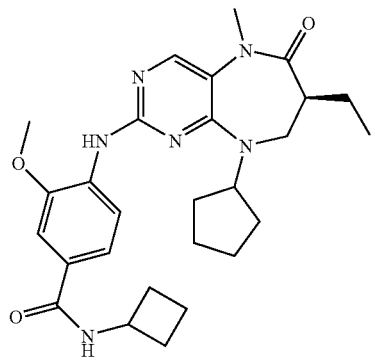

Prepared using the appropriate reagents according to method D. NMR DMSO D$^6$ 1.13 (6H, s), 1.18 (3H, t), 1.44 (2H, br m), 1.57-1.69 (6H, br m), 2.51 (2H, q), 2.64 (3H, m), 2.79 (3H, s), 3.45 (3H, s), 4.95 (1H, m), 7.69 (2H, m), 7.78 (1H, m), 7.87 (1H, s), 8.38 (1H, s); HPLC rt(min): 10.10; MS (ES$^+$) 493, (ES$^-$) 491.

Example 120

4-(9-cyclopentyl-6,7,8,9-tetrahydro-5,7,7-trimethyl-6-oxo-5H-pyrimido[4,5-b][1,4]diazepin-2-ylamino)-3-methoxybenzoic acid (I-120)

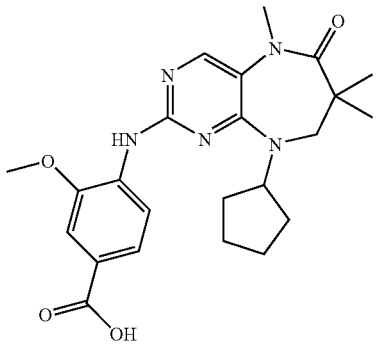

Prepared using the appropriate reagents according to method D. HPLC rt(min): 7.81; MS (ES$^+$) 440, (ES$^-$) 438.

Example 121

3-(2-(pyrrolidin-1-yl)ethoxy)-4-(9-cyclopentyl-6,7,8,9-tetrahydro-5,7,7-trimethyl-6-oxo-5H-pyrimido[4,5-b][1,4]diazepin-2-ylamino)-N-methylbenzamide (I-121)

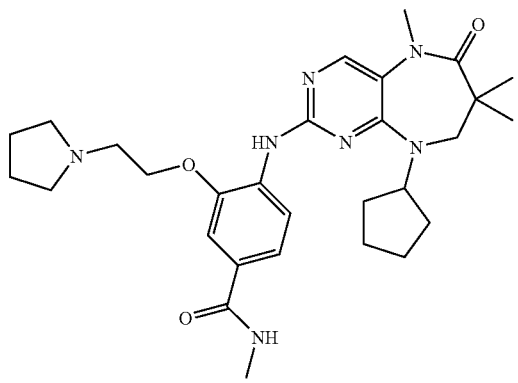

Prepared using the appropriate reagents according to method D. NMR DMSO D$^6$ 1.11 (6H, s), 1.61 (4H, br m), 1.74 (2H, br m), 1.84 (2H, br m), 1.91 (2H, br m), 2.06 (2H, br m), 2.79 (3H, m), 3.19 (5H, m), 3.43 (2H, s), 3.68 (4H, br m), 4.42 (2H, m), 5.14 (1H, m), 7.50-7.55 (2H, m), 8.02 (1H, s), 8.24 (1H, m), 8.38 (1H, s); HPLC rt(min): 8.87; MS (ES$^+$) 536, (ES$^-$) 534.

Example 122

4-(9-benzyl-6,7,8,9-tetrahydro-5,7,7-trimethyl-6-oxo-5H-pyrimido[4,5-b][1,4]diazepin-2-ylamino)-3-methoxy-N-methylbenzamide (I-122)

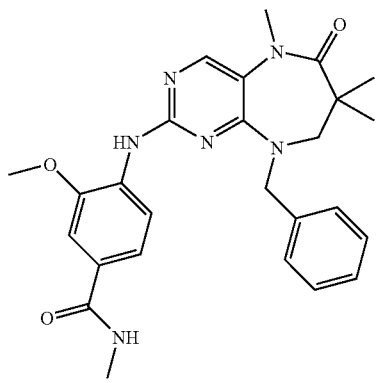

Method N: 2-Chloro-8,9-dihydro-5,7,7-trimethyl-5H-pyrimido[4,5-b][1,4]diazepin-6(7H)-one

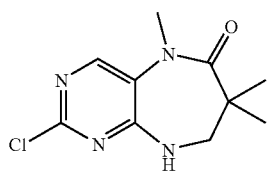

9-allyl-2-chloro-8,9-dihydro-5,7,7-trimethyl-5H-pyrimido[4,5-b][1,4]diazepin-6(7H)-one (1.21 g, 4.34 mmol, prepared by method C) and dichloro(2,7-dimethyl-octa-2,6-diene-1,8-yl) ruthenium (IV) (0.26 g, 0.43 mmol, prepared following Tetrahedron Letters, 1965, 47, 4187) were suspended in dioxane (10 mL) and water (30 mL) in a pressure tube. The resultant suspension was stirred at 100° C. over two nights. The reaction was allowed to cool to room temperature and filtered through celite. The celite was washed copiously with water and DCM. The combined filtrates were concentrated under reduced pressure and partitioned between brine and DCM. The aqueous layer was extracted with dichloromethane (5×20 mL) and the combined organics were dried over sodium sulfate, filtered and concentrated under reduced pressure to give a brown gum. This gum was purified by column chromatography (50% EtOAc in hexanes, loaded on silica, ~100 mL silica) to give a white solid, which was triturated with diethyl ether. The solid was collected by filtration and washed with diethyl ether (1×2 mL) and pentane (3×2 mL) to give a cream powder (351 mg, 34% yield). NMR DMSO D$^6$ 1.09 (6H, s), 3.22 (3H, s), 3.25 (2H, d), 8.08 (1H, s), 8.48 (1H, br d); MS (ES$^+$) 241.

Method O: 9-Benzyl-2-chloro-8,9-dihydro-5,7,7-trimethyl-5H-pyrimido[4,5-b][1,4]diazepin-6(7H)-one

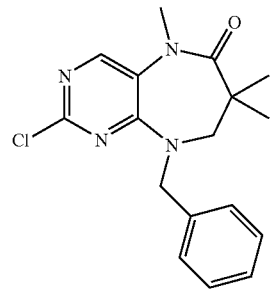

2-Chloro-8,9-dihydro-5,7,7-trimethyl-5H-pyrimido[4,5-b][1,4]diazepin-6(7H)-one (50 mg, 0.21 mmol) and benzylbromide (30 μl, 0.25 mmol) in DMA (0.5 ml) was treated with sodium hydride 60% oil dispersion (9 mg, 0.23 mmol) at room temperature. The mixture was stirred at room temperature for 5 hours. The reaction mixture was concentrated under reduced pressure. The residue was purified by column chromatography (50% EtOAc in hexanes, loaded on silica, ~50 mL silica) to give the title compound as a white solid (63 mg, 91%). NMR DMSO D$^6$ 1.00 (6H, s), 3.22 (3H, s), 3.53 (2H, s), 4.91 (2H, s), 7.28-7.39 (5H, m), 8.12 (1H, s); MS (ES$^+$) 331.

4-(9-benzyl-6,7,8,9-tetrahydro-5,7,7-trimethyl-6-oxo-5H-pyrimido[4,5-b][1,4]diazepin-2-ylamino)-3-methoxy-N-methylbenzamide (I-122)

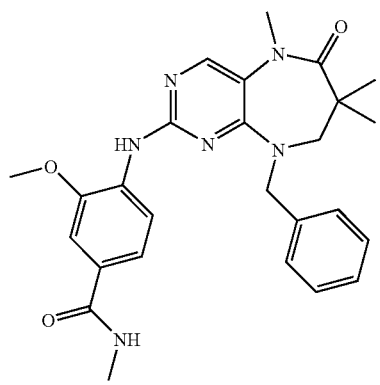

Prepared using the appropriate reagents according to method D. NMR DMSO D$^6$ 1.03 (6H, s), 2.75 (3H, d), 3.23 (3H, s), 3.47 (2H, s), 3.90 (3H, s), 4.98 (2H, br s), 7.2-7.4 (6H, m), 7.45 (1H, s), 7.72 (1H, s), 8.07 (1H, s), 8.19 (1H, d), 8.27 (1H, br d); HPLC rt(min): 9.00; MS (ES⁺) 475, (ES⁻) 473.

Example 123

4-(9-(cyclobutylmethyl)-6,7,8,9-tetrahydro-5,7,7-trimethyl-6-oxo-5H-pyrimido[4,5-b][1,4]diazepin-2-ylamino)-3-methoxy-N-methylbenzamide (I-123)

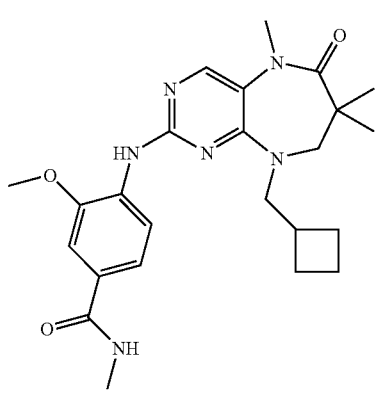

Prepared using the appropriate reagents according to method D. NMR DMSO D⁶ 1.09 (6H, s), 1.84 (4H, br m), 2.05 (2H, br m), 2.78 (4H, br m), 3.18 (3H, s), 3.50 (2H, s), 3.78 (2H, d), 3.94 (3H, s), 7.47 (2H, m), 7.67 (1H, s), 7.97 (1H, s), 8.34 (2H, br m); HPLC rt(min): 9.20; MS (ES⁺) 453, (ES⁻) 451.

Example 124

2-(1-oxoisoindolin-4-ylamino)-9-cyclopentyl-8,9-dihydro-5,7,7-trimethyl-5H-pyrimido[4,5-b][1,4]diazepin-6(7H)-one (I-124)

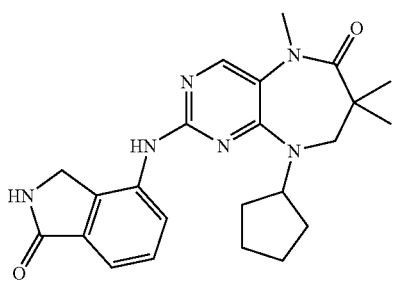

Prepared using the appropriate reagents according to method D. NMR DMSO D⁶ 1.09 (6H, s), 1.52 (4H, br m), 1.69 (2H, br m), 1.76 (2H, br m), 3.18 (3H, s), 3.34 (2H, s), 4.40 (2H, s), 5.15 (1H, m), 7.31 (1H, d), 7.40 (1H, t), 7.96 (1H, s), 8.08 (1H, d), 8.52 (1H, s), 8.86 (1H, s); HPLC rt(min): 8.90; MS (ES⁺) 421, (ES⁻) 419.

Example 125

2-(1-methyl-2-oxoindolin-5-ylamino)-9-cyclopentyl-8,9-dihydro-5,7,7-trimethyl-5H-pyrimido[4,5-b][1,4]diazepin-6(7H)-one (I-125)

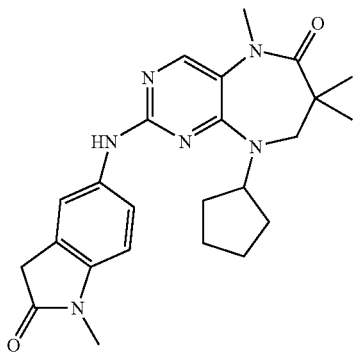

Prepared using the appropriate reagents according to method D. NMR DMSO D⁶ 1.13 (6H, s), 1.54 (4H, br m), 1.62 (2H, br m), 1.82 (2H, br m), 3.12 (3H, s), 3.17 (3H, s), 3.46 (2H, s), 3.55 (2H, s), 5.13 (1H, m), 6.96 (1H, m), 7.39 (1H, m), 7.54 (1H, s), 7.86 (1H, s), 9.89 (1H, s); HPLC rt(min): 9.24; MS (ES⁺) 435, (ES⁻) 433.

Example 126

6-(9-cyclopentyl-6,7,8,9-tetrahydro-5,7,7-trimethyl-6-oxo-5H-pyrimido[4,5-b][1,4]diazepin-2-ylamino)-N-methylpyridine-3-carboxamide (I-126)

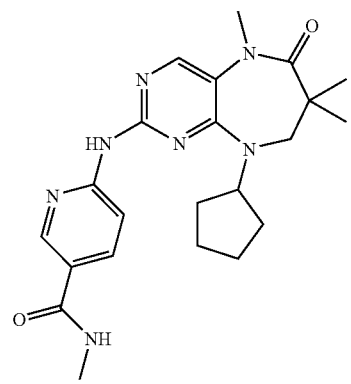

Prepared using the appropriate reagents according to method J. NMR DMSO D⁶ 1.09 (6H, s), 1.61 (4H, br m), 1.74 (2H, br m), 1.90 (2H, br m), 2.79 (3H, m), 3.20 (3H, s), 3.38 (2H, s), 5.20 (1H, m), 8.02 (1H, s), 8.15 (1H, m), 8.24 (1H, m), 8.42 (1H, s), 8.70 (1H, s), 9.71 (1H, s); HPLC rt(min): 8.63; MS (ES⁺) 424, (ES⁻) 422.

Example 127

2-(3-amino-1H-indazol-1-ylamino)-9-cyclopentyl-8,9-dihydro-5,7,7-trimethyl-5H-pyrimido[4,5-b][1,4]diazepin-6(7H)-one (I-127)

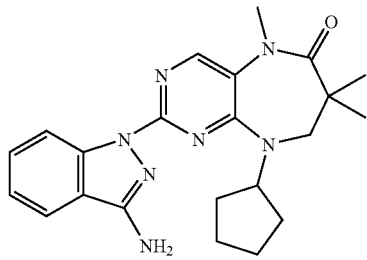

Prepared using the appropriate reagents according to method K. NMR DMSO $D^6$ 1.12 (6H, s), 1.61-1.84 (6H, m), 1.89-1.96 (2H, m), 3.24 (3H, s), 3.43 (2H, s), 5.39 (1H, dt), 6.04 (2H, s, NH2), 7.18 (1H, t), 7.46 (1H, t), 7.85 (1H, d), 8.14 (1H, s), 8.44 (1H, d); HPLC rt(min): 9.84; MS (ES$^+$) 406.

Example 128

2-(3-nitrophenylamino)-9-cyclopentyl-8,9-dihydro-5,7,7-trimethyl-5H-pyrimido[4,5-b][1,4]diazepin-6(7H)-one (I-128)

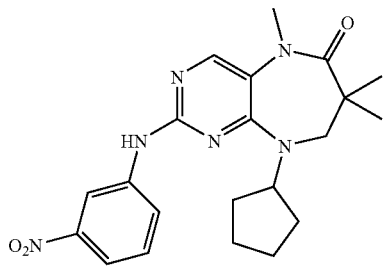

Prepared using the appropriate reagents according to method D. NMR DMSO $D^6$ 1.10 (6H, s), 1.52-1.65 (4H, m), 1.69-1.75 (2H, m), 1.84-1.96 (2H, m), 3.20 (3H, s), 3.39 (2H, s), 5.34 (1H, quint), 7.52 (1H, t), 7.73 (1H, dd), 7.88 (1H, d), 8.02 (1H, s), 8.92 (1H, d), 9.74 (1H, s); HPLC rt(min): 10.50; MS (ES$^+$) 411, (ES$^-$) 409.

Example 129

4-(9-cyclopentyl-6,7,8,9-tetrahydro-5,7,7-trimethyl-6-oxo-5H-pyrimido[4,5-b][1,4]diazepin-2-ylamino)-N-cyclopentyl-3-methoxybenzamide (I-129)

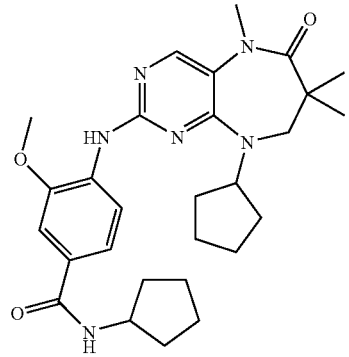

Prepared using the appropriate reagents according to method D. NMR CDCl$_3$ 1.13 (6H, m), 1.36-1.78 (12H, m), 1.88-1.98 (2H, m), 2.00-2.10 (2H, m), 3.22 (3H, s), 3.31 (2H, s), 3.91 (3H, s), 4.28-4.37 (1H, m), 5.18-5.30 (1H, m), 5.93 (1H, d), 7.14 (1H, d), 7.35 (1H, s), 7.64 (1H, br s), 7.77 (1H, s), 8.38 (1H, d); HPLC rt(min): 10.33; MS (ES$^+$) 507, (ES$^-$) 505.

Example 130

4-(9-cyclopentyl-6,7,8,9-tetrahydro-5,7,7-trimethyl-6-oxo-5H-pyrimido[4,5-b][1,4]diazepin-2-ylamino)-N-tert-butyl-3-methoxybenzamide (I-130)

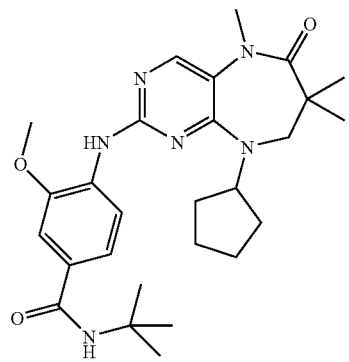

Prepared using the appropriate reagents according to method E. NMR CDCl$_3$ 1.22 (6H, s), 1.51 (9H, s), 1.50-1.87 (6H, m), 1.96-2.06 (2H, m), 3.32 (3H, s), 3.99 (2H, s), 5.26-5.38 (1H, m), 5.95 (1H, s), 7.19 (1H, d), 7.43 (1H, s), 7.22 (1H, br s), 7.86 (1H, s), 8.45 (1H, d); HPLC rt(min): 10.36; MS (ES$^+$) 495, (ES$^-$) 493.

Example 131

4-(9-cyclopentyl-6,7,8,9-tetrahydro-5,7,7-trimethyl-6-oxo-5H-pyrimido[4,5-b][1,4]diazepin-2-ylamino)-N-(cyclopropylmethyl)-3-methoxybenzamide (I-131)

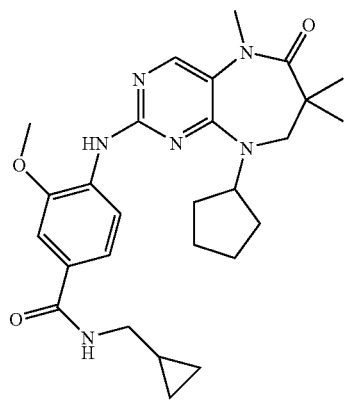

Prepared using the appropriate reagents according to method E. NMR CDCl₃ 0.08-0.13 (2H, m), 0.35-0.41 (2H, m), 0.75-0.84 (1H, m), 1.01 (6H, s), 1.27-1.65 (6H, m), 1.76-1.85 (2H, m), 3.08-3.18 (2H, m), 3.11 (3H, s), 3.19 (2H, s), 3.79 (3H, s), 5.08-5.18 (1H, m), 6.00 (1H, t), 7.09 (1H, d), 7.25 (1H, s), 7.57 (1H, br s), 7.64 (1H, s), 8.26 (1H, d); HPLC rt(min): 10.00; MS (ES⁺) 493, (ES⁻) 491.

Example 132

4-(9-cyclopentyl-6,7,8,9-tetrahydro-5,7,7-trimethyl-6-oxo-5H-pyrimido[4,5-b][1,4]diazepin-2-ylamino)-N-(3,3,3-trifluoropropyl)-3-methoxybenzamide (I-132)

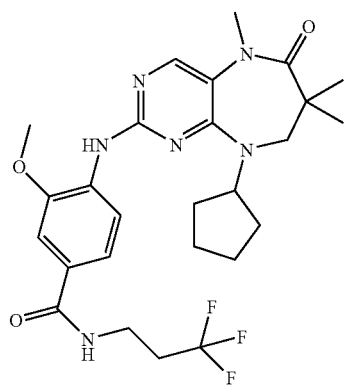

Prepared using the appropriate reagents according to method E. NMR CDCl₃ 1.13 (6H, s), 1.45-1.80 (6H, m), 1.88-1.97 (2H, m), 2.35-2.49 (2H, m), 3.22 (3H, s), 3.31 (2H, s), 3.64-3.70 (2H, m), 3.91 (3H, s), 5.18-5.28 (2H, m), 6.28 (1H, t), 7.17 (1H, d), 7.34 (1H, s), 7.68 (1H, br s), 7.77 (1H, s), 8.41 (1H, d); HPLC rt(min): 10.03; MS (ES⁺) 535, (ES⁻) 533.

Example 133

4-(9-cyclopentyl-6,7,8,9-tetrahydro-5,7,7-trimethyl-6-oxo-5H-pyrimido[4,5-b][1,4]diazepin-2-ylamino)-N-cyclohexyl-3-methoxybenzamide (I-133)

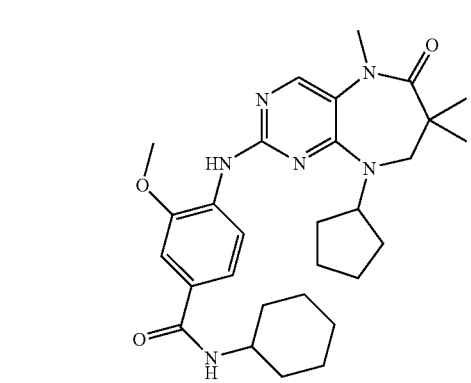

Prepared using the appropriate reagents according to method E. NMR CDCl₃ 1.13 (6H, s), 1.10-1.74 (14H, m), 1.88-2.05 (4H, m), 3.22 (3H, s), 3.31 (2H, s), 3.95-4.00 (1H, m), 3.91 (3H, s), 5.18-5.29 (1H, m), 5.85 (1H, d), 7.14 (1H, d), 7.35 (1H, s), 7.68 (1H, br s), 7.76 (1H, s), 8.37 (1H, d); HPLC rt(min): 10.56; MS (ES⁺) 521, (ES⁻) 519.

Example 134

4-(9-cyclopentyl-6,7,8,9-tetrahydro-5,7,7-trimethyl-6-oxo-5H-pyrimido[4,5-b][1,4]diazepin-2-ylamino)-N-(tetrahydro-2H-pyran-4-yl)-3-methoxybenzamide (I-134)

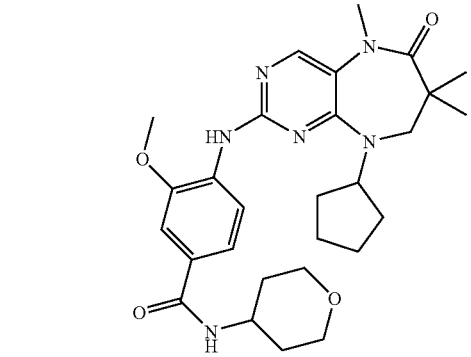

Prepared using the appropriate reagents according to method E. NMR CDCl₃ 1.22 (6H, s), 1.48-1.85 (12H, m), 1.97-2.08 (4H, m), 3.32 (3H, s), 3.40 (2H, s), 3.53-3.61 (2H, m), 3.97-4.07 (2H, m), 4.00 (3H, s), 5.29-5.40 (1H, m), 5.97 (1H, d), 7.24 (1H, d), 7.43 (1H, s), 7.77 (1H, br s), 7.86 (1H, s), 8.48 (1H, d); HPLC rt(min): 9.52; MS (ES⁺) 523, (ES⁻) 521.

Example 135

4-(9-cyclopentyl-6,7,8,9-tetrahydro-5,7,7-trimethyl-6-oxo-5H-pyrimido[4,5-b][1,4]diazepin-2-ylamino)-3-ethoxy-N-(1-isopropylpiperidin-4-yl)benzamide (I-135)

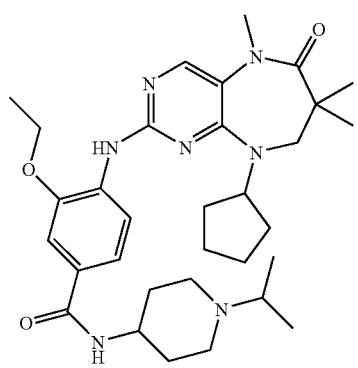

Prepared using the appropriate reagents according to method E. NMR CDCl$_3$ 1.10 (6H, d), 1.22 (6H, s), 1.52 (3H, t), 1.54-1.86 (8H, m), 1.97-2.16 (4H, m), 2.35-2.43 (2H, m), 2.77-2.89 (1H, m), 2.90-3.00 (2H, m), 3.32 (3H, s), 3.40 (2H, s), 3.98-4.07 (1H, m), 4.22 (2H, q), 5.25-5.36 (1H, m), 6.00 (1H, d), 7.23 (1H, d), 7.41 (1H, s), 7.66 (1H, s), 7.87 (1H, s), 8.49 (1H, d); HPLC rt(min): 9.47; MS (ES$^+$) 578, (ES$^-$) 576.

Example 136

4-(9-cyclopentyl-6,7,8,9-tetrahydro-5,7,7-trimethyl-6-oxo-5H-pyrimido[4,5-b][1,4]diazepin-2-ylamino)-N-(1,3-dihydroxy-2-methylpropan-2-yl)-3-methoxybenzamide (I-136)

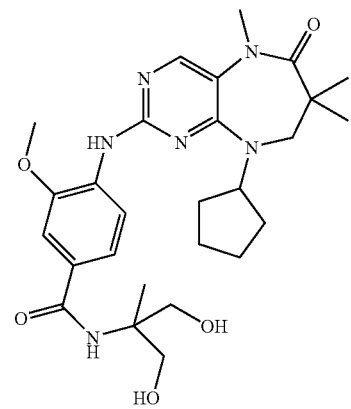

Prepared using the appropriate reagents according to method E. NMR DMSO D$^6$ 1.05 (3H, s), 1.14 (6H, s), 1.55-1.94 (8H, m), 3.13-3.26 (2H, m), 3.18 (3H, s), 3.28-3.37 (2H, m), 3.49 (2H, s), 3.96 (3H, s), 5.10-5.20 (1H, m), 7.54 (1H, d), 7.60 (1H, s), 8.01 (1H, s), 8.15 (1H, d), 8.40-8.47 (1H, m), 8.85 (1H, br s); HPLC rt(min): 9.47; MS (ES$^+$) 527, (ES$^-$) 526.

Example 137

2-(3-(1H-pyrazol-3-yl)phenylamino)-9-cyclopentyl-8,9-dihydro-5,7,7-trimethyl-5H-pyrimido[4,5-b][1,4]diazepin-6(7H)-one (I-137)

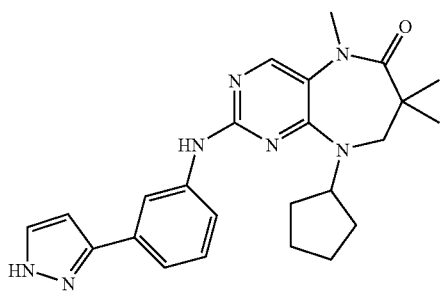

Prepared using the appropriate reagents according to method D. NMR DMSO D$^6$ 1.13 (6H, s), 1.24-1.36 (2H, m), 1.50-1.63 (4H, m), 1.71-1.86 (2H, m), 3.19 (3H, s), 3.47 (2H, s), 5.21 (1H, dt), 6.67 (1H, d), 7.38 (2H, d), 7.48-7.56 (1H, m), 7.75 (1H, s), 7.93 (1H, d), 8.12 (1H, s), 10.01 (1H, br s) HPLC rt(min): 9.58; MS (ES$^+$) 432, (ES$^-$) 430.

Example 138

9-Cyclopentyl-2-(1-methanesulfonyl-2,3-dihydro-1H-indol-5-ylamino)-5,7,7-trimethyl-5,7,8,9-tetrahydro-pyrimido[4,5-b][1,4]diazepin-6-one (I-138)

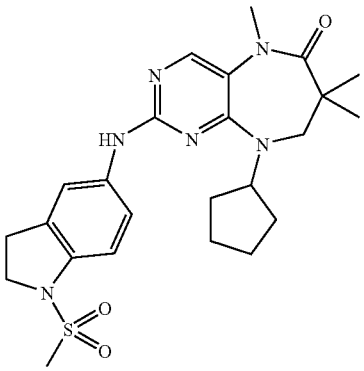

Prepared using the appropriate reagents according to method D. NMR DMSO D$^6$ 1.13 (6H, s), 1.52-1.85 (8H, m), 2.97 (3H, s), 3.11 (2H, t), 3.17 (3H, s), 3.45 (3H, s), 3.95 (2H, t), 5.14 (1H, dt), 7.20 (1H, d), 7.31 (1H, d), 7.62 (1H, s), 7.88 (1H, s), 9.75 (1H, br s); HPLC rt(min): 9.42; MS (ES$^+$) 485, (ES$^-$) 484.

Example 139

5-(9-Cyclopentyl-6,7,8,9-tetrahydro-5,7,7-trimethyl-6-oxo-5H-pyrimido[4,5-b][1,4]diazepin-2-ylamino)indoline-2,3-dione (I-139)

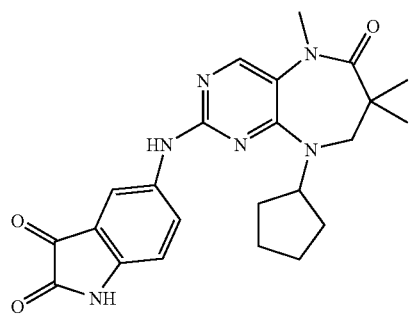

Prepared using the appropriate reagents according to method D. NMR DMSO $D^6$ 1.12 (6H, s), 1.56-1.76 (6H, m), 1.81-1.90 (2H, m), 3.18 (3H, s), 3.42 (2H, s), 5.15 (1H, dt), 6.88 (1H, d), 7.63 (1H, d), 7.92 (1H, s), 7.99 (1H, s), 9.63 (1H, br s), 10.96 (1H, s); HPLC rt(min): 8.75; MS (ES$^+$) 435, (ES$^-$) 433.

Example 140

3-(9-Cyclopentyl-6,7,8,9-tetrahydro-5,7,7-trimethyl-6-oxo-5H-pyrimido[4,5-b][1,4]diazepin-2-ylamino)-5-(trifluoromethyl)-N-methylbenzamide (I-140)

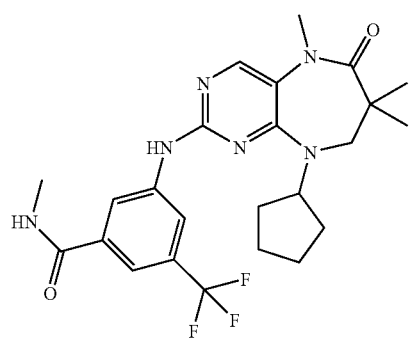

Prepared using the appropriate reagents according to method D. NMR DMSO $D^6$ 1.10 (6H, s), 1.48-1.70 (6H, m), 1.80-1.89 (2H, m), 2.78 (3H, d), 3.19 (3H, s), 3.40 (2H, s), 5.25 (1H, dt), 7.70 (1H, s), 7.99 (1H, s), 8.23 (1H, s), 8.34 (1H, s), 8.58-8.65 (1H, m), 9.87 (1H, br s); HPLC rt(min): 9.99; MS (ES$^+$) 491, (ES$^-$) 490.

Example 141

3-(9-Cyclopentyl-6,7,8,9-tetrahydro-5,7,7-trimethyl-6-oxo-5H-pyrimido[4,5-b][1,4]diazepin-2-ylamino)-N-(tetrahydro-2H-pyran-4-yl)benzamide (I-141)

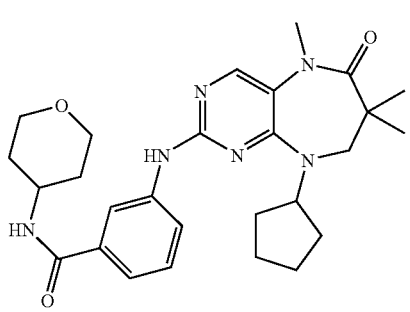

Prepared using the appropriate reagents according to method E. NMR DMSO $D^6$ 1.12 (6H, s), 1.53-1.80 (12H, m), 3.18 (3H, s), 3.36-3.43 (5H, m), 3.90 (2H, m), 3.98 (1H, m), 5.18 (1H, m), 7.39 (1H, m), 7.48 (1H, m), 7.63 (1H, m), 7.93 (1H, s), 8.27 (1H, m), 9.75 (1H, s); HPLC rt(min): 9.07; MS (ES$^+$) 493, (ES$^-$) 492.

Example 142

4-(9-Cyclopentyl-6,7,8,9-tetrahydro-5,7,7-trimethyl-6-oxo-5H-pyrimido[4,5-b][1,4]diazepin-2-ylamino)-N-methyl-3-(trifluoromethoxy)benzamide (I-142)

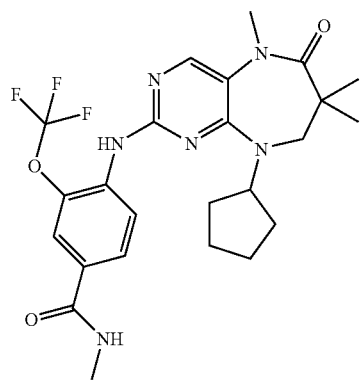

Prepared using the appropriate reagents according to method D. NMR DMSO $D^6$ 1.09 (6H, s), 1.55 (4H, br m), 1.69-1.81 (4H, br m), 2.79 (3H, m), 3.18 (3H, s), 3.36 (2H, s), 5.11 (1H, m), 7.83 (2H, m), 7.98 (1H, s), 8.28 (1H, m), 8.50 (1H, s), 8.64 (1H, s); HPLC rt(min): 9.78; MS (ES$^+$) 507, (ES$^-$) 505.

Example 143

3-[3-(9-Cyclopentyl-5,7,7-trimethyl-6-oxo-6,7,8,9-tetrahydro-5H-pyrimido[4,5-b][1,4]diazepin-2-ylamino)-benzoylamino]-azetidine-1-carboxylic acid tert-butyl ester (I-143)

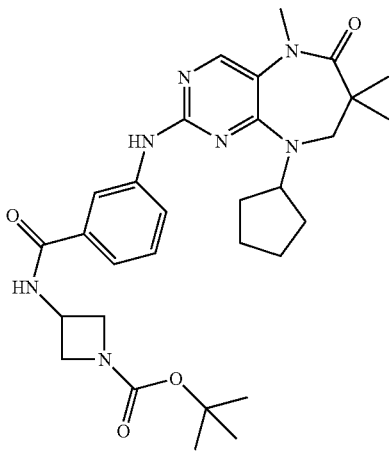

Prepared using the appropriate reagents according to method E. NMR DMSO D$^6$ 1.09 (6H, s), 1.39 (9H, s), 1.53 (4H, m), 1.66 (2H, m), 1.83 (2H, m), 3.19 (3H, s), 3.31 (2H, s), 3.85 (2H, m), 4.10 (2H, m), 4.61 (1H, m), 5.25 (1H, m), 7.30-7.37 (2H, m), 7.68 (1H, m), 7.96 (1H, s), 8.27 (1H, s), 8.89 (1H, m), 9.29 (1H, s); HPLC rt(min): 9.98; MS (ES$^+$) 565, (ES$^-$) 563.

Example 144

3-(9-Cyclopentyl-6,7,8,9-tetrahydro-5,7,7-trimethyl-6-oxo-5H-pyrimido[4,5-b][1,4]diazepin-2-ylamino)-N-(2-methoxyethyl)benzamide (I-144)

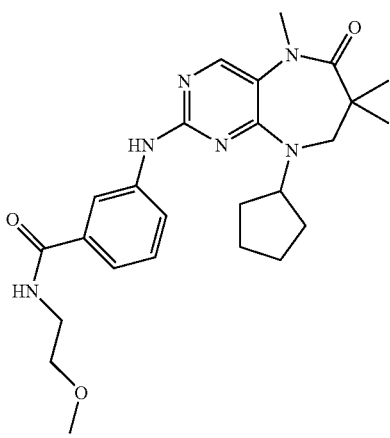

Prepared using the appropriate reagents according to method E. NMR DMSO D$^6$ 1.11 (6H, s), 1.54 (4H, m), 1.67 (2H, m), 1.82 (2H, m), 3.19 (3H, s), 3.27 (2H, m), 3.85 masked signal, 4.10 (2H, m), 5.22 (1H, m), 7.35 (1H, m), 7.46 (1H, m), 7.65 (1H, m), 7.93 (1H, s), 8.20 (1H, s), 8.46 (1H, m), 9.68 (1H, s); HPLC rt(min): 9.04; MS (ES$^+$) 467, (ES$^-$) 466.

Example 145

N-(3-(9-Cyclopentyl-6,7,8,9-tetrahydro-5,7,7-trimethyl-6-oxo-5H-pyrimido[4,5-b][1,4]diazepin-2-ylamino)phenyl-3,3,3-trifluoropropanamide (I-145)

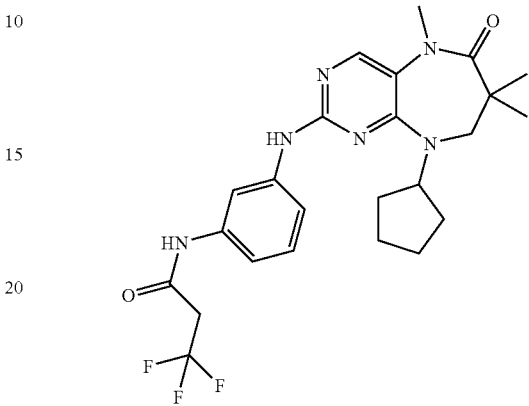

Prepared using the appropriate reagents according to method E. NMR DMSO D$^6$ 1.12 (6H, s), 1.50-1.67 (6H, br m), 1.81 (2H, br m), 3.18 (3H, s), 3.44 (2H, s), 3.50 (2H, m), 5.21 (1H, m), 7.14 (1H, m), 7.28 (2H, m), 7.92 (2H, m), 9.87 (NH), 10.34 (1H, s); HPLC rt(min): 9.63; MS (ES$^+$) 491, (ES$^-$) 489.

Example 146

N-(3-(9-Cyclopentyl-6,7,8,9-tetrahydro-5,7,7-trimethyl-6-oxo-5H-pyrimido[4,5-b][1,4]diazepin-2-ylamino)phenyl)-N-methylacetamide (I-146)

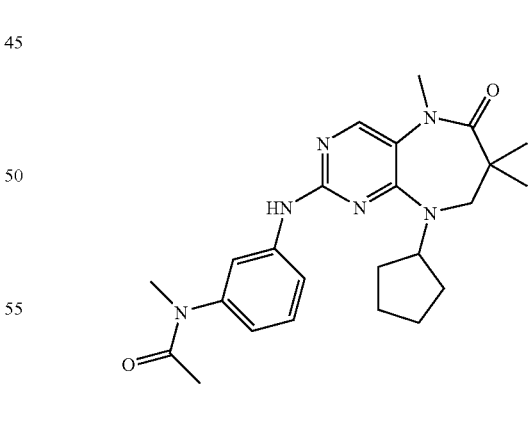

Prepared using the appropriate reagents according to method D. NMR DMSO D$^6$ 1.09 (6H, s), 1.52-1.63 (4H, m), 1.67-1.73 (2H, m), 1.78 (3H, s), 1.81-1.88 (2H, m), 3.14 (3H, s), 3.18 (3H, s), 3.36 (2H, s), 5.23 (1H, quint), 6.84 (1H, d), 7.29 (1H, t), 7.49 (1H, d), 7.93 (1H, s), 7.98 (1H, s), 9.38 (1H, s); HPLC rt(min): 9.40; MS (ES$^+$) 437, (ES$^-$) 435.

Example 147

N-(3-(9-Cyclopentyl-6,7,8,9-tetrahydro-5,7,7-trimethyl-6-oxo-5H-pyrimido[4,5-b][1,4]diazepin-2-ylamino)phenyl)-2-methoxyacetamide (I-147)

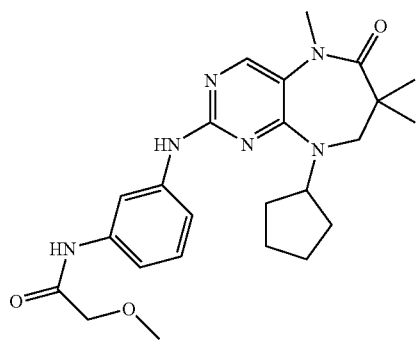

Prepared using the appropriate reagents according to method E. NMR DMSO D$^6$ 1.09 (6H, s), 1.51-1.57 (4H, m), 1.65-1.71 (2H, m), 1.81-1.87 (2H, m), 3.18 (3H, s), 3.32 (2H, s), 3.37 (3H, s), 3.97 (2H, s), 5.26 (1H, quint), 7.10-7.17 (2H, m), 7.34 (1H, d), 7.94 (1H, s), 8.00 (1H, s), 9.14 (1H, s), 9.59 (1H, s); HPLC rt(min): 9.30; MS (ES$^+$) 453, (ES$^-$) 451.

Example 148

3-(9-Cyclopentyl-6,7,8,9-tetrahydro-5,7,7-trimethyl-6-oxo-5H-pyrimido[4,5-b][1,4]diazepin-2-ylamino)-N,N-dimethylbenzamide (I-148)

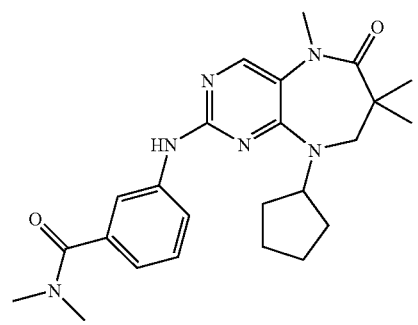

Prepared using the appropriate reagents according to method E. NMR DMSO D$^6$ 1.12 (6H, s), 1.56 (4H, m), 1.70 (2H, m), 1.81 (2H, m), 2.91 (3H, s), 2.98 (3H, s), 3.18 (3H, s), 3.42 (2H, s), 5.19 (1H, m), 7.00 (1H, m), 7.34 (1H, m), 7.53 (1H, m), 7.86 (1H, s), 7.95 (1H, s), 9.70 (1H, s); HPLC rt(min): 9.21; MS (ES$^+$) 437, (ES$^-$) 435.

Example 149

2-(3-(2-oxopyrrolidin-1-yl)phenylamino)-9-cyclopentyl-8,9-dihydro-5,7,7-trimethyl-5H-pyrimido[4,5-b][1,4]diazepin-6(7H)-one (I-149)

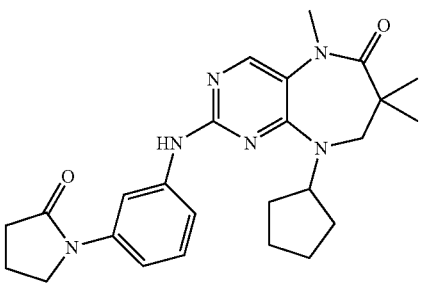

Prepared using the appropriate reagents according to method D. NMR DMSO D$^6$ 1.15 (6H, s), 1.60 (4H, m), 1.77 (2H, m), 1.91 (2H, m), 2.12 (2H, m), 2.51 masked signal, 3.24 (3H, s), 3.37 (2H, s), 3.87 (2H, m), 5.32 (1H, m), 7.19 (1H, m), 7.27 (1H, m), 7.52 (1H, m), 8.01 (1H, s), 8.04 (1H, m), 9.22 (1H, s); HPLC rt(min): 9.52; MS (ES$^+$) 449, (ES$^-$) 447.

Example 150

N-[3-(9-cyclopentyl-5,7,7-trimethyl-6-oxo-6,7,8,9-tetrahydro-5H-pyrimido[4,5-b][1,4]diazepin-2-ylamino)-phenyl]-methanesulfonamide (I-150)

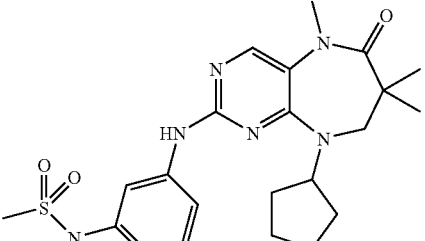

Prepared using the appropriate reagents according to method E. NMR DMSO D$^6$ 1.09 (6H, s), 1.55-1.65 (4H, s), 1.68-1.73 (2H, m), 1.80-1.89 (2H, m), 2.94 (3H, s), 3.18 (3H, s), 3.32 (2H, s), 5.25 (1H, quint), 6.71 (1H, d), 7.15 (1H, t), 7.47 (1H, d), 7.59 (1H, s), 7.93 (1H, s), 9.16 (1H, s), 9.56 (1H, br s); HPLC rt(min): 9.10; MS (ES$^+$) 459, (ES$^-$) 457.

Example 151

N-(3-(9-cyclopentyl-6,7,8,9-tetrahydro-5,7,7-trimethyl-6-oxo-5H-pyrimido[4,5-b][1,4]diazepin-2-ylamino)phenyl)cyclobutanecarboxamide (I-151)

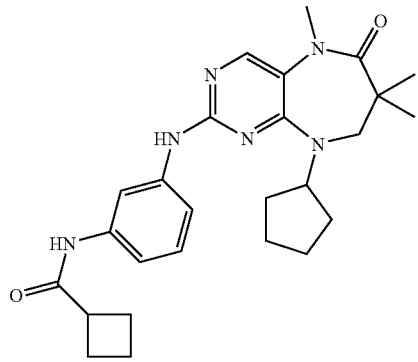

Prepared using the appropriate reagents according to method E. NMR DMSO $D^6$ 1.09 (6H, s), 1.48-1.59 (4H, m), 1.63-1.73 (2H, m), 1.76-1.89 (3H, m), 1.90-1.98 (1H, m), 2.04-2.14 (2H, m), 2.16-2.27 (2H, m), 3.19 (3H, s), 3.18-3.26 (1H, m), 3.34 (2H, s), 5.27 (1H, quint), 7.03-7.12 (2H, m), 7.27 (1H, d), 7.93 (1H, s), 7.99 (1H, s), 9.08 (1H, s), 9.59 (1H, s); HPLC rt(min): 9.80; MS (ES$^+$) 463, (ES$^-$) 461.

Example 152

9-Cyclopentyl-2-[3-(3-cyclopropyl-3-fluoro-azetidine-1-carbonyl)-phenylamino]-5,7,7-trimethyl-5,7,8,9-tetrahydro-pyrimido[4,5-b][1,4]diazepin-6-one (I-152)

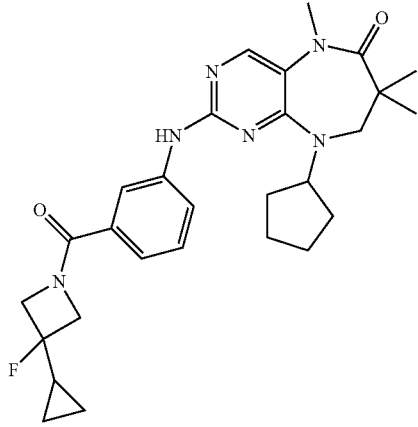

Prepared using the appropriate reagents according to method E. NMR DMSO $D^6$ 0.20 (2H, m), 0.36 (2H, m), 0.86 (6H, s), 1.16 (1H, m), 1.34 (4H, m), 1.46 (2H, m), 1.63 (2H, m), 2.95 (3H, s), 3.08 masked signal, 3.79 (2H, m), 3.96-4.08 (2H, m), 5.01 (1H, m), 6.89 (1H, m), 7.07 (1H, m), 7.73 (1H, s), 7.83 (1H, s), 9.09 (1H, s); HPLC rt(min): 10.03; MS (ES$^+$) 507, (ES$^-$) 505.

Example 153

2-(3-(pyridin-3-yl)phenylamino)-9-cyclopentyl-8,9-dihydro-5,7,7-trimethyl-5H-pyrimido[4,5-b][1,4]diazepin-6(7H)-one (I-153)

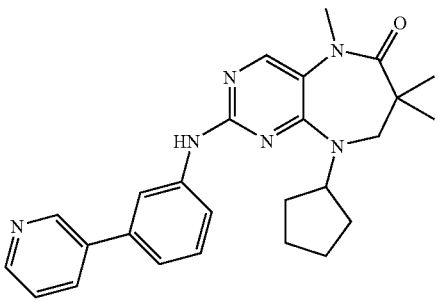

Prepared using the appropriate reagents according to method D. NMR DMSO $D^6$ 1.06 (6H, s), 1.19-1.28 (2H, m), 1.47-1.58 (4H, m), 1.70-1.83 (2H, m), 3.19 (3H, s), 3.33 (2H, s), 5.16-5.24 (1H, m), 7.20 (1H, d), 7.37 (1H, t), 7.49 (1H, dd), 7.62 (1H, d), 7.98 (1H, s), 8.00-8.02 (1H, m), 8.14-8.15 (1H, m), 8.58 (1H, dd), 8.82 (1H, d), 9.30 (1H, s); HPLC rt(min): 10.10; MS (ES$^+$) 443, (ES$^-$) 441.

Example 154

N-(3-(9-cyclopentyl-6,7,8,9-tetrahydro-5,7,7-trimethyl-6-oxo-5H-pyrimido[4,5-b][1,4]diazepin-2-ylamino)phenyl)benzamide (I-154)

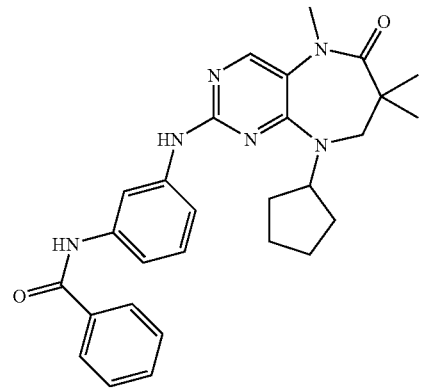

Prepared using the appropriate reagents according to method E. NMR DMSO $D^6$ 1.08 (6H, s), 1.34-1.42 (2H, m), 1.49-1.56 (4H, m), 1.78-1.86 (2H, m), 3.19 (3H, s), 3.33 (2H, s), 5.28 (1H, quint), 7.15-7.22 (2H, m), 7.30-7.32 (1H, m), 7.51-7.61 (3H, m), 7.94-8.00 (3H, m), 8.26 (1H, s), 9.20 (1H, s), 10.17 (1H, s); HPLC rt(min): 9.70; MS (ES$^+$) 485, (ES$^-$) 483.

Example 155

Methyl 3-(9-cyclopentyl-6,7,8,9-tetrahydro-5,7,7-trimethyl-6-oxo-5H-pyrimido[4,5-b][1,4]diazepin-2-ylamino)phenyl)carbamate (I-155)

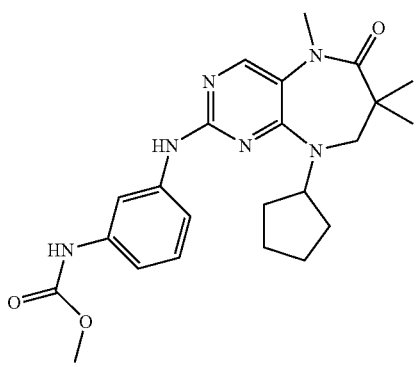

Prepared using the appropriate reagents according to method E. NMR DMSO $D^6$ 1.08 (6H, s), 1.48-1.57 (4H, m), 1.64-1.73 (2H, m), 1.79-1.88 (2H, m), 3.18 (3H, s), 3.29 (2H, s), 3.64 (3H, s), 5.26 (1H, quint), 6.88 (1H, d), 7.11 (1H, t), 7.26 (1H, d), 7.90 (1H, s), 7.93 (1H, s), 9.11 (1H, s), 9.50 (1H, s); HPLC rt(min): 9.40; MS (ES+) 439, (ES−) 437.

Example 156

3-(9-cyclopentyl-6,7,8,9-tetrahydro-5,7,7-trimethyl-6-oxo-5H-pyrimido[4,5-b][1,4]diazepin-2-ylamino)-N-(azetidin-3-yl)benzamide (I-156)

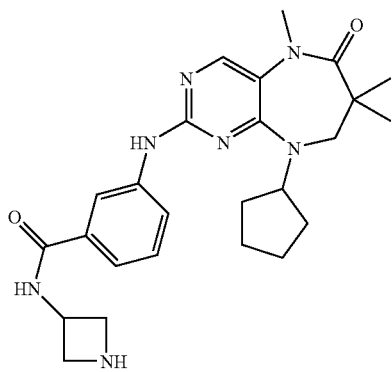

Prepared using the appropriate reagents according to method F. NMR DMSO $D^6$ 1.11 (6H, s), 1.53 (4H, m), 1.67 (2H, m), 1.81 (2H, m), 3.18 (3H, s) 4.07 (4H, m), 4.81 (1H, m), 5.24 (1H, m) 7.41 (2H, m), 7.70 (1H, m), 7.97 (1H, s), 8.24 (1H, m), 8.72 (2H, br s), 9.05 (1H, m), 9.72 (1H, m); HPLC rt(min): 8.38; MS (ES+) 464, (ES−) 463.

Example 157

N-(3-(9-cyclopentyl-6,7,8,9-tetrahydro-5,7,7-trimethyl-6-oxo-5H-pyrimido[4,5-b][1,4]diazepin-2-ylamino)phenyl)-1-methylpiperidine-4-carboxamide (I-157)

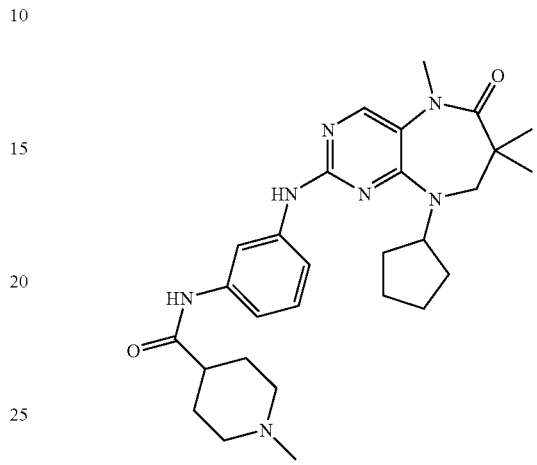

Prepared using the appropriate reagents according to method E. NMR DMSO $D^6$ 1.09 (6H, s), 1.35 (2H, br m), 1.50-1.81 (8H, br m), 1.96 (2H, br m), 2.51 (1H, br m), 2.72 (3H, s), 2.91 (2H, m), 3.12 (3H, s), 3.43 (2H, m), 3.44 (2H, s), 5.07 (1H, m), 7.10 (2H, m), 7.31 (1H, m), 7.73 (1H, s), 7.96 (1H, s), 10.20 (1H, s); HPLC rt(min): 8.96; MS (ES+) 506, (ES−) 504.

Example 158

N-(3-(9-cyclopentyl-6,7,8,9-tetrahydro-5,7,7-trimethyl-6-oxo-5H-pyrimido[4,5-b][1,4]diazepin-2-ylamino)-4-methoxyphenyl)acetamide (I-158)

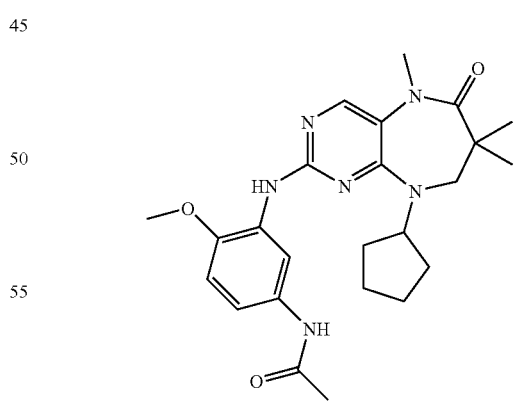

Prepared using the appropriate reagents according to method D. NMR DMSO $D^6$ 1.12 (6H, s), 1.45-1.70 (6H, m), 1.76-1.88 (2H, m), 2.00 (3H, s), 3.17 (3H, s), 3.46 (2H, s), 3.83 (3H, s), 5.21 (1H, dt), 7.01-7.11 (2H, m), 7.93-7.96 (1H, m), 8.26-8.34 (1H, m), 9.84 (1H, s); HPLC rt(min): 8.85; MS (ES+) 453, (ES−) 452.

Example 159

3-(9-cyclopentyl-6,7,8,9-tetrahydro-5,7,7-trimethyl-6-oxo-5H-pyrimido[4,5-b][1,4]diazepin-2-ylamino)-N-cyclopropylbenzamide (I-159)

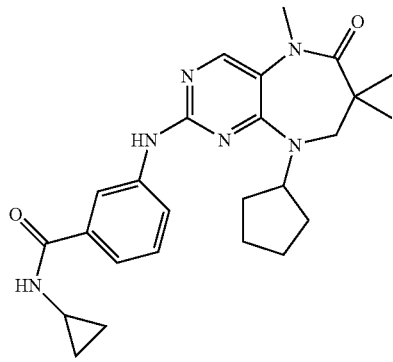

Prepared using the appropriate reagents according to method E. NMR DMSO D⁶ 0.56 (2H, m), 0.68 (2H, m), 1.12 (6H, s), 1.55 (4H, m), 1.67 (2H, m), 1.91 (2H, m), 2.83 (1H, m), 3.18 (3H, s), 3.43 (2H, s), 5.20 (1H, m), 7.36-7.44 (2H, m), 7.60 (1H, m), 7.93 (1H, s), 8.16 (1H, s), 8.38 (1H, m), 9.70 (1H, s); HPLC rt(min): 9.19; MS (ES⁺) 449, (ES⁻) 448.

Example 160

4-(9-(2,2,3,3,3-pentafluoropropyl)-6,7,8,9-tetrahydro-5,7,7-trimethyl-6-oxo-5H-pyrimido[4,5-b][1,4]diazepin-2-ylamino)-3-methoxy-N-methylbenzamide (I-160)

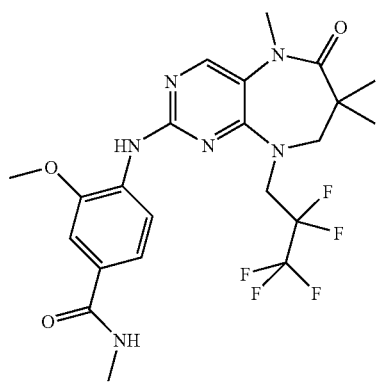

Prepared using the appropriate reagents according to method D. NMR DMSO D⁶ 1.11 (6H, s), 2.79 (3H, d), 3.22 (3H, s), 3.66 (2H, s), 3.92 (3H, s), 4.83 (2H, t), 7.42 (1H, dd), 7.50 (1H, d), 7.89 (1H, s), 8.14 (1H, d), 8.15 (1H, s), 8.35 (1H, q); HPLC rt(min): 9.00; MS (ES⁺) 517, (ES⁻) 515.

Example 161

4-(9-(3-chlorophenyl)-6,7,8,9-tetrahydro-5,7,7-trimethyl-6-oxo-5H-pyrimido[4,5-b][1,4]diazepin-2-ylamino)-3-methoxy-N-methylbenzamide (I-161)

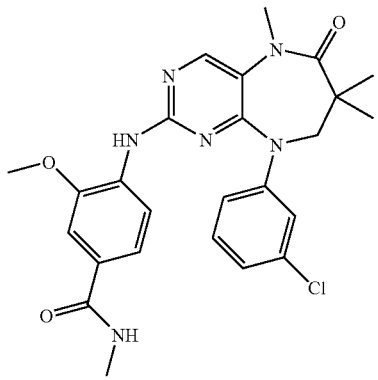

Prepared using the appropriate reagents according to method D. NMR DMSO D⁶ 1.23 (6H, s), 2.77 (3H, d), 3.29 (3H, s), 3.82 (2H, s), 3.87 (3H, s), 6.96 (1H, dd), 7.32 (1H, d), 7.34-7.38 (2H, m), 7.49-7.54 (2H, m), 7.57 (1H, d), 7.60 (1H, s), 8.17 (1H, s), 8.23 (1H, q); HPLC rt(min): 8.99; MS (ES⁺) 495, (ES⁻) 493.

Example 162

N-(5-(9-cyclopentyl-6,7,8,9-tetrahydro-5,7,7-trimethyl-6-oxo-5H-pyrimido[4,5-b][1,4]diazepin-2-ylamino)-2-methylphenyl)acetamide (I-162)

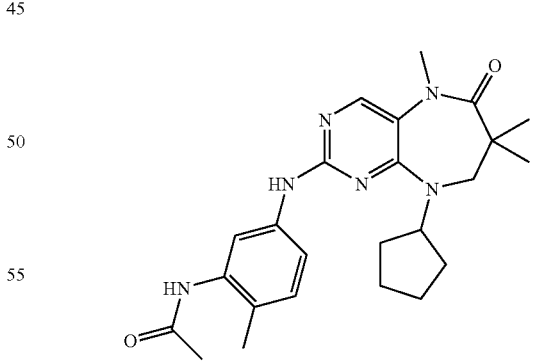

Prepared using the appropriate reagents according to method D. NMR DMSO D⁶ 1.08 (6H, s), 1.57 (4H, br m), 1.70 (2H, br m), 1.84 (2H, br m), 2.02 (3H, s), 2.11 (3H, s), 3.17 (3H, s), 3.34 (2H, s), 5.24 (1H, m), 7.02 (1H, m), 7.28 (1H, m), 7.83 (1H, s), 7.92 (1H, s), 9.09 (1H, s), 9.27 (1H, s); HPLC rt(min): 8.91; MS (ES⁺) 437, (ES⁻) 435.

Example 163

N-(3-(9-cyclopentyl-6,7,8,9-tetrahydro-5,7,7-trimethyl-6-oxo-5H-pyrimido[4,5-b][1,4]diazepin-2-ylamino)-4-methylphenyl)acetamide (I-163)

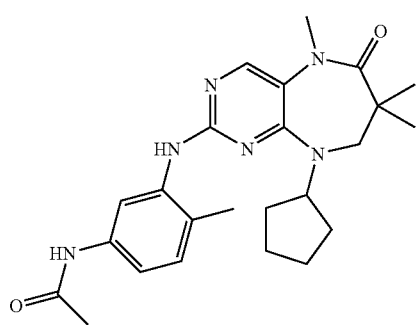

Prepared using the appropriate reagents according to method D. NMR DMSO $D^6$ 1.07 (6H, s), 1.41 (4H, br m), 1.45-1.70 (4H, br m), 1.99 (3H, s), 2.17 (3H, s), 3.17 (3H, s), 3.30 (2H, s), 5.07 (1H, m), 7.04-7.13 (2H, m), 7.89 (2H, m), 8.21 (1H, s), 9.77 (1H, s); HPLC rt(min): 9.01; MS (ES$^+$) 437, (ES$^-$) 435.

Example 164

N-(3-(9-cyclopentyl-6,7,8,9-tetrahydro-5,7,7-trimethyl-6-oxo-5H-pyrimido[4,5-b][1,4]diazepin-2-ylamino)phenyl)piperidine-1-carboxamide (I-164)

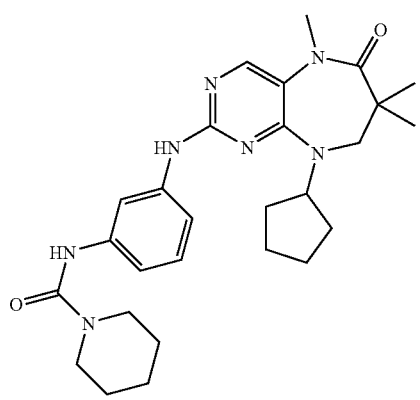

Prepared using the appropriate reagents according to method E. NMR DMSO $D^6$ 1.09 (6H, s), 1.46-1.61 (10H, m), 1.64-1.69 (2H, m), 1.81-1.89 (2H, m), 3.18 (3H, s), 3.32 (2H, s), 3.38-3.41 (4H, m), 5.26 (1H, quint), 6.89 (1H, d), 7.06 (1H, t), 7.16 (1H, d), 7.88-7.90 (1H, m), 7.92 (1H, s), 8.31 (1H, s), 9.03 (1H, s); HPLC rt(min): 9.70; MS (ES$^+$) 492, (ES$^-$) 490.

Example 165

N-(3-(9-cyclopentyl-6,7,8,9-tetrahydro-5,7,7-trimethyl-6-oxo-5H-pyrimido[4,5-b][1,4]diazepin-2-ylamino)-2,6-difluorophenyl)acetamide (I-165)

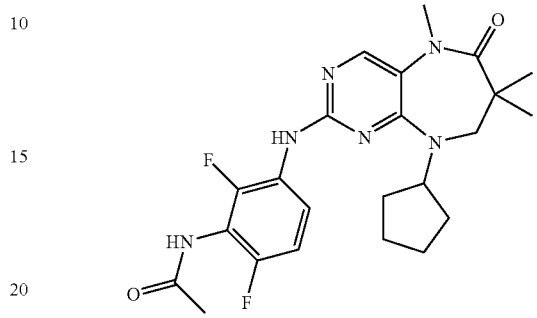

Prepared using the appropriate reagents according to method D. NMR DMSO $D^6$ 1.17 (6H, s), 1.53 (4H, br m), 1.60-1.76 (4H, br m), 2.13 (3H, s), 3.23 (3H, s), 3.48 (2H, s), 5.03 (1H, m), 7.23 (1H, m), 7.64 (1H, m), 7.95 (1H, s), 9.57 (1H, s), 9.83 (1H, s); HPLC rt(min): 8.90; MS (ES$^+$) 459, (ES$^-$) 457.

Example 166

4-(9-cyclopentyl-6,7,8,9-tetrahydro-5,7,7-trimethyl-6-oxo-5H-pyrimido[4,5-b][1,4]diazepin-2-ylamino)-N-(3,3-difluorocyclobutyl)-3-methoxybenzamide (I-166)

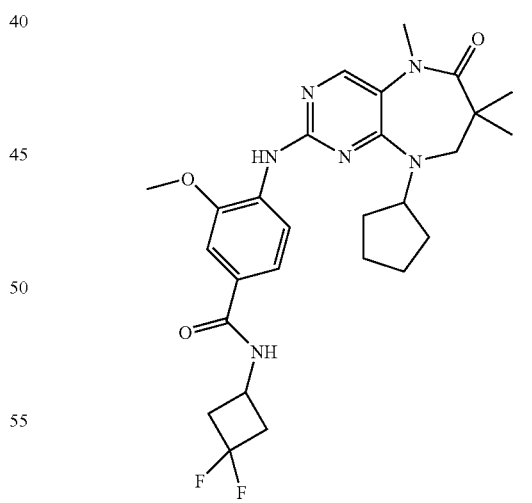

Prepared using the appropriate reagents according to method E. NMR DMSO $D^6$ 1.10 (6H, s), 1.53-1.68 (4H, m), 1.69-1.80 (2H, m), 1.82-1.94 (2H, m), 2.69-2.86 (2H, m), 2.90-3.04 (2H, m), 3.19 (3H, s), 3.38 (2H, s), 3.95 (3H, s), 4.28 (1H, dt), 5.19 (1H, dt), 7.48 (1H, d), 7.49 (1H, s), 7.72 (1H, s), 8.00 (1H, s), 8.40 (1H, d), 8.66 (1H, d); HPLC rt(min): 10.04; MS (ES$^+$) 529, (ES$^-$) 528.

Example 167

4-(9-cyclobutyl-6,7,8,9-tetrahydro-5,7,7-trimethyl-6-oxo-5H-pyrimido[4,5-b][1,4]diazepin-2-ylamino)-3-methoxy-N-methylbenzamide (I-167)

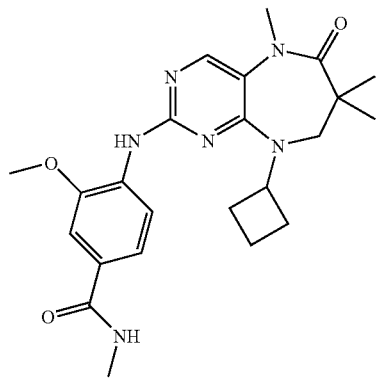

Prepared using the appropriate reagents according to method D. NMR CDCl$_3$ 1.22 (6H, s), 1.76-1.85 (2H, m), 2.14 (2H, dquint), 2.30-2.33 (2H, m), 3.05 (3H, d), 3.32 (3H, s), 3.51 (2H, s), 4.00 (3H, s), 5.09 (1H, quint), 6.14 (1H, q), 7.30 (1H, dd), 7.47 (1H, d), 7.64 (1H, s), 7.90 (1H, s), 8.58 (1H, d); HPLC rt(min): 8.98; MS (ES$^+$) 439, (ES$^-$) 437.

Example 168

4-(6,7,8,9-tetrahydro-5,7,7-trimethyl-9-neopentyl-6-oxo-5H-pyrimido[4,5-b][1,4]diazepin-2-ylamino)-3-methoxy-N-methylbenzamide (I-168)

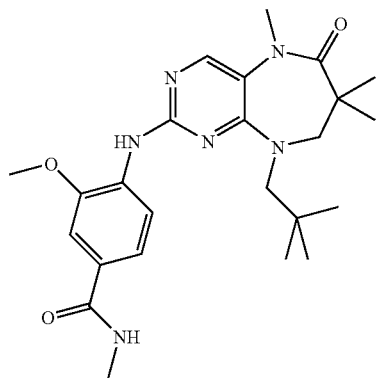

Prepared using the appropriate reagents according to method D. NMR DMSO D$^6$ 0.96 (9H, s), 1.10 (6H, s), 2.78 (3H, s), 3.21 (3H, s), 3.60 (2H, s), 3.79 (2H, s), 3.93 (3H, s), 7.49 (2H, m), 7.71 (1H, s), 8.00 (1H, s), 8.35 (2H, m); HPLC rt(min): 9.30; MS (ES$^+$) 455, (ES$^-$) 453.

Example 169

4-(9-((2,2-difluorocyclopropyl)methyl)-6,7,8,9-tetrahydro-5,7,7-trimethyl-6-oxo-5H-pyrimido[4,5-b][1,4]diazepin-2-ylamino)-3-methoxy-N-methylbenzamide (I-169)

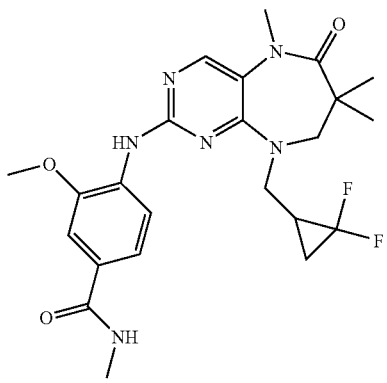

Prepared using the appropriate reagents according to method D. NMR DMSO D$^6$ 1.11 (6H, d), 1.44 (1H, br m), 1.67 (1H, br m), 2.17 (1H, br m), 2.78 (3H, d), 3.20 (3H, s), 3.46 (2H, br m), 3.63 (1H, d), 3.93 (3H, s), 4.14 (1H, br m), 7.46 (2H, br m), 7.76 (1H, s), 8.04 (1H, s), 8.32 (2H, br d); HPLC rt(min): 8.70; MS (ES$^+$) 475, (ES$^-$) 473.

Example 170

4-(9-(3,3-difluorocyclobutyl)-6,7,8,9-tetrahydro-5,7,7-trimethyl-6-oxo-5H-pyrimido[4,5-b][1,4]diazepin-2-ylamino)-3-methoxy-N-methylbenzamide (I-170)

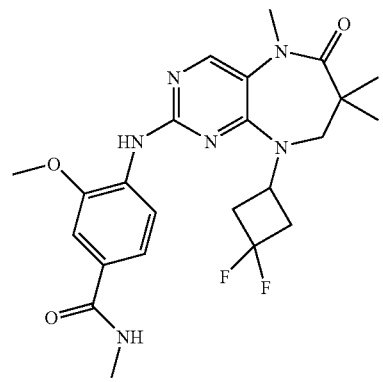

Prepared using the appropriate reagents according to method D. NMR DMSO D$^6$ 1.10 (6H, s), 2.76-2.95 (4H, m), 2.78 (3H, d), 3.21 (3H, s), 3.48 (2H, s), 3.93 (3H, s), 4.58-4.64 (1H, m), 7.43-7.54 (2H, m), 7.87 (1H, s), 8.09 (1H, s), 8.30-8.38 (2H, m); HPLC rt(min): 8.35; MS (ES$^+$) 475, (ES$^-$) 473.

Example 171

4-(9-(3,3-difluorocyclobutyl)-6,7,8,9-tetrahydro-5,7,7-trimethyl-6-oxo-5H-pyrimido[4,5-b][1,4]diazepin-2-ylamino)-N-(tetrahydro-2H-pyran-4-yl)-3-methoxybenzamide (I-171)

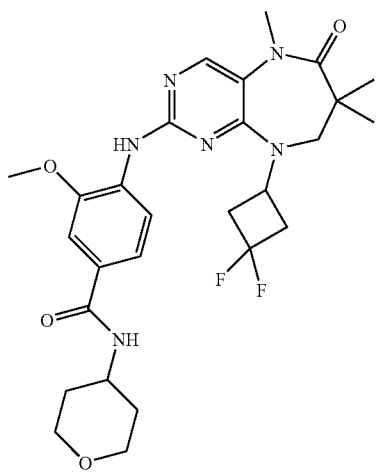

Prepared using the appropriate reagents according to method D. NMR DMSO D$^6$ 1.10 (6H, s), 1.54-1.65 (2H, m), 1.75-1.79 (2H, m), 2.78-2.98 (4H, m), 3.21 (3H, s), 3.34-3.43 (2H, m), 3.48 (2H, s), 3.85-3.89 (1H, m), 3.90-3.93 (1H, m), 3.95 (3H, s), 3.98-4.05 (1H, m), 4.56-4.63 (1H, m), 7.48-7.51 (2H, m), 7.88 (1H, s), 8.10 (1H, s), 8.19 (1H, d), 8.33 (1H, d); HPLC rt(min): 8.86; MS (ES$^+$) 545, (ES$^-$) 544.

Example 172

4-(9-cyclopentyl-6,7,8,9-tetrahydro-5,7,7-trimethyl-6-oxo-5H-pyrimido[4,5-b][1,4]diazepin-2-ylamino)-N—((S)-tetrahydrofuran-3-yl)-3-methoxybenzamide (I-172)

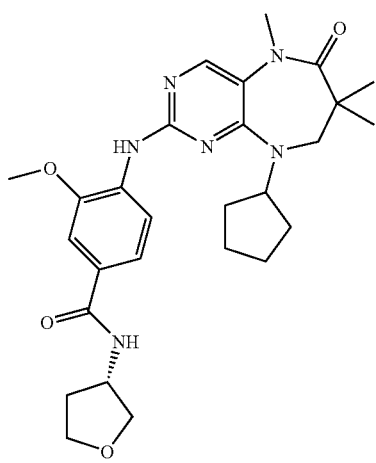

Prepared using the appropriate reagents according to method D. NMR DMSO D$^6$ 1.10 (6H, m), 1.55-1.68 (4H, m), 1.69-1.77 (2H, m), 1.84-1.95 (4H, m), 2.12-2.21 (1H, m), 3.19 (3H, s), 3.38 (2H, s), 3.59 (1H, dd), 3.68-3.76 (1H, m), 3.83-3.91 (2H, m), 3.95 (3H, s), 4.45-4.49 (1H, m), 5.19 (1H, dt), 7.47-7.52 (2H, m), 7.70 (1H, s), 7.99 (1H, s), 8.35-8.41 (2H, m) HPLC rt(min): 9.37; MS (ES$^+$) 509, (ES$^-$) 507.

Example 173

4-((S)-9-cyclopentyl-6,7,8,9-tetrahydro-5,7-dimethyl-6-oxo-5H-pyrimido[4,5-b][1,4]diazepin-2-ylamino)-N-cyclopentyl-3-methoxybenzamide (I-173)

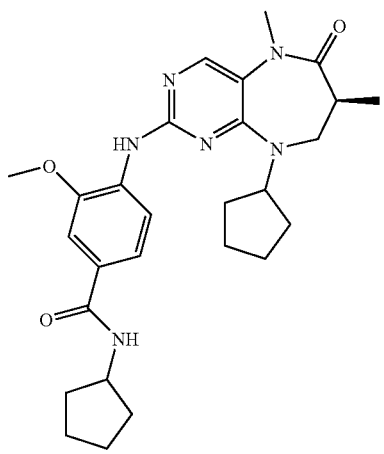

Prepared using the appropriate reagents according to method D. NMR DMSO D$^6$ 1.02 (3H, d), 1.50-1.83 (14H, m), 1.89-1.94 (2H, m), 2.08-2.11 (1H, m), 2.83-2.88 (1H, m), 3.19 (3H, s), 3.37-3.45 (1H, m), 3.95 (3H, s), 4.20-4.26 (1H, m), 4.71-4.76 (1H, m), 7.47 (1H, d), 7.49 (1H, s), 7.75 (1H, s), 8.10 (1H, s), 8.14 (1H, d), 8.38 (1H, d); HPLC rt(min): 10.10; MS (ES$^+$) 493, (ES$^-$) 491.

Example 174

4-((S)-9-cyclopentyl-6,7,8,9-tetrahydro-5,7-dimethyl-6-oxo-5H-pyrimido[4,5-b][1,4]diazepin-2-ylamino)-N-(tetrahydro-2H-pyran-4-yl)-3-methoxybenzamide (I-174)

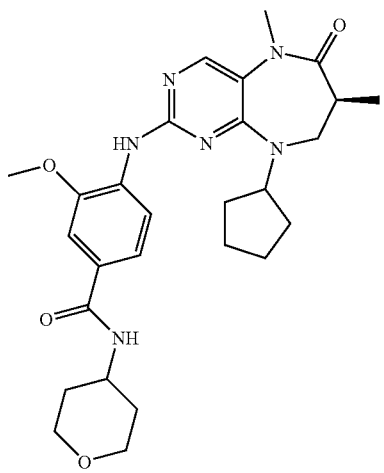

Prepared using the appropriate reagents according to method D. NMR DMSO D$^6$ 1.02 (3H, s), 1.52-1.78 (11H, m), 2.04-2.12 (1H, m), 2.84-2.90 (1H, m), 3.19 (3H, s), 3.39-3.46 (4H, m), 3.89 (2H, br dd), 3.95 (3H, s), 3.96-4.06 (1H, m), 4.74 (1H, quint), 7.49 (1H, d), 7.50 (1H, s), 7.76 (1H, s), 8.10 (1H, s), 8.17 (1H, d), 8.40 (1H, d); HPLC rt(min): 9.20; MS (ES+) 509, (ES−) 507.

Example 175

4-((S)-9-cyclopentyl-6,7,8,9-tetrahydro-5,7-dimethyl-6-oxo-5H-pyrimido[4,5-b][1,4]diazepin-2-ylamino)-N-cyclopropyl-3-methoxybenzamide (I-175)

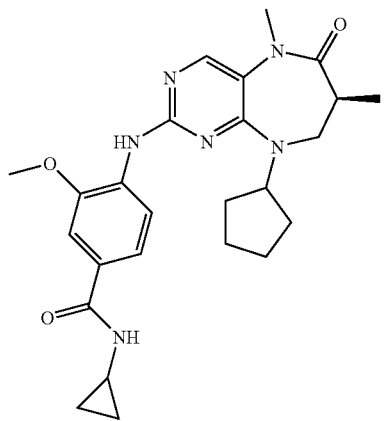

Prepared using the appropriate reagents according to method D. NMR DMSO D$^6$ 0.55-0.59 (2H, m), 0.68-0.73 (2H, m), 1.02 (3H, d), 1.47-1.85 (7H, m), 2.04-2.12 (1H, m), 2.79-2.88 (2H, m), 3.19 (3H, s), 3.36-3.46 (2H, m), 3.94 (3H, s), 4.69-4.75 (1H, m), 7.45 (1H, d), 7.47 (1H, s), 7.75 (1H, s), 8.10 (1H, s), 8.34 (1H, d), 8.38 (1H, d); HPLC rt(min) 9.10; MS (ES+) 465, (ES−) 463.

Example 176

N-cyclopentyl-4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxybenzamide (I-176)

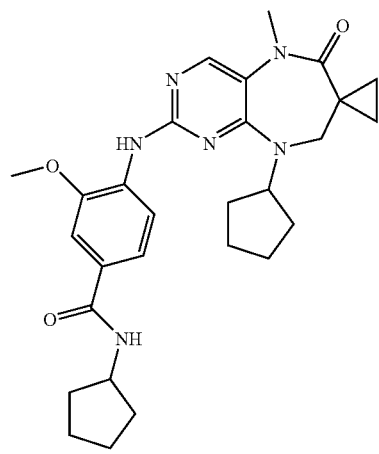

Prepared using the appropriate reagents according to method D. NMR DMSO D$^6$ 0.66-0.69 (2H, m), 0.89-0.91 (2H, m), 1.46-1.71 (12H, m), 1.85-1.95 (4H, m), 3.17 (3H, s), 3.48 (2H, s), 3.95 (3H, s), 4.23 (1H, quint), 4.85 (1H, quint), 7.47 (1H, d), 7.49 (1H, s), 7.66 (1H, s), 7.99 (1H, s), 8.13 (1H, d), 8.38 (1H, d); HPLC rt(min): 10.00; MS (ES+) 505, (ES−) 503.

Example 177

4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxy-N-(tetrahydro-2H-pyran-4-yl)benzamide (I-177)

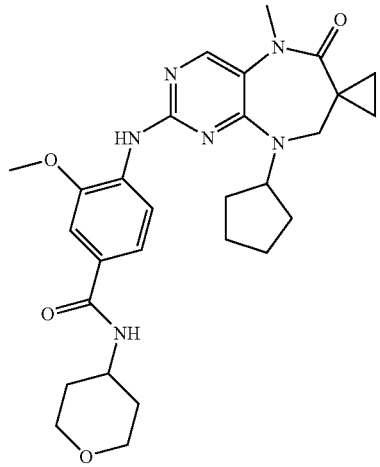

Prepared using the appropriate reagents according to method D. NMR DMSO D$^6$ 0.67 (2H, br t), 0.90 (2H, br t), 1.51-1.78 (11H, m), 1.75-1.85 (2H, m), 3.17 (3H, s), 3.36-3.42 (2H, m), 3.48 (2H, s), 3.89 (2H, br d), 3.99 (3H, s), 3.99-4.03 (1H, m), 4.85 (1H, quint), 7.93 (1H, d), 7.94 (1H, s), 7.70 (1H, s), 7.99 (1H, s), 8.16 (1H, d), 8.40 (1H, d); HPLC rt(min): 9.10; MS (ES+) 521, (ES−) 519.

Example 178

4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-N-cyclopropyl-3-methoxybenzamide (I-178)

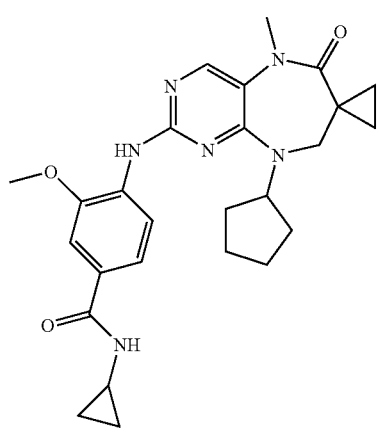

Prepared using the appropriate reagents according to method D. NMR DMSO D$^6$ 0.56-0.59 (2H, m), 0.66-0.73 (4H, m), 0.84-0.91 (2H, m), 1.50-1.76 (6H, m), 1.85-1.95

(2H, m), 2.79-2.83 (1H, m), 3.10 (3H, s), 3.49 (2H, s), 3.94 (3H, s), 4.85 (1H, quint), 7.45 (1H, d), 7.47 (1H, s), 7.69 (1H, s), 7.99 (1H, s), 8.33 (1H, d), 8.38 (1H, d); HPLC rt(min): 9.00; MS (ES$^+$) 477, (ES$^-$) 475.

Example 179

(S)-4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxy-N-(tetrahydrofuran-3-yl)benzamide (I-179)

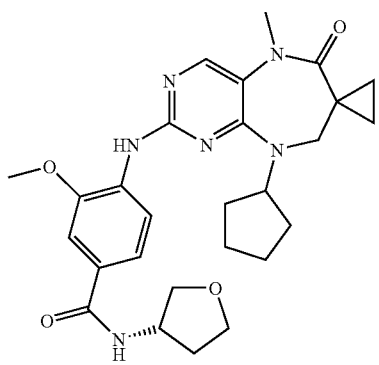

Prepared using the appropriate reagents according to method D. NMR DMSO D$^6$ 0.67 (2H, br m), 0.90 (2H, br m), 1.50-1.69 (6H, br m), 1.88-1.91 (3H, m), 2.16 (1H, m), 3.17 (3H, s), 3.48 (2H, s), 3.60 (1H, m), 3.61 (1H, m), 3.84 (2H, m), 3.95 (3H, s), 4.46 (1H, m), 4.85 (1H, m), 7.50 (2H, m), 7.70 (1H, s), 7.99 (1H, s), 8.38 (1H, m), 8.41 (1H, s); HPLC rt(min): 7.39; MS (ES$^+$) 507, (ES$^-$) 505.

Example 180

4-(6,7,8,9-tetrahydro-9-((S)-tetrahydrofuran-3-yl)-5,7,7-trimethyl-6-oxo-5H-pyrimido[4,5-b][1,4]diazepin-2-ylamino)-3-methoxy-N-methylbenzamide (I-180)

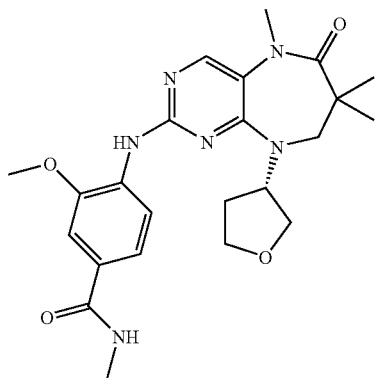

Prepared using the appropriate reagents according to method D. NMR DMSO D$^6$ 1.09 (6H, d), 1.92 (1H, m), 2.31 (1H, m), 2.78 (3H, d), 3.19 (3H, s), 3.47 (2H, m), 3.63 (1H, q), 3.80 (2H, m), 3.93 (3H, s), 3.98 (1H, m), 5.44 (1H, m), 7.48 (2H, m), 7.77 (1H, s), 8.03 (1H, s), 8.35 (2H, m); HPLC rt(min): 7.80; MS (ES$^+$) 455, (ES$^-$) 453.

Example 181

4-(6,7,8,9-tetrahydro-9-((R)-tetrahydrofuran-3-yl)-5,7,7-trimethyl-6-oxo-5H-pyrimido[4,5-b][1,4]diazepin-2-ylamino)-3-methoxy-N-methylbenzamide (I-181)

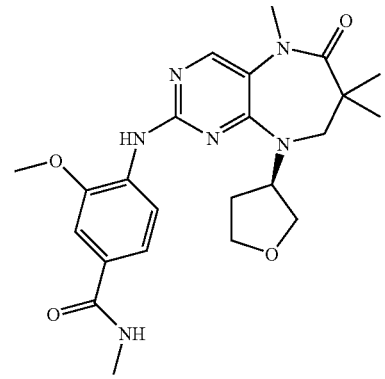

Prepared using the appropriate reagents according to method D. NMR DMSO D$^6$ 1.09 (6H, d), 1.92 (1H, m), 2.31 (1H, m), 2.78 (3H, d), 3.19 (3H, s), 3.47 (2H, m), 3.63 (1H, q), 3.80 (2H, m), 3.93 (3H, s), 3.98 (1H, m), 5.44 (1H, m), 7.48 (2H, m), 7.77 (1H, s), 8.03 (1H, s), 8.35 (2H, m); HPLC rt(min): 7.80; MS (ES$^+$) 455, (ES$^-$) 453.

Example 182

(R)-4-(9-cyclopentyl-5,7-dimethyl-6-oxo-6,7,8,9-tetrahydro-5H-pyrimido[4,5-b][1,4]diazepin-2-ylamino)-3-methoxy-N-(tetrahydro-2H-pyran-4-yl)benzamide (I-182)

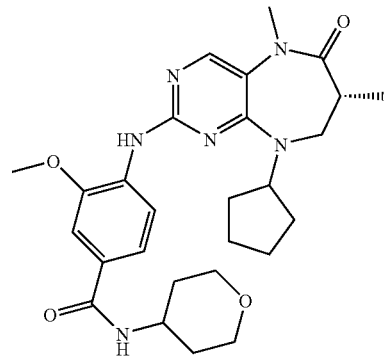

Prepared using the appropriate reagents according to method D. NMR DMSO D$^6$ 1.09 (3H, d), 1.58-1.91 (11H, m), 2.10-2.20 (1H, m), 2.88-2.96 (1H, m), 3.25 (3H, s), 3.36-3.54 (4H, m), 3.90-3.97 (2H, m), 4.02 (3H, s), 4.03-4.12 (1H, m), 4.75-4.85 (1H, m), 7.54-7.57 (2H, m), 7.83 (1H, s), 8.17 (1H, s), 8.24 (1H, d), 8.46 (1H, d); HPLC rt(min): 9.24.

Example 183

4-((R)-9-cyclopentyl-5,7-dimethyl-6-oxo-6,7,8,9-tetrahydro-5H-pyrimido[4,5-b][1,4]diazepin-2-ylamino)-3-methoxy-N—((S)-tetrahydrofuran-3-yl)benzamide (I-183)

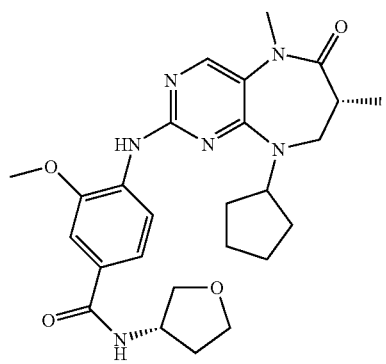

Prepared using the appropriate reagents according to method D. NMR DMSO D⁶ 1.09 (3H, d), 1.48-1.63 (3H, m), 1.65-1.85 (4H, m), 1.85-2.022.10-2.23 (1H, m), 2.30 (3H, s), 2.95-3.05 (1H, m), 3.19 (3H, s), 3.35-3.42 (1H, m), 3.54-3.65 (2H, m), 3.66-3.75 (1H, m), 3.80-3.90 (2H, m), 3.97 (3H, s), 4.42-4.52 (1H, m), 4.76-4.87 (1H, m), 7.52-7.62 (2H, m), 8.04-8.15 (2H, m), 8.52 (1H, d), 9.27 (1H, br s); HPLC rt(min): 9.11.

Example 184

(R)-4-(9-cyclopentyl-5,7-dimethyl-6-oxo-6,7,8,9-tetrahydro-5H-pyrimido[4,5-b][1,4]diazepin-2-ylamino)-N-cyclopropyl-3-methoxybenzamide (I-184)

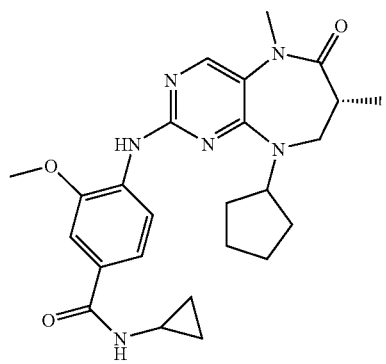

Prepared using the appropriate reagents according to method D. NMR DMSO D⁶ 0.55-0.59 (2H, m), 0.67-0.73 (2H, m), 1.02 (3H, d), 1.52-1.83 (7H, m), 2.05-2.10 (1H, m), 2.79-2.88 (2H, m), 3.19 (3H, s), 3.59-3.45 (2H, m), 3.94 (3H, s), 4.73 (1H, quint), 7.45 (1H, d), 7.47 (1H, s), 7.78 (1H, s), 8.09 (1H, s), 8.33 (1H, d), 8.83 (1H, d); HPLC rt(min): 9.40; MS (ES⁺) 465, (ES⁻) 463.

Example 185

(R)—N-cyclopentyl-4-(9-cyclopentyl-5,7-dimethyl-6-oxo-6,7,8,9-tetrahydro-5H-pyrimido[4,5-b][1,4]diazepin-2-ylamino)-3-methoxybenzamide (I-185)

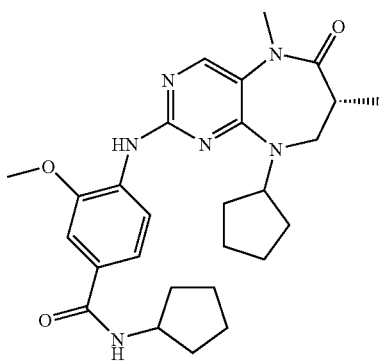

Prepared using the appropriate reagents according to method D. NMR DMSO D⁶ 1.02 (3H, d), 1.50-1.61 (6H, m), 1.63-1.83 (8H, m), 1.86-1.96 (2H, m), 2.04-2.11 (1H, m), 2.83-2.88 (1H, m), 3.19 (3H, s), 3.36-3.46 (1H, m), 3.95 (3H, s), 4.18-4.28 (1H, m), 4.74 (1H, quint), 7.47 (1H, d), 7.48 (1H, s), 7.75 (1H, s), 8.10 (1H, s), 8.15 (1H, s), 8.38 (1H, d); HPLC rt(min): 10.10; MS (ES⁺) 493, (ES⁻) 491.

Example 186

(R)—N-cyclobutyl-4-(9-cyclopentyl-5,7-dimethyl-6-oxo-6,7,8,9-tetrahydro-5H-pyrimido[4,5-b][1,4]diazepin-2-ylamino)-3-methoxybenzamide (I-186)

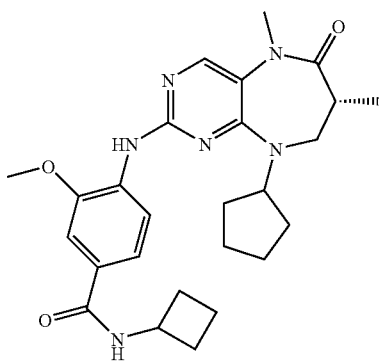

Prepared using the appropriate reagents according to method D. NMR DMSO D⁶ 1.02 (3H, d), 1.50-1.83 (9H, m), 2.03-2.12 (3H, m), 2.19-2.23 (2H, m), 2.81-2.90 (1H, m), 3.19 (3H, s), 3.30-3.33 (1H, m), 3.43 (1H, t), 3.65 (3H, s), 4.43 (1H, q), 4.73 (1H, quint), 7.48 (1H, dd), 7.49 (1H, s), 7.76 (1H, s), 8.10 (1H, s), 8.39 (1H, d), 8.47 (1H, d); HPLC rt(min) 9.90; MS (ES⁺) 479.

Example 187

(R)-4-(9-cyclopentyl-5,7,7-trimethyl-6-oxo-6,7,8,9-tetrahydro-5H-pyrimido[4,5-b][1,4]diazepin-2-ylamino)-3-methoxy-N-(tetrahydrofuran-3-yl)benzamide (I-187)

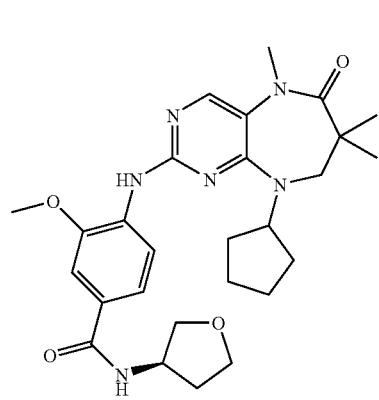

Prepared using the appropriate reagents according to method D. NMR DMSO $D^6$ 1.10 (6H, s), 1.62 (4H, br m), 1.74 (2H, br m), 1.89 (3H, br m), 2.16 (1H, br m), 3.19 (3H, s), 3.38 (2H, s), 3.60 (1H, m), 3.71 (1H, m), 3.86 (2H, m), 3.95 (3H, s), 4.45 (1H, m), 5.20 (1H, m), 7.51 (2H, m), 7.70 (1H, s), 7.99 (1H, s), 8.39 (2H, m); HPLC rt(min): 9.40; MS (ES$^+$) 509.

Example 188

9-cyclopentyl-2-(2-methoxyphenylamino)-5-methyl-8,9-dihydro-5H-pyrimido[4,5-b][1,4]diazepin-6(7H)-one (I-188)

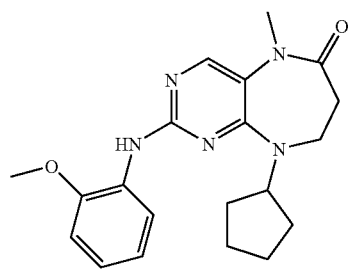

Prepared using the appropriate reagents according to method D. NMR DMSO $D^6$ 1.52-1.75 (6H, m), 1.85-1.95 (2H, m), 2.52-2.58 (2H, m), 3.16 (3H, s), 3.58-3.62 (2H, m), 3.86 (3H, s), 4.75 (1H, quint), 6.93 (2H, dt) 7.02 (1H, dd), 7.61 (1H, s), 8.04 (1H, s), 8.21 (1H, dd); HPLC rt(min): 10.07; MS (ES$^+$) 368.

Example 189

2-(2-methoxyphenylamino)-5,9-dimethyl-8,9-dihydro-5H-pyrimido[4,5-b][1,4]diazepin-6(7H)-one (I-189)

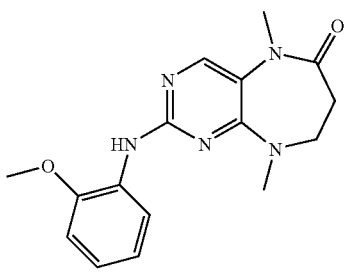

Prepared using the appropriate reagents according to method D. NMR DMSO $D^6$ 2.58-2.61 (2H, m), 3.03 (3H, s), 3.17 (3H, s), 3.65-3.69 (2H, m), 3.87 (3H, s), 6.90-6.97 (2H, m) 7.01-7.03 (1H, m), 7.62 (1H, s), 8.07 (1H, s), 8.30-8.33 (1H, m); HPLC rt(min): 8.61; MS (ES$^+$) 314.

Example 190

4-(9-cyclopentyl-7-ethyl-5-methyl-6-oxo-6,7,8,9-tetrahydro-5H-pyrimido[4,5-b][1,4]diazepin-2-ylamino)-3-methoxy-N-methylbenzamide (I-190)

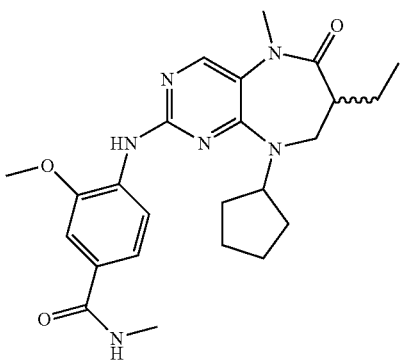

Prepared using the appropriate reagents according to method D. NMR DMSO $D^6$ 0.87 (3H, t), 1.09 (1H, t), 1.28 (1H, m), 1.69 (8H, br m), 2.07 (1H, br m), 2.60 (1H, m), 2.78 (3H, d), 3.19 (3H, s), 3.40 (2H, m), 3.94 (3H, s), 4.77 (1H, br m), 7.48 (2H, m), 7.76 (1H, s), 8.11 (1H, s), 8.33 (1H, br d), 8.38 (1H, d); HPLC rt(min): 9.40; MS (ES$^+$) 453.

Example 191

4-(9-(bicyclo[2.2.1]heptan-2-yl)-5,7,7-trimethyl-6-oxo-6,7,8,9-tetrahydro-5H-pyrimido[4,5-b][1,4]diazepin-2-ylamino)-3-methoxy-N-methylbenzamide (I-191)

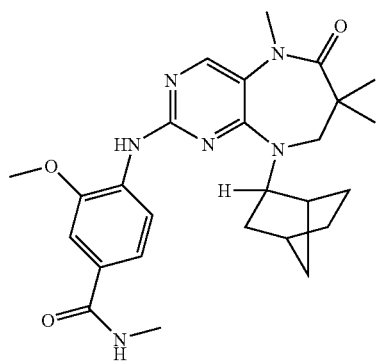

Prepared using the appropriate reagents according to method D. NMR DMSO D$^6$ 0.95-1.08 (2H, m), 1.06 (3H, s), 1.08 (3H, s), 1.16-1.58 (6H, m), 1.95-2.06 (1H, m), 2.18-2.23 (1H, m), 2.58-2.65 (1H, m), 2.79 (3H, d), 3.22 (3H, s), 3.30 (1H, d), 3.52 (1H, d), 3.94 (3H, s), 4.24-4.31 (1H, m), 7.44-7.51 (2H, m), 7.77 (1H, s), 8.12 (1H, s), 8.30-8.36 (1H, m), 8.39 (1H, d); HPLC rt(min): 9.78; MS (ES$^+$) 479.

Example 192

3-methoxy-N-methyl-4-(5,7,7-trimethyl-9-(morpholin-2-ylmethyl)-6-oxo-6,7,8,9-tetrahydro-5H-pyrimido[4,5-b][1,4]diazepin-2-ylamino)benzamide (I-192)

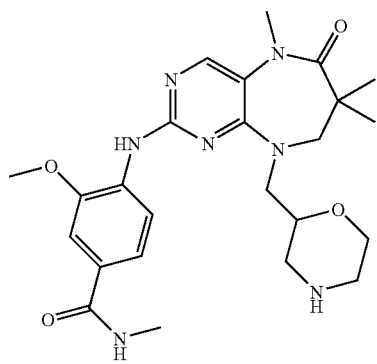

Prepared using the appropriate reagents according to method O. NMR DMSO D$^6$ 1.10 (6H, s), 2.40-2.48 (1H, m), 2.60-2.69 (2H, m), 2.78 (3H, d), 2.78-2.85 (1H, m), 3.19 (3H, s), 3.34 (2H, s), 3.34-3.44 (1H, m), 3.52-3.60 (2H, m), 3.68-3.78 (2H, m), 3.85-3.95 (1H, m), 3.93 (3H, s), 7.45 (1H, d), 7.48 (1H, d), 7.69 (1H, s), 7.99 (1H, s), 8.30-8.35 (1H, m), 8.31 (1H, d); HPLC rt(min): 6.88; MS (ES$^+$) 484.

Example 193

4-(9-cyclopentyl-5,7,7-trimethyl-6-oxo-6,7,8,9-tetrahydro-5H-pyrimido[4,5-b][1,4]diazepin-2-ylamino)-N-(furan-2-ylmethyl)-3-methoxybenzamide (I-193)

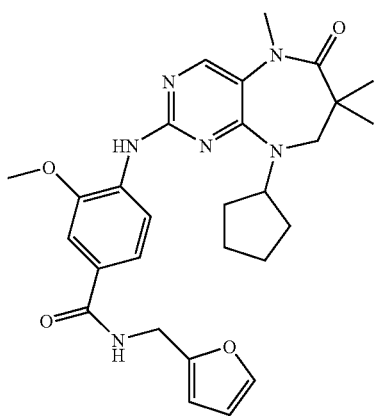

Prepared using the appropriate reagents according to method E. HPLC rt(min): 9.90; MS (ES$^+$) 519.

Example 194

4-(9-cyclopentyl-5,7,7-trimethyl-6-oxo-6,7,8,9-tetrahydro-5H-pyrimido[4,5-b][1,4]diazepin-2-ylamino)-3-methoxy-N-((tetrahydrofuran-2-yl)methyl)benzamide (I-194)

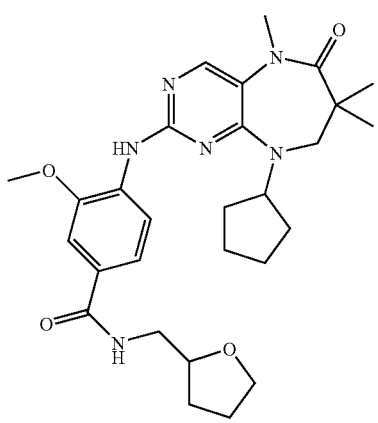

Prepared using the appropriate reagents according to method E. HPLC rt(min): 9.70; MS (ES$^+$) 523.

Example 195

4-(9-cyclopentyl-5,7,7-trimethyl-6-oxo-6,7,8,9-tetrahydro-5H-pyrimido[4,5-b][1,4]diazepin-2-ylamino)-3-methoxy-N-((tetrahydrofuran-2H-pyran-4-yl)methyl)benzamide (I-195)

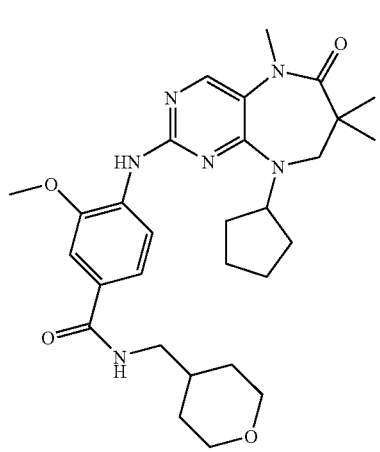

Prepared using the appropriate reagents according to method E. HPLC rt(min): 9.60; MS (ES$^+$) 537.

Example 196

N-(cyclohexylmethyl)-4-(9-cyclopentyl-5,7,7-trimethyl-6-oxo-6,7,8,9-tetrahydro-5H-pyrimido[4,5-b][1,4]diazepin-2-ylamino)-3-methoxybenzamide (I-196)

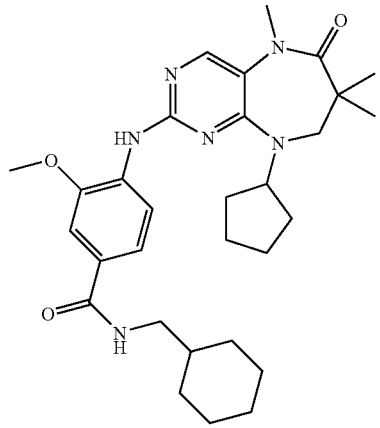

Prepared using the appropriate reagents according to method E. NMR DMSO D$^6$ 0.90-0.96 (2H, m), 1.10 (6H, s), 1.15-1.14 (3H, m), 1.54-1.73 (12H, m), 1.84-1.91 (2H, m), 3.11 (2H, t), 3.19 (3H, s), 3.38 (2H, s), 3.94 (3H, s), 5.18 (1H, quint), 7.47 (1H, d), 7.50 (1H, s), 7.69 (1H, s), 7.99 (1H, s), 8.32-8.37 (2H, m); HPLC rt(min): 10.90; MS (ES$^+$) 535.

Example 197

4-(9-cyclopentyl-5,7,7-trimethyl-6-oxo-6,7,8,9-tetrahydro-5H-pyrimido[4,5-b][1,4]diazepin-2-ylamino)-3-methoxy-N-(2-methoxyethyl)benzamide (I-197)

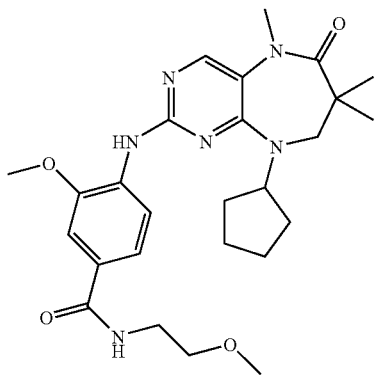

Prepared using the appropriate reagents according to method E. HPLC rt(min): 9.40; MS (ES$^+$) 497.

Example 198

4-(9-cyclopentyl-5,7,7-trimethyl-6-oxo-6,7,8,9-tetrahydro-5H-pyrimido[4,5-b][1,4]diazepin-2-ylamino)-3-methoxy-N-(3-methoxypropyl)benzamide (I-198)

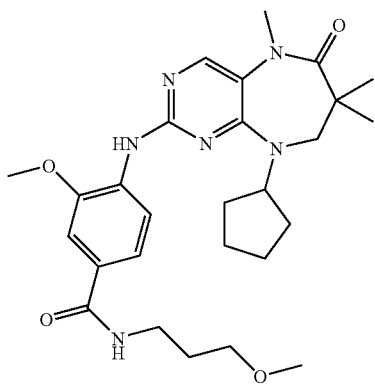

Prepared using the appropriate reagents according to method E. HPLC rt(min): 9.60; MS (ES$^+$) 511.

Example 199

9-cyclopentyl-2-(2-methoxy-4-(morpholine-4-carbonyl)phenylamino)-5,7,7-trimethyl-8,9-dihydro-5H-pyrimido[4,5-b][1,4]diazepin-6(7H)-one (I-199)

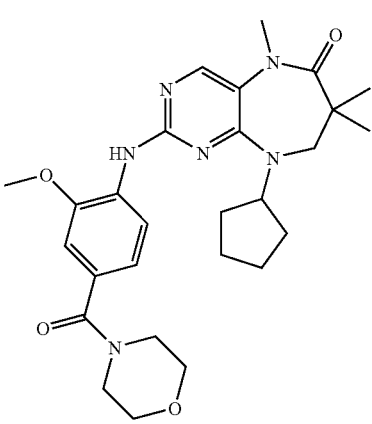

Prepared using the appropriate reagents according to method E. HPLC rt(min): 9.50; MS (ES+) 509.

Example 200

4-(9-cyclopentyl-5,7,7-trimethyl-6-oxo-6,7,8,9-tetrahydro-5H-pyrimido[4,5-b][1,4]diazepin-2-ylamino)-3-methoxy-N-phenylbenzamide (I-200)

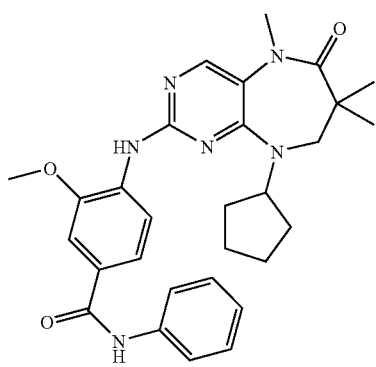

Prepared using the appropriate reagents according to method E. HPLC rt(min): 10.30; MS (ES+) 515.

Example 201

4-(9-cyclopentyl-5,7,7-trimethyl-6-oxo-6,7,8,9-tetrahydro-5H-pyrimido[4,5-b][1,4]diazepin-2-ylamino)-3-methoxy-N-((tetrahydrofuran-2-yl)methyl)benzamide (I-201)

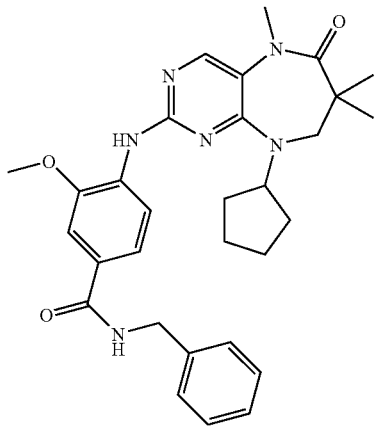

Prepared using the appropriate reagents according to method E. HPLC rt(min): 10.20; MS (ES+) 529.

Example 202

4-(9-cyclopentyl-5,7,7-trimethyl-6-oxo-6,7,8,9-tetrahydro-5H-pyrimido[4,5-b][1,4]diazepin-2-ylamino)-3-methoxy-N-(pyridin-3-ylmethyl)benzamide (I-202)

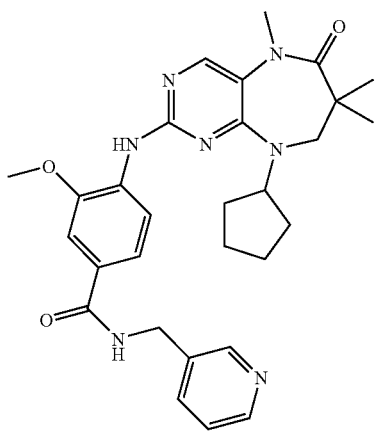

Prepared using the appropriate reagents according to method E. HPLC rt(min): 9.50; MS (ES+) 530.

Example 203

4-(9-cyclopentyl-5,7,7-trimethyl-6-oxo-6,7,8,9-tetrahydro-5H-pyrimido[4,5-b][1,4]diazepin-2-ylamino)-3-methoxy-N-phenethylbenzamide (I-203)

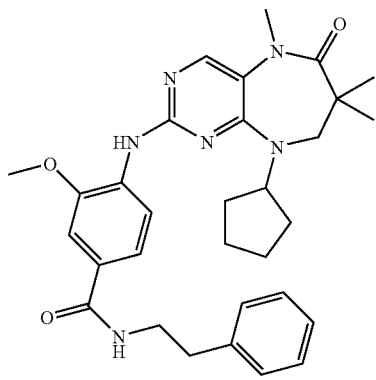

Prepared using the appropriate reagents according to method E. NMR DMSO $D^6$ 1.10 (6H, s), 1.58-1.66 (4H, m), 1.70-1.78 (2H, m), 1.84-1.92 (2H, m), 2.85 (2H, t), 3.19 (3H, s), 3.38 (2H, s), 3.48 (2H, q), 3.94 (3H, s), 5.18 (1H, quint), 7.19-7.33 (5H, m), 7.45 (1H, d), 7.49 (1H, s), 7.70 (1H, s), 7.99 (1H, s), 8.37 (1H, d), 8.47 (1H, br t); HPLC rt(min): 10.40; MS (ES$^+$) 543.

Example 204

4-(9-cyclopentyl-5,7,7-trimethyl-6-oxo-6,7,8,9-tetrahydro-5H-pyrimido[4,5-b][1,4]diazepin-2-ylamino)-N-((1R,4R)-4-hydroxycyclohexyl)-3-methoxybenzamide (I-204)

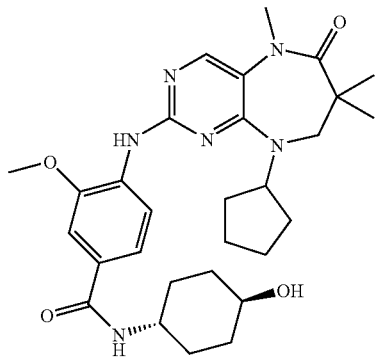

Prepared using the appropriate reagents according to method E. NMR DMSO $D^6$ 1.09 (6H, s), 1.19-1.43 (4H, m), 1.55-1.93 (12H, m), 3.19 (3H, s), 3.34-3.45 (1H, m), 3.38 (2H, s), 3.68-3.79 (1H, m), 3.94 (3H, s), 4.57 (1H, d), 5.19 (1H, dt), 7.46 (1H, d), 7.47 (1H, s), 7.68 (1H, s), 7.99 (1H, s), 8.02 (1H, s), 8.36 (1H, d); HPLC rt(min): 9.21; MS (ES$^+$) 537.

Example 205

4-(9-cyclopentyl-5,7,7-trimethyl-6-oxo-6,7,8,9-tetrahydro-5H-pyrimido[4,5-b][1,4]diazepin-2-ylamino)-N-((1-hydroxycyclohexyl)methyl)-3-methoxy-benzamide (I-205)

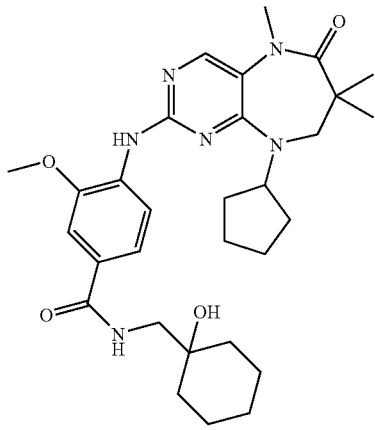

Prepared using the appropriate reagents according to method E. NMR DMSO $D^6$ 1.10 (6H, s), 1.16-1.26 (1H, m), 1.29-1.80 (15H, m), 1.82-1.92 (2H, m), 3.19 (3H, s), 3.28 (2H, d), 3.38 (2H, s), 3.95 (3H, s), 4.43 (1H, s), 5.19 (1H, dt), 7.51 (1H, d), 7.53 (1H, s), 7.70 (1H, s), 7.99 (1H, s), 8.16 (1H, t), 8.38 (1H, d); HPLC rt(min): 10.06; MS (ES$^+$) 551.

Example 206

4-(9-cyclopentyl-5,7,7-trimethyl-6-oxo-6,7,8,9-tetrahydro-5H-pyrimido[4,5-b][1,4]diazepin-2-ylamino)-3-methoxy-N-(pyrrolidin-1-yl)benzamide (I-206)

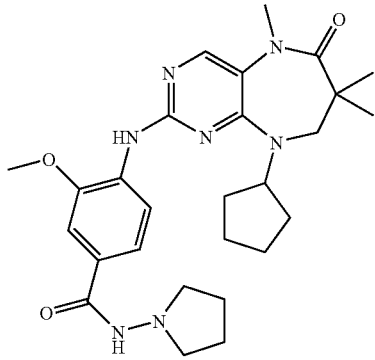

Prepared using the appropriate reagents according to method E. NMR DMSO $D^6$ 1.10 (6H, s), 1.57-1.92 (12H, m), 2.90-2.99 (4H, m), 3.19 (3H, s), 3.38 (2H, s), 3.94 (3H, s), 5.18 (1H, dt), 7.41 (1H, d), 7.43 (1H, s), 7.69 (1H, s), 7.99 (1H, s), 8.37 (1H, d), 9.27 (1H, s); HPLC rt(min): 9.57; MS (ES$^+$) 508.

Example 207

4-(9-cyclopentyl-5,7,7-trimethyl-6-oxo-6,7,8,9-tetrahydro-5H-pyrimido[4,5-b][1,4]diazepin-2-ylamino)-3-methoxy-N-(pyridin-3-yl)benzamide (I-207)

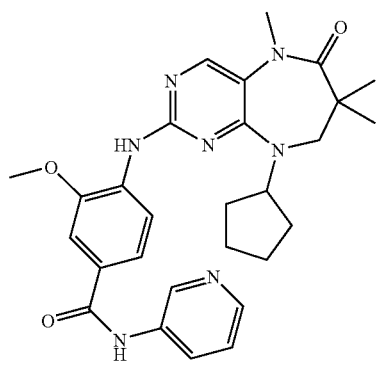

Prepared using the appropriate reagents according to method E. HPLC rt(min): 9.85; MS (ES+) 516.

Example 208

9-cyclopentyl-2-(4-(3-cyclopropyl-3-fluoroazetidine-1-carbonyl)-2-methoxyphenylamino)-5,7,7-trimethyl-8,9-dihydro-5H-pyrimido[4,5-b][1,4]diazepin-6(7)-one (I-208)

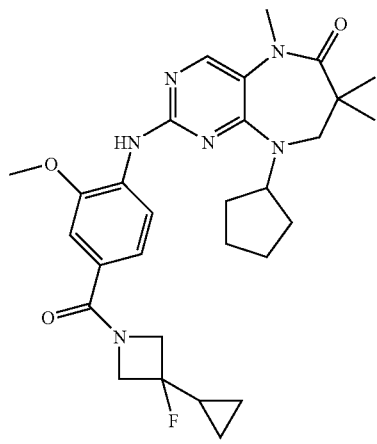

Prepared using the appropriate reagents according to method E. NMR DMSO D$^6$ 0.44 (2H, br s), 0.61 (2H, d), 1.09 (6H, s), 1.35-1.45 (1H, m), 1.53-1.80 (6H, m), 1.82-1.92 (2H, m), 3.19 (3H, s), 3.38 (2H, s), 3.94 (3H, s), 3.96-4.13 (2H, m), 4.20-4.51 (2H, m), 5.19 (1H, dt), 7.24 (1H, s), 7.25 (1H, d), 7.73 (1H, s), 7.99 (1H, s), 8.37 (1H, d); HPLC rt(min): 10.37; MS (ES+) 537.

Example 209

(R)-4-(9-cyclopentyl-5,7,7-trimethyl-6-oxo-6,7,8,9-tetrahydro-5H-pyrimido[4,5-b][1,4]diazepin-2-ylamino)-N-(2,3-dihydro-1H-inden-1-yl)-3-methoxybenzamide (I-209)

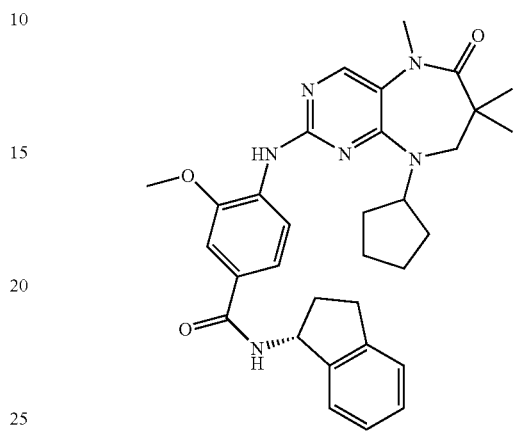

Prepared using the appropriate reagents according to method E. NMR DMSO D$^6$ 1.10 (6H, m), 1.55-1.79 (6H, m), 1.82-1.95 (2H, m), 1.96-2.06 (1H, m), 2.43-2.51 (1H, m), 2.82-2.93 (1H, m), 2.96-3.07 (1H, m), 3.19 (3H, s), 3.38 (2H, s), 3.94 (3H, s), 5.19 (1H, dt), 5.61 (1H, q), 7.18-7.31 (4H, m), 7.55-7.60 (2H, m), 7.71 (1H, s), 8.00 (1H, s), 8.39 (1H, d), 8.67 (1H, d); HPLC rt(min): 10.60; MS (ES+) 555.

Example 210

N-(bicyclo[2.2.1]heptan-2-yl)-4-(9-cyclopentyl-5,7,7-trimethyl-6-oxo-6,7,8,9-tetrahydro-5H-pyrimido[4,5-b][1,4]diazepin-2-ylamino)-3-methoxybenzamide (I-210)

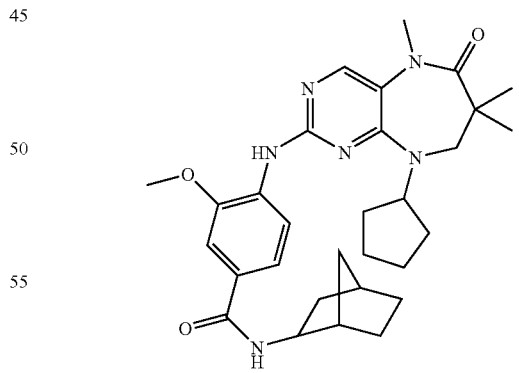

Prepared using the appropriate reagents according to method E. NMR DMSO D$^6$ 1.09 (6H, s), 1.12-1.23 (3H, m), 1.48-1.75 (11H, m), 1.84-1.92 (2H, m), 2.18-2.28 (2H, m), 3.18 (3H, s), 3.37 (2H, s), 3.67-3.75 (1H, m), 3.94 (3H, s), 5.18 (1H, quint), 7.46 (1H, d), 7.47 (1H, s), 7.68 (1H, s), 7.91 (1H, d), 7.98 (1H, s), 8.34 (1H, d); HPLC rt(min): 10.70; MS (ES+) 533.

Example 211

4-(9-cyclopentyl-5,7,7-trimethyl-6-oxo-6,7,8,9-tetrahydro-5H-pyrimido[4,5-b][1,4]diazepin-2-ylamino)-N-(3-hydroxy-2,2-dimethylpropyl)-3-methoxybenzamide (I-211)

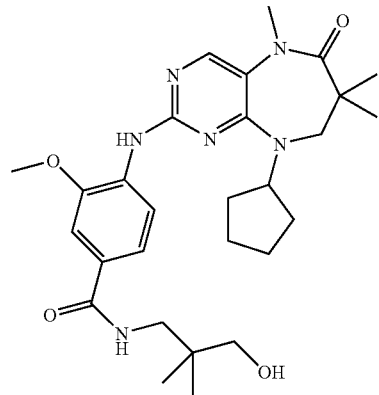

Prepared using the appropriate reagents according to method E. NMR DMSO $D^6$ 0.84 (6H, s), 1.09 (6H, s), 1.55-1.65 (4H, m), 1.70-1.77 (2H, m), 1.84-1.92 (2H, m), 3.10 (2H, d), 3.15 (2H, d), 3.19 (3H, s), 3.38 (2H, s), 3.95 (3H, s), 4.69 (1H, t), 5.18 (1H, quint), 7.48 (1H, d), 7.50 (1H, s), 7.71 (1H, s), 7.99 (1H, s), 8.33-8.39 (2H, m); HPLC rt(min): 9.80; MS (ES$^+$) 525.

Example 212

4-(9-cyclopentyl-5,7,7-trimethyl-6-oxo-6,7,8,9-tetrahydro-5H-pyrimido[4,5-b][1,4]diazepin-2-ylamino)-3-methoxy-N-(pyridin-4-ylmethyl)benzamide (I-212)

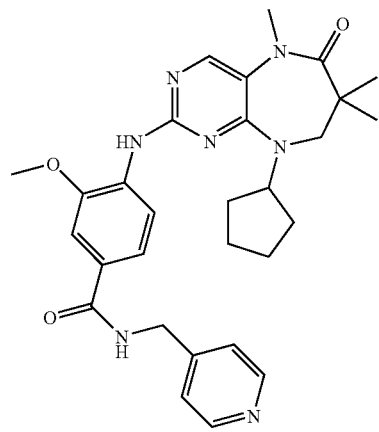

Prepared using the appropriate reagents according to method E. NMR DMSO $D^6$ 1.10 (6H, s), 1.56-1.67 (4H, m), 1.69-1.75 (2H, m), 1.84-1.93 (2H, m), 3.19 (3H, s), 3.38 (2H, s), 3.95 (3H, s), 4.51 (2H, d), 5.19 (1H, quint), 7.31 (2H, d), 7.55 (1H, d), 7.56 (1H, s), 7.73 (1H, s), 8.00 (1H, s), 8.41 (1H, d), 8.51 (2H, d), 9.02 (1H, t); HPLC rt(min): 9.40; MS (ES$^+$) 530.

Example 213

4-(9-cyclopentyl-5,7,7-trimethyl-6-oxo-6,7,8,9-tetrahydro-5H-pyrimido[4,5-b][1,4]diazepin-2-ylamino)-3-methoxy-N-(4-methoxybenzyl)benzamide (I-213)

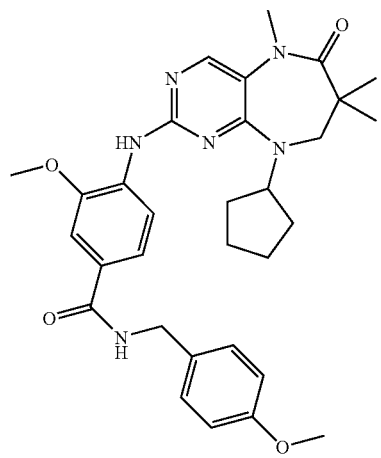

Prepared using the appropriate reagents according to method E. HPLC rt(min): 10.20; MS (ES$^+$) 559.

Example 214

4-(9-cyclopentyl-5,7,7-trimethyl-6-oxo-6,7,8,9-tetrahydro-5H-pyrimido[4,5-b][1,4]diazepin-2-ylamino)-3-methoxy-N-(4-(methylsulfonyl)benzyl)benzamide (I-214)

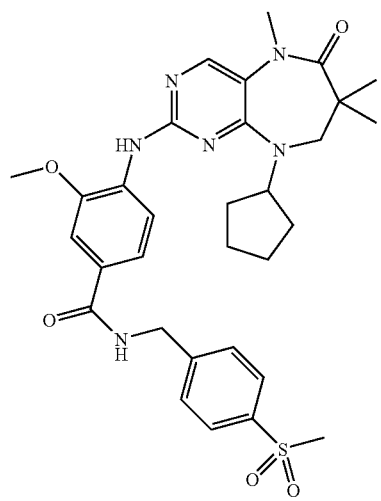

Prepared using the appropriate reagents according to method E. HPLC rt(min): 9.40; MS (ES$^+$) 607.

Example 215

4-(9-cyclopentyl-5,7,7-trimethyl-6-oxo-6,7,8,9-tetrahydro-5H-pyrimido[4,5-b][1,4]diazepin-2-ylamino)-3-methoxy-N,N-dimethylbenzamide (I-215)

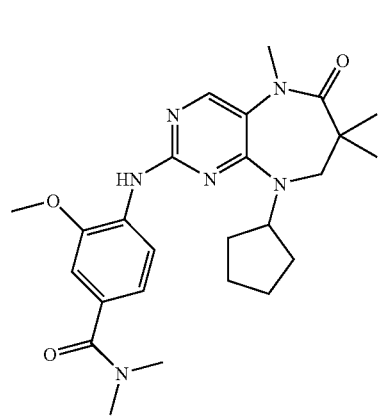

Prepared using the appropriate reagents according to method E. HPLC rt(min): 9.70; MS (ES$^+$) 467.

Example 216

4-(9-cyclopentyl-5,7,7-trimethyl-6-oxo-6,7,8,9-tetrahydro-5H-pyrimido[4,5-b][1,4]diazepin-2-ylamino)-N-(((1S,2S)-2-hydroxycyclohexyl)methyl)-3-methoxybenzamide (I-216)

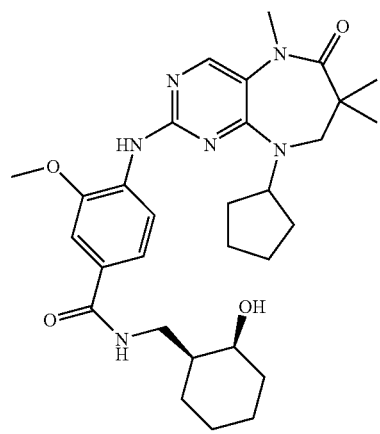

Prepared using the appropriate reagents according to method E. NMR DMSO D$^6$ 1.09 (6H, s), 1.14-1.25 (1H, m), 1.28-1.40 (4H, m), 1.51-1.67 (10H, m), 1.84-1.92 (2H, m), 3.09-3.19 (1H, m), 3.19 (3H, s), 3.24-3.31 (1H, m), 3.38 (2H, s), 3.73 (1H, br s), 3.94 (3H, s), 4.42 (1H, d), 5.18 (1H, quint), 7.47 (1H, d), 7.50 (1H, s), 7.70 (1H, s), 7.99 (1H, s), 8.36-8.38 (2H, m); HPLC rt(min): 10.20; MS (ES$^+$) 551.

Example 217

(S)-4-(9-cyclopentyl-5,7,7-trimethyl-6-oxo-6,7,8,9-tetrahydro-5H-pyrimido[4,5-b][1,4]diazepin-2-ylamino)-3-methoxy-N-(1-methoxypropan-2-yl)benzamide (I-217)

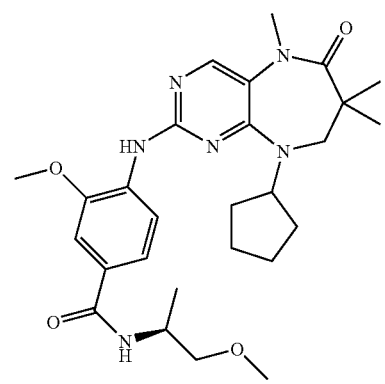

Prepared using the appropriate reagents according to method E. HPLC rt(min): 9.80; MS (ES$^+$) 511.

Example 218

4-(9-cyclopentyl-5,7,7-trimethyl-6-oxo-6,7,8,9-tetrahydro-5H-pyrimido[4,5-b][1,4]diazepin-2-ylamino)-3-methoxy-N-propylbenzamide (I-218)

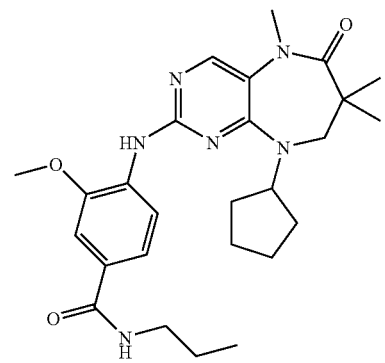

Prepared using the appropriate reagents according to method E. NMR DMSO D$^6$ 0.89 (3H, t), 1.09 (6H, s), 1.53 (2H, dt), 1.53-1.77 (6H, m), 1.82-1.92 (2H, m), 3.19 (3H, s), 3.18-3.25 (2H, m), 3.38 (2H, s), 3.94 (3H, s), 5.18 (1H, dt), 7.47 (1H, d), 7.50 (1H, s), 7.69 (1H, s), 7.99 (1H, s), 8.32-8.39 (2H, m); HPLC rt(min): 9.97; MS (ES$^+$) 481.

Example 219

4-(9-cyclopentyl-5,7,7-trimethyl-6-oxo-6,7,8,9-tetrahydro-5H-pyrimido[4,5-b][1,4]diazepin-2-ylamino)-N-ethyl-3-methoxybenzamide (I-219)

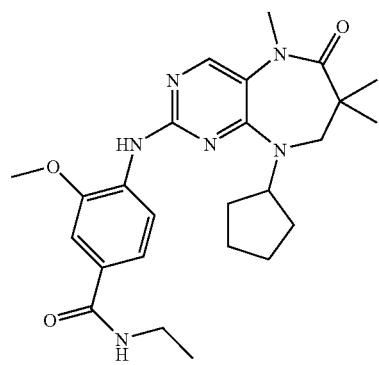

Prepared using the appropriate reagents according to method E. NMR DMSO D$^6$ 1.09 (6H, s), 1.13 (3H, t), 1.57-1.78 (6H, m), 1.82-1.92 (2H, m), 3.18 (3H, s), 3.24-3.34 (2H, m), 3.38 (2H, s), 3.94 (3H, s), 5.18 (1H, dt), 7.47 (1H, d), 7.49 (1H, s), 7.69 (1H, s), 7.99 (1H, s), 8.35-8.39 (2H, m); HPLC rt(min): 9.65; MS (ES$^+$) 467.

Example 220

9-cyclopentyl-2-(2-methoxy-4-(3-methoxyazetidine-1-carbonyl)phenylamino)-5,7,7-trimethyl-8,9-dihydro-5H-pyrimido[4,5-b][1,4]diazepin-6(7H)-one (I-220)

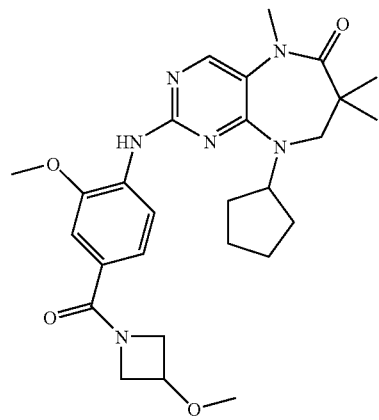

Prepared using the appropriate reagents according to method E. NMR DMSO D$^6$ 1.09 (6H, s), 1.53-1.77 (6H, m), 1.82-1.92 (2H, m), 3.18 (3H, s), 3.22 (3H, s), 3.37 (2H, s), 3.79-3.89 (1H, m), 3.92 (3H, s), 4.13-4.27 (3H, m), 4.43-4.53 (1H, m), 5.17 (1H, dt), 7.21 (1H, d), 7.23 (1H, s), 7.71 (1H, s), 7.98 (1H, s), 8.35 (1H, d); HPLC rt(min): 9.69; MS (ES$^+$) 509.

Example 221

4-(9-cyclopentyl-5,7,7-trimethyl-6-oxo-6,7,8,9-tetrahydro-5H-pyrimido[4,5-b][1,4]diazepin-2-ylamino)-3-methoxy-N-(pyridin-2-yl)benzamide (I-221)

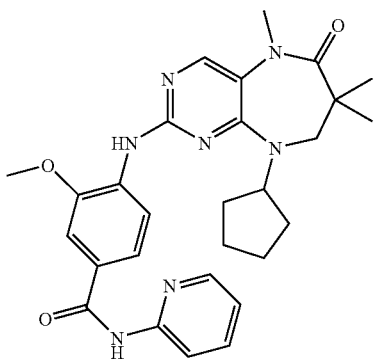

Prepared using the appropriate reagents according to method E. NMR DMSO D$^6$ 1.10 (6H, s), 1.56-1.77 (6H, m), 1.86-1.94 (2H, m), 3.20 (3H, s), 3.42 (2H, s), 4.00 (3H, s), 5.21 (1H, quint), 7.16 (1H, dd), 7.72-7.77 (3H, m), 7.82-7.86 (1H, m), 8.01 (1H, s), 8.21 (1H, d), 8.38 (1H, dd), 8.46 (1H, d), 10.69 (1H, s); HPLC rt(min): 10.30; MS (ES$^+$) 516.

Example 222

4-(9-cyclopentyl-5,7,7-trimethyl-6-oxo-6,7,8,9-tetrahydro-5H-pyrimido[4,5-b][1,4]diazepin-2-ylamino)-3-methoxy-N-(pyrimidin-4-yl)benzamide (I-222)

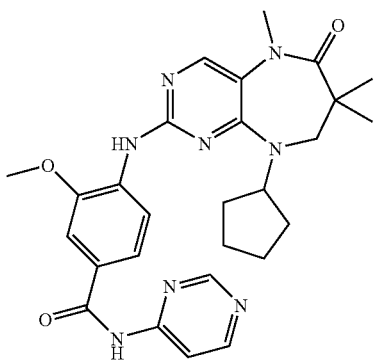

Prepared using the appropriate reagents according to method E. NMR DMSO D$^6$ 1.03 (6H, s), 1.51-1.70 (6H, m), 1.79-1.86 (2H, m), 3.13 (3H, s), 3.32 (2H, s), 3.93 (3H, s), 5.13 (1H, quint), 7.66-7.69 (2H, m), 7.74 (1H, s), 7.95 (1H, s), 8.16 (1H, d), 8.40-8.43 (1H, m), 8.64 (1H, d), 8.88 (1H, s), 11.07 (1H, s); HPLC rt(min): 10.10; MS (ES$^+$) 517.

Example 223

4-(9-cyclopentyl-5,7,7-trimethyl-6-oxo-6,7,8,9-tetrahydro-5H-pyrimido[4,5-b][1,4]diazepin-2-ylamino)-3-methoxy-N-(thiazol-2-yl)benzamide (I-223)

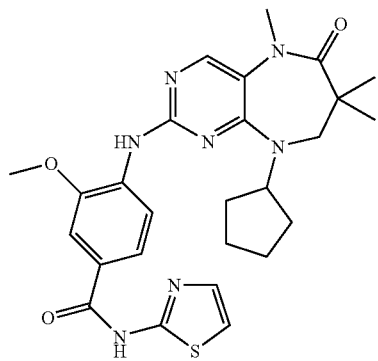

Prepared using the appropriate reagents according to method E. NMR DMSO $D^6$ 1.03 (6H, s), 1.52-1.73 (6H, m), 1.78-1.84 (2H, m), 3.13 (3H, s), 3.32 (2H, s), 3.93 (3H, s), 5.13 (1H, quint), 7.19 (1H, d), 7.49 (1H, d), 7.71-7.74 (3H, m), 7.95 (1H, s), 8.44 (1H, d), 12.42 (1H br s); HPLC rt(min): 10.30; MS (ES$^+$) 522.

Example 224

4-(9-cyclopentyl-5,7,7-trimethyl-6-oxo-6,7,8,9-tetrahydro-5H-pyrimido[4,5-b][1,4]diazepin-2-ylamino)-3-methoxy-N-(pyrazin-2-yl)benzamide (I-224)

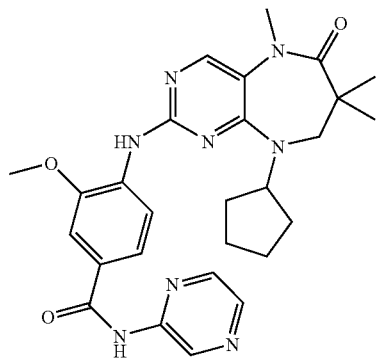

Prepared using the appropriate reagents according to method E. NMR DMSO $D^6$ 1.14 (6H, s), 1.58-1.80 (6H, m), 1.82-1.92 (2H, m), 3.19 (3H, s), 3.50 (2H, s), 4.01 (3H, s), 5.17 (1H, dt), 7.79 (1H, d), 7.83 (1H, s), 8.05 (1H, s), 8.29 (1H, t), 8.43 (1H, d), 8.50 (1H, s), 9.46 (1H, s), 11.12 (1H, s); HPLC rt(min): 9.99; MS (ES$^+$) 517.

Example 225

4-(9-cyclopentyl-5,7,7-trimethyl-6-oxo-6,7,8,9-tetrahydro-5H-pyrimido[4,5-b][1,4]diazepin-2-ylamino)-3-methoxy-N-((1R,2S)-2-phenylcyclopropyl)benzamide (I-225)

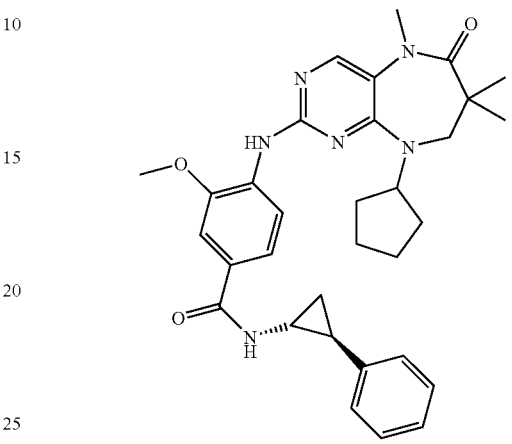

Prepared using the appropriate reagents according to method E. NMR DMSO $D^6$ 1.09 (6H, s), 1.21-1.27 (1H, m), 1.32-1.39 (1H, m), 1.56-1.79 (6H, m), 1.82-1.92 (2H, m), 2.03-2.11 (1H, m), 2.86-3.04 (1H, m), 3.19 (3H, s), 3.38 (2H, s), 3.94 (3H, s), 5.19 (1H, dt), 7.15-7.20 (3H, m), 7.24-7.32 (2H, m), 7.45-7.51 (2H, m), 7.70 (1H, s), 7.99 (1H, s), 8.38 (1H, d), 8.57 (1H, d); HPLC rt(min): 10.50; MS (ES$^+$) 555.

Example 226

(R)-4-(9-cyclopentyl-5,7,7-trimethyl-6-oxo-6,7,8,9-tetrahydro-5H-pyrimido[4,5-b][1,4]diazepin-2-ylamino)-3-methoxy-N-(1-phenylethyl)benzamide (I-226)

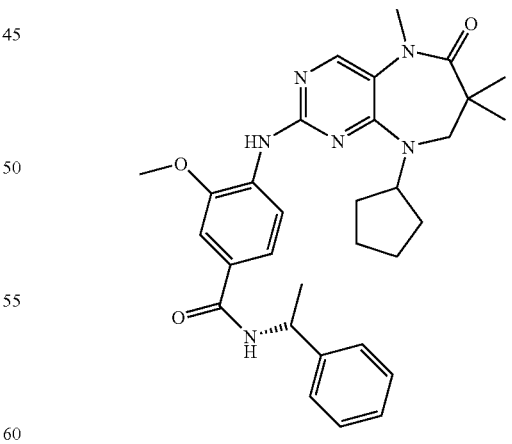

Prepared using the appropriate reagents according to method E. NMR DMSO $D^6$ 1.09 (6H, s), 1.50 (3H, d), 1.53-1.78 (6H, m), 1.82-1.92 (2H, m), 3.19 (3H, s), 3.38 (2H, s), 3.95 (3H, s), 5.16-5.23 (2H, m), 7.23 (1H, t), 7.33 (2H, t), 7.39 (2H, d), 7.53 (2H, d), 7.71 (1H, s), 7.99 (1H, s), 8.38 (1H, d), 8.66 (1H, d); HPLC rt(min): 10.39; MS (ES$^+$) 543.

Example 227

N-(2-chloropyridin-4-yl)-4-(9-cyclopentyl-5,7,7-trimethyl-6-oxo-6,7,8,9-tetrahydro-5H-pyrimido[4,5-b][1,4]diazepin-2-ylamino)-3-methoxybenzamide (I-227)

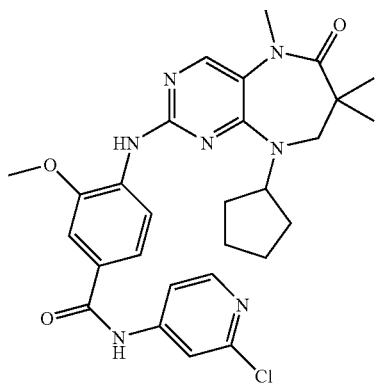

Prepared using the appropriate reagents according to method E. NMR DMSO $D^6$ 1.14 (6H, s), 1.58-1.80 (6H, m), 1.82-1.92 (2H, m), 3.19 (3H, s), 3.51 (2H, s), 4.01 (3H, s), 5.17 (1H, dt), 7.66 (1H, s), 7.67 (1H, d), 7.77 (1H, dd), 7.95 (1H, s), 8.05 (1H, d), 8.27 (1H, t), 8.33 (1H, d), 10.69 (1H, s); HPLC rt(min): 10.46; MS (ES$^+$) 550.

Example 228

4-(9-cyclopentyl-5,7,7-trimethyl-6-oxo-6,7,8,9-tetrahydro-5H-pyrimido[4,5-b][1,4]diazepin-2-ylamino)-3-methoxy-N-(2-methoxypyridin-3-yl)benzamide (I-228)

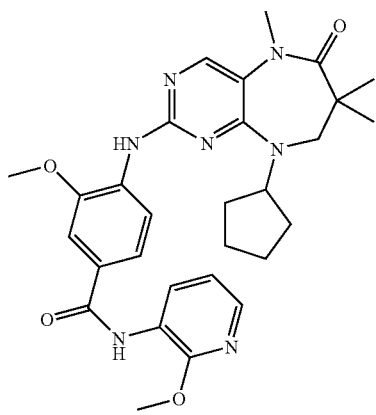

Prepared using the appropriate reagents according to method E. NMR DMSO $D^6$ 1.14 (6H, s), 1.58-1.80 (6H, m), 1.82-1.92 (2H, m), 3.19 (3H, s), 3.50 (2H, s), 3.93 (3H, s), 3.99 (3H, s), 5.15 (1H, dt), 7.06 (1H, dd), 7.66 (1H, d), 7.69 (1H, s), 7.98-8.05 (3H, m), 8.23 (1H, t), 8.88 (1H, bs), 9.64 (1H, s); HPLC rt(min): 10.51; MS (ES$^+$) 546.

Example 229

4-(9-cyclopentyl-5,7,7-trimethyl-6-oxo-6,7,8,9-tetrahydro-5H-pyrimido[4,5-b][1,4]diazepin-2-ylamino)-N-(((1S,2R)-2-hydroxycyclohexyl)methyl)-3-methoxybenzamide (I-229)

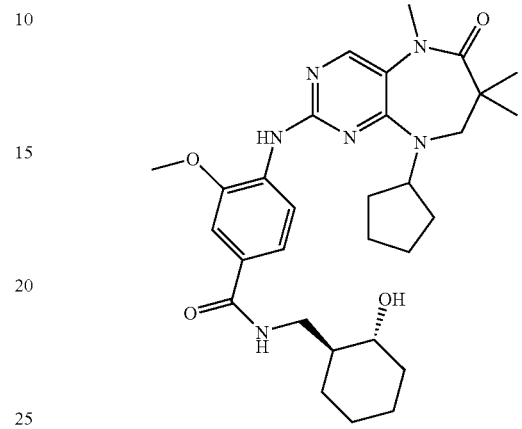

Prepared using the appropriate reagents according to method E. NMR DMSO $D^6$ 0.93-0.99 (1H, m), 1.09 (6H, s), 1.10-1.20 (2H, m), 1.36-1.46 (1H, m), 1.52-1.91 (12H, m), 3.07-3.13 (1H, m), 3.19 (3H, s), 3.35-3.45 (2H, m), 3.38 (2H, s), 3.94 (3H, s), 4.82 (1H, d), 5.18 (1H, dt), 7.48 (1H, d), 7.50 (1H, s), 7.70 (1H, s), 7.99 (1H, s), 8.32 (1H, t), 8.36 (1H, d); HPLC rt(min): 10.17; MS (ES$^+$) 551.

Example 230

4-(9-cyclopentyl-5,7,7-trimethyl-6-oxo-6,7,8,9-tetrahydro-5H-pyrimido[4,5-b][1,4]diazepin-2-ylamino)-N-(cyclopentylmethyl)-3-methoxybenzamide (I-230)

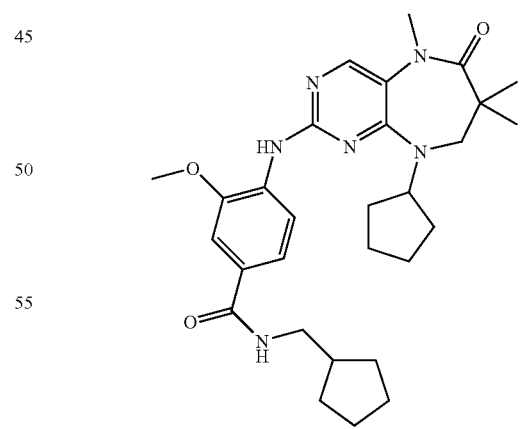

Prepared using the appropriate reagents according to method E. NMR DMSO $D^6$ 1.09 (6H, s), 1.21-1.30 (2H, m), 1.43-1.79 (12H, m), 1.83-1.96 (2H, m), 2.11-2.19 (1H, m), 3.15-3.22 (2H, m), 3.19 (3H, s), 3.38 (2H, s), 3.94 (3H, s), 5.18 (1H, dt), 7.47 (1H, d), 7.50 (1H, s), 7.69 (1H, s), 7.99 (1H, s), 8.36 (1H, d); HPLC rt(min): 10.65; MS (ES$^+$) 521.

Example 231

4-(9-cyclopentyl-5,7,7-trimethyl-6-oxo-6,7,8,9-tetrahydro-5H-pyrimido[4,5-b][1,4]diazepin-2-ylamino)-3-methoxy-N-(5-methyl-1H-pyrazol-3-yl)benzamide (I-231)

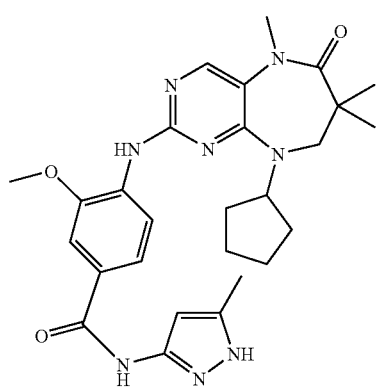

Prepared using the appropriate reagents according to method E. NMR DMSO $D^6$ 1.14 (6H, s), 1.59-1.90 (8H, m), 2.23 (3H, s), 3.18 (3H, s), 3.50 (2H, s), 3.99 (3H, s), 5.15 (1H, dt), 6.41 (1H, br s), 7.70 (1H, d), 7.76 (1H, s), 8.03 (1H, s), 8.19 (1H, d), 10.69 (1H, s); HPLC rt(min): 9.57; MS (ES$^+$) 519.

Example 232

4-(9-cyclopentyl-5,7,7-trimethyl-6-oxo-6,7,8,9-tetrahydro-5H-pyrimido[4,5-b][1,4]diazepin-2-ylamino)-3-methoxy-N-(3-methylisothiazol-5-yl)benzamide (I-232)

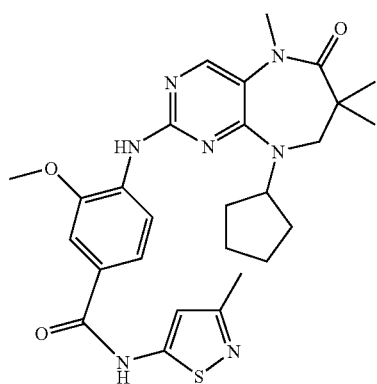

Prepared using the appropriate reagents according to method E. NMR DMSO $D^6$ 1.14 (6H, s), 1.59-1.82 (6H, m), 1.84-1.98 (2H, m), 2.36 (3H, s), 3.19 (3H, s), 3.51 (2H, s), 4.01 (3H, s), 5.16 (1H, dt), 6.93 (1H, s), 7.74 (1H, d), 7.75 (1H, s), 8.05 (1H, s), 8.27 (1H, d), 9.01 (1H, br s), 12.19 (1H, s); HPLC rt(min): 10.15; MS (ES$^+$) 53.6.

Example 233

N-(cyanomethyl)-4-(9-cyclopentyl-5,7,7-trimethyl-6-oxo-6,7,8,9-tetrahydro-5H-pyrimido[4,5-b][1,4]diazepin-2-ylamino)-3-methoxybenzamide (I-233)

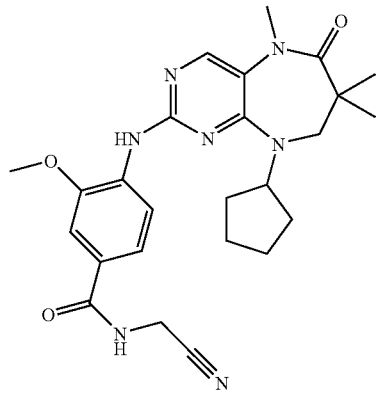

Prepared using the appropriate reagents according to method E. NMR DMSO $D^6$ 1.09 (6H, s), 1.56-1.80 (6H, m), 1.82-1.88 (2H, m), 3.19 (3H, s), 3.38 (2H, s), 3.95 (3H, s), 4.31 (2H, d), 5.18 (1H, dt), 7.50 (1H, d), 7.52 (1H, s), 7.75 (1H, s), 8.00 (1H, s), 8.43 (1H, d), 9.07 (1H, t); HPLC rt(min): 9.34; MS (ES$^+$) 478.

Example 234

4-(9-cyclopentyl-5,7,7-trimethyl-6-oxo-6,7,8,9-tetrahydro-5H-pyrimido[4,5-b][1,4]diazepin-2-ylamino)-3-methoxy-N-(3-trifluoromethyl)pyridin-4-yl))benzamide (I-234)

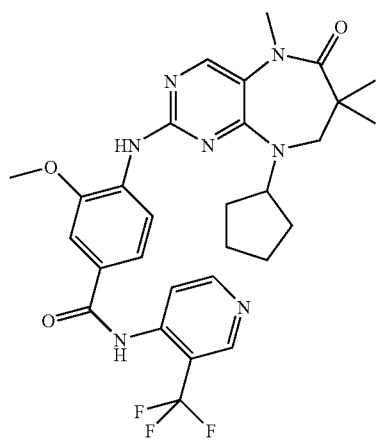

Prepared using the appropriate reagents according to method E. NMR DMSO $D^6$ 1.15 (6H, s), 1.58-1.78 (6H, m), 1.82-1.92 (2H, m), 3.19 (3H, s), 3.52 (2H, s), 3.99 (3H, s), 5.14 (1H, quint), 7.64-7.69 (2H, m), 7.75-7.79 (1H, m), 8.05 (1H, d), 8.20-8.24 (1H, m), 8.89 (1H, d), 9.00 (1H, s), 9.15 (1H, br s), 10.23 (1H, br s); HPLC rt(min): 10.70; MS (ES$^+$) 584.

Example 235

4-(9-cyclopentyl-5,7,7-trimethyl-6-oxo-6,7,8,9-tetrahydro-5H-pyrimido[4,5-b][1,4]diazepin-2-ylamino)-3-methoxy-N-((5-methylisoxazol-3-yl)methyl)benzamide (I-235)

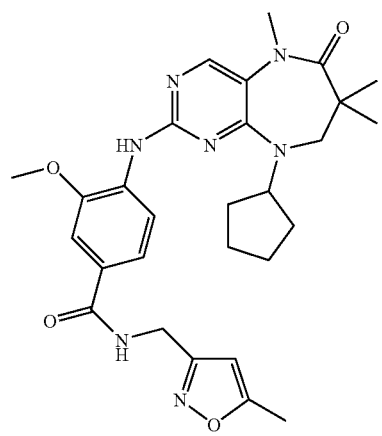

Prepared using the appropriate reagents according to method E. NMR DMSO D$^6$ 1.10 (6H, s), 1.54-1.67 (4H, m), 1.69-1.76 (2H, m), 1.82-1.93 (2H, m), 2.37 (3H, s), 3.19 (3H, s), 3.38 (2H, s), 3.94 (3H, s), 4.46 (2H, d), 5.18 (1H, quint), 6.15 (1H, s), 7.52 (1H, d), 7.53 (1H, s), 7.72 (1H, s), 7.99 (1H, s), 8.40 (1H, d), 8.96 (1H, t); HPLC rt(min): 9.70; MS (ES$^+$) 534.

Example 236

4-(9-cyclopentyl-5,7,7-trimethyl-6-oxo-6,7,8,9-tetrahydro-5H-pyrimido[4,5-b][1,4]diazepin-2-ylamino)-3-methoxy-N-(5-methylthiazol-2-yl)benzamide (I-236)

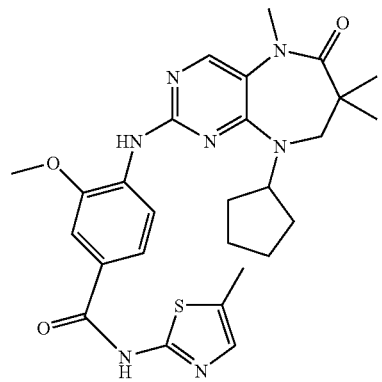

Prepared using the appropriate reagents according to method E. NMR DMSO D$^6$ 1.12 (6H, s), 1.58-1.82 (6H, s), 1.83-1.91 (2H, m), 2.38 (3H, s), 3.19 (3H, s), 3.50 (2H, s), 4.00 (3H, s), 5.16 (1H, quint), 7.24 (1H, s), 7.79 (1H, d), 7.85 (1H, s), 8.05 (1H, s), 8.27 (1H, d), 8.78 (1H, br s), 12.44 (1H, br s); HPLC rt(min): 10.50; MS (ES$^+$) 536.

Example 237

4-(9-cyclopentyl-5,7,7-trimethyl-6-oxo-6,7,8,9-tetrahydro-5H-pyrimido[4,5-b][1,4]diazepin-2-ylamino)-N-(2-(2-hydroxyethoxy)ethyl)-3-methoxybenzamide (I-237)

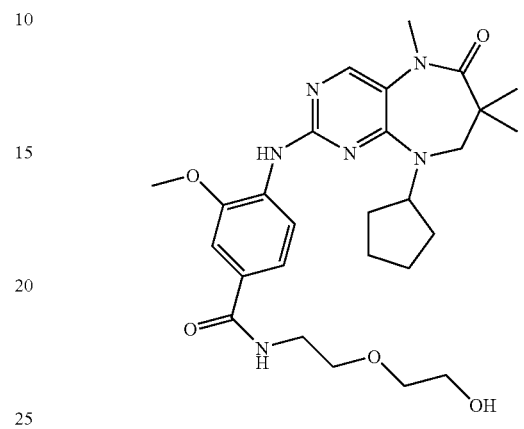

Prepared using the appropriate reagents according to method E. NMR DMSO D$^6$ 1.09 (6H, s), 1.54-1.69 (4H, s), 1.70-1.81 (2H, m), 1.84-1.93 (2H, m), 3.19 (3H, s), 3.38 (2H, s), 3.40-3.47 (4H, m), 3.49-3.55 (4H, m), 3.94 (3H, s), 4.62 (1H, t), 5.18 (1H, quint), 7.48 (1H, d), 7.51 (1H, s), 7.70 (1H, s), 7.99 (1H, s), 8.38 (1H, d), 8.42 (1H, t); HPLC rt(min): 9.00; MS (ES$^+$) 527.

Example 238

4-(9-cyclopentyl-5,7,7-trimethyl-6-oxo-6,7,8,9-tetrahydro-5H-pyrimido[4,5-b][1,4]diazepin-2-ylamino)-N-isopropyl-3-methoxybenzamide (I-238)

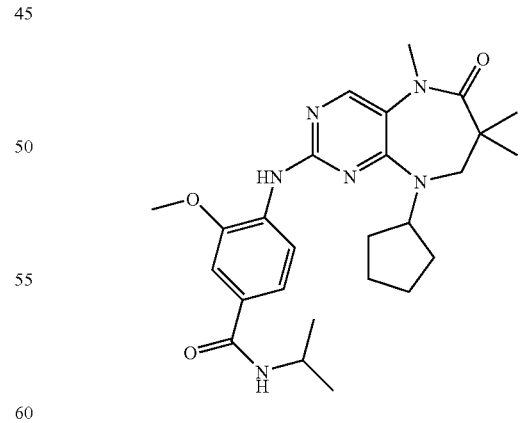

Prepared using the appropriate reagents according to method E. NMR DMSO D$^6$ 1.09 (6H, s), 1.17 (6H, s), 1.54-1.69 (4H, m), 1.72-1.79 (2H, m), 1.82-1.93 (2H, m), 3.19 (3H, s), 3.38 (2H, s), 3.94 (3H, s), 4.11 (1H, dt), 5.19 (1H, quint), 7.48 (1H, d), 7.49 (1H, s), 7.68 (1H, s), 7.99 (1H, s), 8.08 (1H, d), 8.36 (1H, d); HPLC rt(min): 10.10; MS (ES$^+$) 481.

Example 239

(S)-4-(9-cyclopentyl-5,7,7-trimethyl-6-oxo-6,7,8,9-tetrahydro-5H-pyrimido[4,5-b][1,4]diazepin-2-ylamino)-N-(1-hydroxy-3-methylbutan-2-yl)-3-methoxybenzamide (I-239)

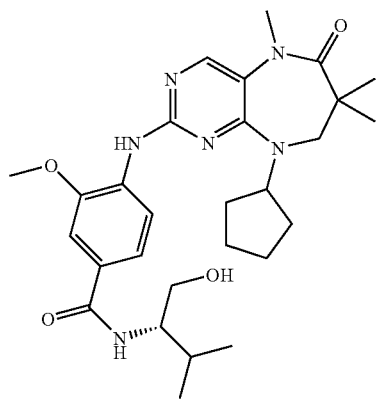

Prepared using the appropriate reagents according to method E. NMR DMSO D$^6$ 0.89 (3H, d), 0.91 (3H, d), 1.09 (6H, s), 1.58-1.77 (6H, m), 1.83-1.97 (3H, m), 3.19 (3H, s), 3.38 (2H, s), 3.53 (2H, t), 3.76-3.85 (1H, m), 3.95 (3H, s), 4.60 (1H, t), 5.19 (1H, dt), 7.51 (1H, d), 7.52 (1H, s), 7.69 (1H, s), 7.86 (1H, d), 7.99 (1H, s), 8.36 (1H, d); HPLC rt(min): 9.75; MS (ES$^+$) 525.

Example 240

4-(9-cyclopentyl-5,7,7-trimethyl-6-oxo-6,7,8,9-tetrahydro-5H-pyrimido[4,5-b][1,4]diazepin-2-ylamino)-N-(1-hydroxy-2-methylpropan-2-yl)-3-methoxybenzamide (I-240)

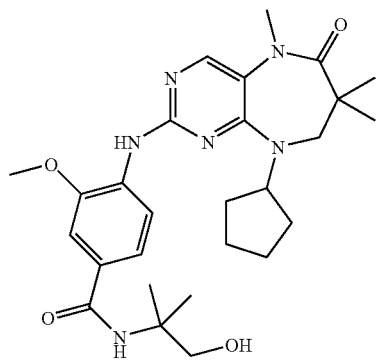

Prepared using the appropriate reagents according to method E. NMR DMSO D$^6$ 1.09 (6H, s), 1.32 (6H, s), 1.57-1.90 (8H, m), 3.18 (3H, s), 3.38 (2H, s), 3.52 (2H, d), 3.94 (3H, s), 4.96 (1H, t), 5.19 (1H, dt), 7.40-7.44 (3H, m), 7.68 (1H, s), 7.99 (1H, s), 8.36 (1H, d); HPLC rt(min): 9.61; MS (ES$^+$) 511.

Example 241

4-(9-cyclopentyl-5,7,7-trimethyl-6-oxo-6,7,8,9-tetrahydro-5H-pyrimido[4,5-b][1,4]diazepin-2-ylamino)-N-(3-hydroxypropyl)-3-methoxy-N-(thiazol-2-yl)benzamide (I-241)

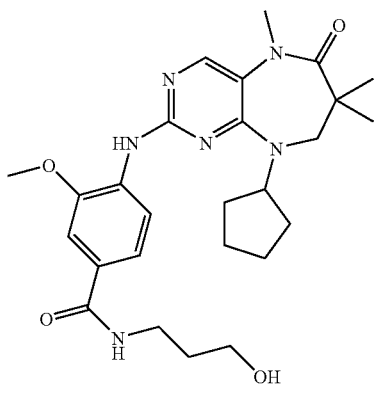

Prepared using the appropriate reagents according to method E. NMR DMSO D$^6$ 1.09 (6H, s), 1.54-1.79 (8H, m), 1.82-1.93 (2H, m), 3.18 (3H, s), 3.28-3.36 (2H, m), 3.38 (2H, s), 3.46 (2H, dd), 3.94 (3H, s), 4.50 (1H, t), 5.18 (1H, dt), 7.47 (1H, d), 7.50 (1H, s), 7.69 (1H, s), 7.99 (1H, s), 8.34-8.39 (2H, m); HPLC rt(min): 9.02; MS (ES$^+$) 497.

Example 242

(S)-4-(9-cyclopentyl-5,7,7-trimethyl-6-oxo-6,7,8,9-tetrahydro-5H-pyrimido[4,5-b][1,4]diazepin-2-ylamino)-N-(2,3-dihydroxypropyl)-3-methoxybenzamide (I-242)

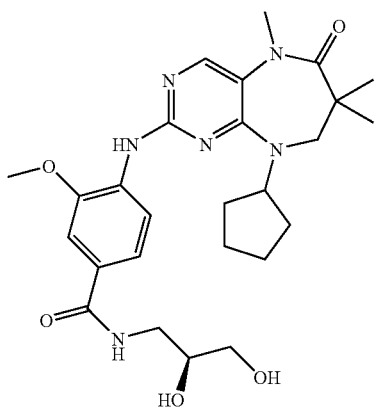

Prepared using the appropriate reagents according to method E. NMR DMSO D$^6$ 1.09 (6H, s), 1.53-1.77 (6H, m), 1.82-1.94 (2H, m), 3.19 (3H, s), 3.18-3.24 (1H, m), 3.38 (2H, s), 3.30-3.43 (3H, m), 3.60-3.66 (1H, m), 3.94 (3H, s), 4.61 (1H, t), 4.85 (1H, d), 5.19 (1H, dt), 7.50 (1H, d), 7.53 (1H, s), 7.70 (1H, s), 7.99 (1H, s), 8.34-8.41 (2H, m); HPLC rt(min): 8.62; MS (ES$^+$) 513.

Example 243

4-(9-cyclopentyl-5,7,7-trimethyl-6-oxo-6,7,8,9-tetrahydro-5H-pyrimido[4,5-b][1,4]diazepin-2-ylamino)-N-(3-hydroxybutyl)-3-methoxybenzamide (I-243)

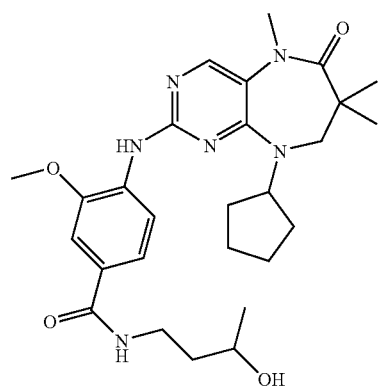

Prepared using the appropriate reagents according to method E. NMR DMSO D$^6$ 1.07-1.10 (3H, m), 1.09 (6H, s), 1.51-1.89 (10H, m), 3.18 (3H, s), 3.28-3.38 (2H, m), 3.39 (2H, s), 3.63-3.70 (1H, m), 3.93 (3H, s), 4.54 (1H, d), 5.18 (1H, dt), 7.46 (1H, d), 7.49 (1H, s), 7.69 (1H, s), 7.99 (1H, s), 8.32-8.39 (2H, m); HPLC rt(min): 9.31; MS (ES$^+$) 511.

Example 244

4-(9-cyclopentyl-5,7,7-trimethyl-6-oxo-6,7,8,9-tetrahydro-5H-pyrimido[4,5-b][1,4]diazepin-2-ylamino)-N-((1R,2R)-2-hydroxycyclopentyl)-3-methoxybenzamide (I-244)

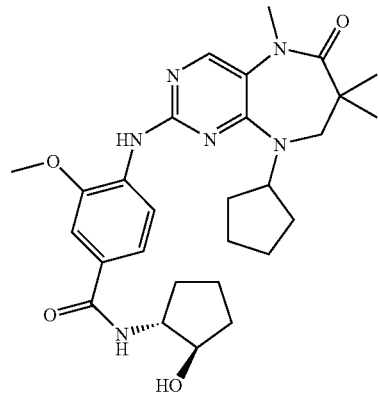

Prepared using the appropriate reagents according to method E. NMR DMSO D$^6$ 1.09 (6H, s), 1.44-1.52 (2H, m), 1.53-1.78 (8H, m), 1.81-1.96 (3H, m), 1.97-2.04 (1H, m), 3.18 (3H, s), 3.38 (2H, s), 3.94 (3H, s), 3.94-4.03 (2H, m), 4.80 (1H, d), 5.19 (1H, dt), 7.48 (1H, d), 7.49 (1H, s), 7.69 (1H, s), 7.99 (1H, s), 8.11 (1H, d), 8.36 (1H, d); HPLC rt(min): 9.55; MS (ES$^+$) 523.

Example 245

4-(9-cyclopentyl-5,7,7-trimethyl-6-oxo-6,7,8,9-tetrahydro-5H-pyrimido[4,5-b][1,4]diazepin-2-ylamino)-N-((2,2-difluorocyclopropyl)methyl)-3-methoxybenzamide (I-245)

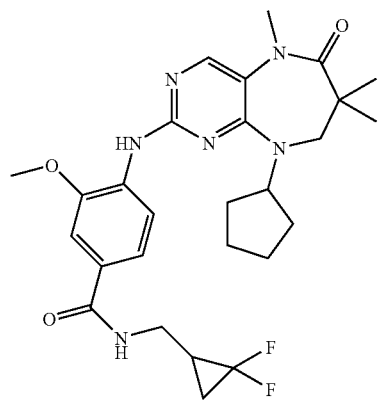

Prepared using the appropriate reagents according to method E. NMR DMSO D$^6$ 1.10 (6H, s), 1.26-1.36 (1H, m), 1.55-1.70 (5H, m), 1.70-1.79 (2H, m), 1.82-1.94 (2H, m), 1.95-2.09 (1H, m), 3.19 (3H, s), 3.31-3.39 (2H, m), 3.39 (2H, s), 3.95 (3H, s), 5.18 (1H, dt), 7.50 (1H, d), 7.52 (1H, s), 7.76 (1H, bs), 7.99 (1H, s), 8.38 (1H, d), 8.65 (1H, t); HPLC rt(min) 10.00; MS (ES$^+$) 529.

Example 246

N-(cyclobutylmethyl)-4-(9-cyclopentyl-5,7,7-trimethyl-6-oxo-6,7,8,9-tetrahydro-5H-pyrimido[4,5-b][1,4]diazepin-2-ylamino)-3-methoxybenzamide (I-246)

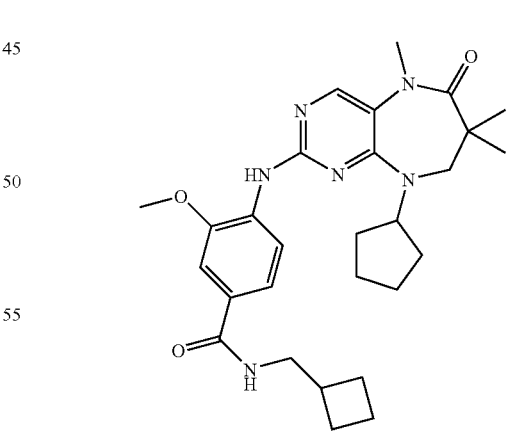

Prepared using the appropriate reagents according to method E. NMR DMSO D$^6$ 1.09 (6H, s), 1.58-2.04 (14H, m), 2.50-2.56 (1H, m), 3.18 (3H, s), 3.30 (2H, t), 3.38 (2H, s), 3.94 (3H, s), 5.18 (1H, dt), 7.47 (1H, d), 7.49 (1H, s), 7.69 (1H, s), 7.99 (1H, s), 8.32-8.38 (2H, m); HPLC rt(min): 10.42; MS (ES$^+$) 507.

Example 247

4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxy-N-(pyridin-4-ylmethyl)benzamide (I-247)

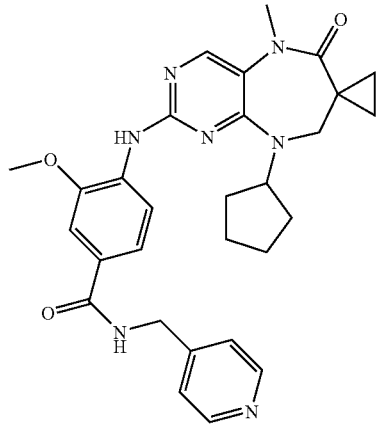

Prepared using the appropriate reagents according to method E. NMR DMSO D⁶ 0.66-0.69 (2H, m), 0.89-0.91 (2H, m), 1.51-1.55 (2H, m), 1.60-1.64 (2H, m), 1.69 (2H, m), 1.89 (2H, m), 3.17 (3H, s), 3.44 (2H, m), 3.95 (3H, s), 4.50-4.52 (2H, m), 4.85 (1H, m), 7.30-7.31 (2H, m), 7.55-7.57 (2H, m), 7.73 (1H, s), 8.00 (1H, s), 8.44 (1H, s), 8.50-8.51 (2H, m), 9.03 (1H, m); HPLC rt(min): 9.08; MS (ES⁺) 528.

Example 248

4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-N-(furan-2-ylmethyl)-3-methoxybenzamide (I-248)

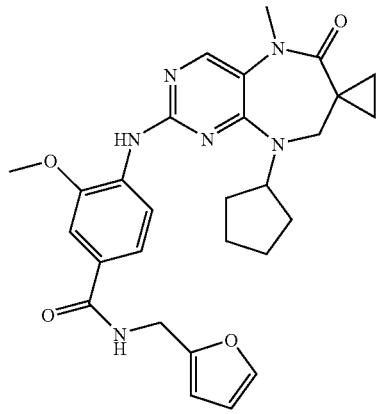

Prepared using the appropriate reagents according to method E. NMR DMSO D⁶ 0.72 (2H, m), 0.90 (2H, m), 1.50-1.54 (2H, m), 1.60-1.64 (2H, m), 1.69 (2H, m), 1.89 (2H, m), 3.17 (3H, s), 3.48 (2H, br s), 3.94 (3H, s), 4.47-4.48 (2H, m), 4.85 (1H, m), 6.27 (1H, m), 6.41 (1H, m), 7.53 (2H, m), 7.59 (1H, br s), 7.70 (1H, br s), 7.99 (1H, br s), 8.41 (1H, d); HPLC rt(min): 9.58; MS (ES⁺) 517.

Example 249

4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxy-N-(pyridin-3-ylmethyl)benzamide (I-249)

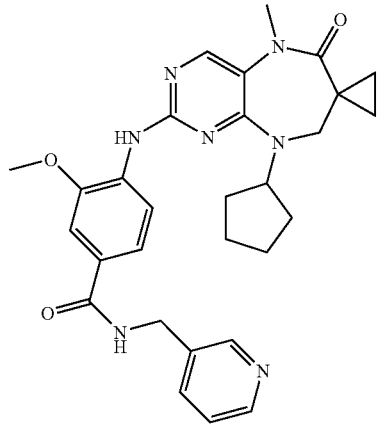

Prepared using the appropriate reagents according to method E. NMR DMSO D⁶ 0.67-0.68 (2H, m), 0.90-0.91 (2H, m), 1.50-1.54 (2H, m), 1.59-1.64 (2H, m), 1.69 (2H, m), 1.89 (2H, m), 3.17 (3H, s), 3.45-3.48 (2H, m), 3.94 (3H, s), 4.50-4.51 (2H, m), 4.58 (1H, m), 7.37 (1H, m), 7.52-7.55 (2H, m), 7.71-7.73 (2H, m), 7.99 (1H, s), 8.42-8.47 (2H, m), 8.56 (1H, s), 9.00 (1H, m); HPLC rt(min): 9.12; MS (ES⁺) 528.

Example 250

2-(4-(1H-imidazole-2-yl)-2-methoxyphenylamino)-9-cyclopentyl-5,7,7-trimethyl-8,9-dihydro-5H-pyrimido[4,5-b][1,4]diazepin-6(7H)-one (I-250)

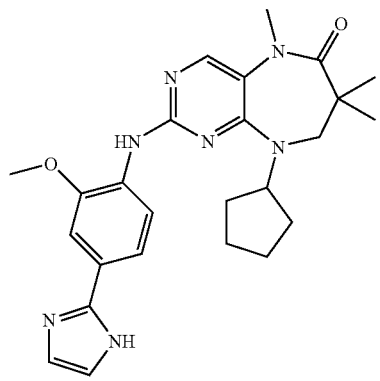

Prepared using the appropriate reagents according to method D. NMR DMSO D⁶ 1.09 (6H, s), 1.56-1.81 (6H, m), 1.82-1.97 (2H, m), 3.19 (3H, s), 3.30-3.40 (2H, m), 3.94 (3H, s), 5.14-5.25 (1H, m), 7.1 (2H, br s), 7.49-7.54 (1H, m), 7.59-7.65 (2H, m), 7.97 (1H, s), 8.30-8.36 (1H, m), 12.40 (1H, s); HPLC rt(min): 9.50; MS (ES⁺) 462.

Example 251

4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-N-((1R,4R)-4-hydroxycyclohexyl)-3-methoxybenzamide (I-251)

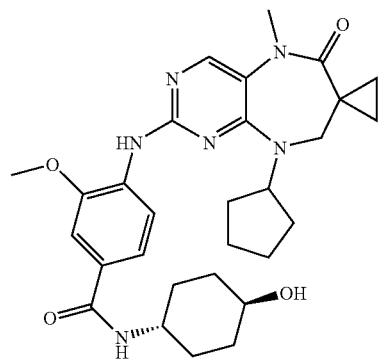

Prepared using the appropriate reagents according to method E. NMR DMSO $D^6$ 0.67 (2H, m), 0.90 (2H, m), 1.20-1.28 (2H, m), 1.34-1.43 (2H, m), 1.50-1.54 (2H, m), 1.59-1.87 (10H, m), 3.16 (3H, s), 3.47 (2H, m), 3.73 (1H, m), 3.94 (3H, s), 4.58 (1H, m), 4.86 (1H, m), 7.45-7.47 (2H, m), 7.68 (1H, m), 7.98-8.04 (2H, m), 8.38 (1H, m); HPLC rt(min): 8.84; MS (ES$^+$) 535.

Example 252

4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-N-(((1S,2S)-2-hydroxycyclohexyl)methyl)-3-methoxybenzamide (I-252)

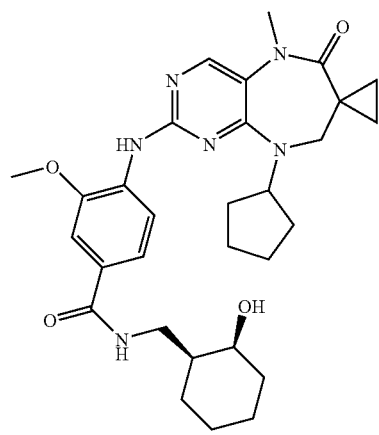

Prepared using the appropriate reagents according to method E. NMR DMSO $D^6$ 0.66-0.67 (2H, m), 0.90-0.91 (2H, m), 1.15-1.18 (2H, m), 1.23-1.35 (4H, m), 1.501-1.69 (10H, m), 1.88 (2H, m), 3.17 (3H, s), 3.48 (2H, m), 3.73 (1H, m), 3.94 (3H, s), 4.42 (1H, m), 4.84 (1H, m), 7.46-7.50 (2H, m), 7.70 (1H, br s), 7.99 (1H, br s), 8.36-8.41 (2H, m); HPLC rt(min): 9.85; MS (ES$^+$) 549.

Example 253

4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxy-N-(pyrrolidin-1-yl)benzamide (I-253)

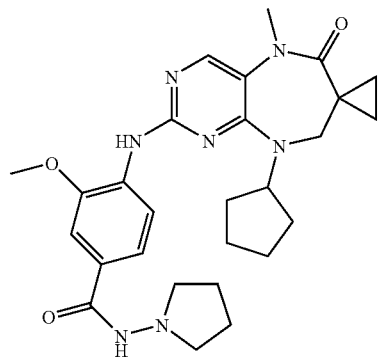

Prepared using the appropriate reagents according to method E. NMR DMSO $D^6$ 0.66-0.68 (2H, m), 0.90-0.91 (2H, m), 1.49 (2H, m), 1.50-1.54 (2H, m), 1.60-1.61 (2H, m), 1.64-1.78 (4H, m), 1.88 (2H, m), 2.95 (4H, m), 3.17 (3H, s), 3.48 (2H, m), 3.94 (3H, s), 4.84 (1H, m), 7.41 (2H, m), 7.69 (1H, s), 7.99 (1H, s), 8.40 (1H, m), 9.28 (1H, s); HPLC rt(min): 9.20; MS (ES$^+$) 506.

Example 254

4-(9-cyclopentyl-5,7,7-trimethyl-6-oxo-6,7,8,9-tetrahydro-5H-pyrimido[4,5-b][1,4]diazepin-2-ylamino)-N-(1-(hydroxymethyl)cyclopentyl)-3-methoxybenzamide (I-254)

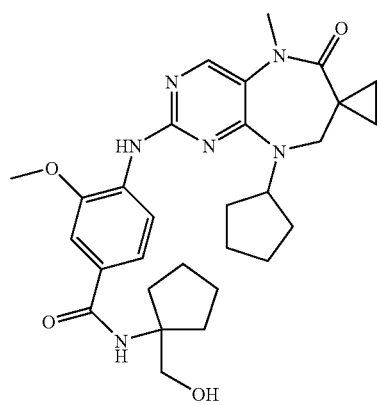

Prepared using the appropriate reagents according to method E. NMR DMSO $D^6$ 1.09 (6H, s), 1.52-1.78 (12H, m), 1.83-1.92 (2H, m), 1.95-2.05 (2H, m), 3.19 (3H, s), 3.38 (2H, s), 3.58 (2H, d), 3.94 (3H, s), 4.89 (1H, t), 5.19 (1H, quint), 7.44-7.46 (2H, m), 7.63 (1H, s), 7.68 (1H, s), 7.99 (1H, s), 8.36 (1H, d); HPLC rt(min): 10.10; MS (ES$^+$) 537.

Example 255

4-(9-cyclopentyl-5,7,7-trimethyl-6-oxo-6,7,8,9-tetrahydro-5H-pyrimido[4,5-b][1,4]diazepin-2-ylamino)-3-methoxy-N-(pyridin-2-ylmethyl)benzamide (I-255)

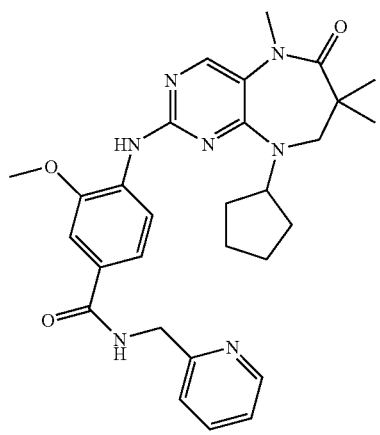

Prepared using the appropriate reagents according to method E. NMR DMSO D⁶ 1.08 (6H, s), 1.54-1.67 (4H, m), 1.68-1.78 (2H, m), 1.85-1.93 (2H, m), 3.16 (3H, s), 3.38 (2H, s), 3.95 (3H, s), 4.57 (2H, d), 5.19 (1H, quint), 7.25-7.28 (1H, m), 7.32 (1H, d), 7.57 (1H, d), 7.58 (1H, s), 7.74 (1H, s), 7.76 (1H, t), 8.00 (1H, s), 8.41 (1H, d), 8.51 (1H, d), 9.04 (1H, t); HPLC rt(min): 9.60; MS (ES⁺) 530.

Example 256

9-cyclopentyl-2-(4-(4,5-dihydro-1H-imidazol-2-yl)-2-methoxyphenylamino)-5,7,7-trimethyl-8,9-dihydro-5H-pyrimido[4,5-b][1,4]diazepin-6(7H)-one (I-256)

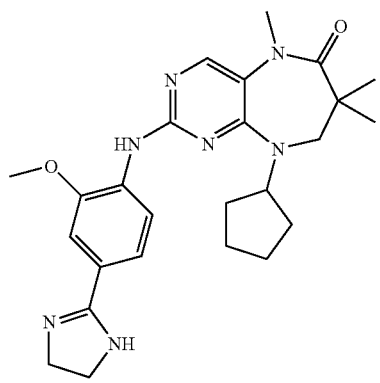

Prepared using the appropriate reagents according to method D. NMR DMSO D⁶ 1.09 (6H, s), 1.55-1.95 (8H, m), 3.19 (3H, s), 3.38 (2H, s), 3.65 (4H, s), 3.92 (3H, s), 5.20 (1H, quint), 7.42 (1H, d) 7.50 (1H, s), 7.71 (1H, s), 7.99 (1H, s), 8.38 (1H, d); HPLC rt(min): 9.06; MS (ES⁺) 464.

Example 257

9-cyclopentyl-2-(4-(5,5-dimethyl-4,5-dihydro-1H-imidazol-2-yl)-2-methoxyphenylamino)-5,7,7-trimethyl-8,9-dihydro-5H-pyrimido[4,5-b][1,4]diazepin-6(7H)-one (I-257)

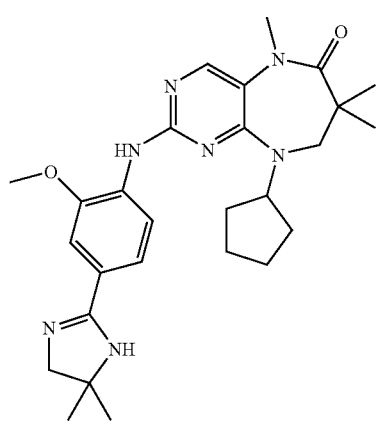

Prepared using the appropriate reagents according to method D. NMR DMSO D⁶ 1.09 (6H, s), 1.24 (6H, s), 1.55-1.95 (8H, m), 3.18 (3H, s), 3.32 (2H, s), 3.38 (2H, s), 3.92 (3H, s), 5.18 (1H, quint), 7.38 (1H, dd) 7.46 (1H, s), 7.67 (1H, s), 7.99 (1H, s), 8.36 (1H, d); HPLC rt(min): 9.43; MS (ES⁺) 492.

Example 258

4-(9-cyclopentyl-5,7,7-trimethyl-6-oxo-6,7,8,9-tetrahydro-5H-pyrimido[4,5-b][1,4]diazepin-2-ylamino)-N-((1R,3R)-3-(hydroxycyclopentyl)-3-methoxybenzamide (I-258)

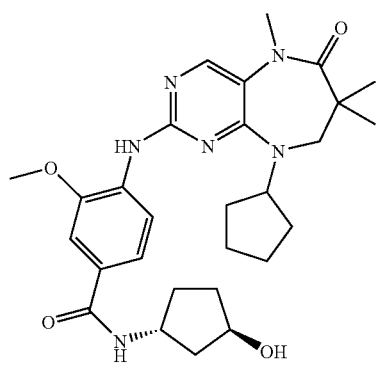

Prepared using the appropriate reagents according to method E. NMR DMSO D⁶ 0.87 (6H, s), 1.21-1.31 (2H, m), 1.37-1.53 (7H, m), 1.60-1.74 (4H, m), 1.80-1.87 (1H, m), 2.96 (3H, s), 3.16 (2H, s), 3.72 (3H, s), 4.00 (1H, br s), 4.23 (1H, dd), 4.31 (1H, d), 4.96 (1H, quint), 7.23 (1H, d), 7.25 (1H, s), 7.46 (1H, s), 7.77 (1H, s), 7.91 (1H, d), 8.13 (1H, d); HPLC rt(min): 9.20; MS (ES⁺) 523.

Example 259

4-(9-cyclopentyl-5,7,7-trimethyl-6-oxo-6,7,8,9-tetrahydro-5H-pyrimido[4,5-b][1,4]diazepin-2-ylamino)-N-((1R,3R)-3-(hydroxycyclopentyl)methyl)-3-methoxybenzamide (I-259)

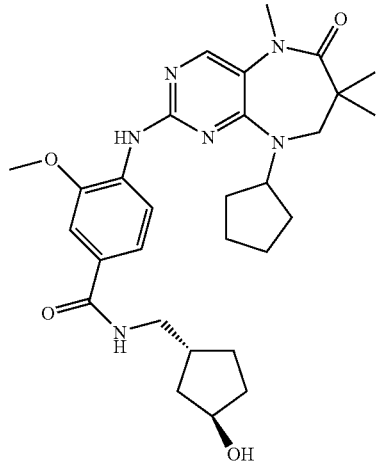

Prepared using the appropriate reagents according to method E. NMR DMSO $D^6$ 1.09 (6H, s), 1.18-1.27 (1H, m), 1.34-1.47 (2H, m), 1.57-1.69 (5H, m), 1.72-0.93 (6H, m), 2.33-2.41 (1H, m), 3.19 (3H, s), 3.34 (2H, s), 3.39 (2H, s), 3.94 (3H, s), 4.14 (1H, br d), 4.38 (1H, d), 5.18 (1H, quint), 7.47 (1H, d), 7.50 (1H, s), 7.69 (1H, s), 7.99 (1H, s), 8.35-8.37 (2H, m); HPLC rt(min): 9.30; MS (ES+) 537.

Example 260

4-(9-cyclopentyl-5,7,7-trimethyl-6-oxo-6,7,8,9-tetrahydro-5H-pyrimido[4,5-b][1,4]diazepin-2-ylamino)-N-((1R,3R)-3-(hydroxymethyl)cyclopentyl)-3-methoxybenzamide (I-260)

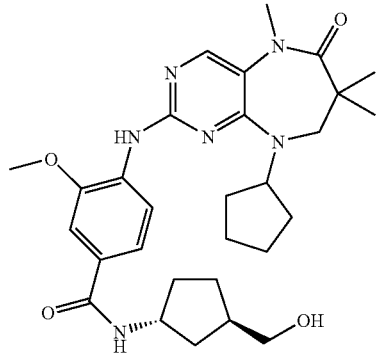

Prepared using the appropriate reagents according to method E. NMR DMSO $D^6$ 1.08 (6H, s), 1.23-1.29 (1H, m), 1.50-1.68 (6H, m), 1.70-1.76 (2H, m), 1.78-1.98 (5H, m), 2.16-2.24 (1H, m), 3.19 (3H, s), 3.30 (2H, t), 3.38 (2H, s), 3.94 (3H, s), 4.22-4.28 (1H, m), 4.55 (1H, t), 5.18 (1H, quint), 7.46 (1H, d), 7.47 (1H, s), 7.68 (1H, s), 7.99 (1H, s), 8.13 (1H, d), 8.35 (1H, d); HPLC rt(min): 9.40; MS (ES+) 537.

Example 261

4-(9-cyclopentyl-5,7,7-trimethyl-6-oxo-6,7,8,9-tetrahydro-5H-pyrimido[4,5-b][1,4]diazepin-2-ylamino)-3-methoxy-N-(4-methoxyphenyl)benzamide (I-261)

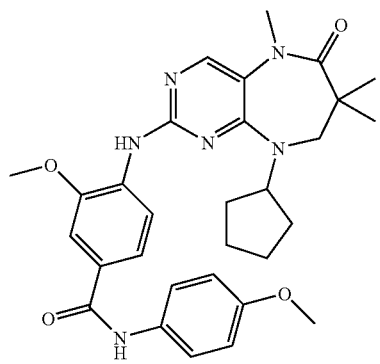

Prepared using the appropriate reagents according to method E. NMR DMSO $D^6$ 1.10 (6H, s), 1.56-1.69 (4H, m), 1.70-1.79 (2H, m), 1.83-1.93 (2H, m), 3.19 (3H, s), 3.39 (2H, s), 3.75 (3H, s), 3.98 (3H, s), 5.21 (1H, quint), 6.93 (2H, d), 7.59-7.66 (4H, m), 7.76 (1H, s), 8.01 (1H, s), 8.44 (1H, d), 9.98 (1H, s); HPLC rt(min): 10.19; MS (ES+) 545.

Example 262

4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-N-(3-hydroxypropyl)-3-methoxybenzamide (I-262)

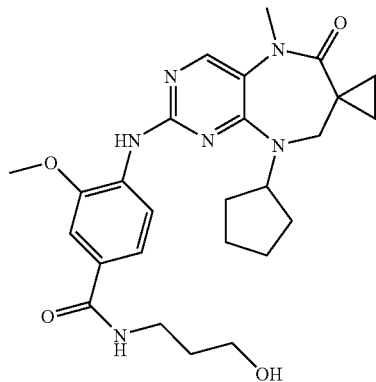

Prepared using the appropriate reagents according to method E. NMR DMSO $D^6$ 0.67 (2H, m), 0.90 (2H, m), 1.50-1.71 (6H, m), 1.89-1.91 (2H, m), 3.17 (3H, s), 3.29-3.34 (4H, m), 3.44-3.47 (4H, m), 3.94 (3H, s), 4.50 (1H, m), 4.84 (1H, m), 7.46-7.50 (2H, m), 7.69 (1H, s), 7.99 (1H, s), 8.35-8.41 (2H, m); HPLC rt(min): 8.58; MS (ES+) 495.

Example 263

4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-N-isopropyl-3-methoxybenzamide (I-263)

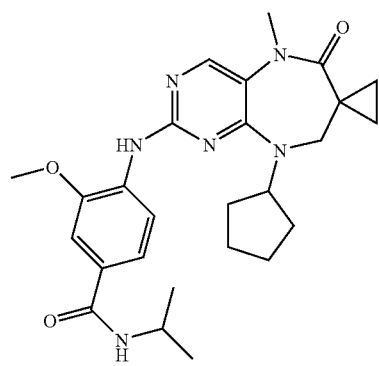

Prepared using the appropriate reagents according to method E. NMR DMSO D$^6$ 0.67 (2H, m), 0.90 (2H, m), 1.17 (3H, s), 1.18 (3H, s), 1.50-1.70 (6H, m), 1.80 (2H, m), 3.17 (3H, s), 3.48 (2H, s), 3.95 (3H, s), 4.10 (1H, m), 4.85 (1H, m), 7.49 (2H, m), 7.69 (1H, s), 7.99 (1H, s), 8.10 (1H, d), 8.40 (1H, d); HPLC rt(min): 9.58; MS (ES$^+$) 479.

Example 264

4-(9-cyclopentyl-5,7,7-trimethyl-6-oxo-6,7,8,9-tetrahydro-5H-pyrimido[4,5-b][1,4]diazepin-2-ylamino)-N-(2-hydroxyethyl)-3-methoxybenzamide (I-264)

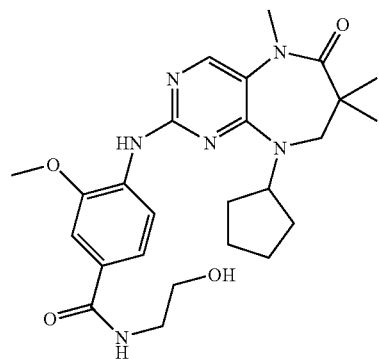

Prepared using the appropriate reagents according to method E. NMR DMSO D$^6$ 0.19 (6H, s), 1.52-1.67 (4H, m), 1.69-1.81 (2H, m), 1.82-1.94 (2H, m), 3.19 (3H, s), 3.30-3.34 (2H, br m), 3.38 (2H, s), 3.48-3.53 (2H, m), 3.94 (3H, s), 4.75 (1H, t), 5.18 (1H, quint), 7.49 (1H, d), 7.51 (1H, s), 7.69 (1H, s), 7.99 (1H, s), 8.35 (1H, s), 8.37 (1H, d); HPLC rt(min): 8.87; MS (ES$^+$) 483.

Example 265

(S)-4-(9-cyclopentyl-5,7,7-trimethyl-6-oxo-6,7,8,9-tetrahydro-5H-pyrimido[4,5-b][1,4]diazepin-2-ylamino)-N-(1-(hydroxypropan-2-yl)-3-methoxybenzamide (I-265)

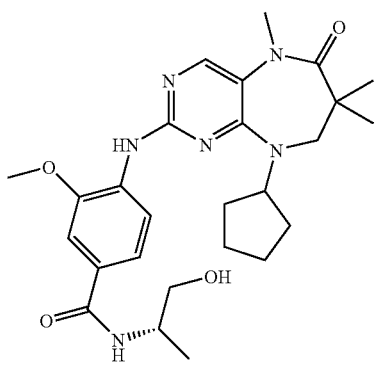

Prepared using the appropriate reagents according to method E. NMR DMSO D$^6$ 1.10 (6H, s), 1.14 (3H, d), 1.52-1.67 (4H, m), 1.69-1.81 (2H, m), 1.82-1.94 (2H, m), 3.19 (3H, s), 3.31-3.34 (1H, m), 3.38 (2H, s), 3.44-3.50 (1H, m), 3.95 (3H, s), 3.99-4.06 (1H, m), 4.74 (1H, t), 5.19 (1H, quint), 7.49 (1H, d), 7.50 (1H, s), 7.69 (1H, s), 7.96 (1H, s), 7.99 (1H, s), 8.37 (1H, d); HPLC rt(min) 9.15; MS (ES$^+$) 497.

Example 266

4-(9-cyclopentyl-5,7,7-trimethyl-6-oxo-6,7,8,9-tetrahydro-5H-pyrimido[4,5-b][1,4]diazepin-2-ylamino)-N-(1-(hydroxymethyl)cyclopentyl)-3-methoxybenzamide (I-266)

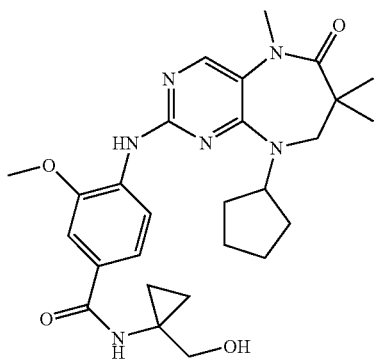

Prepared using the appropriate reagents according to method E. NMR DMSO D$^6$ 0.65-0.72 (2H, m), 0.75-0.80 (2H, m), 1.09 (6H, s), 1.57-1.94 (8H, m), 3.18 (3H, s), 3.38 (2H, s), 3.53 (2H, d), 3.93 (3H, s), 4.80 (1H, t), 5.18 (1H, dt), 7.50 (1H, d), 7.52 (1H, s), 7.68 (1H, s), 7.99 (1H, s), 8.37 (1H, d), 8.61 (1H, s); HPLC rt(min): 9.26; MS (ES$^+$) 510, (ES$^-$) 508.

Example 267

4-(9-cyclopentyl-5,7,7-trimethyl-6-oxo-6,7,8,9-tetrahydro-5H-pyrimido[4,5-b][1,4]diazepin-2-ylamino)-N-((1S,4S)-4-fluorocylohexyl)-3-methoxybenzamide (I-267)

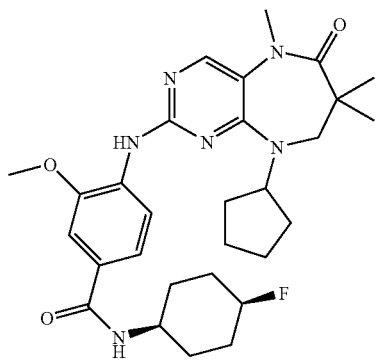

Prepared using the appropriate reagents according to method E. NMR DMSO D$^6$ 1.09 (6H, s), 1.55-1.79 (12H, m), 1.85-2.02 (4H, m), 3.19 (3H, s), 3.38 (2H, s), 3.85-3.94 (1H, m), 3.94 (3H, s), 4.85 (1H, d), 5.19 (1H, dt), 7.49 (1H, d), 7.50 (1H, s), 7.69 (1H, s), 7.99 (1H, s), 8.13 (1H, d), 8.37 (1H, d); HPLC rt(min): 10.17; MS (ES$^+$) 540, (ES$^-$) 538.

Example 268

4-(9-cyclopentyl-5,7,7-trimethyl-6-oxo-6,7,8,9-tetrahydro-5H-pyrimido[4,5-b][1,4]diazepin-2-ylamino)-N-((1R,2R)-2-hydroxycyclohexyl)-3-methoxybenzamide (I-268)

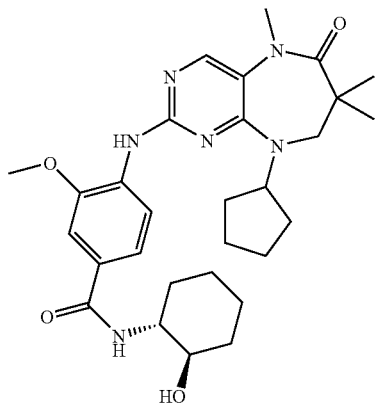

Prepared using the appropriate reagents according to method E. NMR DMSO D$^6$ 1.09 (6H, s), 1.19-1.30 (4H, m), 1.55-1.79 (8H, m), 1.81-1.96 (4H, m), 3.19 (3H, s), 3.38 (2H, m), 3.38-3.48 (1H, m), 3.56-3.67 (1H, m), 3.95 (3H, s), 4.62 (1H, d), 5.19 (1H, dt), 7.49 (1H, d), 7.51 (1H, s), 7.69 (1H, s), 7.98 (1H, d), 7.99 (1H, s), 8.37 (1H, d); HPLC rt(min): 9.74; MS (ES$^+$) 538, (ES$^-$) 536.

Example 269

4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-N-(3,3-difluorocyclobutyl)-3-methoxybenzamide (I-269)

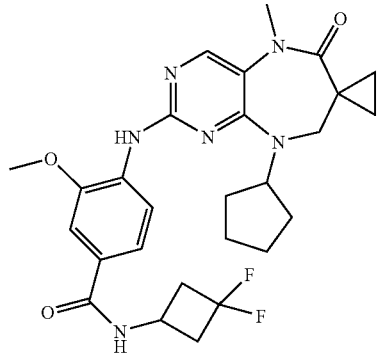

Prepared using the appropriate reagents according to method E. NMR DMSO D$^6$ 0.63-0.71 (2H, m), 0.87-0.93 (2H, m), 1.44-1.76 (6H, m), 1.84-1.94 (2H, m), 2.70-2.82 (2H, m), 2.90-3.02 (2H, m), 3.17 (3H, s), 3.48 (2H, s), 3.95 (3H, s), 4.23-4.31 (1H, m), 4.85 (1H, dt), 7.48 (1H, d), 7.49 (1H, s), 7.72 (1H, s), 7.99 (1H, s), 8.43 (1H, d), 8.66 (1H, d); HPLC rt(min): 9.75; MS (ES$^+$) 528, (ES$^-$) 526.

Example 270

(S)-4-(9-cyclopentyl-5,7,7-trimethyl-6-oxo-6,7,8,9-tetrahydro-5H-pyrimido[4,5-b][1,4]diazepin-2-ylamino)-N-(2-hydroxypropyl)-3-methoxybenzamide (I-270)

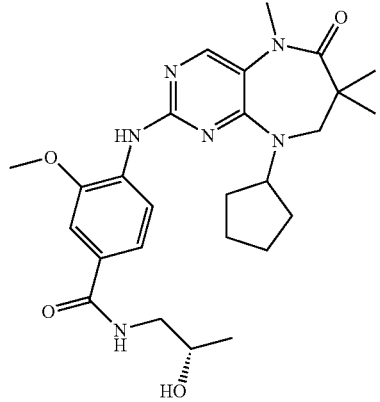

Prepared using the appropriate reagents according to method E. NMR DMSO D$^6$ 1.06 (3H, d), 1.14 (6H, s), 1.54-1.78 (6H, m), 1.82-1.94 (2H, m), 3.13-3.24 (2H, m), 3.16 (3H, s), 3.38 (2H, s), 3.73-3.82 (1H, m), 3.95 (3H, s), 4.77 (1H, d), 5.18 (1H, dt), 7.50 (1H, d), 7.52 (1H, s), 7.69 (1H, s), 7.99 (1H, s), 8.30-8.40 (2H, m); HPLC rt(min): 9.10; MS (ES$^+$) 498, (ES$^-$) 496.

Example 271

4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-N-(1-hydroxy-2-methylpropan-2-yl)-3-methoxybenzamide (I-271)

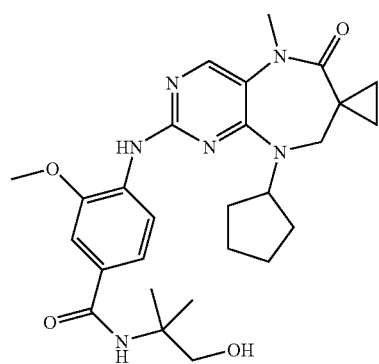

Prepared using the appropriate reagents according to method E. NMR DMSO $D^6$ 0.66-0.69 (2H, m), 0.89-0.92 (2H, m), 1.32 (6H, s), 1.48-1.69 (6H, m), 1.89 (2H, m), 3.17 (3H, s), 3.44-3.48 (2H, m), 3.51-3.52 (2H, m), 3.95 (3H, s), 4.85 (1H, m), 4.96 (1H, m), 7.42-7.43 (3H, m), 7.68 (1H, s), 7.99 (1H, s), 8.38 (1H, d); HPLC rt(min): 9.23; MS (ES$^+$) 510, (ES$^-$) 508.

Example 272

4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-N-((1R,2R)-2-hydroxycyclopentyl)-3-methoxybenzamide (I-272)

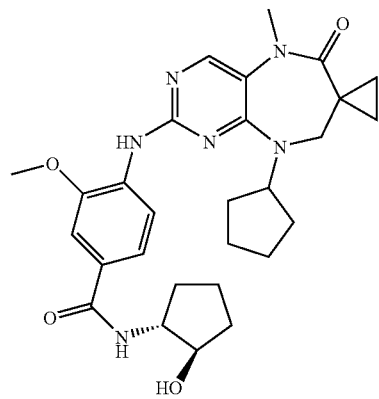

Prepared using the appropriate reagents according to method E. NMR DMSO $D^6$ 0.67 (2H, m), 0.90 (2H, m), 1.49-1.50 (2H, m), 1.55-1.68 (8H, m), 1.86-1.89 (3H, m), 2.00-2.01 (1H, m), 3.17 (3H, s), 3.48 (2H, m), 3.95 (3H, s), 3.97-4.00 (2H, m), 4.80 (1H, m), 4.85 (1H, m), 7.47-7.49 (2H, m), 7.69 (1H, s), 7.99 (1H, s), 8.11 (1H, m), 8.39 (1H, d); HPLC rt(min): 9.16; MS (ES$^+$) 522, (ES$^-$) 520.

Example 273

4-(9-cyclopentyl-5,7,7-trimethyl-6-oxo-6,7,8,9-tetrahydro-5H-pyrimido[4,5-b][1,4]diazepin-2-ylamino)-3-methoxy-N-(3,3,3-trifluoro-2-hydroxypropyl)benzamide (I-278)

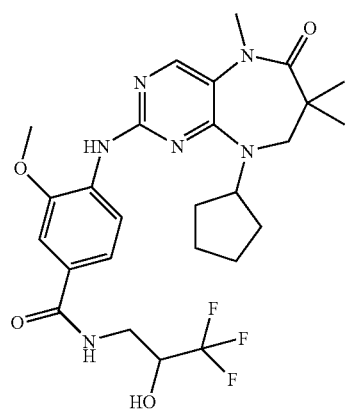

Prepared using the appropriate reagents according to method E. NMR DMSO $D^6$ 1.09 (6H, s), 1.57-1.94 (8H, m), 3.19 (3H, s), 3.21-3.28 (1H, m), 3.38 (2H, s), 3.59-3.68 (1H, m), 3.94 (3H, s), 4.12-4.24 (1H, m), 5.18 (1H, dt), 6.54 (1H, d), 7.52 (1H, d), 7.53 (1H, s), 7.72 (1H, s), 7.99 (1H, s), 8.39 (1H, d), 8.65 (1H, t); HPLC rt(min): 9.67; MS (ES$^+$) 552, (ES$^-$) 550.

Example 274

4-(9-cyclopentyl-5,7,7-trimethyl-6-oxo-6,7,8,9-tetrahydro-5H-pyrimido[4,5-b][1,4]diazepin-2-ylamino)-N-(2-fluoroethyl)-3-methoxybenzamide (I-279)

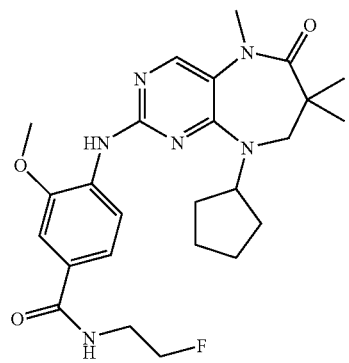

Prepared using the appropriate reagents according to method E. NMR DMSO $D^6$ 1.09 (6H, s), 1.55-1.80 (6H, m), 1.82-1.93 (2H, m), 3.19 (3H, s), 3.38 (2H, s), 3.53 (1H, q), 3.60 (1H, q), 3.94 (3H, s), 4.48 (1H, t), 4.60 (1H, t), 5.18 (1H, dt), 7.52 (1H, d), 7.53 (1H, s), 7.71 (1H, s), 7.99 (1H, s), 8.39 (1H, d), 8.61 (1H, t); HPLC rt(min): 9.54; MS (ES$^+$) 486, (ES$^-$) 484.

Example 275

3-(4-(9-cyclopentyl-5,7,7-trimethyl-6-oxo-6,7,8,9-tetrahydro-5H-pyrimido[4,5-b][1,4]diazepin-2-ylamino)-3-methoxybenzamido)propyl acetate (I-273)

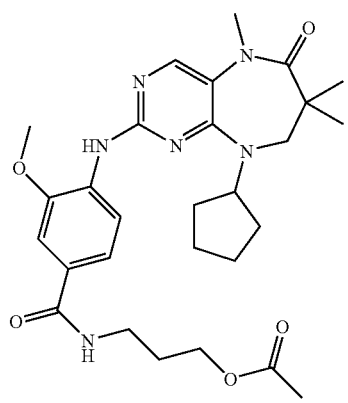

Prepared using the appropriate reagents according to method E. NMR DMSO $D^6$ 1.15 (6H, s), 1.58-1.70 (8H, m), 1.83-1.87 (2H, m), 2.01 (3H, s), 3.18 (3H, s), 3.33-3.37 (2H, m), 3.47-3.52 (2H, m), 3.94 (3H, s), 4.04-4.08 (2H, m), 5.11 (1H, m), 7.52 (1H, d), 7.59 (1H, s), 8.03 (2H, m), 8.54 (1H, m), 9.28 (1H, br s); HPLC rt(min): 9.64; MS (ES$^+$) 540, (ES$^-$) 538.

Example 276

(1r,4r)-4-(4-(9-cyclopentyl-5,7,7-trimethyl-6-oxo-6,7,8,9-tetrahydro-5H-pyrimido[4,5-b][1,4]diazepin-2-ylamino)-3-methoxybenzamido)cyclohexyl acetate (I-280)

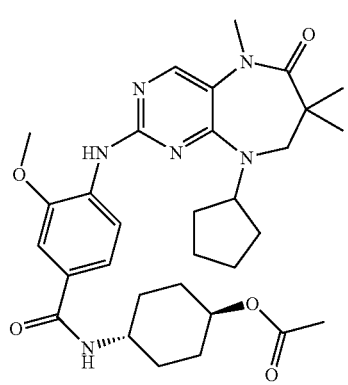

Prepared using the appropriate reagents according to method E. NMR DMSO $D^6$ 1.14 (6H, s), 1.44-1.96 (15H, m), 2.00 (3H, s), 3.17 (3H, s), 3.50 (3H, s), 3.82 (1H, m), 3.95 (3H, s), 4.59 (1H, m), 5.13 (1H, m), 7.50-7.55 (2H, m), 8.01 (1H, s), 8.08 (1H, d), 8.20 (1H, d), 9.00 (1H, br s); HPLC rt(min) 10.04; MS (ES$^+$) 580, (ES$^-$) 578.

Example 277

4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-N-((1s,4s)-4-fluorocyclohexyl)-3-methoxybenzamide (I-281)

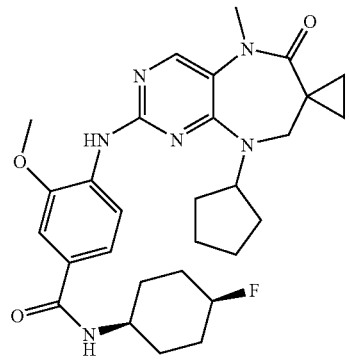

Prepared using the appropriate reagents according to method E. NMR DMSO $D^6$ 0.63-0.71 (2H, m), 0.86-0.94 (2H, m), 1.47-1.99 (16H, m), 3.17 (3H, s), 3.47 (2H, s), 3.83-3.91 (1H, m), 3.95 (3H, s), 4.78-4.89 (2H, m), 7.49 (1H, d), 7.50 (1H, s), 7.69 (1H, s), 7.99 (1H, s), 8.13 (1H, d), 8.39 (1H, d); HPLC rt(min): 9.88; MS (ES$^+$) 538, (ES$^-$) 536.

Example 278

4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-N-((1R,3R)-3-hydroxycyclopentyl)-3-methoxybenzamide (I-282)

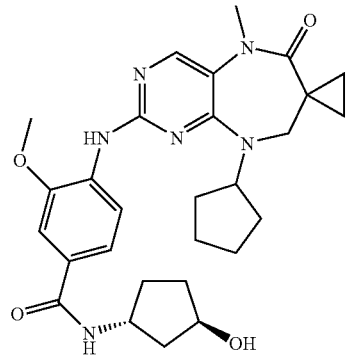

Prepared using the appropriate reagents according to method E. NMR DMSO $D^6$ 0.63-0.69 (2H, m), 0.86-0.93 (2H, m), 1.43-1.75 (9H, m), 1.83-2.09 (5H, m), 3.17 (3H, s), 3.48 (2H, s), 3.94 (3H, s), 4.19-4.26 (1H, m), 4.46 (1H, dt), 4.53 (1H, d), 4.85 (1H, dt), 7.46 (1H, d), 7.48 (1H, s), 7.69 (1H, s), 7.99 (1H, s), 8.14 (1H, d), 8.39 (1H, d); HPLC rt(min): 8.83; MS (ES$^+$) 522, (ES$^-$) 520.

Example 279

PLK1 Assay

The compounds of the present invention are evaluated as inhibitors of human PLK kinase using the following assays.

Plk1 Inhibition Assay:

Compounds were screened for their ability to inhibit Plk1 using a radioactive-phosphate incorporation assay. Assays were carried out in a mixture of 25 mM HEPES (pH 7.5), 10 mM $MgCl_2$, and 1 mM DTT. Final substrate concentrations were 50 μM [γ-33P]ATP (136 mCi 33P ATP/mmol ATP, Amersham Pharmacia Biotech/Sigma Chemicals) and 10 μM peptide (SAM68 protein Δ332-443). Assays were carried out at 25° C. in the presence of 15 nM Plk1 (A20-K338). An assay stock buffer solution was prepared containing all of the reagents listed above, with the exception of ATP and the test compound of interest. 30 μL of the stock solution was placed in a 96 well plate followed by addition of 2 μL of DMSO stock containing serial dilutions of the test compound (typically starting from a final concentration of 10 μM with 2-fold serial dilutions) in duplicate (final DMSO concentration 5%). The plate was pre-incubated for 10 minutes at 25° C. and the reaction initiated by addition of 8 μL [γ-33P]ATP (final concentration 50 μM).

The reaction was stopped after 60 minutes by the addition of 100 μL 0.14M phosphoric acid. A multiscreen phosphocellulose filter 96-well plate (Millipore, Cat no. MAPHN0B50) was pretreated with 100 μL 0.2M phosphoric acid prior to the addition of 125 μL of the stopped assay mixture. The plate was washed with 4×200 μL 0.2M phosphoric acid. After drying, 100 μL Optiphase 'SuperMix' liquid scintillation cocktail (Perkin Elmer) was added to the well prior to scintillation counting (1450 Microbeta Liquid Scintillation Counter, Wallac).

After removing mean background values for all of the data points, Ki(app) data were calculated from non-linear regression analysis of the initial rate data using the Prism software package (GraphPad Prism version 3.0cx for Macintosh, GraphPad Software, San Diego Calif., USA).

Plk1 Inhibition Assay:

Compounds were screened for their ability to inhibit Plk1 using a radioactive-phosphate incorporation assay. Assays were carried out in a mixture of 25 mM HEPES (pH 7.5), 10 mM $MgCl_2$, 0.1% BSA, and 2 mM DTT. Final substrate concentrations were 150 μM (350 μM for determining values of <1 nM) [γ-33P]ATP (115 mCi 33P ATP/mmol ATP, Amersham Pharmacia Biotech/Sigma Chemicals) and 300 μM (450 μM for determining values of <1 nM) peptide (KKKIS-DELMDATFADQEAK; SEQ ID NO: 1). Assays were carried out at 25° C. in the presence of 4 nM (1 nM for determining values of <1 nM) Plk1. An assay stock buffer solution was prepared containing all of the reagents listed above, with the exception of ATP and the test compound of interest. 30 μL of the stock solution was placed in a 96 well plate followed by addition of 2 μL of DMSO stock containing serial dilutions of the test compound (typically starting from a final concentration of 10 μM with 2-fold serial dilutions) in duplicate (final DMSO concentration 5%). The plate was pre-incubated for 10 minutes at 25° C. and the reaction initiated by addition of 8 μL [γ-33P]ATP (final concentration 150 μM (350 μM for determining values of <nM))).

The reaction was stopped after 90 minutes (240 minutes for determining values of <1 nM) by the addition of 100 μL 0.14M phosphoric acid. A multiscreen phosphocellulose filter 96-well plate (Millipore, Cat no. MAPHNOB50) was pretreated with 100 μL 0.2M phosphoric acid prior to the addition of 125 μL of the stopped assay mixture. The plate was washed with 4×200 μL 0.2M phosphoric acid. After drying, 100 μL Optiphase 'SuperMix' liquid scintillation cocktail (Perkin Elmer) was added to the well prior to scintillation counting (1450 Microbeta Liquid Scintillation Counter, Wallac).

After removing mean background values for all of the data points, Ki(app) data were calculated from non-linear regression analysis of the initial rate data using the Prism software package (GraphPad Prism version 3.0cx for Macintosh, GraphPad Software, San Diego Calif., USA).

In general, compounds of the invention are effective for the inhibition of Plk1. The following compounds showed Ki below 10 nM in the radioactive incorporation assay: I-2, I-5, I-4, I-6, I-9, I-11, I-12, I-16, I-17, I-18, I-21, I-22, I-23, I-24, I-25, I-26, I-27, I-28, I-31, I-32, I-33, I-34, I-36, I-37, I-38, I-39, I-47, I-48, I-51, I-52, I-53, I-58, I-59, I-60, I-62, I-64, I-67, I-68, I-69, I-70, I-71, I-72, I-73, I-74, I-75, I-76, I-77, I-80, I-85, I-87, I-93, I-94, I-95, I-96, I-99, I-101, I-103, I-104, I-105, I-108, I-113, I-118, I-119, I-123, I-129, I-130, I-131, I-132, I-133, I-134, I-135, I-136, I-157, I-158, I-163, I-166, I-167, I-169, I-170, I-171, I-172, I-173, I-174, I-175, I-176, I-177, I-178, I-179, I-180, I-181, I-182, I-183, I-184, I-185, I-186, I-187, I-190, I-191, I-192, I-193, I-194, I-195, I-196, I-197, I-198, I-199, I-200, I-201, I-202, I-203, I-204, I-205, I-206, I-207, I-208, I-209, I-210, I-211, I-212, I-213, I-214, I-216, I-217, I-218, I-219, I-220, I-221, I-222, I-223, I-224, I-225, I-226, I-227, I-228, I-229, I-230, I-231, I-232, I-233, I-234, I-235, I-236, I-237, I-238, I-239, I-240, I-241, I-242, I-243, I-244, I-245, I-246, I-247, I-248, I-249, I-250, I-251, I-252, I-253, I-254, I-255, I-256, I-257, I-258, I-259, I-260, I-261, I-262, I-263, I-264, I-265, I-266, I-267, I-268, I-269, I-270, I-271, I-272, I-273, I-278, I-279, I-280, I-282. The following compounds showed Ki between 10 nM and 100 nM in the radioactive incorporation assay: I-1, I-3, I-7, I-8, I-10, I-14, I-15, I-19, I-20, I-30, I-35, I-40, I-42, I-43, I-44, I-45, I-46, I-49, I-50, I-56, I-63, I-65, I-66, I-78, I-79, I-81, I-86, I-89, I-90, I-91, I-92, I-97, I-98, I-102, I-109, I-110, I-111, I-112, I-114, I-116, I-117, I-120, I-122, I-124, I-125, I-137, I-138, I-139, I-141, I-143, I-144, I-145, I-147, I-149, I-150, I-151, I-152, I-153, I-154, I-155, I-156, I-159, I-160, I-161, I-162, I-164, I-165, I-168, I-188, I-192, I-215. The following compounds showed Ki between 100 nM and 4 μM in the radioactive incorporation assay: I-29, I-41, I-54, I-55, I-57, I-61, I-82, I-83, I-84, I-88, I-100, I-106, I-115, I-121, I-127, I-128, I-140, I-146, I-148, I-189. The following compounds were not soluble under the assay conditions: I-126 and I-142. The following compounds were not active within the limits of the assay: I-13 and I-107.

Plk2 Inhibition Assay:

Compounds were screened for their ability to inhibit Plk2 using a radioactive-phosphate incorporation assay. Assays were carried out in a mixture of 25 mM HEPES (pH 7.5), 10 mM $MgCl_2$, 0.1% BSA, and 2 mM DTT. Final substrate concentrations were 200 μM [γ-33P]ATP (57 mCi 33P ATP/mmol ATP, Amersham Pharmacia Biotech/Sigma Chemicals) and 300 μM peptide (KKKISDELMDATFADQEAK; SEQ ID NO: 1). Assays were carried out at 25° C. in the presence of 25 nM Plk2. An assay stock buffer solution was prepared containing all of the reagents listed above, with the exception of ATP and the test compound of interest. 30 μL of the stock solution was placed in a 96 well plate followed by addition of 2 μL of DMSO stock containing serial dilutions of the test compound (typically starting from a final concentration of 10 μM with 2-fold serial dilutions) in duplicate (final DMSO concentration 5%). The plate was pre-incubated for 10 minutes at 25° C. and the reaction initiated by addition of 8 µL [γ-33P]ATP (final concentration 200 µM).

The reaction was stopped after 90 minutes by the addition of 100 µL 0.14M phosphoric acid. A multiscreen phosphocellulose filter 96-well plate (Millipore, Cat no. MAPHN0B50) was pretreated with 100 µL 0.2M phosphoric acid prior to the addition of 125 µL of the stopped assay mixture. The plate was washed with 4×200 µL 0.2M phosphoric acid. After drying, 100 µL Optiphase 'SuperMix' liquid scintillation cocktail (Perkin Elmer) was added to the well prior to scintillation counting (1450 Microbeta Liquid Scintillation Counter, Wallac).

After removing mean background values for all of the data points, Ki(app) data were calculated from non-linear regression analysis of the initial rate data using the Prism software package (GraphPad Prism version 3.0cx for Macintosh, GraphPad Software, San Diego Calif., USA).

Plk3 Inhibition Assay:

Compounds were screened for their ability to inhibit Plk3 using a radioactive-phosphate incorporation assay. Assays were carried out in a mixture of 25 mM HEPES (pH 7.5), 10 mM $MgCl_2$, and 1 mM DTT. Final substrate concentrations were 75 µM [γ-33P]ATP (60 mCi 33P ATP/mmol ATP, Amersham Pharmacia Biotech/Sigma Chemicals) and 10 µM peptide (SAM68 protein Δ332-443). Assays were carried out at 25° C. in the presence of 5 nM Plk3 (S38-A340). An assay stock buffer solution was prepared containing all of the reagents listed above, with the exception of ATP and the test compound of interest. 30 µL of the stock solution was placed in a 96 well plate followed by addition of 2 µL of DMSO stock containing serial dilutions of the test compound (typically starting from a final concentration of 10 µM with 2-fold serial dilutions) in duplicate (final DMSO concentration 5%). The plate was pre-incubated for 10 minutes at 25° C. and the reaction initiated by addition of 8 µL [γ-33P]ATP (final concentration 75 µM).

The reaction was stopped after 60 minutes by the addition of 100 µL 0.14M phosphoric acid. A multiscreen phosphocellulose filter 96-well plate (Millipore, Cat no. MAPHN0B50) was pretreated with 100 µL 0.2M phosphoric acid prior to the addition of 125 µL of the stopped assay mixture. The plate was washed with 4×200 µL 0.2M phosphoric acid. After drying, 100 µL Optiphase 'SuperMix' liquid scintillation cocktail (Perkin Elmer) was added to the well prior to scintillation counting (1450 Microbeta Liquid Scintillation Counter, Wallac).

After removing mean background values for all of the data points, Ki(app) data were calculated from non-linear regression analysis of the initial rate data using the Prism software package (GraphPad Prism version 3.0cx for Macintosh, GraphPad Software, San Diego Calif., USA).

Plk4 Inhibition Assay:

Compounds were screened for their ability to inhibit Plk4 using a radioactive-phosphate incorporation assay. Assays were carried out in a mixture of 8 mM MOPS (pH 7.5), 10 mM $MgCl_2$, 0.1% BSA and 2 mM DTT. Final substrate concentrations were 15 µM [γ-33P]ATP (227 mCi 33P ATP/mmol ATP, Amersham Pharmacia Biotech/Sigma Chemicals) and 300 µM peptide (KKKMDATFADQ; SEQ ID NO: 2). Assays were carried out at 25° C. in the presence of 25 nM Plk4. An assay stock buffer solution was prepared containing all of the reagents listed above, with the exception of ATP and the test compound of interest. 3 µL of the stock solution was placed in a 96 well plate followed by addition of 2 µL of DMSO stock containing serial dilutions of the test compound (typically starting from a final concentration of 10 µM with 2-fold serial dilutions) in duplicate (final DMSO concentration 5%). The plate was pre-incubated for 10 minutes at 25° C. and the reaction initiated by addition of 8 µL [γ-33P]ATP (final concentration 15 µM).

The reaction was stopped after 180 minutes by the addition of 100 µL 0.14M phosphoric acid. A multiscreen phosphocellulose filter 96-well plate (Millipore, Cat no. MAPHNOB50) was pretreated with 100 µL 0.2M phosphoric acid prior to the addition of 125 µL of the stopped assay mixture. The plate was washed with 4×200 µL 0.2M phosphoric acid. After drying, 100 µL Optiphase 'SuperMix' liquid scintillation cocktail (Perkin Elmer) was added to the well prior to scintillation counting (1450 Microbeta Liquid Scintillation Counter, Wallac).

After removing mean background values for all of the data points, Ki(app) data were calculated from non-linear regression analysis of the initial rate data using the Prism software package (GraphPad Prism version 3.0cx for Macintosh, GraphPad Software, San Diego, Calif., USA).

While we have described a number of embodiments of this invention, it is apparent that our basic examples may be altered to provide other embodiments that utilize or encompass the compounds, methods, and processes of this invention. Therefore, it will be appreciated that the scope of this invention is to be defined by the appended claims.

We claim:

1. A compound of formula I:

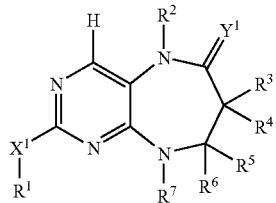

I wherein $X^1$ is a bond, O, $NR^8$, S, SO, or $SO_2$;

$Y^1$ is O or $NR^9$;

$R^1$ is H, $C_{1-10}$aliphatic, $C_{3-10}$cycloaliphatic, $C_{6-10}$aryl, 5-10 membered heteroaryl, or 3-10 membered heterocyclyl; wherein said $R^1$ is optionally substituted with 0-5 $J^1$; provided that when $X^1$ is a bond, $R^1$ is not H;

$R^2$ is H, $C_{1-10}$aliphatic, $-(C_{3-10}$aliphatic)-$(C_{3-10}$cycloaliphatic), $C_{3-8}$cycloaliphatic, halo$C_{1-4}$ aliphatic; wherein said $R^2$ is optionally substituted with 0-4 $J^2$;

each $R^3$, $R^4$, $R^5$, and $R^6$ is independently H, $C_{1-10}$aliphatic, $C_{3-10}$cycloaliphatic, $C_{6-10}$aryl, or 5-10 membered heteroaryl; wherein each $R^3$, $R^4$, $R^5$, and $R^6$ is optionally and independently substituted with 0-5 $J^3$, $J^4$, $J^5$, and $J^6$ respectively; and $R^7$ is H, C(O)R, C(O)OR, or C(O)NRR', $C_{1-10}$aliphatic, $C_{3-10}$cycloaliphatic, $C_{6-10}$aryl, 5-10 membered heteroaryl, 3-10 membered heterocyclyl, $-(C_{1-6}$aliphatic)-$(C_{3-10}$cycloaliphatic), $-(C_{1-6}$aliphatic)-$(C_{6-10}$aryl), or $-(C_{1-6}$aliphatic)-(5-10 membered heteroaryl), or $-(C_{1-6}$aliphatic)-(3-6 membered heterocyclyl; wherein said $R^7$ is optionally substituted with 0-5 $J^7$; or $R^3$ and $R^4$, together with the carbon atom to which they are attached, optionally form a 3-8 membered saturated or partially unsaturated monocyclic ring containing 0-4 heteroatoms independently selected from O, N, and S; said monocyclic ring formed by $R^3$ and $R^4$ is optionally substituted with 0-4 $J^{34}$;

$R^5$ and $R^6$, together with the carbon atom to which they are attached, optionally form a 3-8 membered saturated or partially unsaturated monocyclic ring containing 0-4 heteroatoms independently selected from O, N, and S; said monocyclic ring formed by $R^5$ and $R^6$ is optionally substituted with 0-4 $J^{56}$;

$R^3$ and $R^5$, together with the carbon atoms to which they are attached, optionally form a 3-8 membered saturated or partially unsaturated monocyclic ring containing 0-4 heteroatoms independently selected from O, N, and S; said monocyclic ring formed by $R^3$ and $R^5$ is optionally substituted with 0-4 $J^{35}$;

$R^3$ and $R^7$, together with the atoms to which they are attached, optionally form a 4-8 membered saturated or partially unsaturated monocyclic ring containing 0-4 heteroatoms independently selected from O, N, and S; said monocyclic ring formed by $R^3$ and $R^7$ is optionally substituted with 0-4 $J^{37}$;

$R^5$ and $R^7$, together with the atoms to which they are attached, optionally form a 3-8 membered saturated or partially unsaturated monocyclic ring containing 0-4 heteroatoms independently selected from O, N, and S; said monocyclic ring formed by $R^5$ and $R^7$ is optionally substituted with 0-4 $J^{57}$;

$R^8$ is H, $C_{1-6}$aliphatic, $C_{3-8}$cycloaliphatic, C(O)R, C(O)OR, or C(O)NRR';

$R^9$ is H or unsubstituted $C_{1-6}$aliphatic; or $R^2$ and $R^9$, together with the atoms to which they are attached, optionally form a 5-8 membered aromatic or nonaromatic monocyclic ring containing 2-4 heteroatoms independently selected from O, N, and S; said monocyclic ring formed by $R^2$ and $R^9$ is optionally substituted with 0-4 $J^{29}$;

each $J^1$ is independently $C_{1-6}$haloalkyl, halo, $NO_2$, CN, Q, or -Z-Q; or, two $J^1$ taken together can optionally form =O;

Z is $C_{1-6}$aliphatic optionally replaced with 0-3 occurrences of —NR—, —O—, —S—, —C(O)—, —C(=NR)—, —C(=NOR)—, —SO—, or —$SO_2$—; each Z is optionally substituted with 0-2 $J^Z$;

Q is H; $C_{1-6}$ aliphatic; a 3-8-membered aromatic or nonaromatic monocyclic ring having 0-3 heteroatoms independently selected from O, N, and S; or an 7-12 membered aromatic or nonaromatic bicyclic ring system having 0-5 heteroatoms independently selected from O, N, and S; each Q is optionally substituted with 0-5 $J^Q$;

each $J^2$ is halo or halo$C_{1-4}$ aliphatic;

each $J^3$, $J^4$, $J^5$, and $J^6$ is independently $C_{1-6}$ aliphatic, $C_{3-6}$cycloaliphatic, or —$C_{1-4}$alkyl)$_n$—$V^1$;

wherein n is O or 1;

$V^1$ is halo($C_{1-4}$ aliphatic), —O(halo$C_{1-4}$ aliphatic), halo, $NO_2$, CN, OH, OR", SH, SR", $NH_2$, NHR", N(R")$_2$, COH, COR", $CO_2$H, $CO_2$R", $CONH_2$, CONHR", CONR"$_2$, OCOR", $OCONH_2$, OCONHR", OCON(R")$_2$, NHCOR", NR"COR", NHCO$_2$R", NR"CO$_2$R", NHCO$_2$H, NR"CO$_2$H, NHCONH$_2$, NHCONHR", NHCON(R")$_2$, SO$_2$NH$_2$, SO$_2$NHR", SO$_2$N(R")$_2$, NHSO$_2$R", NR"SO$_2$R";

or V$^1$ is a cyclic group selected from C$_{3-6}$cycloaliphatic, phenyl, 5-6 membered heteroaryl, or 3-6 membered heterocyclyl; wherein said cyclic group is optionally substituted with 0-3 J$^V$;

R" is unsubstituted C$_{1-4}$ aliphatic;

or two of the same J$^3$, J$^4$, J$^5$, or J$^6$, bonded to the same atom, together can optionally form =O;

each J$^Z$ and J$^V$ is independently halo, C$_{1-6}$ aliphatic, C$_{3-6}$cycloaliphatic, NO$_2$, CN, —NH$_2$, —NH(C$_{1-4}$ aliphatic), —N(C$_{1-4}$ aliphatic)$_2$, —OH, —O(C$_{1-4}$ aliphatic), —CO$_2$H, —CO$_2$(C$_{1-4}$ aliphatic), —O(haloC$_{1-4}$ aliphatic), or halo(C$_{1-4}$ aliphatic);

each J$^Q$, J$^7$, J$^{29}$, J$^{34}$, J$^{56}$, J$^{35}$, J$^{37}$, and J$^{57}$ is independently M or —Y-M;

each Y is independently an unsubstituted C$_{1-6}$aliphatic optionally replaced with 0-3 occurrences of —NR—, —O—, —S—, —C(O)—, —SO—, or —SO$_2$—;

each M is independently H, C$_{1-6}$ aliphatic, C$_{3-6}$cycloaliphatic, halo(C$_{1-4}$ aliphatic), —O(haloC$_{1-4}$ aliphatic), 3-6 membered heterocyclyl, C$_{6-10}$aryl, halo, NO$_2$, CN, OH, OR', SH, SR', NH$_2$, NHR', N(R')$_2$, COH, COR', CO$_2$H, CO$_2$R', CONH$_2$, CONHR', CONR'$_2$, OCOR', OCONH$_2$, OCONHR', OCON(R')$_2$, NHCOR', NR'COR', NHCO$_2$R', NR'CO$_2$R', NHCO$_2$H, NR'CO$_2$H, NHCONH$_2$, NHCONHR', NHCON(R')$_2$, SO$_2$NH$_2$, SO$_2$NHR', SO$_2$N(R')$_2$, NHSO$_2$R', or NR'SO$_2$R', or two M taken together can optionally form =O;

R is H or unsubstituted C$_{1-6}$aliphatic;

R' is unsubstituted C$_{1-6}$aliphatic; or two R' groups, together with the atom to which they are bound, form an unsubstituted 3-8 membered saturated or partially unsaturated monocyclic ring having 0-1 heteroatoms independently selected from O, N, and S.

2. The compound of claim 1, wherein:

R$^1$ is H, C$_{1-10}$aliphatic, C$_{6-10}$aryl, 5-10 membered heteroaryl, or 3-10 membered heterocyclyl;
  wherein said R$^1$ is optionally substituted with 0-5 J$^1$;
  provided that when X$^1$ is a bond, R$^1$ is not H;

R$^7$ is H, C(O)R, C(O)OR, or C(O)NRR', C$_{1-10}$aliphatic, C$_{3-10}$cycloaliphatic, C$_{6-10}$aryl, 5-10 membered heteroaryl, 3-10 membered heterocyclyl, —(C$_{1-6}$aliphatic)-(C$_{3-10}$cycloaliphatic), —(C$_{1-6}$aliphatic)-(C$_{6-10}$aryl), or —(C$_{1-6}$aliphatic)-(5-10 membered heteroaryl); wherein said R$^7$ is optionally substituted with 0-5 J$^7$;

Q is H; C$_{1-6}$ aliphatic; a 3-8-membered aromatic or nonaromatic monocyclic ring having 0-3 heteroatoms independently selected from O, N, and S; or an 8-12 membered aromatic or nonaromatic bicyclic ring system having 0-5 heteroatoms independently selected from O, N, and S; each Q is optionally substituted with 0-5 J$^Q$; and each M is independently H, C$_{1-6}$ aliphatic, C$_{3-6}$cycloaliphatic, halo(C$_{1-4}$ aliphatic), —O(haloC$_{1-4}$ aliphatic), 3-6 membered heterocyclyl, halo, NO$_2$, CN, OH, OR', SH, SR', NH$_2$, NHR', N(R')$_2$, COH, COR', CO$_2$H, CO$_2$R', CONH$_2$, CONHR', CONR'$_2$, OCOR', OCONH$_2$, OCONHR', OCON(R')$_2$, NHCOR', NR'COR', NHCO$_2$R', NR'CO$_2$R', NHCO$_2$H, NR'CO$_2$H, NHCONH$_2$, NHCONHR', NHCON(R')$_2$, SO$_2$NH$_2$, SO$_2$NHR', SO$_2$N(R')$_2$, NHSO$_2$R', or NR'SO$_2$R'.

3. The compound of claim 2, wherein X$^1$ is NR$^8$.

4. The compound of claim 2, wherein Y$^1$ is O.

5. The compound of claim 4, wherein R$^1$ is C$_{6-10}$aryl or 5-10 membered heteroaryl, wherein R$^1$ is substituted with 0-5 J$^1$.

6. The compound of claim 5, wherein R$^2$ is C$_{1-10}$aliphatic or C$_{3-10}$cycloaliphatic, wherein R$^2$ is substituted with 0-4 J$^2$.

7. The compound of claim 6, wherein R$^2$—CH$_3$.

8. The compound of claim 6, wherein R$^3$ and R$^4$, together with the carbon atom to which they are attached, form a 3-6 membered monocyclic ring substituted with 0-5 R$^3$ or R$^4$.

9. The compound of claim 6, wherein R$^3$ and R$^5$, together with the carbon atoms to which they are attached, form a 3-6 membered monocyclic ring substituted with 0-5 R$^3$ or R$^5$.

10. The compound of claim 6, wherein each R$^3$, R$^4$, R$^5$, and R$^6$ is independently a group selected from H, C$_{1-10}$aliphatic, C$_{3-10}$cycloaliphatic, C$_{6-10}$aryl, or 5-10 membered heteroaryl, wherein each R$^3$, R$^4$, R$^5$, and R$^6$ is independently substituted with 0-5 J$^3$, J$^4$, J$^5$, and J$^6$, respectively.

11. The compound of claim 6, wherein each R$^3$ and R$^4$ is independently H, C$_{1-6}$aliphatic, or C$_{3-8}$cycloaliphatic, wherein each R$^3$ and R$^4$ is independently substituted with 0-5 J$^3$ and J$^4$, respectively.

12. The compound of claim 6, wherein one of R$^3$ and R$^4$ is H and the other is C$_{1-6}$aliphatic or C$_{3-8}$cycloaliphatic wherein the R$^3$ and R$^4$ that is not H is independently substituted with 0-5 J$^3$ and J$^4$, respectively.

13. The compound of claim 1, wherein each J$^3$ and J$^4$ is independently halo.

14. The compound of claim 1, wherein R$^5$ and R$^7$, together with the atoms to which they are attached, form a 3-6 membered saturated or partially unsaturated monocyclic ring substituted with 0-5 J$^5$ or J$^7$.

15. The compound of claim 6, wherein R$^7$ is a group selected from C$_{1-10}$aliphatic, C$_{3-10}$cycloaliphatic, C$_{6-10}$aryl, 5-10 membered heteroaryl, and 3-10 membered heterocyclyl, wherein R$^7$ is substituted with 0-5 J$^7$.

16. The compound of claim 6, wherein R$^7$ is a group selected from C$_{1-10}$aliphatic, C$_{3-8}$cycloaliphatic, phenyl, a 5-membered heteroaryl, 2-pyridyl, 3-pyridyl, 4-pyridyl, 2,5-pyridazinyl, 3,5-pyrimidyl, and a 3-8 membered heterocyclyl, wherein R$^7$ is substituted with 0-5 J$^7$.

17. The compound of claim 1, wherein R$^7$ is not 3-amino-2,4-pyrimidine.

18. The compound of claim 6, wherein R$^7$ is a group selected from C$_{3-6}$alkyl, C$_{3-6}$cycloalkyl, phenyl, or 5-6 membered heterocyclyl, wherein the heterocyclyl contains 1 oxygen heteroatom and wherein R$^7$ is substituted with 0-5 J$^7$.

19. The compound of claim 6, wherein R$^7$ is a C$_{4-5}$cycloalkyl, wherein R$^7$ is substituted with 0-5 J$^7$.

20. The compound of claim 6, wherein R$^7$ is C$_{4-5}$cycloalkyl substituted with 1 or 2 —F.

21. The compound of claim 6, wherein R$^7$ is an unsubstituted C$_{4-5}$cycloalkyl.

22. The compound of claim 6, wherein R$^7$ is cyclopentyl substituted with 0-5 J$^7$.

23. The compound of claim 6, wherein R$^7$ is cyclopentyl substituted with 1 or 2 —F.

24. The compound of claim 6, wherein R$^7$ is an unsubstituted cyclopentyl.

25. The compound of claim 1, wherein R$^8$ is H.

26. The compound of claim 1, represented by formula II;

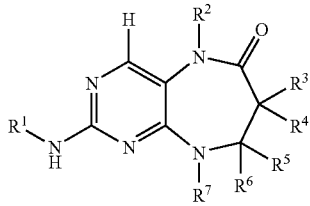

II wherein
R¹ is optionally substituted C₆₋₁₀aryl or optionally substituted 5-10 membered heteroaryl;
R² is H or an optionally substituted group selected from C₁₋₁₀aliphatic and C₃₋₁₀cycloaliphatic;
each R³, R⁴, R⁵, and R⁶ is independently H, C₁₋₁₀aliphatic, or C₃₋₁₀ cycloaliphatic;
wherein each R³, R⁴, R⁵, and R⁶ is optionally substituted with 0-5 J³, J⁴, J⁵, and J⁶ respectively; or
R³ and R⁴, together with the carbon atom to which they are attached, can form an optionally substituted 3-6 membered saturated or partially unsaturated monocyclic ring;
R³ and R⁵, together with the carbon atoms to which they are attached, can form an optionally substituted 3-6 membered saturated or partially unsaturated monocyclic ring;
R⁵ and R⁷, together with the atoms to which they are attached, can form an optionally substituted 3-6 membered saturated or partially unsaturated monocyclic ring;
R² and R⁹, together with the atoms to which they are attached, can form an optionally substituted 5-8 membered saturated or partially unsaturated monocyclic ring.

27. The compound of claim 1, represented by formula III;

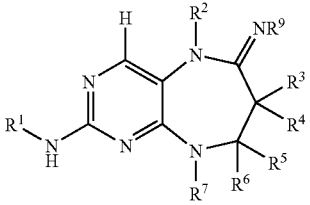

III wherein
R¹ is optionally substituted C₆₋₁₀aryl or optionally substituted 5-10 membered heteroaryl;
R² is H or an optionally substituted group selected from C₁₋₁₀aliphatic and C₃₋₁₀cycloaliphatic;
each R³, R⁴, R⁵, and R⁶ is independently H, C₁₋₁₀aliphatic, or C₃₋₁₀cycloaliphatic;
wherein each R³, R⁴, R⁵, and R⁶ is optionally substituted with 0-5 J³, J⁴, J⁵, and J⁶ respectively; or
R³ and R⁴, together with the carbon atom to which they are attached, can form an optionally substituted 3-6 membered saturated or partially unsaturated monocyclic ring;
R³ and R⁵, together with the carbon atoms to which they are attached, can form an optionally substituted 3-6 membered saturated or partially unsaturated monocyclic ring;

R⁵ and R⁷, together with the atoms to which they are attached, can form an optionally substituted 3-6 membered saturated or partially unsaturated monocyclic ring;
R² and R⁹, together with the atoms to which they are attached, can form an optionally substituted 5-8 membered saturated or partially unsaturated monocyclic ring.

28. The compound according to claim 1, wherein
each J³, J⁴, J⁵, and J⁶ is independently C₁₋₆ aliphatic, C₃₋₆cycloaliphatic, or —(C₁₋₄alkyl)ₙ—V¹;
wherein
n is 0 or 1;
V¹ is halo(C₁₋₄ aliphatic), —O(haloC₁₋₄ aliphatic), halo, NO₂, CN, OH, OR", SH, SR", NH₂, NHR", N(R")₂, COH, COR", CO₂H, CO₂R", CONH₂, CONHR", CONR"₂, OCOR", OCONH₂, OCONHR", OCON(R")₂, NHCOR", NR"COR", NHCO₂R", NR"CO₂R", NHCO₂H, NR"CO₂H, NHCONH₂, NHCONHR", NHCON(R")₂, SO₂NH₂, SO₂NHR", SO₂N(R")₂, NHSO₂R", NR"SO₂R";
R" is unsubstituted C₁₋₄ aliphatic;
or two of the same J³, J⁴, J⁵, or J⁶, bonded to the same atom, together can optionally form =O.

29. A compound selected from the following:

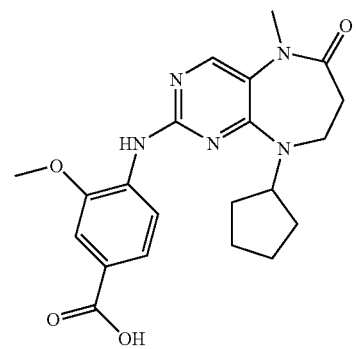

I-1

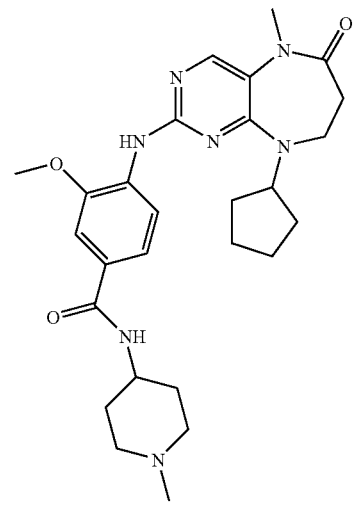

I-2

-continued
I-3
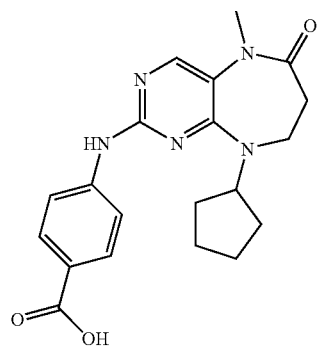
I-4
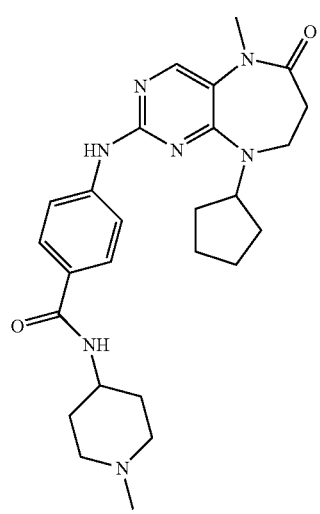
I-5
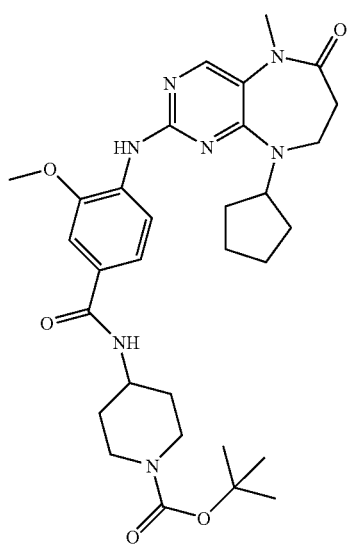
-continued
I-6
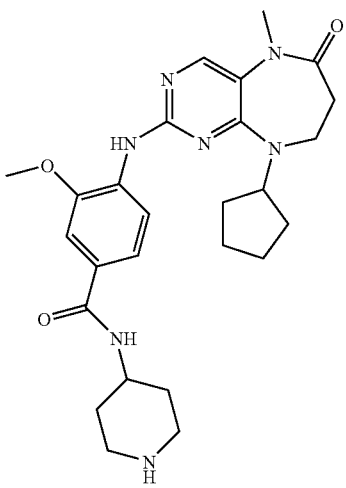
I-7
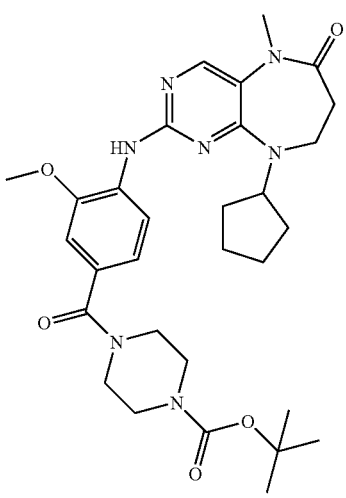
I-8
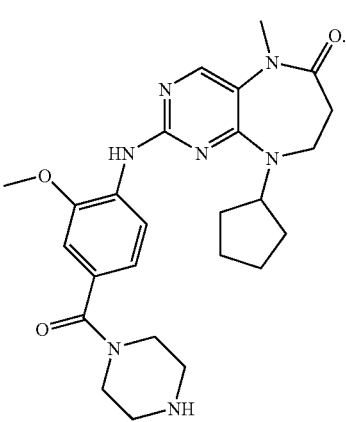

30. The compound of claim 1 selected from the following:
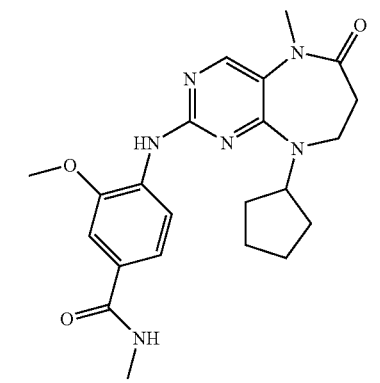
I-9
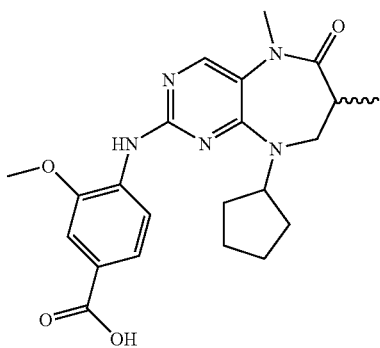
I-10
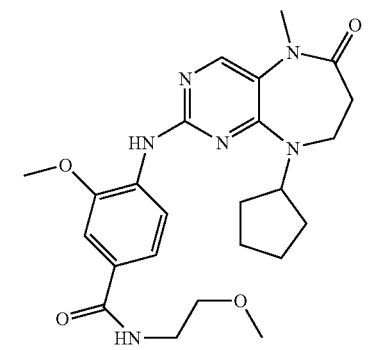
I-11
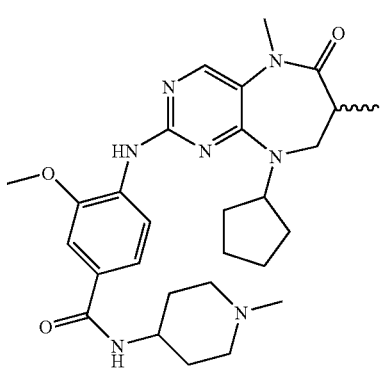
I-12
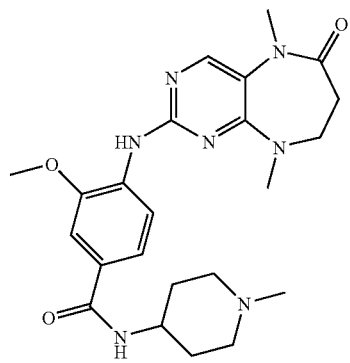
I-14
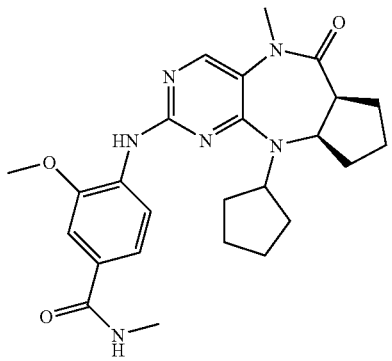
I-15
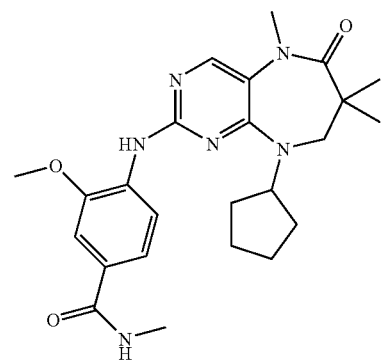
I-16
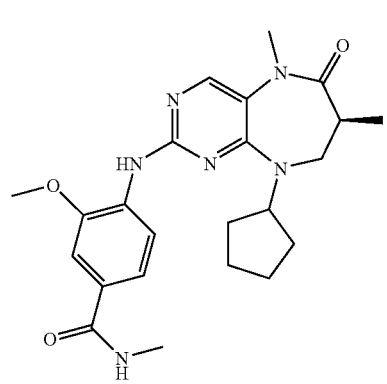
I-17

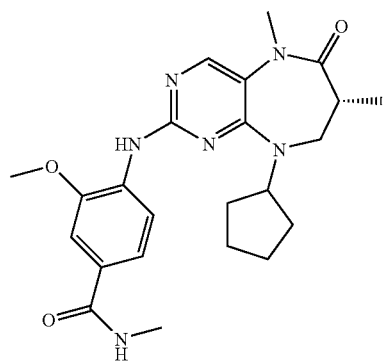
I-18
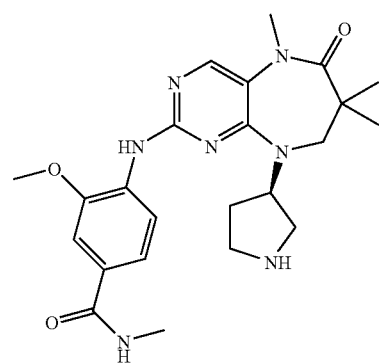
I-19
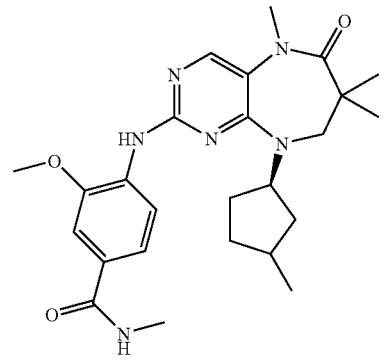
I-20
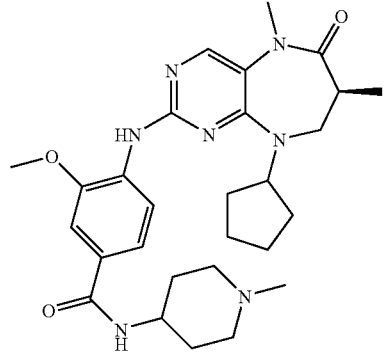
I-21
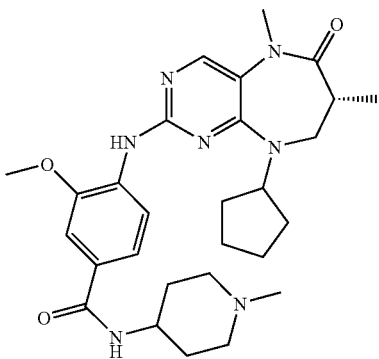
I-22
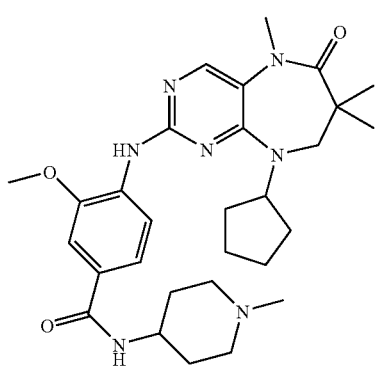
I-23
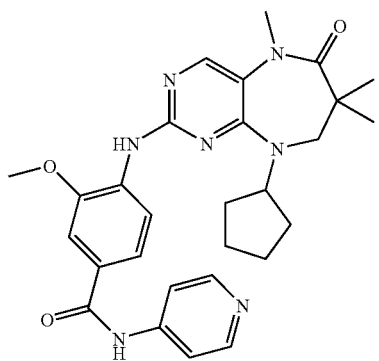
I-24
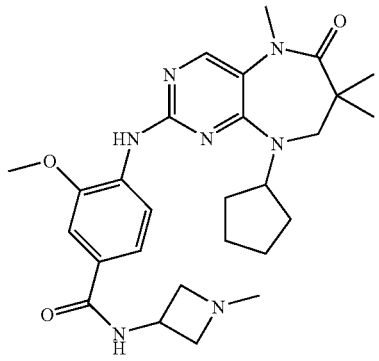
I-25

-continued
I-26
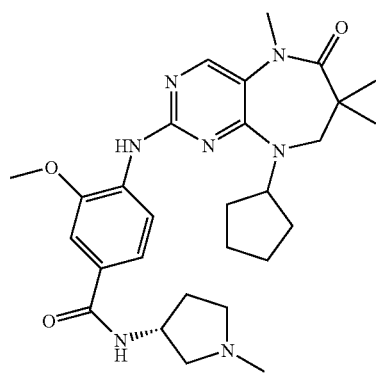
I-27
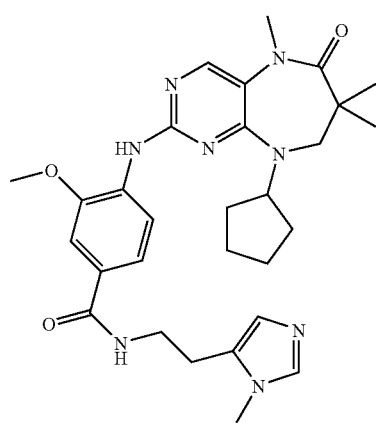
I-28
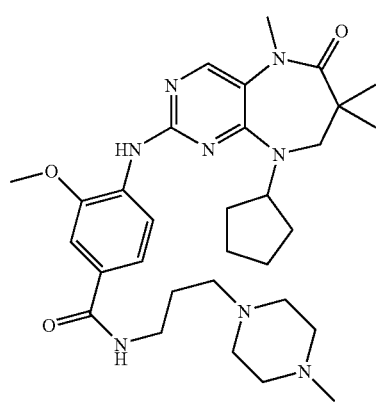
I-29
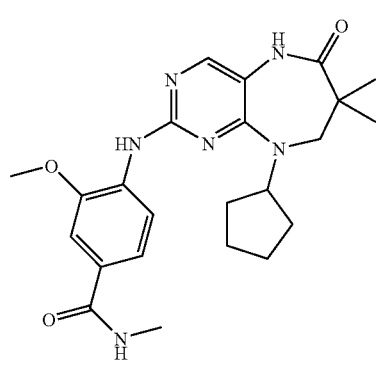
-continued
I-30
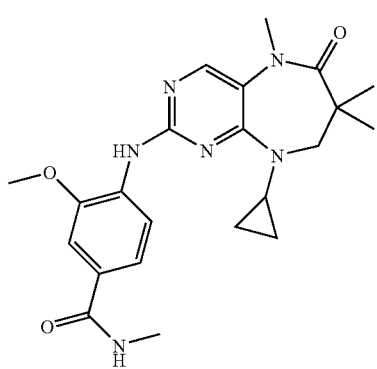
I-31
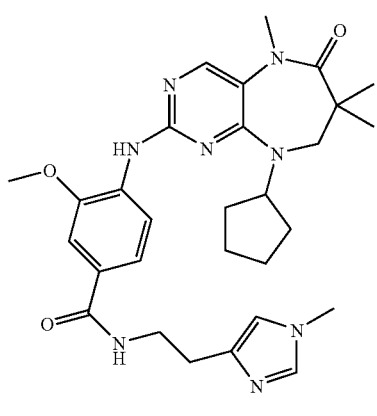
I-32
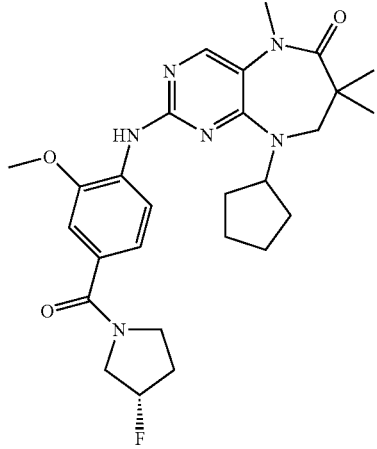
I-33
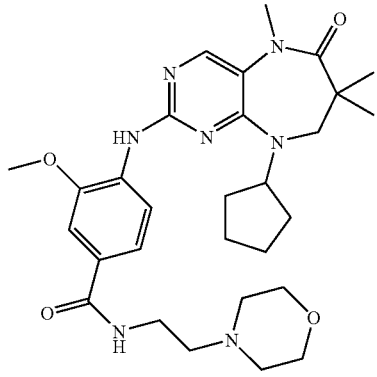

I-34
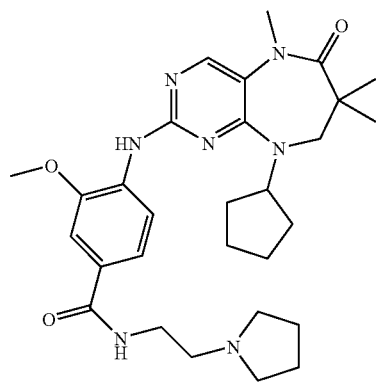
I-35
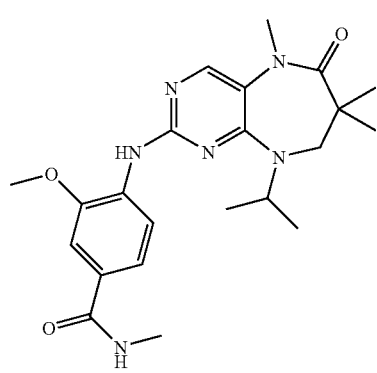
I-36
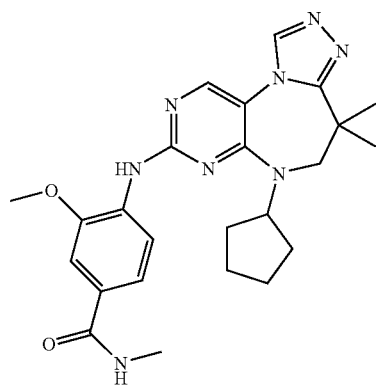
I-37
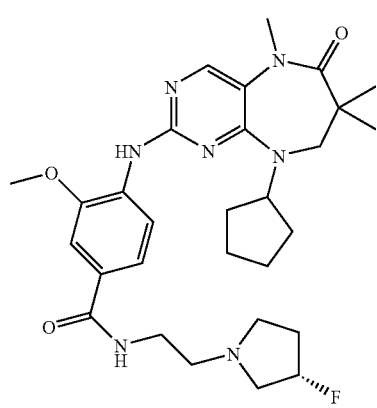
I-38
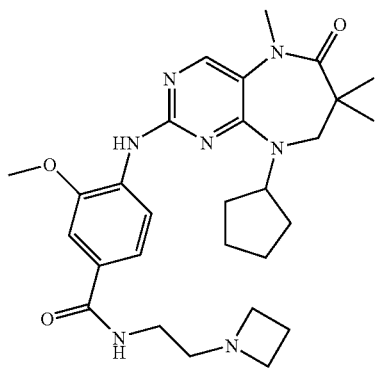
I-39
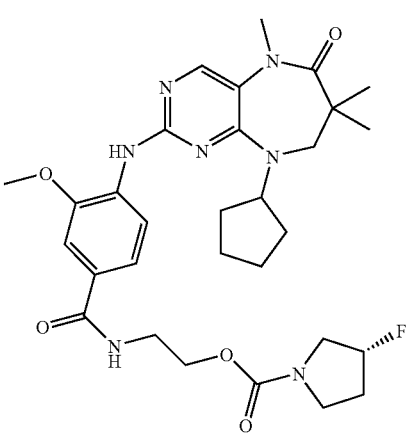
I-40
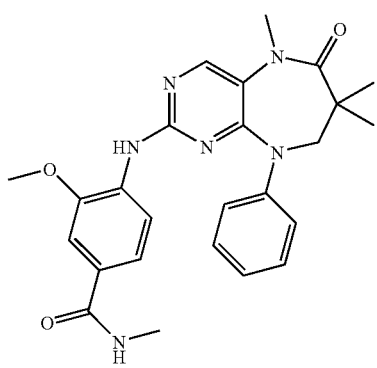
I-41
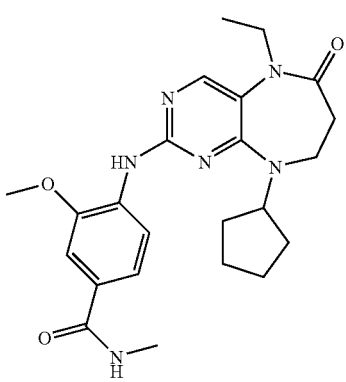

-continued
I-42
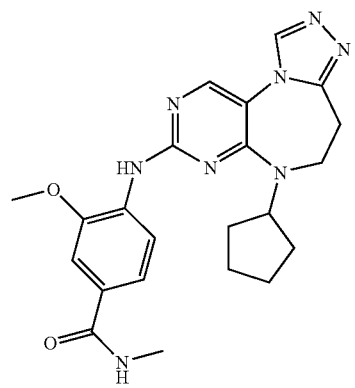
I-43
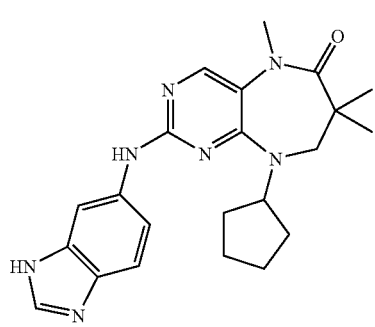
I-44
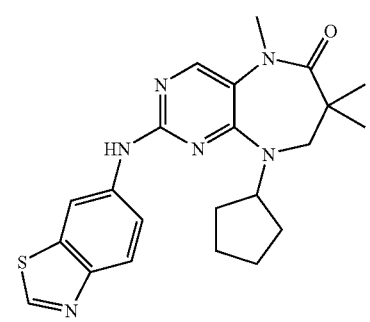
I-45
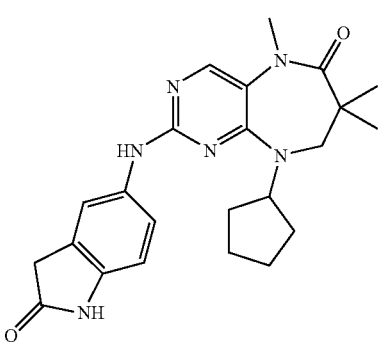
-continued
I-46
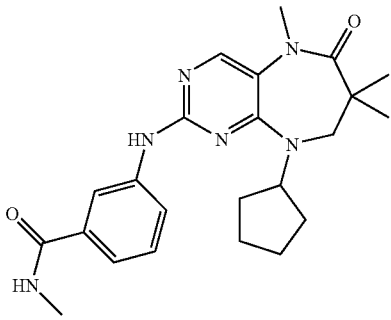
I-47
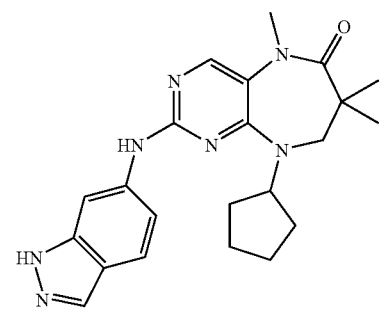
I-48
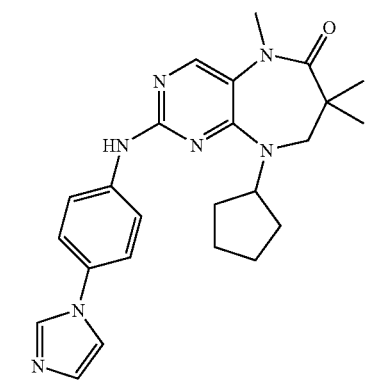
I-49
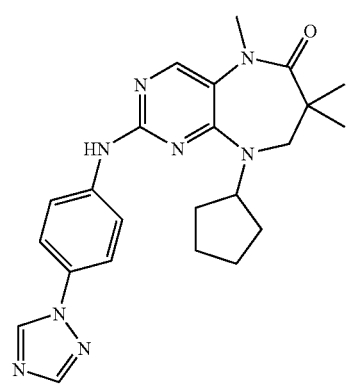

-continued
I-50
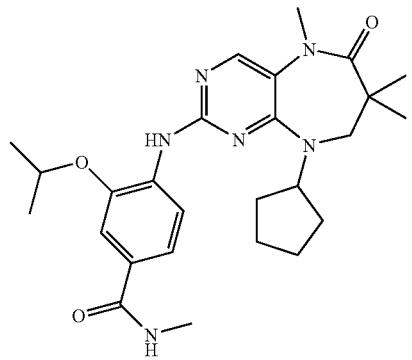
I-51
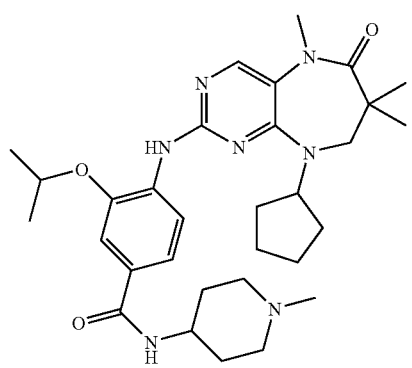
I-52
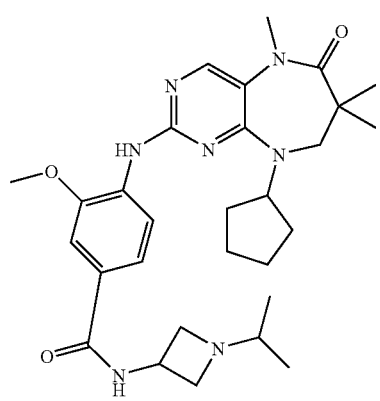
I-53
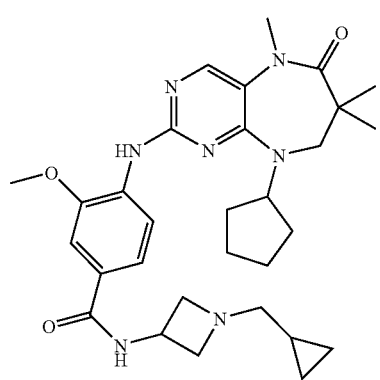
-continued
I-54
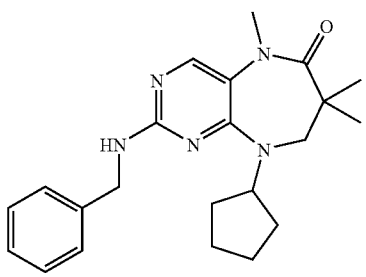
I-55
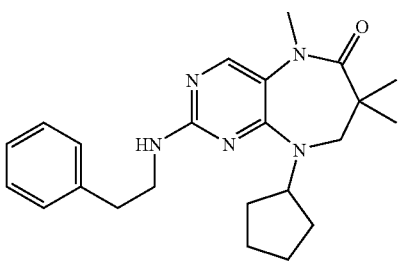
I-56
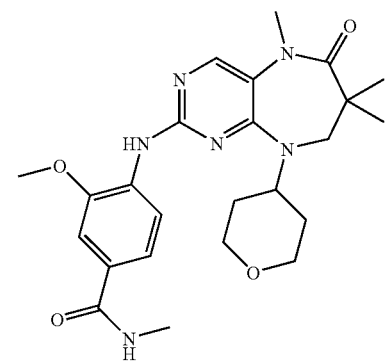
I-57
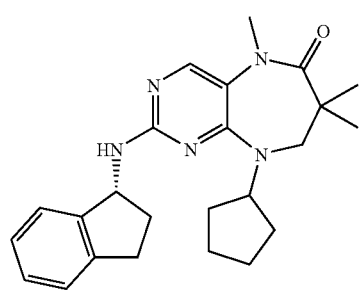
I-58
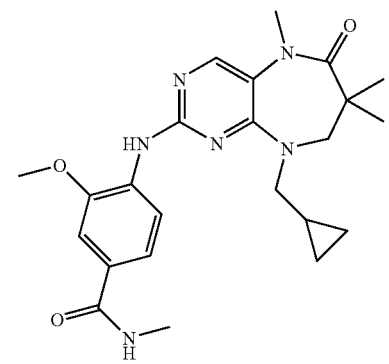

-continued
I-59
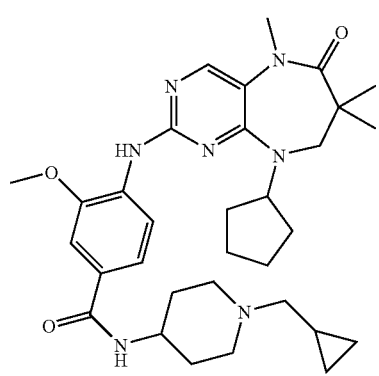
I-60
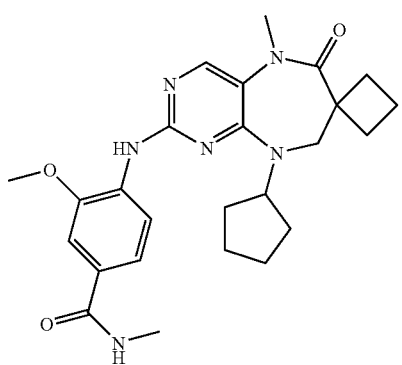
I-61
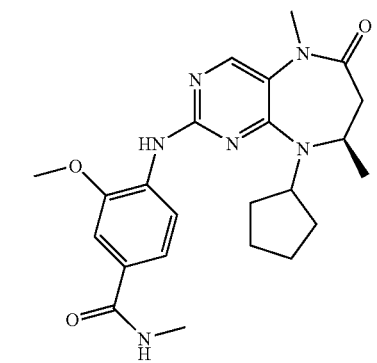
I-62
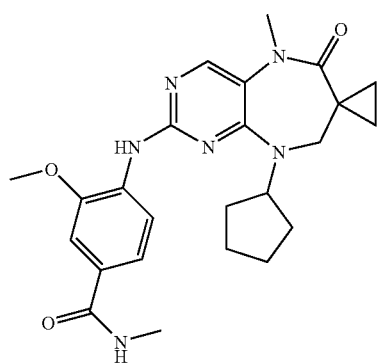
-continued
I-63
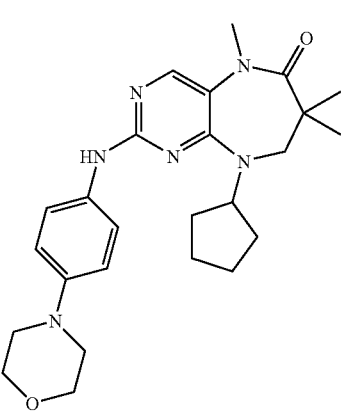
I-64
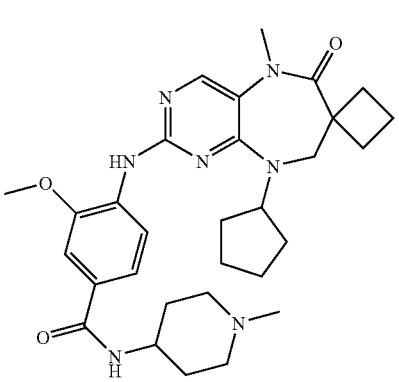
I-65
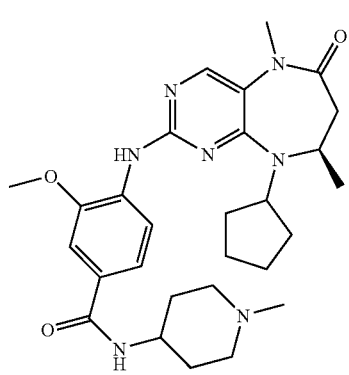
I-66
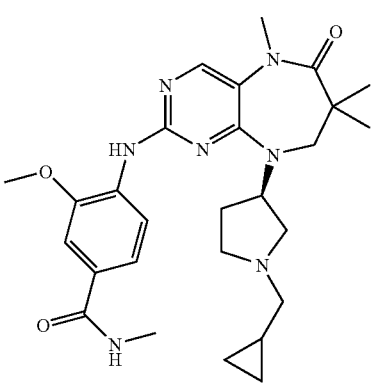

-continued
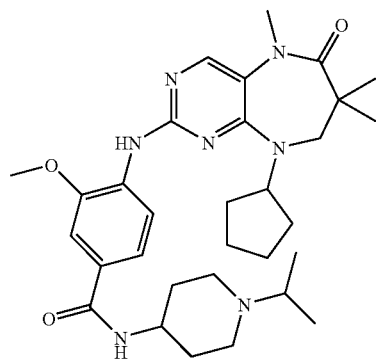
I-67
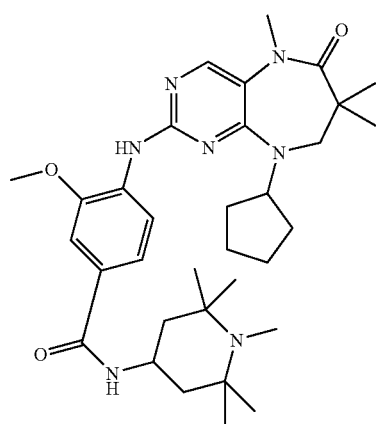
I-68
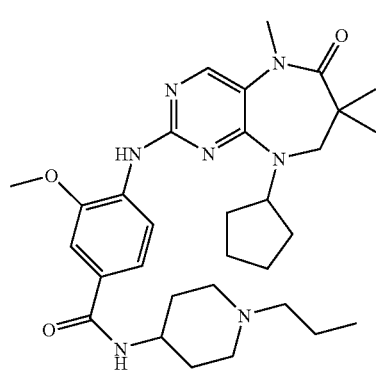
I-69
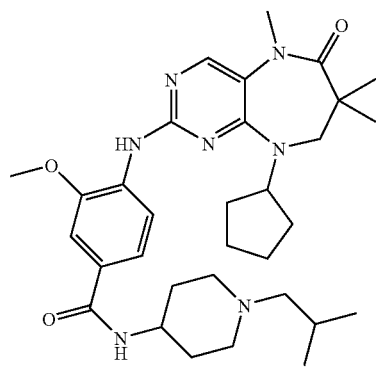
I-70
-continued
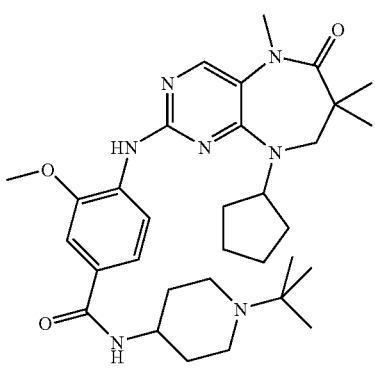
I-71
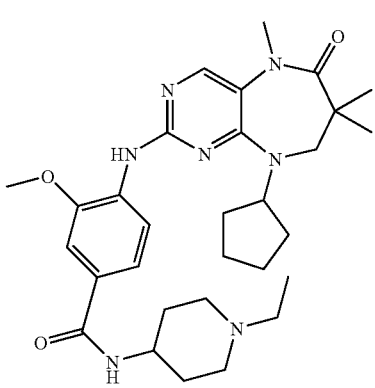
I-72
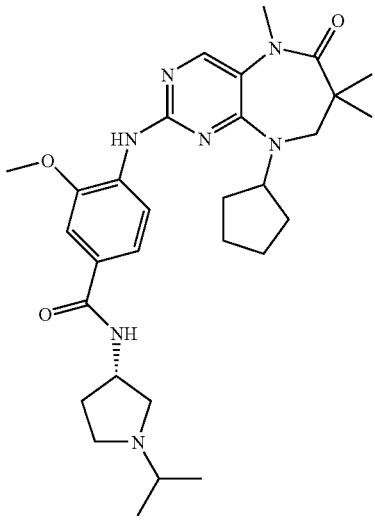
I-73
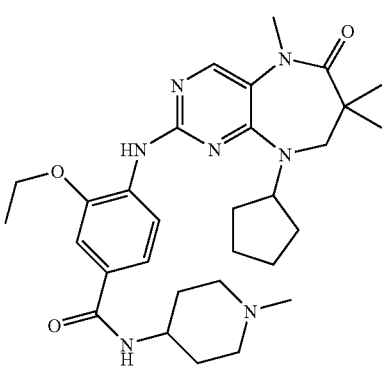
I-74

I-75
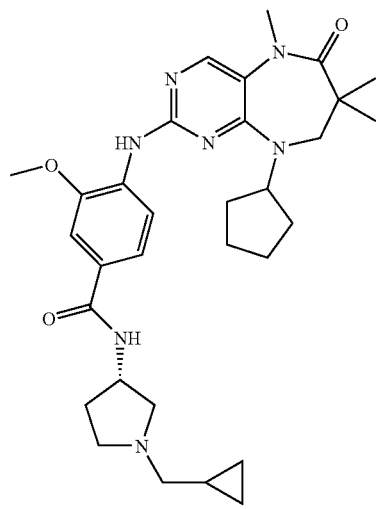
I-76
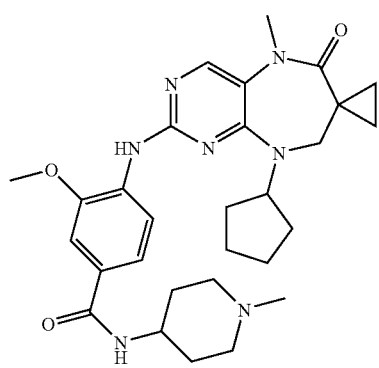
I-77
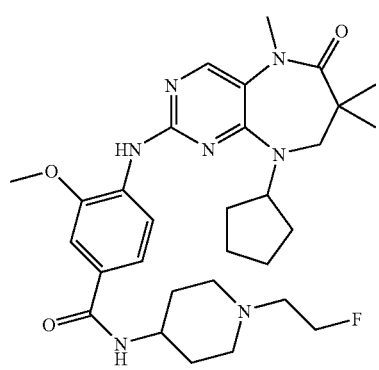
I-78
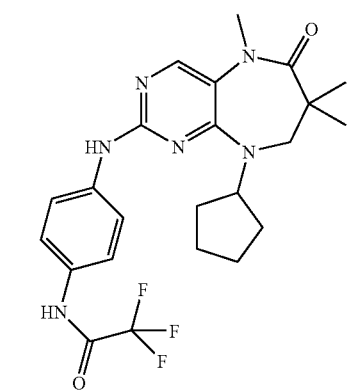
I-79
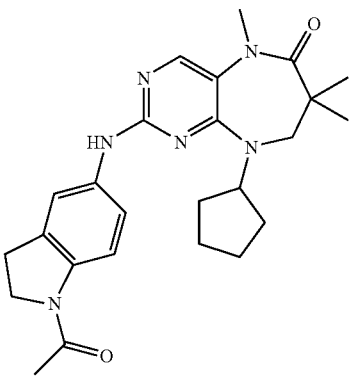
I-80
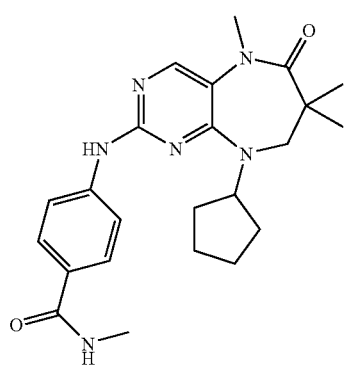
I-81
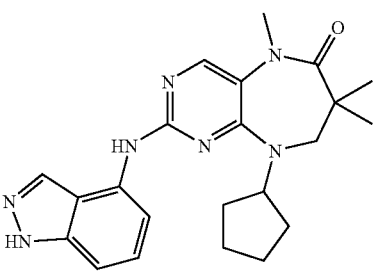
I-82
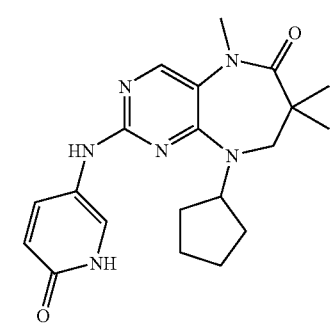

-continued
I-83
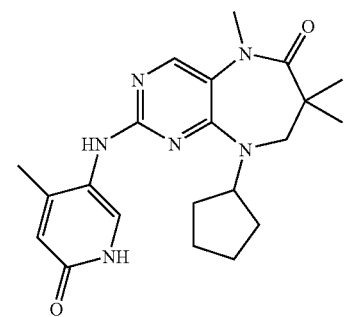
I-84
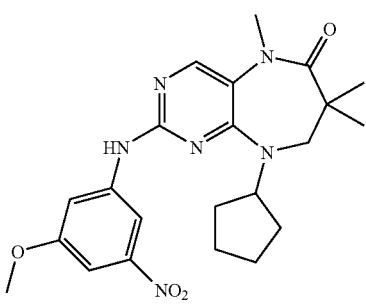
I-85
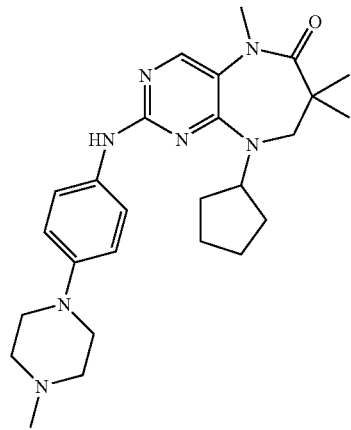
I-86
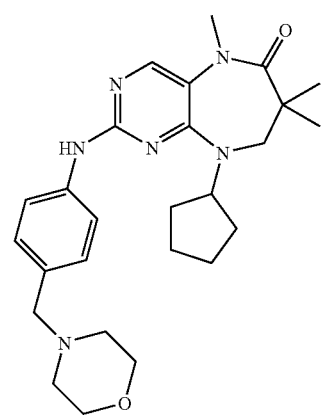
-continued
I-87
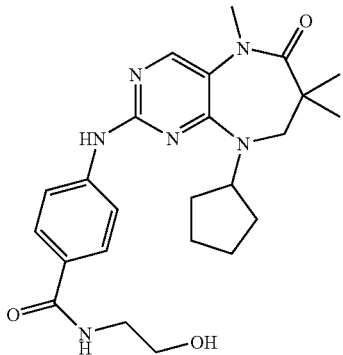
I-88
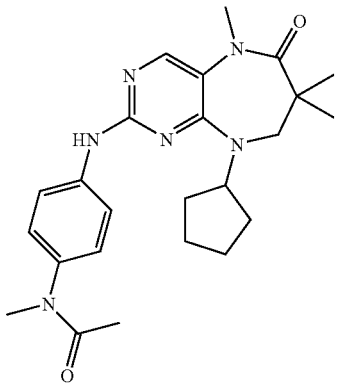
I-89
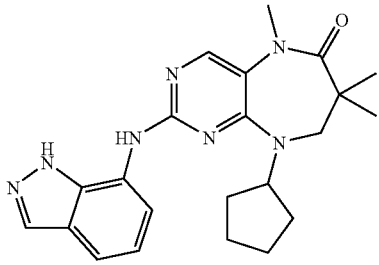
I-90
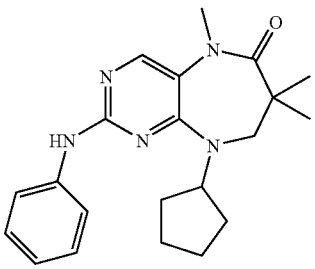
I-91
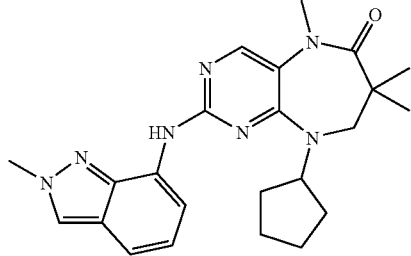

I-92
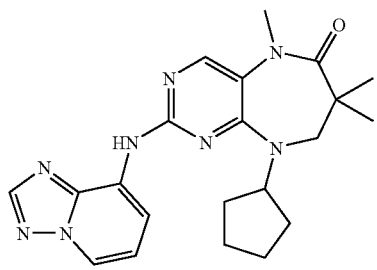
I-93
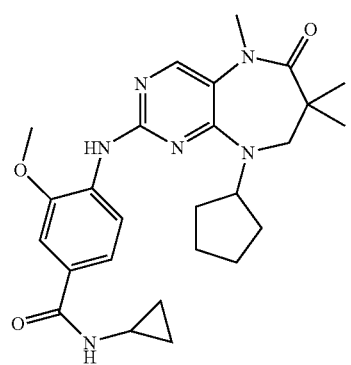
I-94
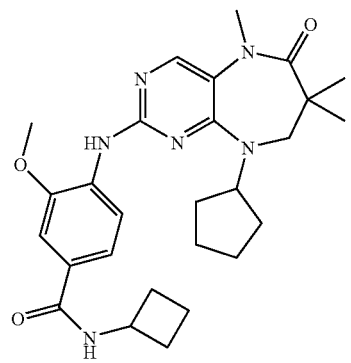
I-95
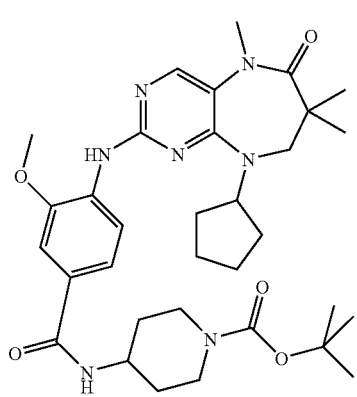
I-96
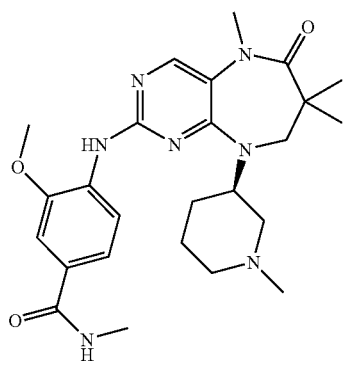
I-97
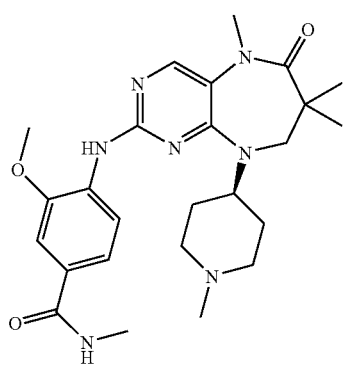
I-98
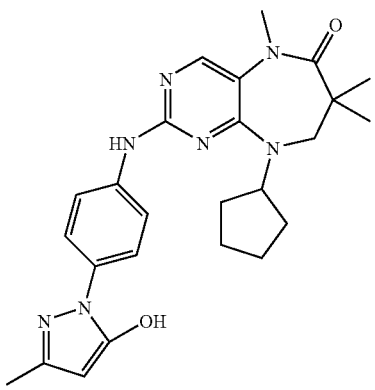
I-99
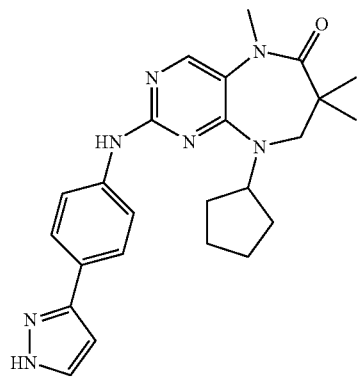

-continued
I-100
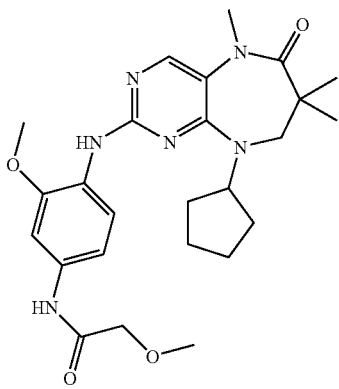
I-101
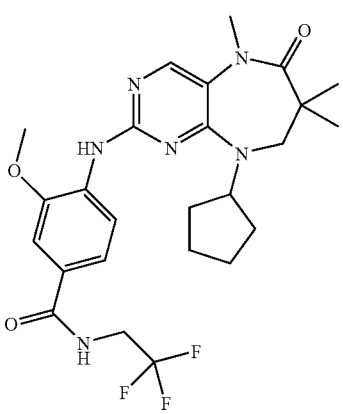
I-102
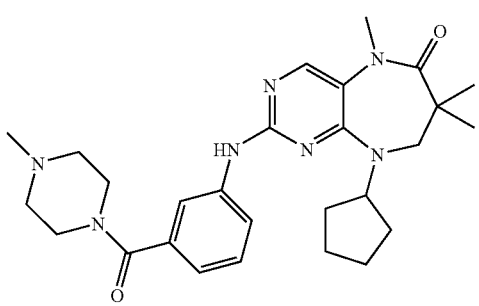
I-103
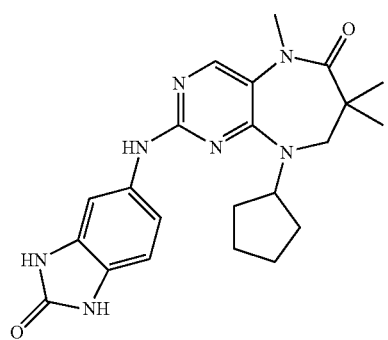
-continued
I-104
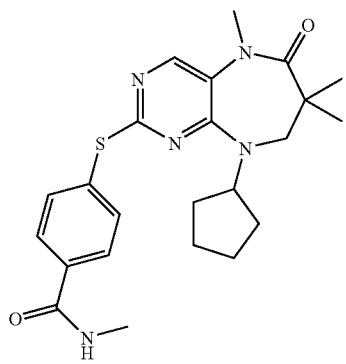
I-105
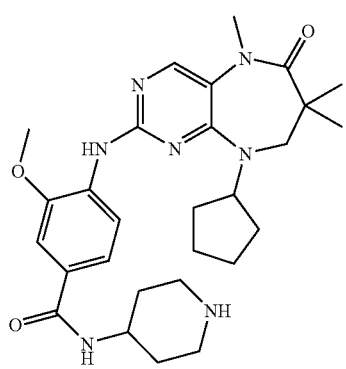
I-106
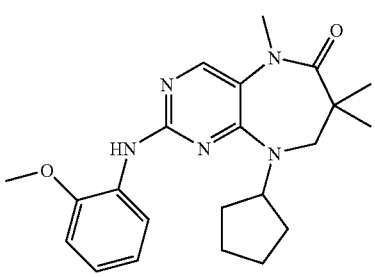
I-108
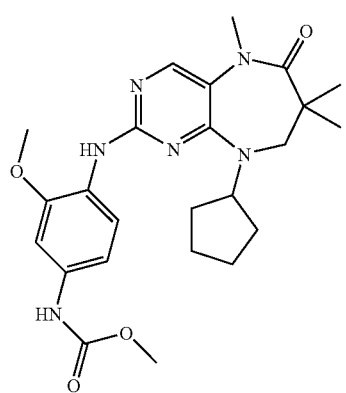

-continued
I-109
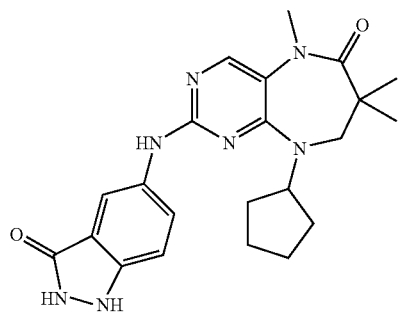
I-110
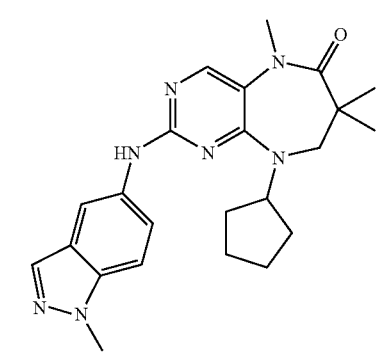
I-111
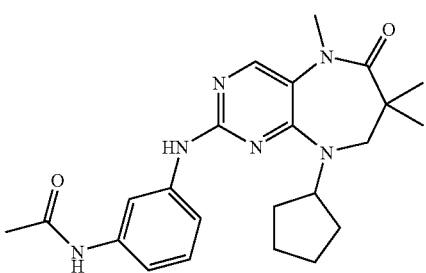
I-112
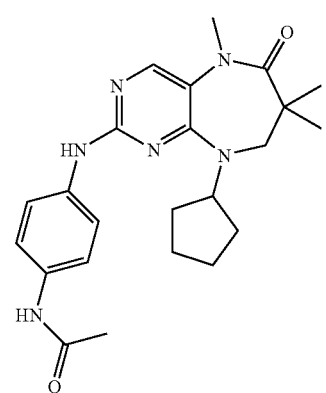
-continued
I-113
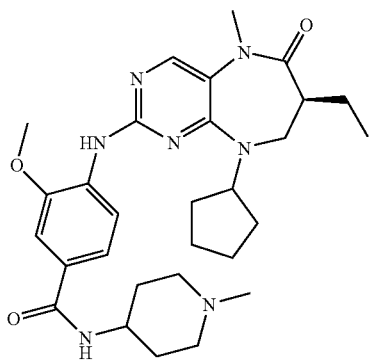
I-114
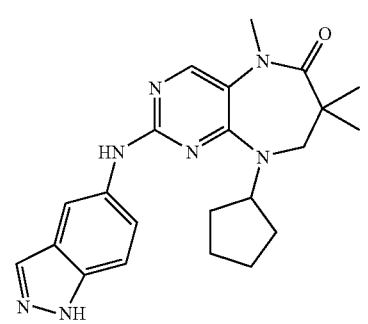
I-115
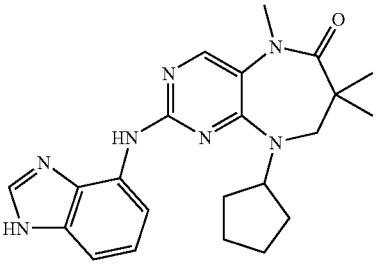
I-116
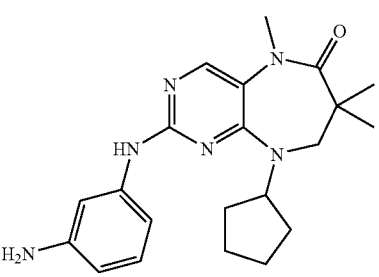
I-117
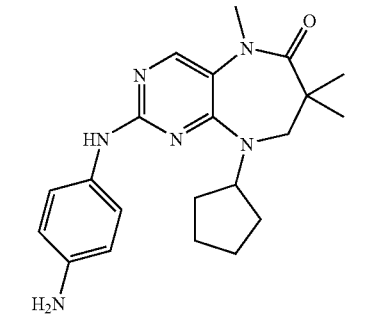

I-118
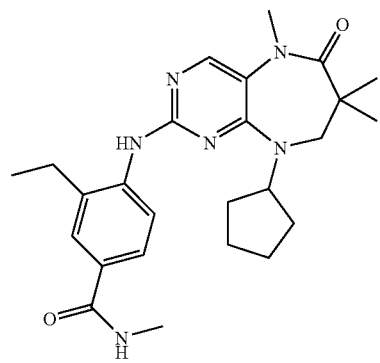
I-119
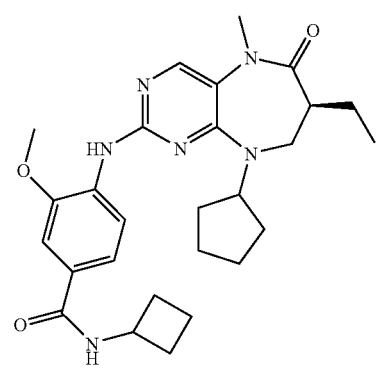
I-120
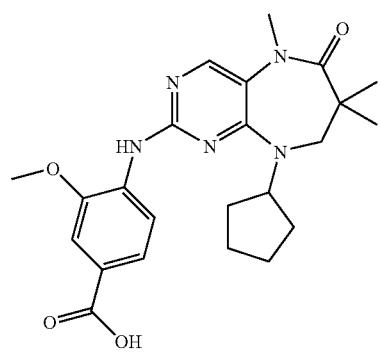
I-121
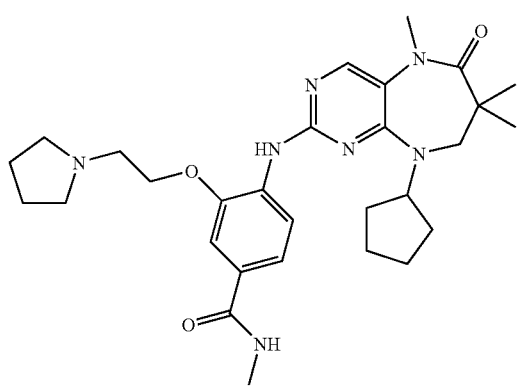
I-122
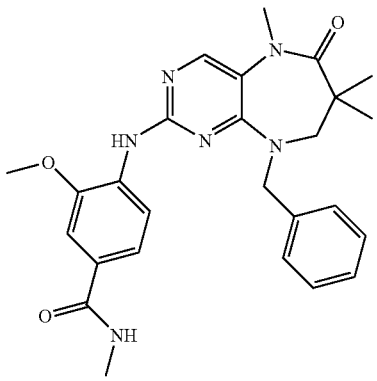
I-123
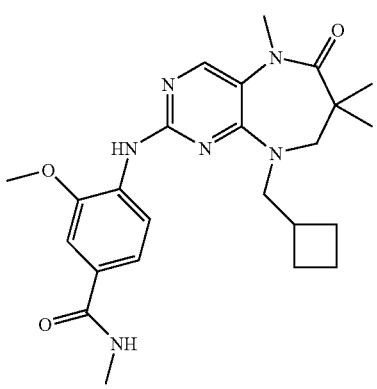
I-124
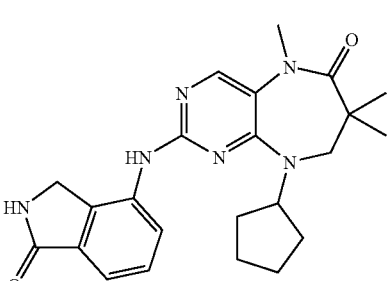
I-125
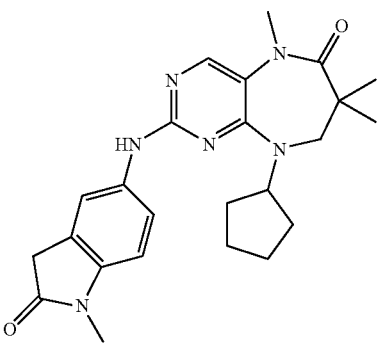

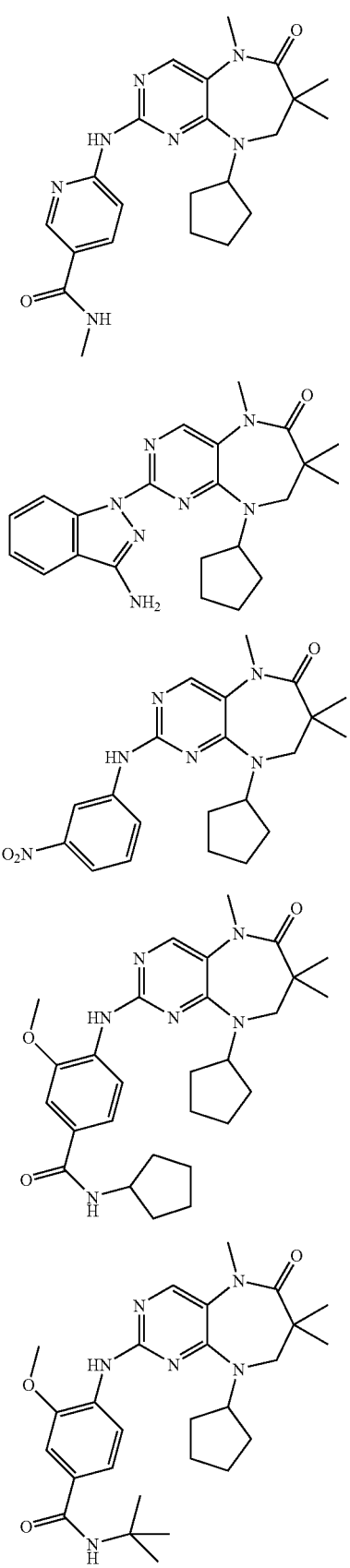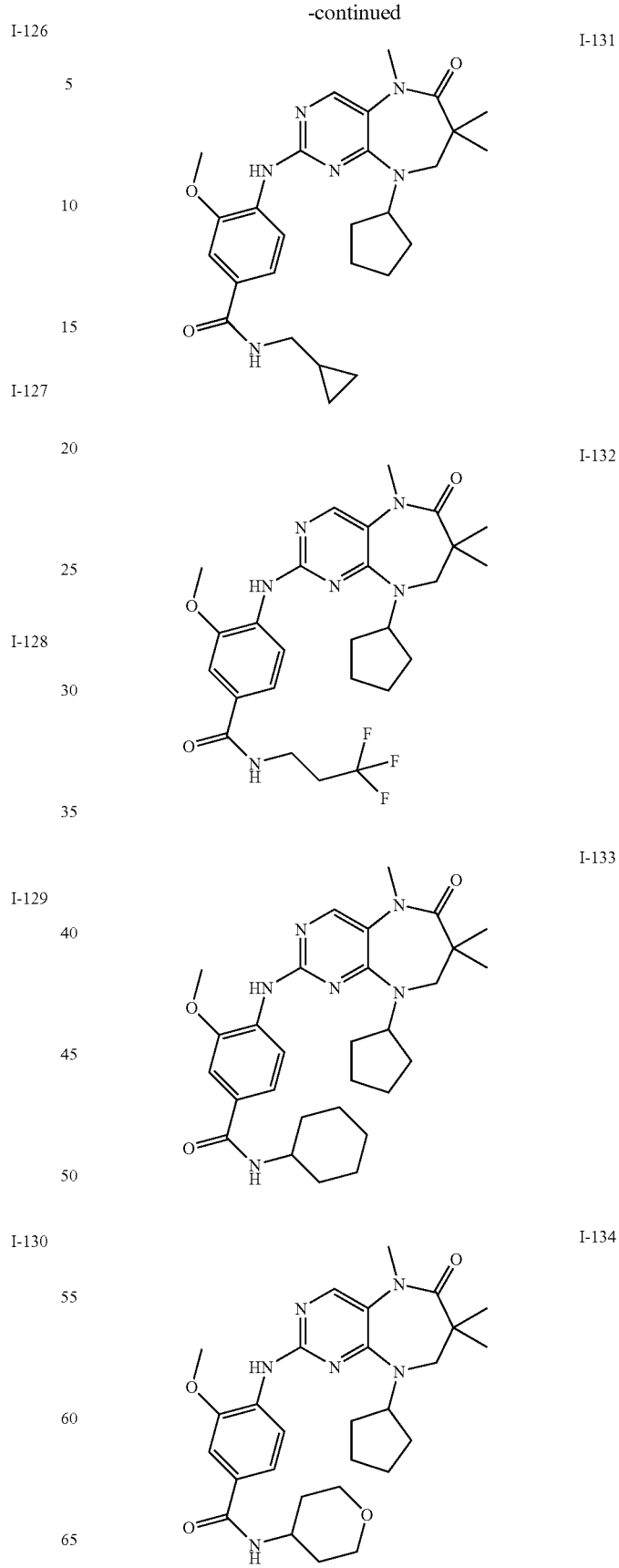

I-135 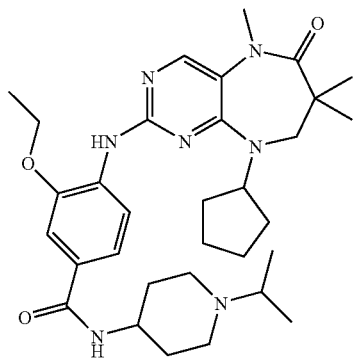
I-136 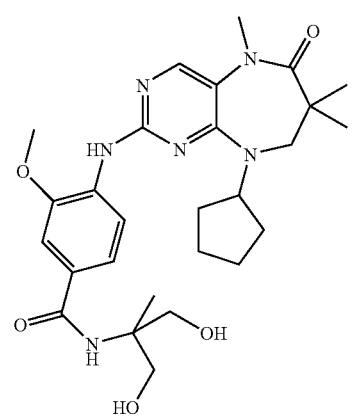
I-137 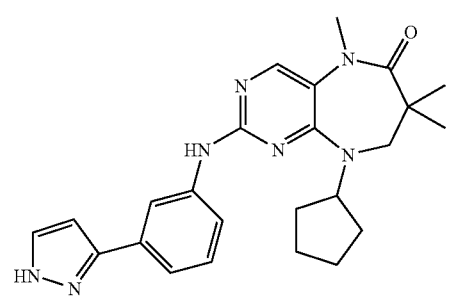
I-138 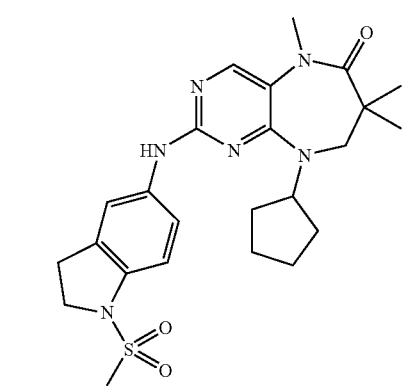
I-139 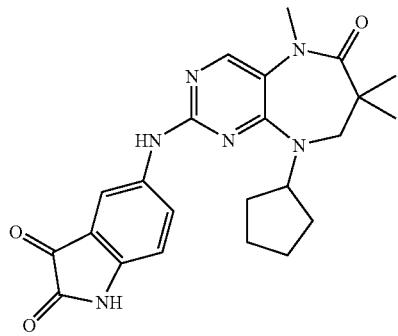
I-140 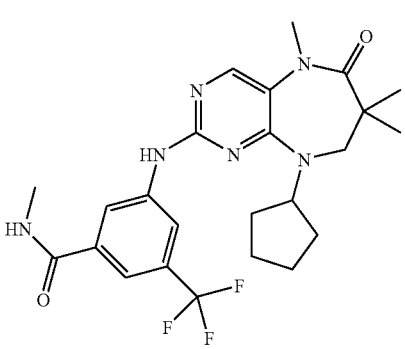
I-141 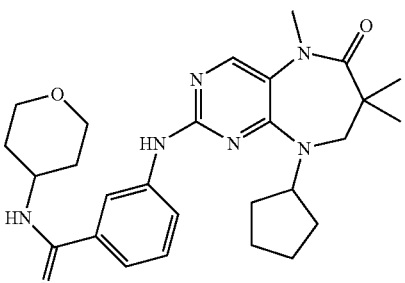
I-142 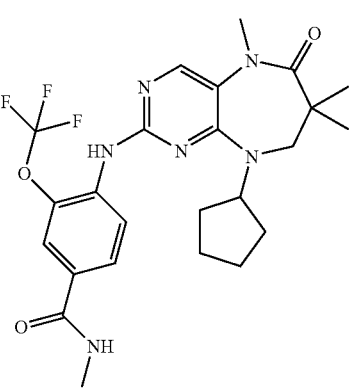

-continued
I-143
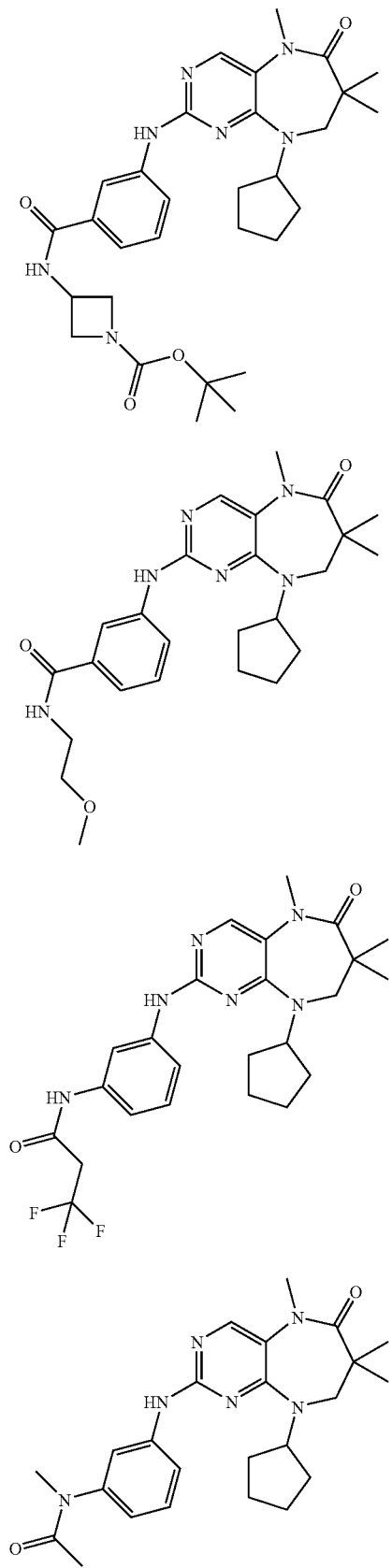
I-144
I-145
I-146
-continued
I-147
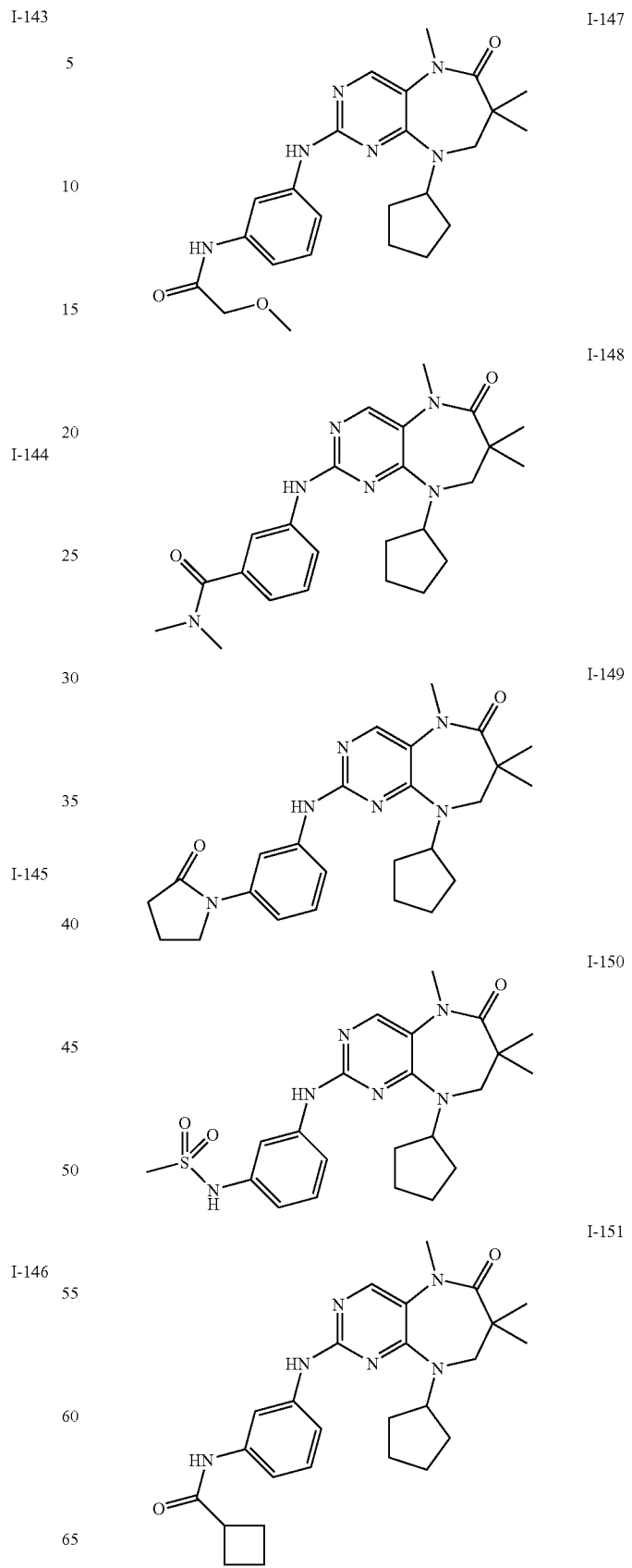
I-148
I-149
I-150
I-151

-continued
I-152
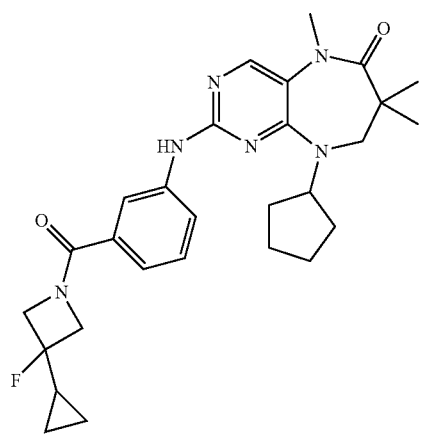
I-153
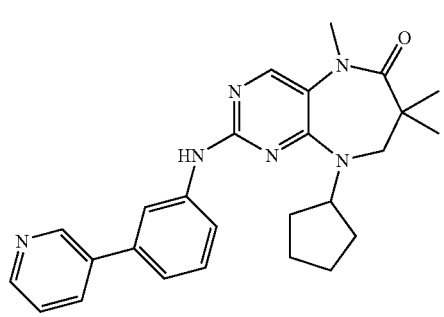
I-154
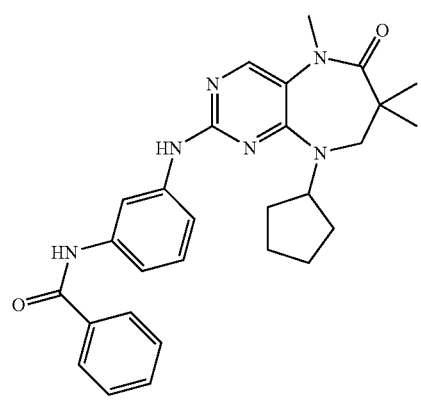
I-155
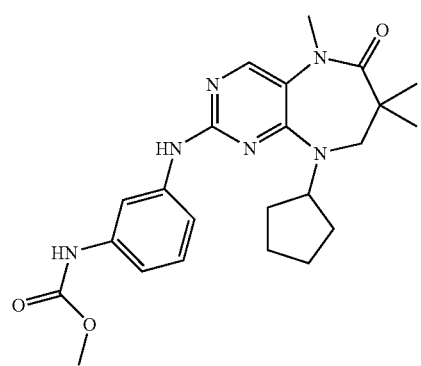
-continued
I-156
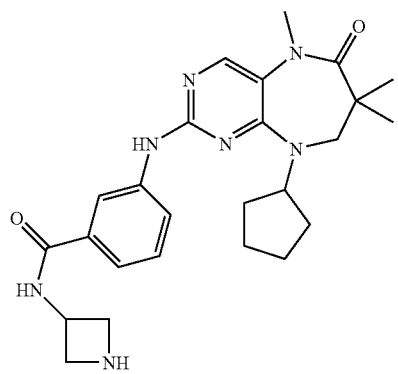
I-157
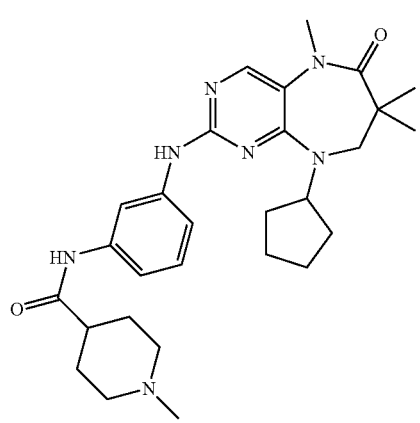
I-158
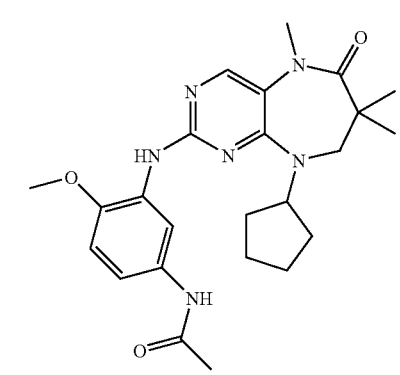
I-159
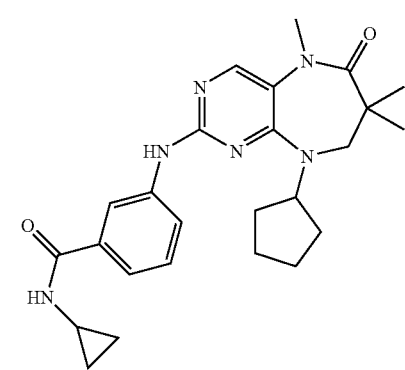

-continued
I-160
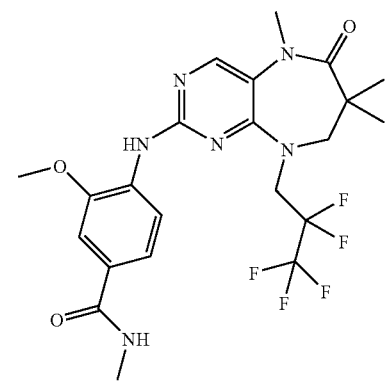
I-161
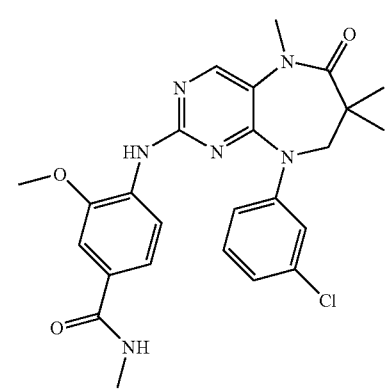
I-162
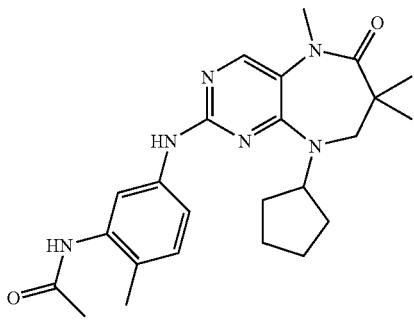
I-163
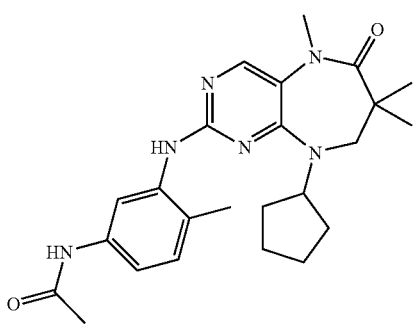
-continued
I-164
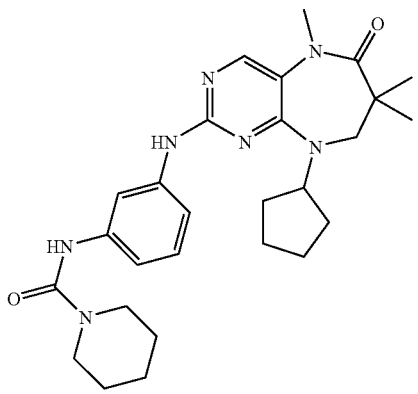
I-165
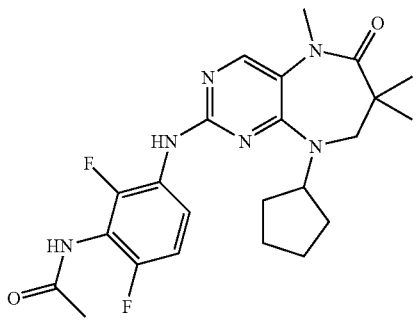
I-166
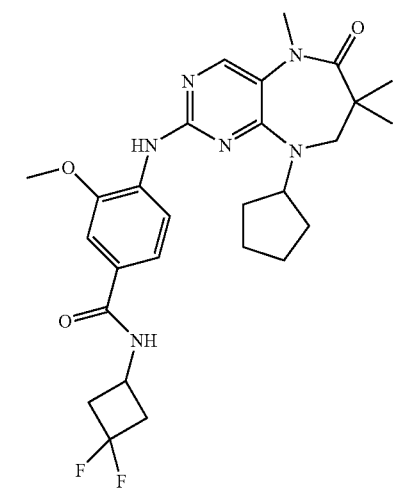
I-167
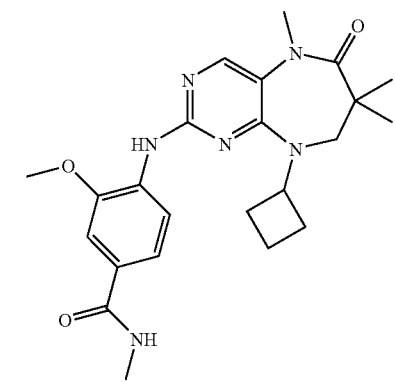

-continued
I-168
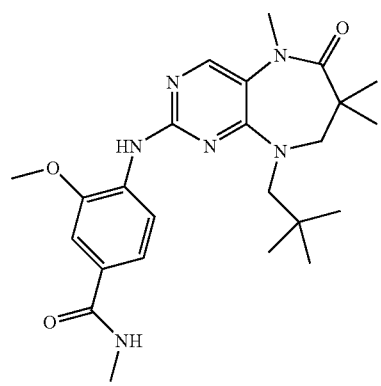
I-169
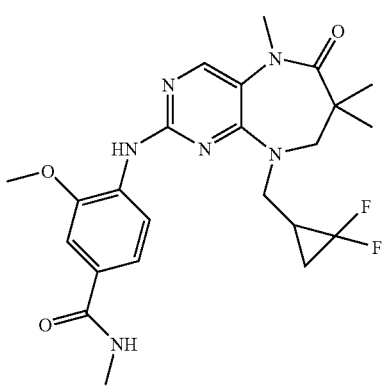
I-170
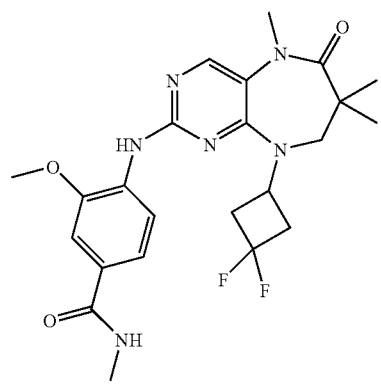
I-171
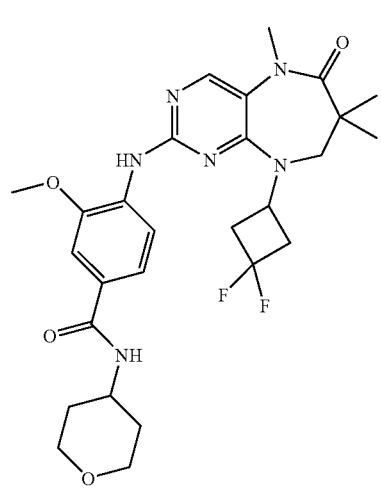
-continued
I-172
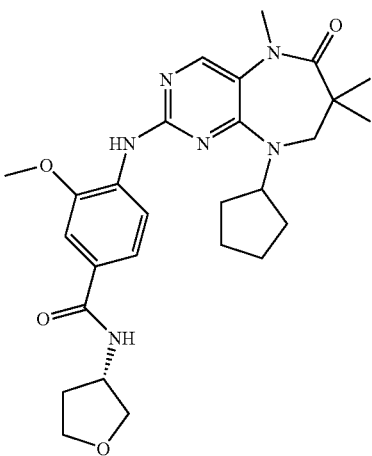
I-173
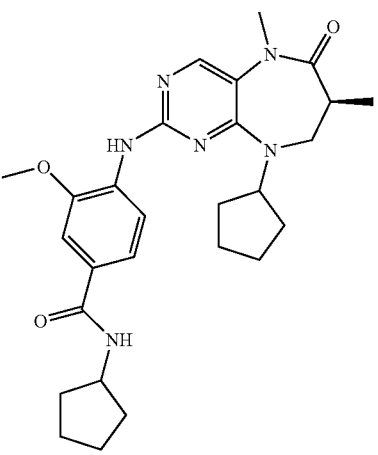
I-174
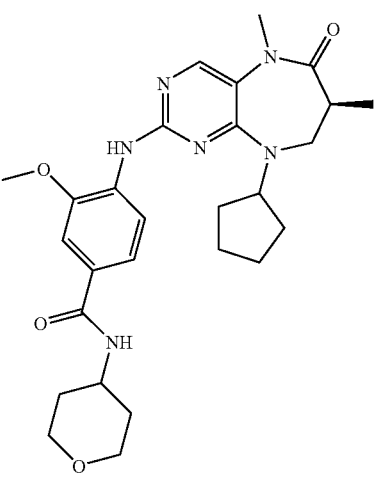

-continued
I-175
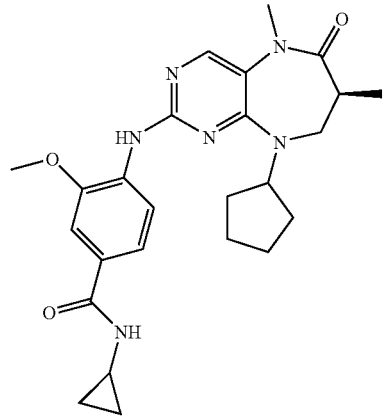
I-176
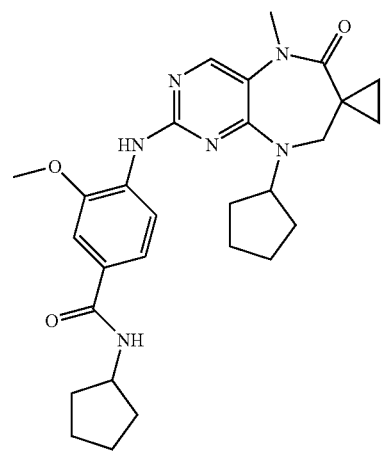
I-177
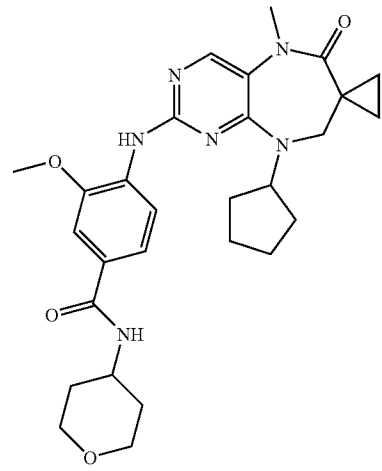
-continued
I-178
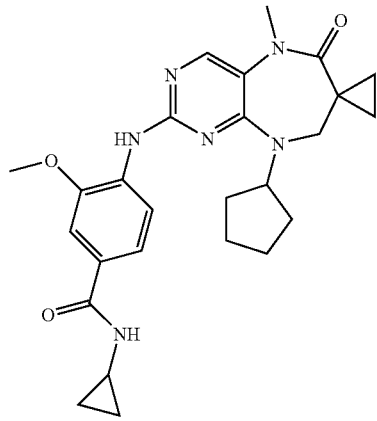
I-179
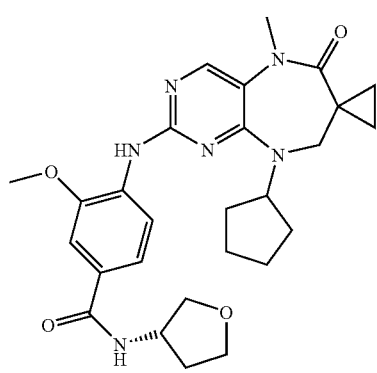
I-180
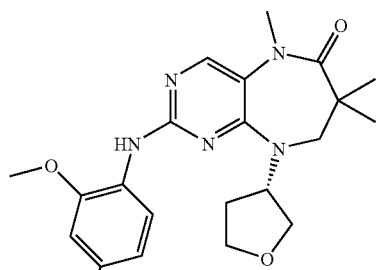
I-181
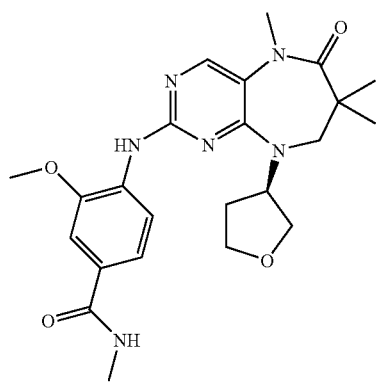

I-182 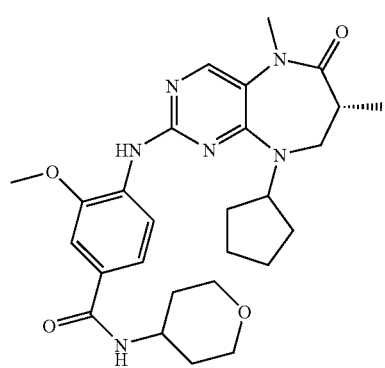
I-183 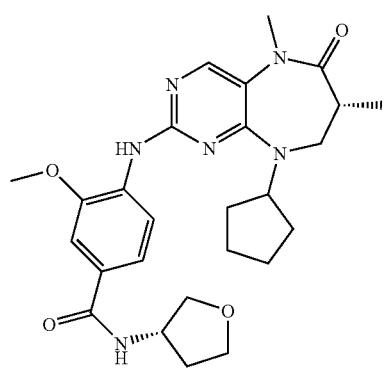
I-184 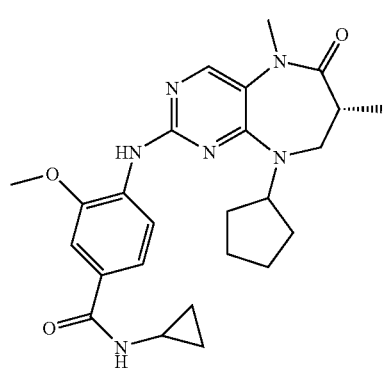
I-185 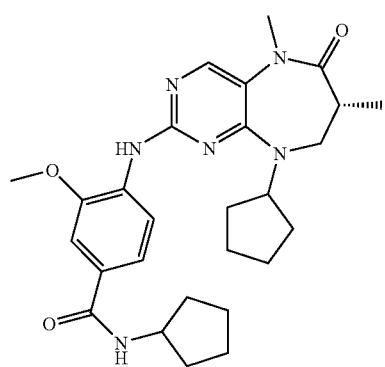
I-186 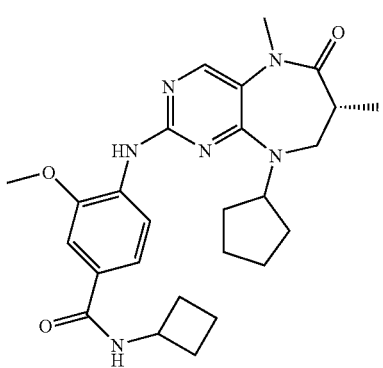
I-187 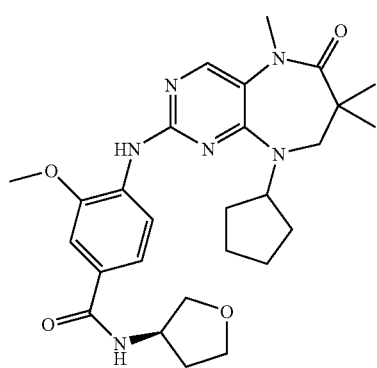
I-188 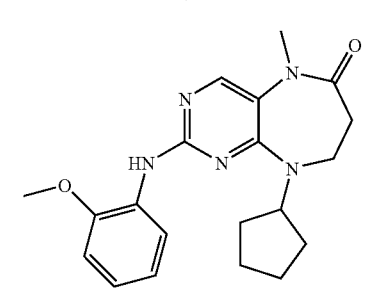
I-189 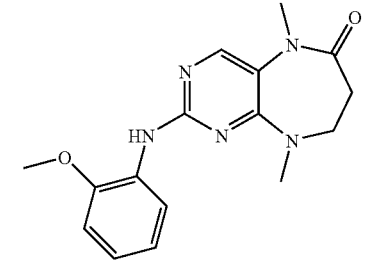
I-190 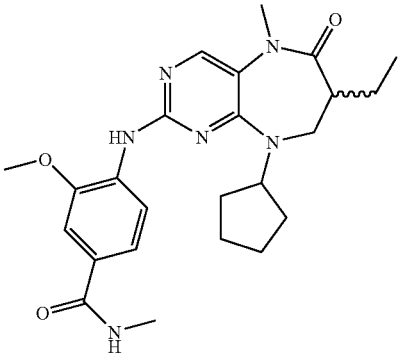

| 309 | 310 |
|---|---|
| -continued | -continued |
I-191
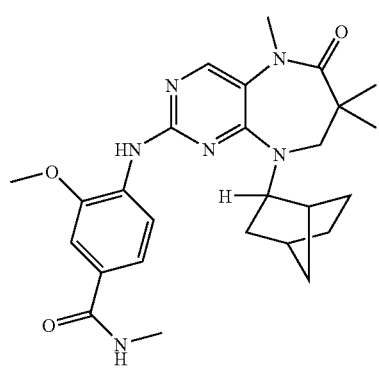
I-192
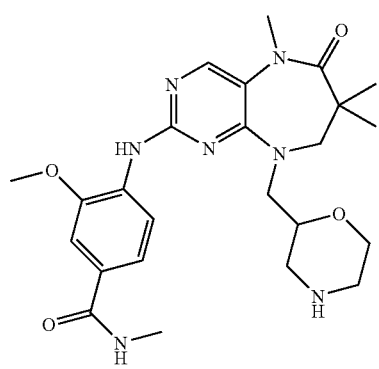
I-193
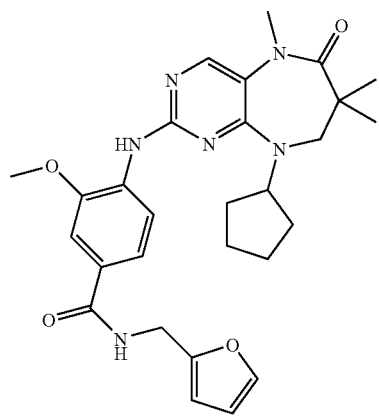
I-194
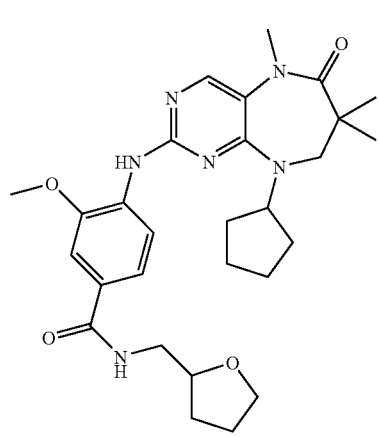
I-195
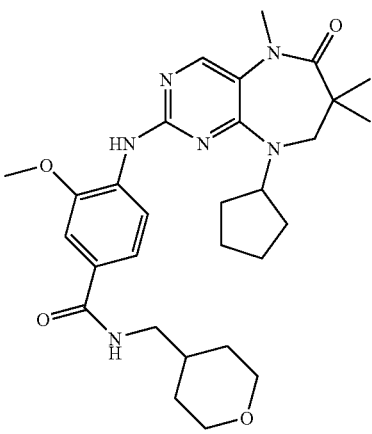
I-196
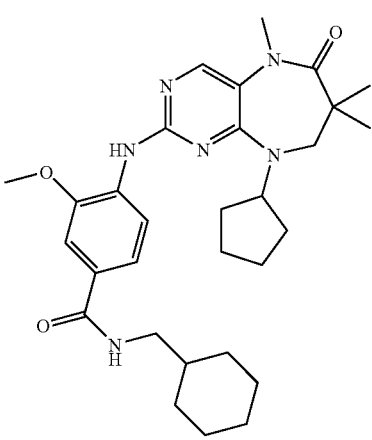
I-197
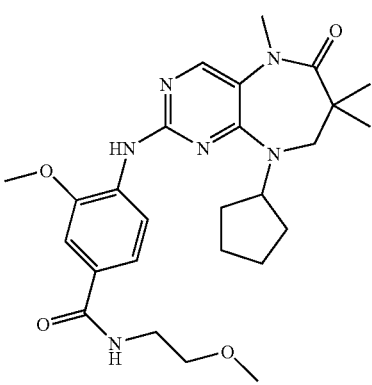
I-198
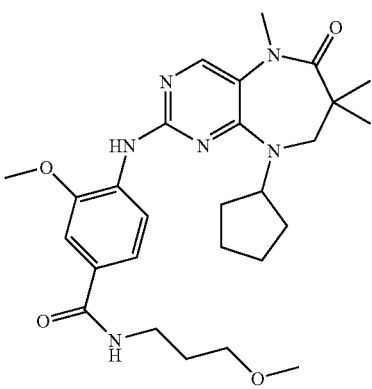

-continued
I-199
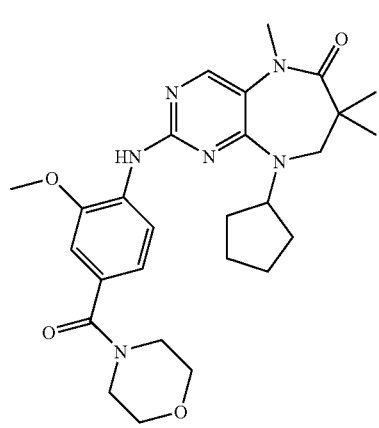
I-200
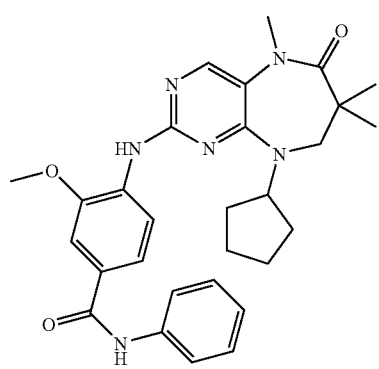
I-201
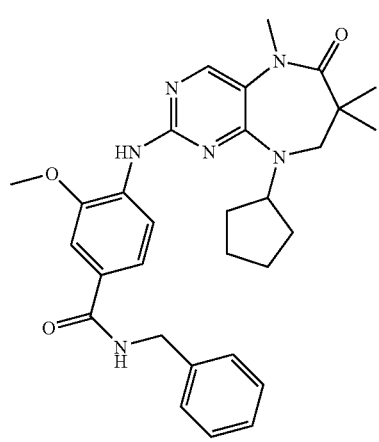
I-202
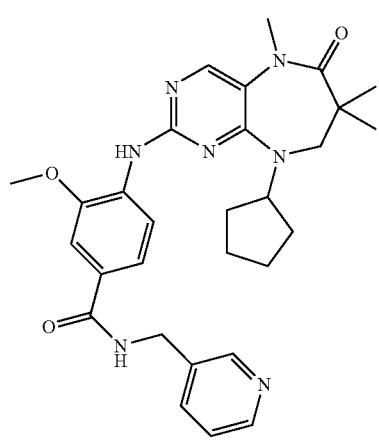
-continued
I-203
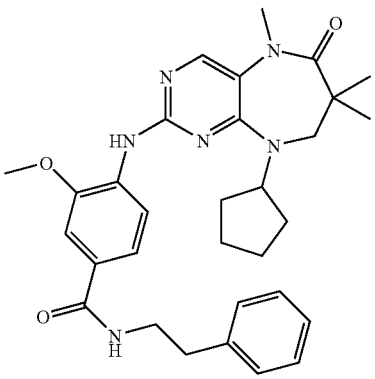
I-204
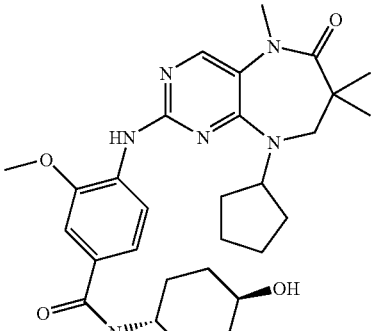
I-205
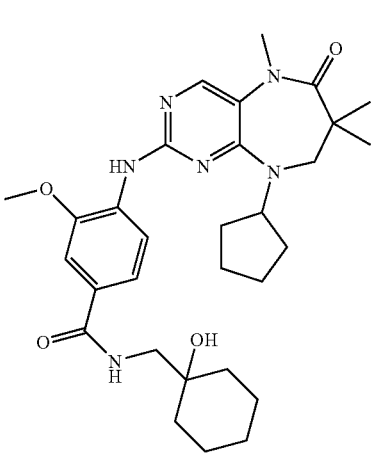
I-206
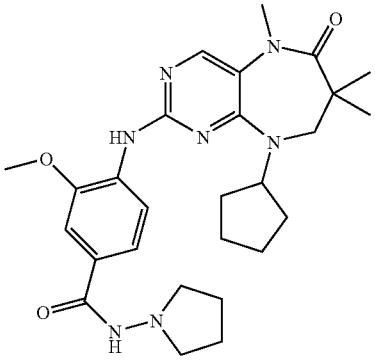

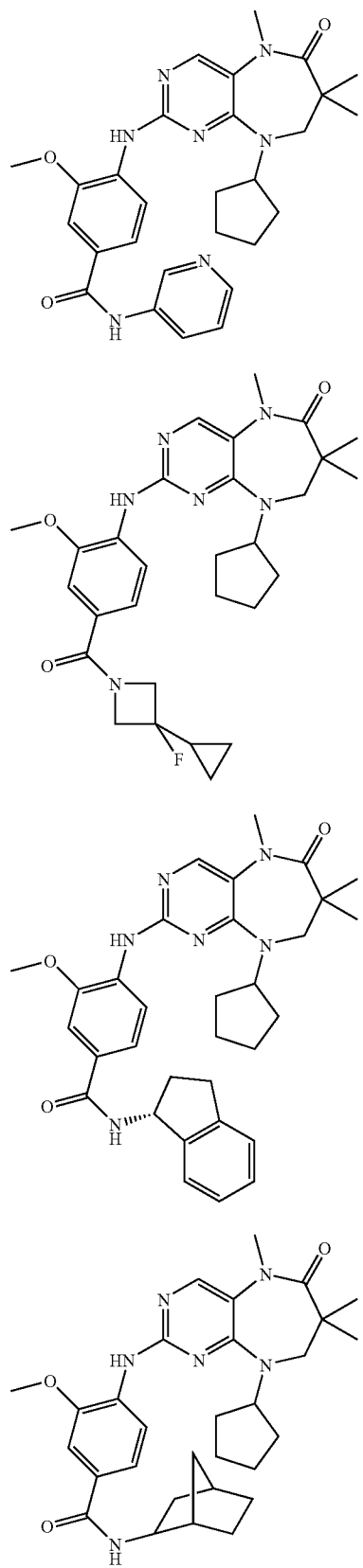
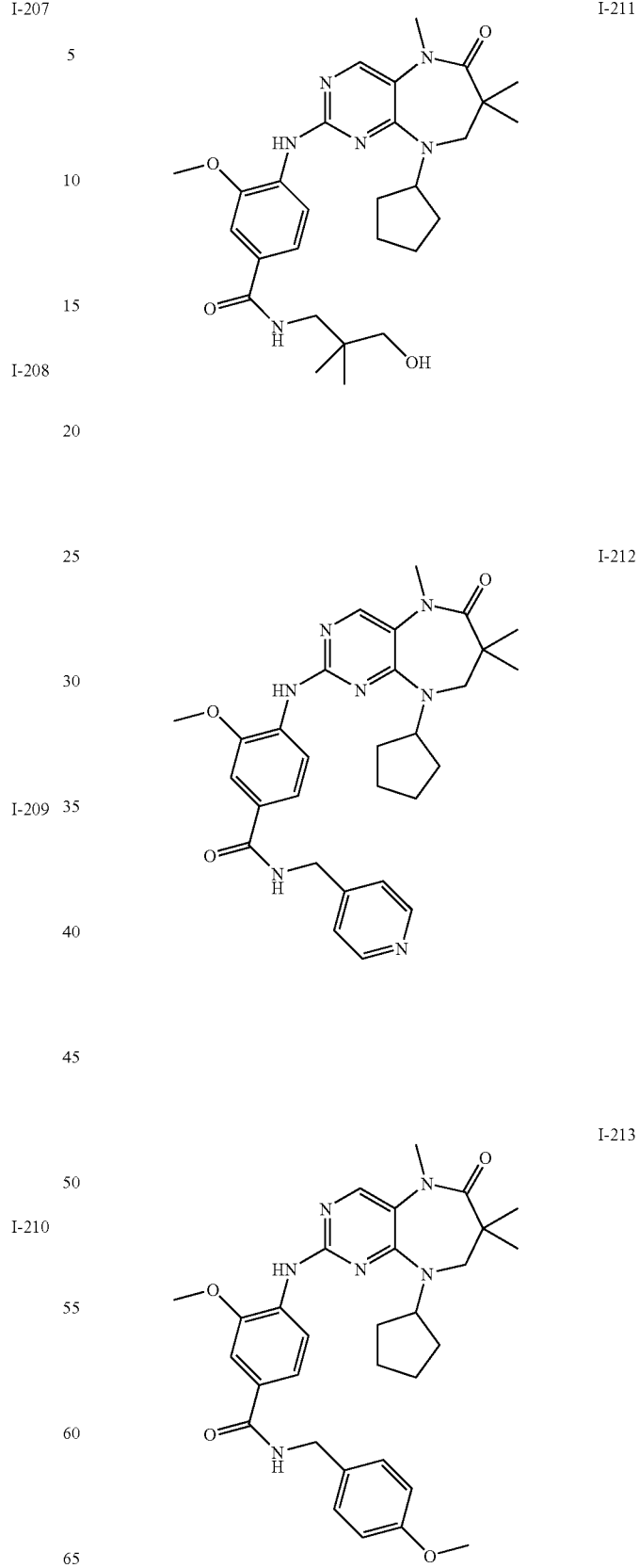

I-214
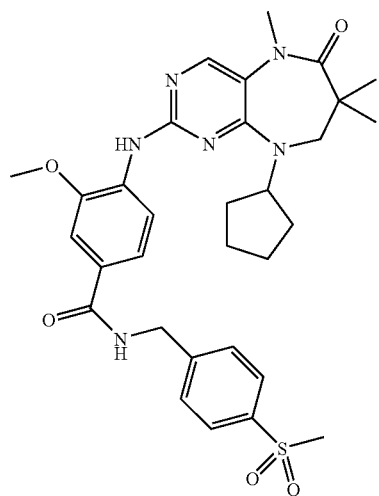
I-215
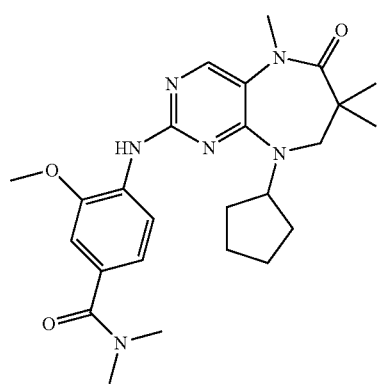
I-216
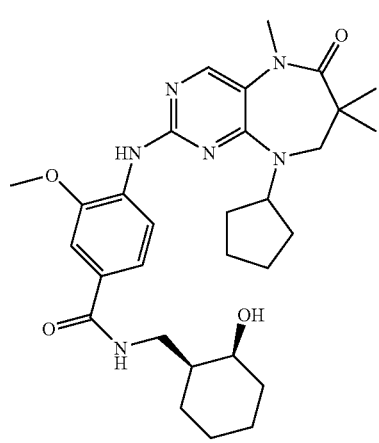
I-217
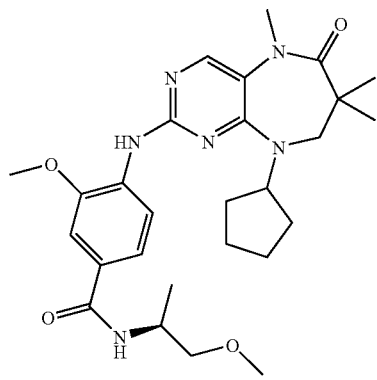
I-218
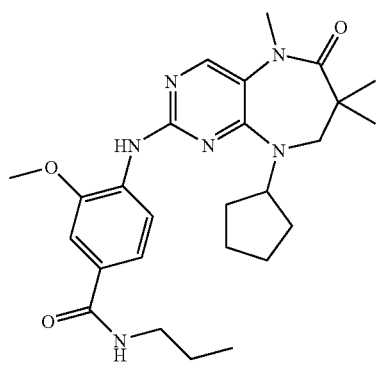
I-219
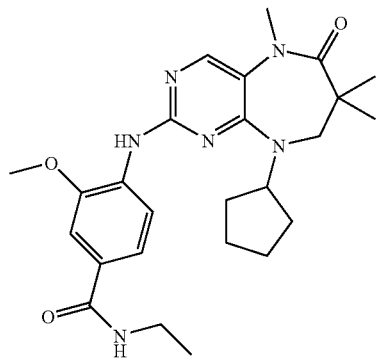
I-220
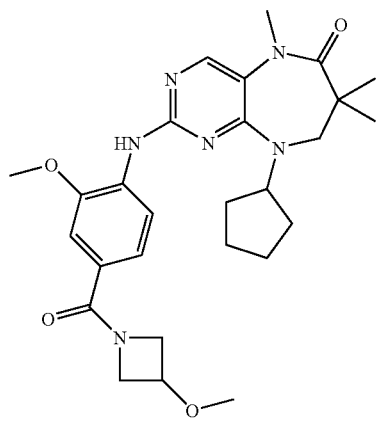

-continued
I-221
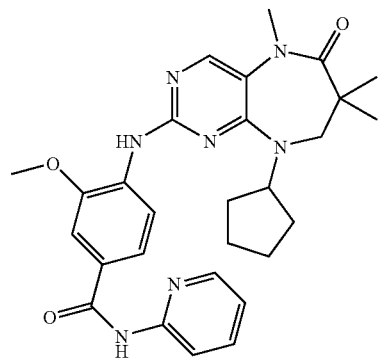
I-222
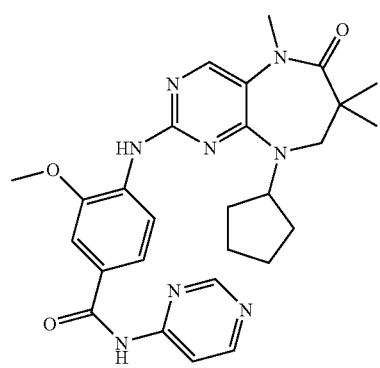
I-223
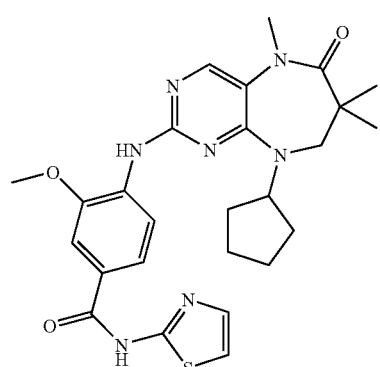
I-224
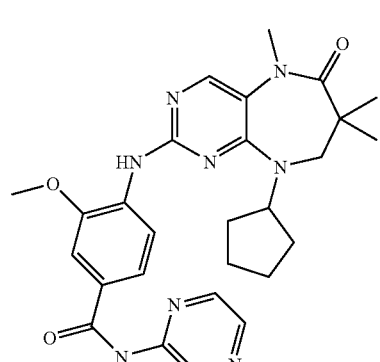
-continued
I-225
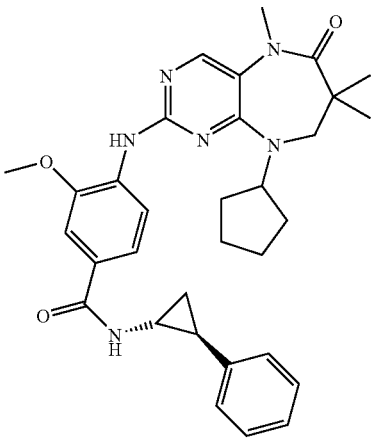
I-226
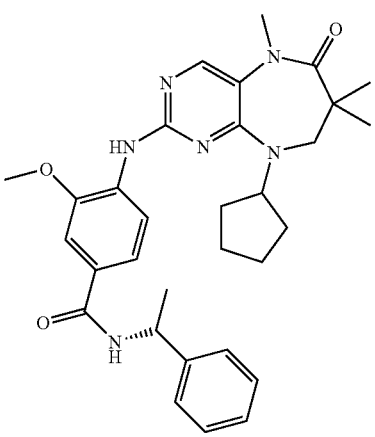
I-227
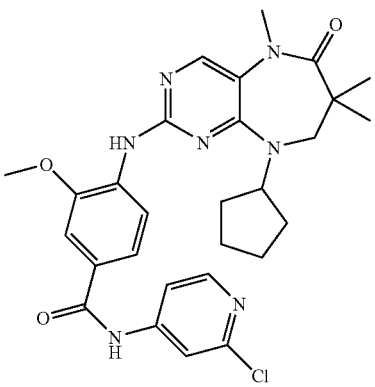

-continued
I-228
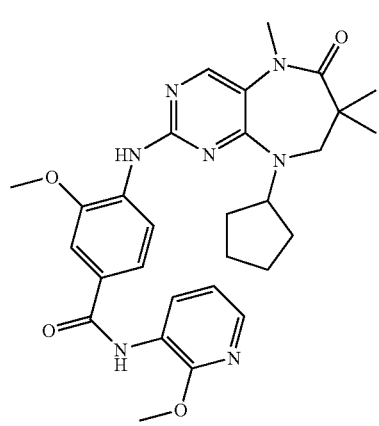
I-229
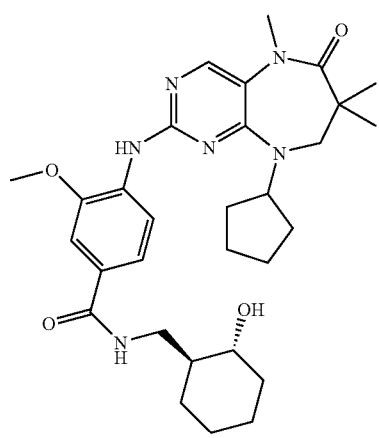
I-230
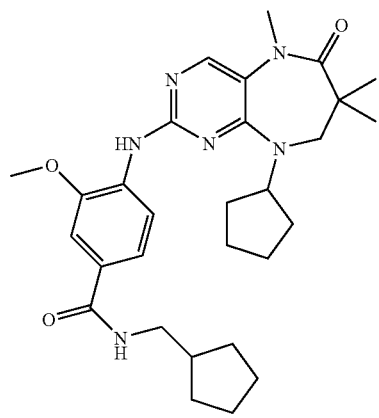
I-231
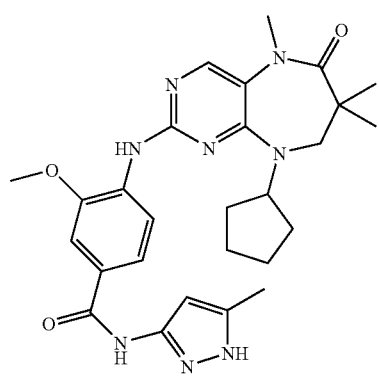
-continued
I-232
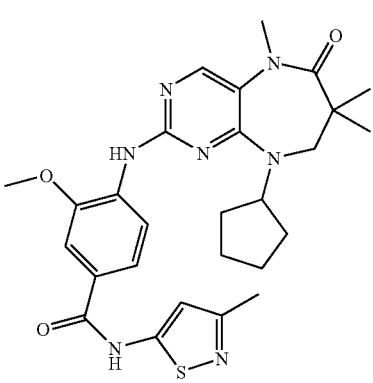
I-233
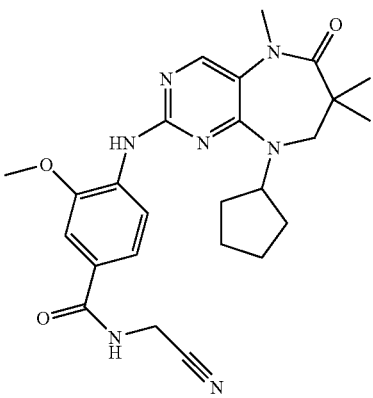
I-234
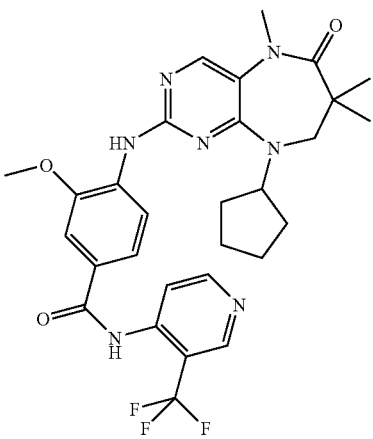
I-235
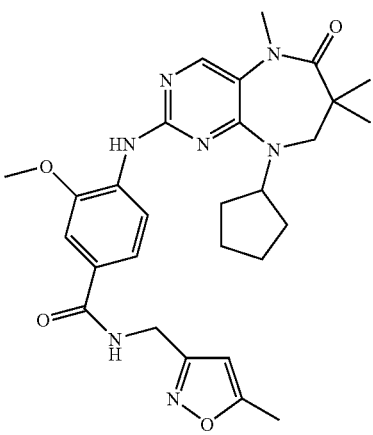

I-236
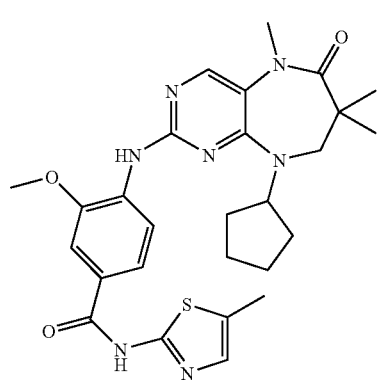
I-237
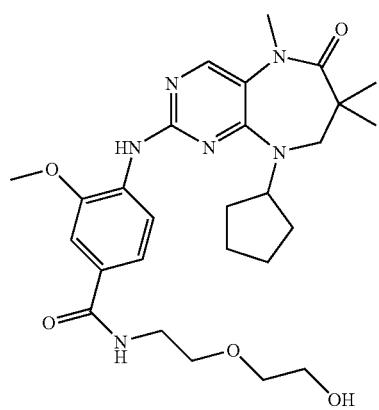
I-238
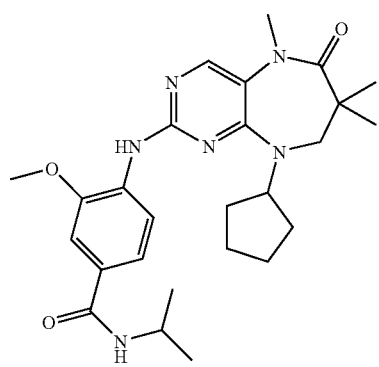
I-239
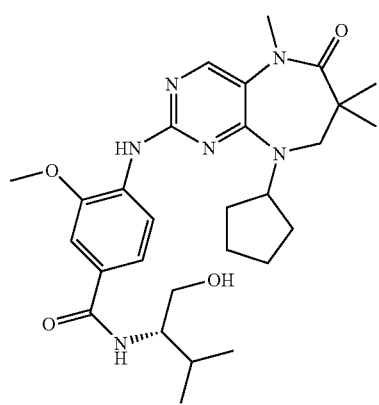
I-240
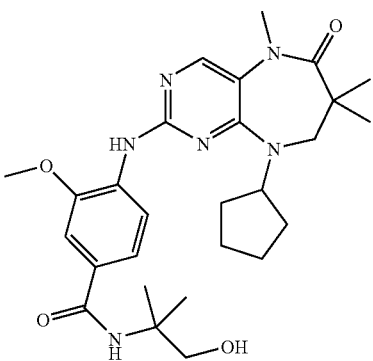
I-241
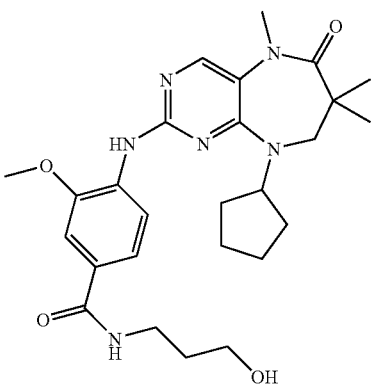
I-242
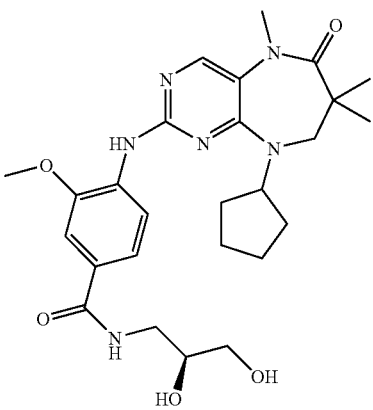
I-243
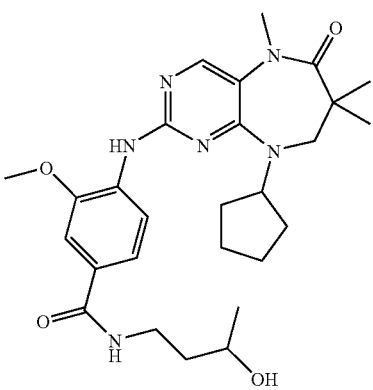

I-244
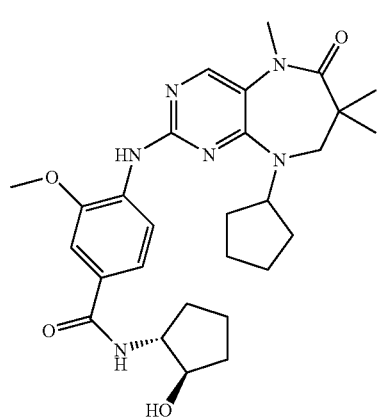
I-245
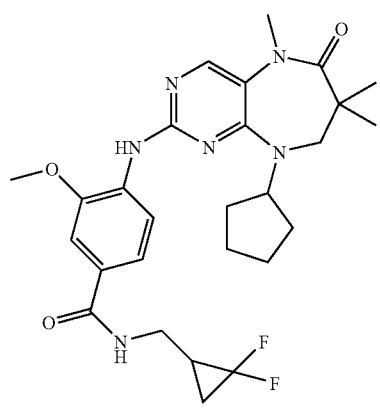
I-246
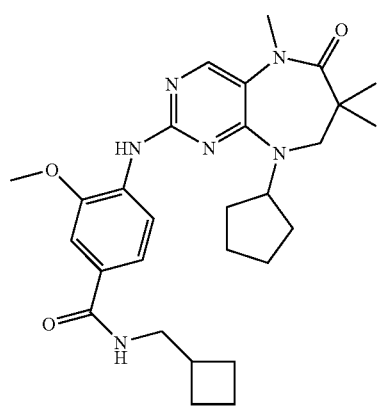
I-247
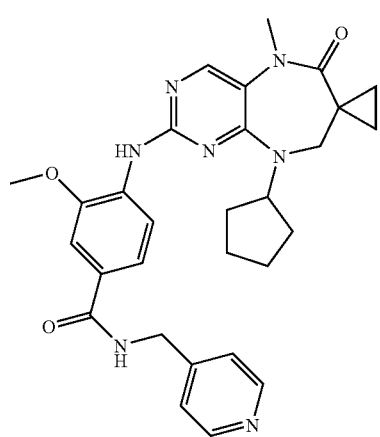
I-248
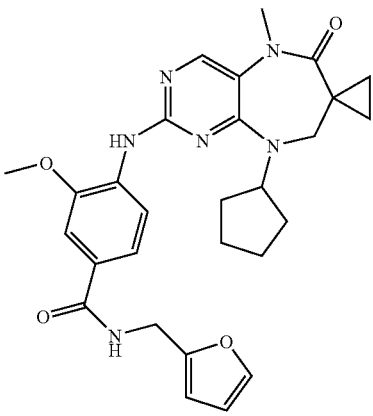
I-249
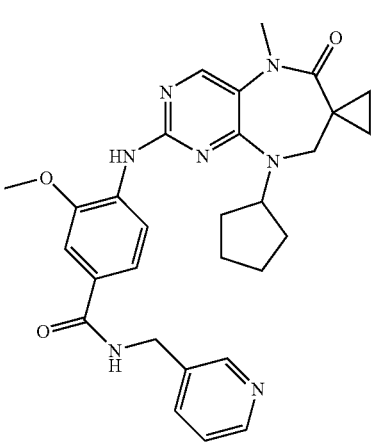
I-250
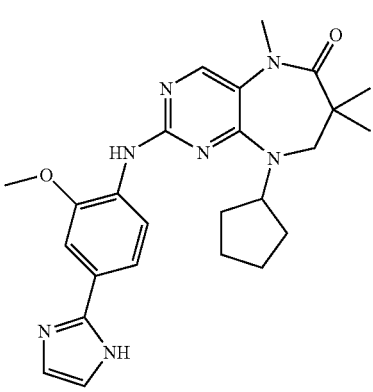
I-251
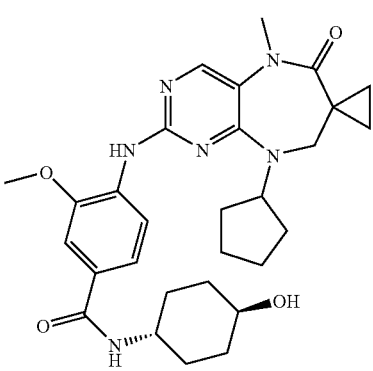

-continued
I-252
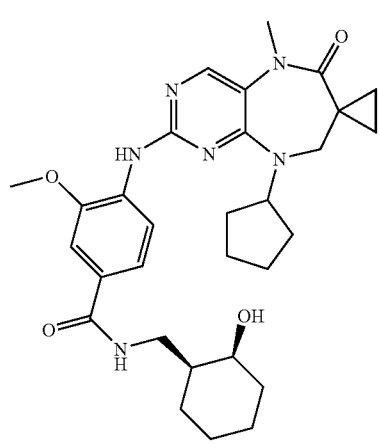
I-253
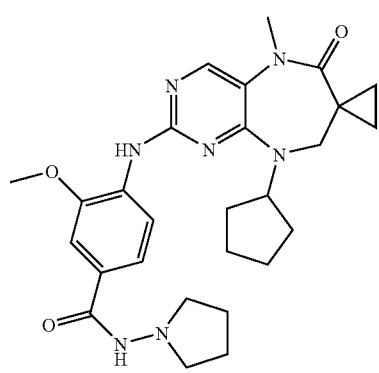
I-254
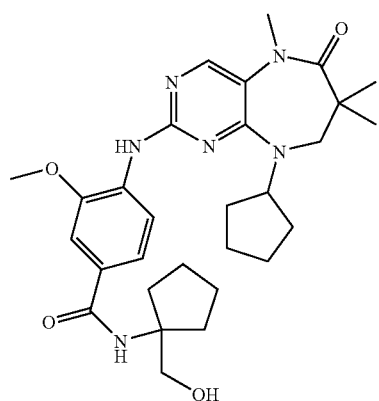
I-255
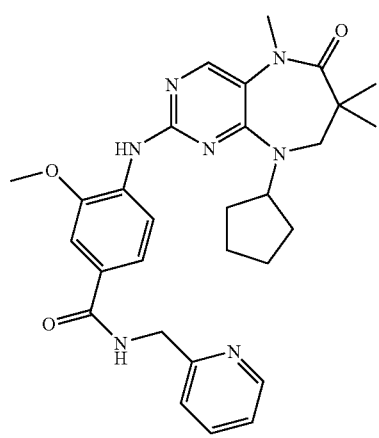
-continued
I-256
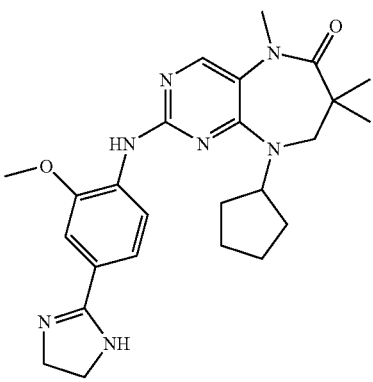
I-257
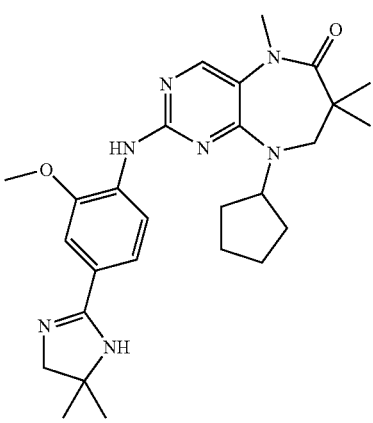
I-258
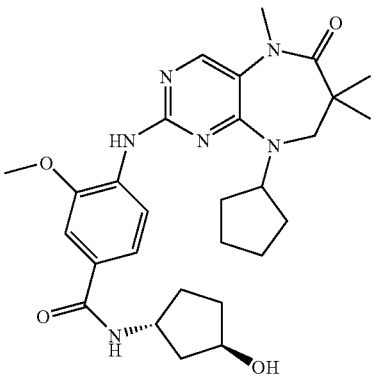
I-259
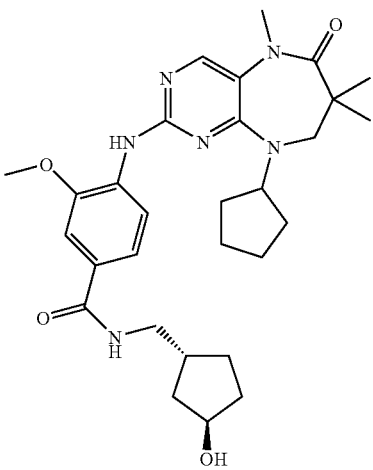

I-260 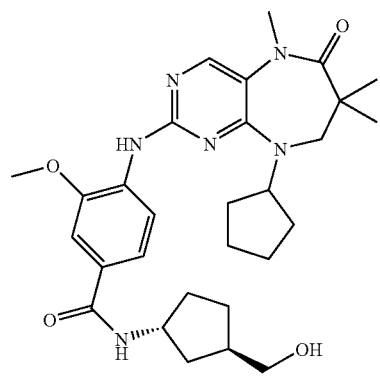
I-261 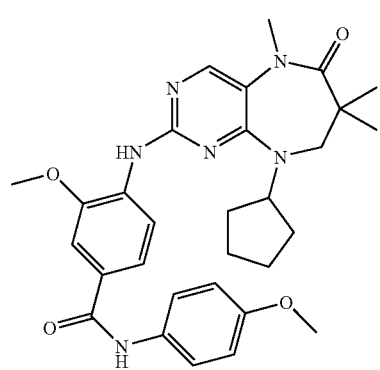
I-262 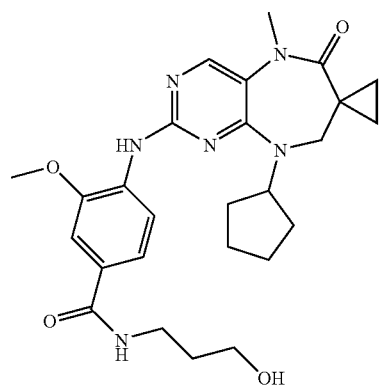
I-263 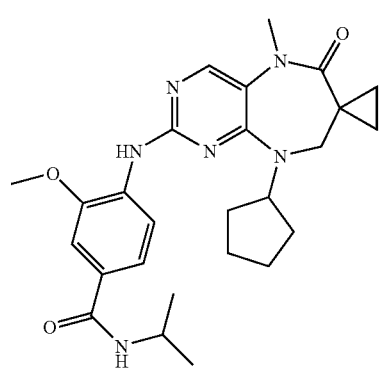
I-264 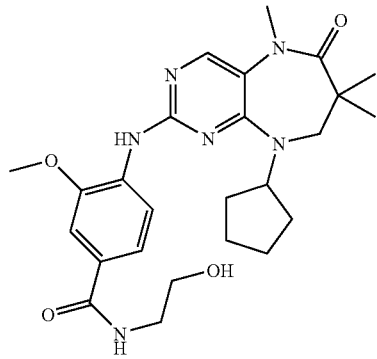
I-265 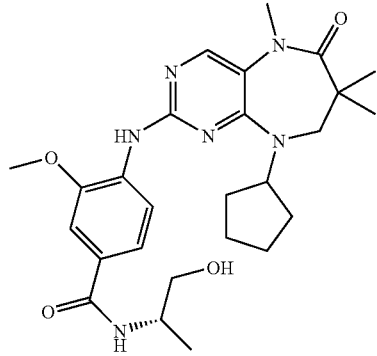
I-266 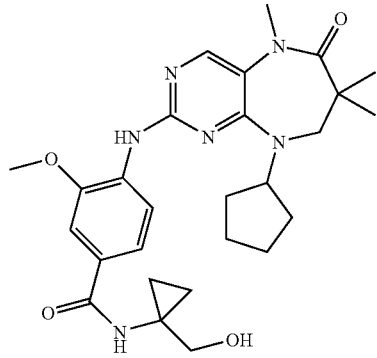
I-267 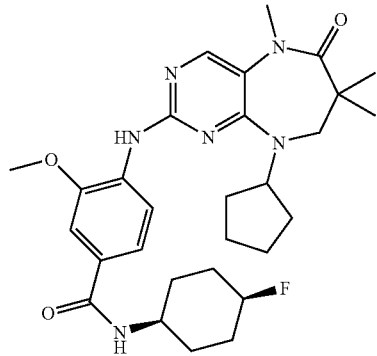

-continued
I-268
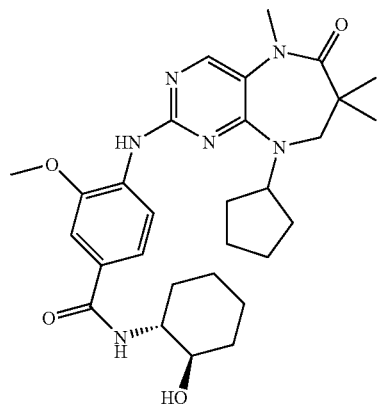
I-269
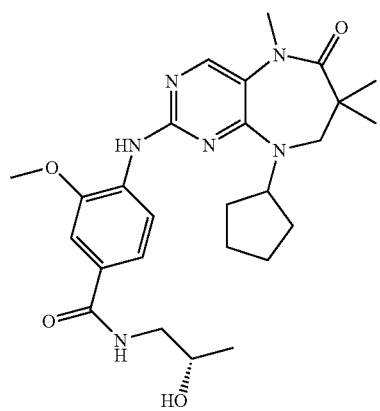
I-270
I-271
-continued
I-272
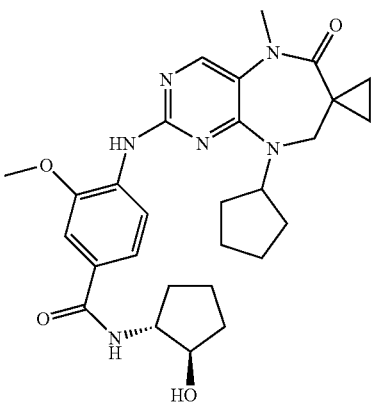
I-273
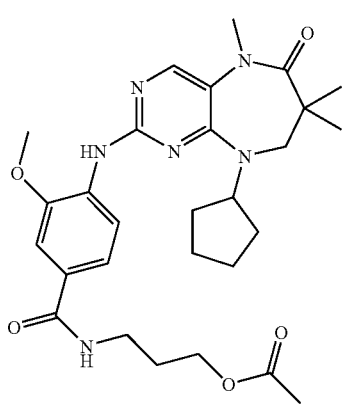
I-274
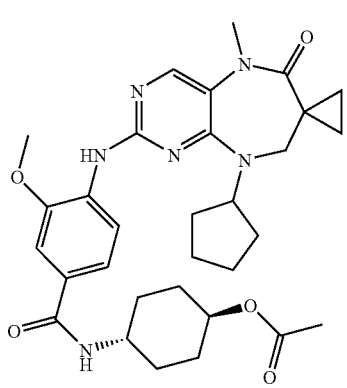
I-275
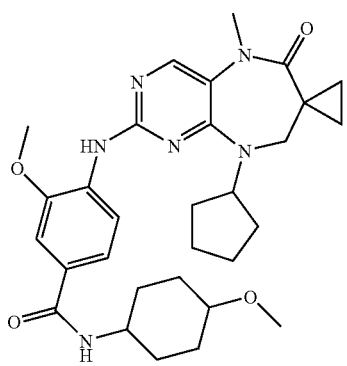

I-276
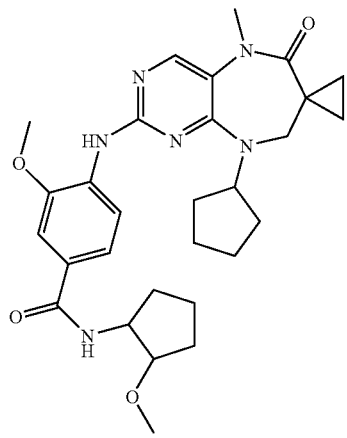
I-277
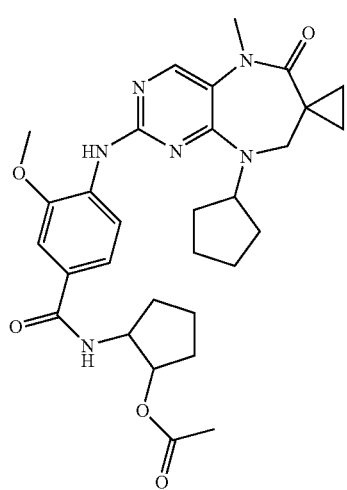
I-278
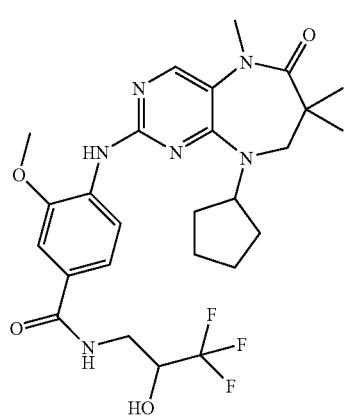
I-279
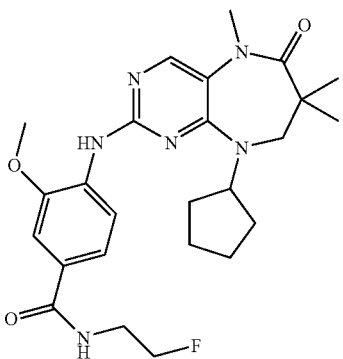
I-280
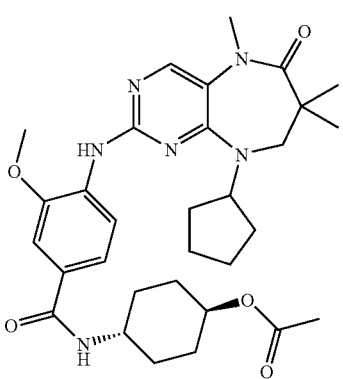
I-281
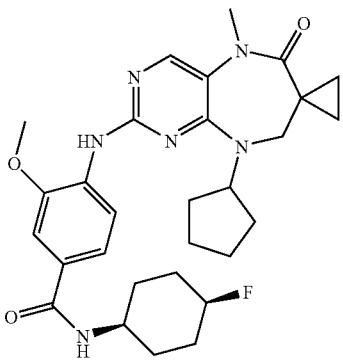
I-282
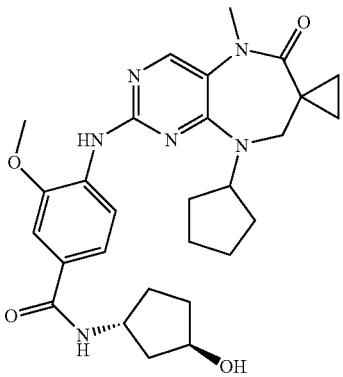

31. A composition comprising a compound of any one of claims 1-30, and a pharmaceutically acceptable carrier, adjuvant, or vehicle.

32. A process for preparing a compound of formula I:

wherein
Y$^1$ is O and X$^1$, R$^1$, R$^2$, R$^3$, R$^4$, R$^5$, R$^6$, and R$^7$ are as defined according to any one of claims 1-30;
comprising reacting a compound of formula 5;

wherein
R$^2$, R$^3$, R$^4$, R$^5$, R$^6$, and R$^7$ are as defined according to any one of claims 1-29; and LG$_2$ is a suitable leaving group;
with X$^1$R$^1$ under suitable conditions to form the compound of formula I.

33. The process of claim 32, further comprising the step of reacting a compound of formula 4;

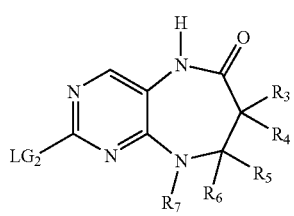

with $R^2$-$LG_3$, wherein $LG_3$ is a leaving group capable of being displaced by an NH-amide; to form the compound of formula 5.

34. The process of claim 33, further comprising cyclizing a compound of formula 3-a;

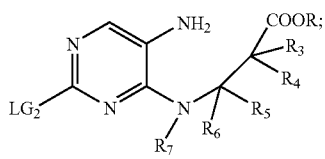

wherein $LG_2$ is a suitable leaving group and R is H or unsubstituted $C_{1-6}$aliphatic; under cyclo-condensation conditions to form a compound of formula 4.

35. The process of claim 34, further comprising the step reacting a compound of formula 3;

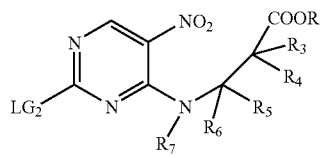

under suitable reduction conditions to form a compound of formula 3-a.

36. The process of claim 34, further comprising
(a) functionalizing the amino group in the compound of formula 3-a under suitable conditions to form a compound of formula 3-b;

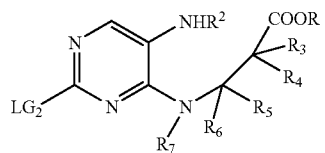

(b) cyclizing the compound of formula 3-b under suitable cyclo-condensation conditions to form a compound of formula 4.

37. The process of claim 35, further comprising reacting a compound of formula 2;

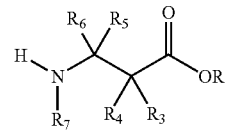

with a compound of formula 1;

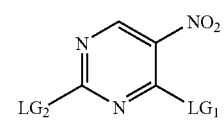

wherein $LG_1$ and $LG_2$ are each independently suitable leaving groups; under suitable displacement conditions to form the compound of formula 3.

38. A process for preparing a compound of formula I:

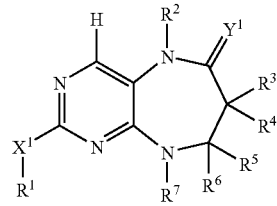

wherein $Y^1$ is $NR^9$ and $X^1$, $R^1$, $R^2$, $R^3$, $R^4$, $R^5$, $R^6$, and $R^7$ are as defined according to any one of claims 1-29;
comprising reacting the compound of formula I wherein $Y^1$ is O and $X^1$, $R^1$, $R^2$, $R^3$, $R^4$, $R^5$, $R^6$, and $R^7$ are as defined according to any one of claims 1-29;
under suitable conditions known in the art for converting amides into amidines, to form a compound of formula I wherein $Y^1$ is $NR^9$.

39. A process for preparing a compound of formula 5-a:

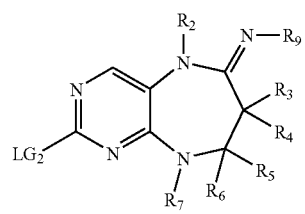

wherein $LG_2$ is a suitable leaving group and $R^2$, $R^3$, $R^4$, $R^5$, $R^6$, $R^7$, and $R^9$ are as defined according to any one of claims 1-29;

comprising reacting a compound of formula 5

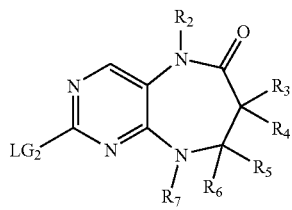

wherein $LG_2$ is a suitable leaving group and $R^2$, $R^3$, $R^4$, $R^5$, $R^6$ and $R^7$ are as defined according to any one of claims 1-29;

under suitable conditions known in the art for converting amides into amidines, to form a compound of formula 5-a.

40. The process of claim 39, further comprising displacing $LG_2$ with $X^1R^1$ to form a compound of formula I wherein $Y^1$ is $NR^9$, $X^1$ is a bond, O, $NR^8$, S, SO, or $SO_2$;

$R^1$ is H, $C_{1-10}$aliphatic, $C_{3-10}$cycloaliphatic, $C_{6-10}$aryl, 5-10 membered heteroaryl, or 3-10 membered heterocyclyl; wherein said $R^1$ is optionally substituted with 0-5 $J^1$; provided that when $X^1$ is a bond, $R^1$ is not H;

each $J^1$ is independently $C_{1-6}$haloalkyl, halo, $NO_2$, CN, Q, or -Z-Q; or, two $J^1$ taken together can optionally form =O;

Z is $C_{1-6}$aliphatic optionally replaced with 0-3 occurrences of —NR—, —O—, —S—, —C(O)—, —C(=NR)—, —C(=NOR)—, —SO—, or —SO)—; each Z is optionally substituted with 0-2 $J^Z$;

Q is H; $C_{1-6}$ aliphatic; a 3-8-membered aromatic or non-aromatic monocyclic ring having 0-3 heteroatoms independently selected from O, N, and S; or an 7-12 membered aromatic or nonaromatic bicyclic ring system having 0-5 heteroatoms independently selected from O, N, and S; each O is optionally substituted with 0-5 $J^Q$; and each $J^Z$ is independently halo, $C_{1-6}$ aliphatic, $C_{3-6}$cycloaliphatic, $NO_2$, CN, —$NH_2$, —NH($C_{1-4}$ aliphatic), —N($C_{1-4}$ aliphatic)$_2$, —OH, —O($C_{1-4}$ aliphatic), —$CO_2$H, —$CO_2$($C_{1-4}$ aliphatic), —O(halo$C_{1-4}$ aliphatic), or halo($C_{1-4}$ aliphatic).

41. The process of claim 38, wherein $R^2$ and $R^9$ are taken together to form Ring A, and wherein suitable conditions known in the art for converting amides into amidines comprise a multi-step cyclisation sequence to form ring A.

42. The process of claim 39, wherein $R^2$ and $R^9$ are taken together to form Ring A, and wherein suitable conditions known in the art for converting amides into amidines comprise a multi-step cyclisation sequence to form ring A.

\* \* \* \* \*

SEQUENCE LISTING

```
<160> NUMBER OF SEQ ID NOS: 2

<210> SEQ ID NO 1
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Lys Lys Ile Ser Asp Glu Leu Met Asp Ala Thr Phe Ala Asp Gln
1               5                   10                  15

Glu Ala Lys
```

```
<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Lys Lys Met Asp Ala Thr Phe Ala Asp Gln
1               5                   10
```